US012448430B2

(12) United States Patent
Schmitt et al.

(10) Patent No.: US 12,448,430 B2
(45) Date of Patent: Oct. 21, 2025

(54) HIGH AVIDITY WT1 T CELL RECEPTORS AND USES THEREOF

(71) Applicant: FRED HUTCHINSON CANCER CENTER, Seattle, WA (US)

(72) Inventors: Thomas M. Schmitt, Seattle, WA (US); Aude G. Chapuis, Seattle, WA (US); Philip D. Greenberg, Mercer Island, WA (US)

(73) Assignee: FRED HUTCHINSON CANCER CENTER, Seattle, WA (US)

(*) Notice: Subject to any disclaimer, the term of this patent is extended or adjusted under 35 U.S.C. 154(b) by 910 days.

(21) Appl. No.: 17/438,380

(22) PCT Filed: Mar. 10, 2020

(86) PCT No.: PCT/US2020/021916

§ 371 (c)(1),
(2) Date: Sep. 10, 2021

(87) PCT Pub. No.: WO2020/185796

PCT Pub. Date: Sep. 17, 2020

(65) Prior Publication Data

US 2022/0160764 A1 May 26, 2022

Related U.S. Application Data

(60) Provisional application No. 62/816,746, filed on Mar. 11, 2019.

(51) Int. Cl.

| | |
|---|---|
| ***A61K 35/17*** | (2025.01) |
| ***A61K 40/11*** | (2025.01) |
| ***A61K 40/32*** | (2025.01) |
| ***A61K 40/42*** | (2025.01) |
| ***A61P 35/00*** | (2006.01) |
| ***C07K 14/725*** | (2006.01) |
| ***C12N 5/0783*** | (2010.01) |
| *A61K 38/00* | (2006.01) |

(52) U.S. Cl.

CPC .......... *C07K 14/7051* (2013.01); *A61K 40/11* (2025.01); *A61K 40/32* (2025.01); *A61K 40/4243* (2025.01); *A61P 35/00* (2018.01); *C12N 5/0636* (2013.01); *A61K 38/00* (2013.01); *A61K 2239/49* (2023.05); *A61K 2239/54* (2023.05)

(58) Field of Classification Search

CPC ............................ C07K 14/7051; A61P 35/00
See application file for complete search history.

(56) References Cited

U.S. PATENT DOCUMENTS

| | | | |
|---|---|---|---|
| 5,283,173 | A | 2/1994 | Fields et al. |
| 5,420,032 | A | 5/1995 | Marshall et al. |
| 5,468,614 | A | 11/1995 | Fields et al. |
| 6,833,252 | B1 | 12/2004 | Dujon et al. |
| 7,342,092 | B2 | 3/2008 | Sugiyama |
| 7,608,685 | B1 | 10/2009 | Sugiyama et al. |
| 7,622,119 | B2 | 11/2009 | Sugiyama |
| 8,119,772 | B2 | 2/2012 | Yang et al. |
| 8,697,359 | B1 | 4/2014 | Zhang |
| 9,574,000 | B2 | 2/2017 | Langermann et al. |
| 2004/0002092 | A1 | 1/2004 | Arnould et al. |
| 2004/0087025 | A1 | 5/2004 | June et al. |
| 2006/0078552 | A1 | 4/2006 | Arnould et al. |
| 2006/0153826 | A1 | 7/2006 | Arnould et al. |
| 2006/0206949 | A1 | 9/2006 | Arnould et al. |
| 2007/0117128 | A1 | 5/2007 | Smith et al. |
| 2011/0189141 | A1 | 8/2011 | Kieback et al. |
| 2011/0243972 | A1 | 10/2011 | Jaffee |
| 2011/0301073 | A1 | 12/2011 | Gregory et al. |
| 2014/0068797 | A1 | 3/2014 | Doudna et al. |
| 2014/0186843 | A1 | 7/2014 | Zhang et al. |
| 2017/0088895 | A1* | 3/2017 | Han .................... C12Q 1/6883 |
| 2019/0085081 | A1 | 3/2019 | Bicknell et al. |

FOREIGN PATENT DOCUMENTS

| | | | |
|---|---|---|---|
| JP | WO 2017501130 | A | 1/2017 |
| WO | WO 9709433 | A1 | 3/1997 |
| WO | WO 2005056595 | A2 | 6/2005 |
| WO | WO 2010084158 | A1 | 7/2010 |
| WO | WO 2013025779 | A1 | 2/2013 |
| WO | WO 2015071474 | A2 | 5/2015 |
| WO | WO 2015077615 | A1 | 5/2015 |
| WO | WO 2016022400 | A1 | 2/2016 |

(Continued)

OTHER PUBLICATIONS

Milighetti et al. Intra- and inter-chain contacts determine TCR specificity: applying protein co-evolution methods to TCRab pairing. bioRxiv doi: https://doi.org/10.1101/2024.05.24.595718; posted May 29, 2024. p. 1-51 (Year: 2024).*

Seladi-Schulman. Curing Cancer: Newer Treatments to Keep an Eye On. Downloaded from https://www.healthline.com/health/is-there-a-cure-for-cancer#overview. Published online May 19, 2023. p. 1-10. (Year: 2023).*

Altschul et al., "Gapped BLAST and PSI-BLAST: a new generation of protein database search programs," *Nucleic Acids Research* 25(17):3389-3402, 1997. (14 pages).

Argast et al., "I-PpoI and I-CreI Homing Site Sequence Degeneracy Determined by Random Mutagenesis and Sequential in Vitro Enrichment," *J. Mol. Biol.* 280:345-353, 1998. (9 pages).

Ashworth et al., "Computational redesign of endonuclease DNA binding and cleavage specificity," *Nature* 441(7093):656-659, Jun. 1, 2006. (NIH Public Access, Author Manuscript, available in PMC Dec. 9, 2010) (11 pages).

(Continued)

*Primary Examiner* — James D Schultz
*Assistant Examiner* — Jianjian Zhu
(74) *Attorney, Agent, or Firm* — Seed IP Law Group LLP

(57) ABSTRACT

The present disclosure provides T cell receptors (TCRs) and related binding proteins with high functional avidity against tumor associated antigen p37 from Wilms tumor protein 1 (WT1), T cells expressing such high affinity WT1 specific TCRs, nucleic acids encoding the same, and compositions for use in treating diseases or disorders in which cells overexpress WT1 and/or produce the p37 antigen, such as in cancer.

49 Claims, 12 Drawing Sheets

Specification includes a Sequence Listing.

(56) References Cited

FOREIGN PATENT DOCUMENTS

| | | | |
|---|---|---|---|
| WO | WO 2016040724 | A1 | 3/2016 |
| WO | WO 2016054638 | A1 | 4/2016 |
| WO | WO 2016134333 | A1 | 8/2016 |
| WO | WO 2016141357 | A1 | 9/2016 |
| WO | WO 2017021526 | A1 | 2/2017 |
| WO | WO 2017059084 | A1 | 4/2017 |
| WO | WO 2017112944 | A1 | 6/2017 |
| WO | WO 2018058002 | A1 | 3/2018 |
| WO | WO 2018197492 | A1 | 11/2018 |
| WO | WO 2019178427 | A1 | 9/2019 |

OTHER PUBLICATIONS

Belfort et al., "Homing endonucleases: keeping the house in order," *Nucleic Acids Research* 25(17):3379-3388, 1997. (10 pages).

Betts et al., "The Functional Profile of Primary Human Antiviral CD8+ T Cell Effector Activity Is Dictated by Cognate Peptide Concentration," *The Journal of Immunology* 172:6407-6417, 2004. (12 pages).

Cavallo et al., "2011: the immune hallmarks of cancer," *Cancer Immunol. Immunother.* 60:319-326, 2011. (8 pages).

Cawthon et al., "Peptide Requirement for CTL Activation Reflects the Sensitivity to CD3 Engagement: Correlation with CD8αβ Versus CD8aa Expression," *The Journal of Immunology* 167:2577-2584, 2001. (9 pages).

Chapuis et al., "Transferred melanoma-specific CD8+ T cells persist, mediate tumor regression, and acquire central memory phenotype," *PNAS* 109(12):4592-4597, Mar. 20, 2012. (6 pages).

Chapuis et al., "Transferred WT1-reactive CD8+ T cells can mediate antileukemic activity and persist in post-transplant patients," *Sci. Transl. Med.* 5(174):174ra27, Feb. 27, 2013. (NIH Public Access, Author Manuscript, available in PMC Jun. 11, 2013) (25 pages).

Cheever et al., "The Prioritization of Cancer Antigens: A National Cancer Institute Pilot Project for the Acceleration of Translational Research," *Clin. Cancer Res.* 15(17):5323-5337, Sep. 1, 2009. (15 pages).

Chen et al., "Oncology Meets Immunology: The Cancer-Immunity Cycle," *Immunity* 39:1-10, Jul. 25, 2013. (10 pages).

Chevalier et al., "Design, Activity, and Structure of a Highly Specific Artificial Endonuclease," *Molecular Cell* 10:895-905, Oct. 2002. (11 pages).

Chothia et al., "The outline structure of the T-cell αβ receptor," *The EMBO Journal* 7(12):3745-3755, 1988. (11 pages).

Cole et al., "CD8: Adhesion Molecule, Co-Receptor and Immuno-Modulator," *Cellular & Molecular Immunology* 1(2):81-88, Apr. 2004. (8 pages).

Coosemans et al., "Wilms' tumor gene 1 immunotherapy in pelvic gynecological malignancies," *Expert Rev. Clin. Immunol.* 10(6): 705-711, 2014. (8 pages).

Dangaj et al., "Novel Recombinant Human B7-H4 Antibodies Overcome Tumoral Immune Escape to Potentiate T-Cell Antitumor Responses," *Cancer Res* 73(15):4820-4829, Aug. 1, 2013. (10 pages).

Desjarlais et al., "Use of a zinc-finger consensus sequence framework and specificity rules to design specific DNA binding proteins," *Proc. Natl. Acad. Sci. USA* 90:2256-2260, Mar. 1993. (5 pages).

Di Stasi et al., "Inducible Apoptosis as a Safety Switch for Adoptive Cell Therapy," *The New England Journal of Medicine* 365(18):1673-1683, Nov. 3, 2011. (11 pages).

Dossett et al., "Adoptive Immunotherapy of Disseminated Leukemia With TCR-transduced, CD8+ T Cells Expressing a Known Endogenous TCR," *Molecular Therapy* 17(4):742-749, Apr. 2009. (8 pages).

Dudley et al., "Adoptive Cell Therapy for Patients With Metastatic Melanoma: Evaluation of Intensive Myeloablative Chemoradiation Preparative Regimens," *Journal of Clinical Oncology* 26(32):5233-5239, Nov. 10, 2008. (7 pages).

Dujon et al., "Mobile introns: definition of terms and recommended nomenclature," *Gene* 82:115-118, 1989. (4 pages).

Epinat et al., "A novel engineered meganuclease induces homologous recombination in yeast and mammalian cells," *Nucleic Acids Research* 31(11):2952-2962, 2003. (11 pages).

Fehse et al., "CD34 Splice Variant: An Attractive Marker for Selection of Gene-Modified Cells," *Molecular Therapy* 1(5):448-456, May 2000. (9 pages).

Floros et al., "Anticancer Cytokines: Biology and Clinical Effects of IFN-α2, IL-2, IL-15, IL-21, and IL-12," *Semin Oncol.* 42(4):539-548, Aug. 2015. (HHS Public Access, Author Manuscript, available in PMC Aug. 1, 2016) (17 pages).

Gao et al., "Molecular interactions of coreceptor CD8 and MCH class I: the molecular basis for functional coordination with the T-cell receptor," *Immunology Today* 21(12):630-636, Dec. 2000. (7 pages).

Gimble et al., "Substrate Recognition and Induced DNA Distortion by the PI-SceI Endonuclease, an Enzyme Generated by Protein Splicing," *J. Mol. Biol.* 263:163-180, 1996. (18 pages).

Govers et al., "T cell receptor gene therapy: strategies for optimizing transgenic TCR pairing," *Trends in Molecular Medicine* 16(2):77-87, 2010. (11 pages).

Green et al., "Mitichondria and Apoptosis," *Science* 281:1309-1312, Aug. 28, 1998. (4 pages).

Hanahan et al., "Hallmarks of Cancer: The Next Generation," *Cell* 144:646-674, Mar. 4, 2011. (29 pages).

Hanahan et al., "The Hallmarks of Cancer," *Cell* 100:57-70, Jan. 7, 2000. (14 pages).

Harris et al., "Adoptive T Cell Therapies: A Comparison of T Cell Receptors and Chimeric Antigen Receptors," *Trends in Pharmacological Sciences* 37(3):220-230, Mar. 2016. (11 pages).

Heemskerk et al., "Redirection of antileukemic reactivity of peripheral T lymphocytes using gene transfer of minor histocompatibility antigen HA-2-specific T-cell receptor complexes expressing a conserved alpha joining region," *Blood* 102(10):3530-3540, Nov. 15, 2003. (11 pages).

Ho et al., "In vitro methods for generating CD8+ T-cell clones for immunotherapy from the naïve repertoire," *Journal of Immunological Methods* 310:40-52, 2006. (13 pages).

Howie et al., "High-throughput pairing of T cell receptor a and B sequences," *Science Translational Medicine* 7(301):301ra131, Aug. 19, 2015. (12 pages).

Hylander et al., "Expression of Wilms tumor gene (WT1) in epithelial ovarian cancer," *Gynecologic Oncology* 101:12-17, 2006. (6 pages).

International Search Report and Written Opinion, mailed Sep. 14, 2020, for International Application No. PCT/US2020/021916. (25 pages).

Jaigirdar et al., "A high avidity WTI reactive T cell receptor mediates recognition of peptide and processed antigen but not naturally occurring WTI positive tumor cells," *J. Immunother.* 39(3):105-116, Apr. 2016. (HHS Public Access, Author Manuscript, available in PMC Apr. 1, 2017) (26 pages).

Jasin, "Genetic manipulation of genomes with rare-cutting endonucleases," *TIG* 12(6):224-228, Jun. 1996. (5 pages).

Jinek et al., "A programmable dual RNA-guided DNA endonuclease in adaptive bacterial immunity," *Science* 337(6096):816-821, Aug. 17, 2012. (HHMI Public Access, Author Manuscript, available in PMC Dec. 7, 2018) (14 pages).

Jores et al., "Resolution of hypervariable regions in T-cell receptor β chains by a modified Wu-Kabat index of amino acid diversity," *Proc. Natl. Acad. Sci. USA* 87:9138-9142, Dec. 1990. (5 pages).

Kalos et al., "T Cells with Chimeric Antigen Receptors Have Potent Antitumor Effects and Can Establish Memory in Patients with Advanced Leukemia," *Sci. Transl. Med.* 3(95):95ra73, Aug. 10, 2011. (NIH Public Access, Author Manuscript, available in PMC Aug. 10, 2012) (21 pages).

Kieback et al., "A safeguard eliminates T cell receptor gene-modified autoreactive T cells after adoptive transfer," *PNAS* 105(2):623-628, Jan. 15, 2008. (6 pages).

(56) References Cited

OTHER PUBLICATIONS

Kochenderfer et al., "Eradication of B-lineage cells and regression of lymphoma in a patient treated with autologous T cells genetically engineered to recognize CD19," *Blood* 116(20):4099-4102, Nov. 18, 2010. (4 pages).
Kuball et al., "Facilitating matched pairing and expression of TCR chains introduced into human T cells," *Blood* 109(6):2331-2338, Mar. 15, 2007. (8 pages).
Kyrgidis et al., "Melanoma: Stem cells, sun exposure and hallmarks for carcinogenesis, molecular concepts and future clinical implications," *Journal of Carcinogenesis* 9(3):1-15, Apr. 1, 2010. (15 pages).
Langenkamp et al., "T cell priming by dendritic cells: thresholds for proliferation, differentiation and death and intraclonal functional diversification," *Eur. J. Immunol.* 32:2046-2054, 2002. (9 pages).
Leen et al., "Improving T Cell Therapy for Cancer," *Annu. Rev. Immunol.* 25:243-265, 2007. (26 pages).
Lefranc et al., "IMGT unique numbering for immunoglobulin and T cell receptor variable domains and Ig superfamily V-like domains," *Developmental and Comparative Immunology* 27:55-77, 2003. (23 pages).
Liu et al., "Selective inhibition of IDO1 effectively regulates mediators of antitumor immunity," *Blood* 115(17):3520-3530, Apr. 29, 2010. (11 pages).
Luescher et al., "CD8 modulation of T-cell antigen receptor-ligand interactions on living cytotoxic T lymphocytes," *Nature* 373:353-356, Jan. 26, 1995. (4 pages).
Mautino et al., "Abstract 491: NLG919, a novel indoleamine-2,3-dioxygenase (IDO)-pathway inhibitor drug candidate for cancer therapy," Proceedings: AACR 104th Annual Meeting 2013, American Association for Cancer Research, Washington, DC, Apr. 6-10, 2013, *Cancer Res.* 73(8 Suppl): Abstract nr 491. (4 pages).
Mavilio et al., "Peripheral Blood Lymphocytes as Target Cells of Retroviral Vector-Mediated Gene Transfer," *Blood* 83(7):1988-1997, Apr. 1, 1994. (10 pages).
Menssen et al., "Presence of Wilms' tumor gene (wt1) transcripts and the WTI nuclear protein in the majority of human acute leukemias," *Leukemia* 9:1060-1067, 1995. (8 pages).
Morgan et al., "Cancer Regression in Patients After Transfer of Genetically Engineered Lymphocytes," *Science* 314(5796):126-129, Oct. 6, 2006. (NIH Public Access, Author Manuscript, available in PMC Mar. 12, 2008) (10 pages).
Nakatsuka et al., "Immunohistochemical detection of WT1 protein in a variety of cancer cells," *Modern Pathology* 19:804-814, 2006. (11 pages).
Oji et al., "Expression of the Wilms' Tumor Gene WTI in Solid Tumors and Its Involvement in Tumor Cell Growth," *Jpn. J. Cancer Res.* 90:194-204, Feb. 1999. (11 pages).
Oji et al., "Overexpression of the Wilms' Tumor Gene WTI in De Novo Lung Cancers," *Int. J. Cancer* 100:297-303, 2002. (7 pages).
Pardoll, "The blockade of immune checkpoints in cancer immunotherapy," Nature Reviews *Cancer* 12:252-264, Apr. 2012. (13 pages).
Park et al., "Cancer Stem Cell-Directed Therapies: Recent Data From the Laboratory and Clinic," *Molecular Therapy* 17(2):219-230, Feb. 2009. (12 pages).
Penix et al., "Two Essential Regulatory Elements in the Human Interferon γ Promoter Confer Activation Specific Expression in T Cells," *The Journal of Experimental Medicine* 178:1483-1496, Nov. 1993. (14 pages).
Perler et al., "Protein splicing elements: inteins and exteins—a definition of terms and recommended nomenclature," *Nucleic Acids Research* 22(7):1125-1127, 1994. (3 pages).
Philip et al., "A highly compact epitope-based marker/suicide gene for easier and safer T-cell therapy," *Blood* 124(8):1277-1287, Aug. 21, 2014. (11 pages).
Pittet et al., "α3 Domain Mutants of Peptide/MHC Class I Multimers Allow the Selective Isolation of High Avidity Tumor-Reactive CD8 T Cells," *The Journal of Immunology* 171:1844-1849, 2003. (7 pagse).
Porter et al., "Chimeric Antigen Receptor-Modified T Cells in Chronic Lymphoid Leukemia," *The New England Journal of Medicine* 365(8):725-733, Aug. 25, 2011. (9 pages).
Porteus et al., "Gene targeting using zinc finger nucleases," *Nature Biotechnology*23(8):967-973, Aug. 2005. (7 pages).
Pâques et al., "Meganucleases and DNA Double-Strand Break-Induced Recombination: Perspectives for Gene Therapy," *Current Gene Therapy* 7(1):49-66, 2007. (18 pages).
Ren et al., "Multiplex genome editing to generate universal Car T cells resistant to PD1 inhibition," *Clin Cancer Res* 23(9):2255-2266, May 1, 2017. (HHS Public Access, Author Manuscript, available in PMC May 1, 2018) (21 pages).
Robbins et al., "Tumor Regression in Patients With Metastatic Synovial Cell Sarcoma and Melanoma Using Genetically Engineered Lymphocytes Reactive With NY-ESO-1," *Journal of Clinical Oncology* 29(7):917-924, Mar. 1, 2011. (8 pages).
Robins et al., "Comprehensive assessment of T-cell receptor β-chain diversity in αβ T cells," *Blood* 114(19):4099-4107, Nov. 5, 2009. (9 pages).
Robins et al., "Overlap and effective size of the human CD8+ T-cell receptor repertoire," *Sci. Transl. Med.* 2(47):47ra64, Sep. 1, 2010. (NIH Public Access, Author Manuscript, available in PMC Nov. 9, 2011) (9 pages).
Robins et al., "Ultra-sensitive detection of rare T cell clones," *J. Immunol. Methods* 375(0):14-19, Jan. 31, 2012. (NIH Public Access, Author Manuscript, available in PMC Jul. 24, 2013) (9 pages).
Sadelain et al., "The basic principles of chimeric antigen receptor (CAR) design," *Cancer Discov.* 3(4):388-398, Apr. 2013. (NIH Public Access, Author Manuscript, available in PMC Apr. 2, 2014) (21 pages).
Salter et al., "Impaired assembly and transport of HLA-A and -B antigens in a mutant TxB cell hybrid," *The EMBO Journal* 5(5):943-949, 1986. (7 pages).
Schmied et al., "Analysis of the functional WT1-specific T-cell repertoire in healthy donors reveals a discrepancy between $CD4^+$ and $CD8^+$ memory formation," *Immunology* 145:558-569, 2015. (12 pages).
Schmitt et al., "Generation of TCRs of higher affinity by antigen-driven differentiation of progenitor T cells in vitro," *Nat. Biotechnol.* 35(12):1188-1195, Dec. 2017. (HHS Public Access, Author Manuscript, available in PMC May 6, 2018) (21 pages).
Schmitt et al., "T Cell Receptor Gene Therapy for Cancer," *Human Gene Therapy* 20:1240-1248, Nov. 2009. (9 pages).
Scholten et al., "Codon modification of T cell receptors allows enhanced functional expression in transgenic human T cells," *Clinical Immunology* 119:135-145, 2006. (11 pages).
Stone et al., "A novel T cell receptor single-chain signaling complex mediates antigen-specific T cell activity and tumor control," *Cancer Immunol. Immunother.* 63(11):1163-1176, Nov. 2014. (NIH Public Access, Author Manuscript, available in PMC Nov. 1, 2015) (23 pages).
Stone et al., "Role of T cell receptor affinity in the efficacy and specificity of adoptive T cell therapies," *Frontiers in Immunology* 4:244, Aug. 21, 2013. (16 pages).
Straathof et al., "An inducible caspase 9 safety switch for T-cell therapy," *Blood* 105(11):4247-4254, Jun. 1, 2005. (8 pages).
Stromnes et al., "Abrogation of SHP-1 in tumor-specific T cells improves efficacy of adoptive immunotherapy by enhancing the effector function and accumulation of short-lived effector T cells in vivo," *J. Immunol.* 189(4):1812-1825, Aug. 15, 2012. (NIH Public Access, Author Manuscript, available in PMC Aug. 15, 2013) (31 pages).
Sussman et al., "Isolation and Characterization of New Homing Endonuclease Specificites at Individual Target Site Positions," *J. Mol. Biol.* 342:31-41, 2004. (11 pages).
Terentis et al., "The Selenazal Drug Ebselen Potently Inhibits Indoleamine 2,3-Dioxygenase by Targeting Enzyme Cysteine Residues," *Biochemistry* 49(3):591-600, 2010. (10 pages).
Thompson et al., "cis-Acting Sequences Required for Inducible Interleukin-2 Enhancer Function Bind a Novel Ets-Related Protein, Elf-1," *Molecular and Cellular Biology* 12(3):1043-1053, Mar. 1992. (11 pages).

(56) References Cited

OTHER PUBLICATIONS

Till et al., "Adoptive immunotherapy for indolent non-Hodgkin lymphoma and mantle cell lymphoma using genetically modified autologous CD20-specific T cells," *Blood* 112(6):2261-2271, Sep. 15, 2008. (11 pages).
Todd et al., "Transcription of the Interleukin 4 Gene Is Regulated by Multiple Promoter Elements," *J. Exp. Med.* 177:1663-1674, Jun. 1993. (12 pages).
Torikai et al., "A foundation for universal T-cell based immunotherapy: T cells engineered to express a CD19-specific chimeric-antigen-receptor and eliminate expression of endogenous TCR," *Blood* 119(24):5697-5705, Jun. 14, 2012. (10 pages).
Torikai et al., "Genetic editing of HLA expression in hematopoietic stem cells to broaden their human application," *Nature Scientific Reports* 6:21757, Feb. 23, 2016. (11 pages).
Torikai et al., "Toward eliminating HLA class I expression to generate universal cells from allogeneic donors," *Blood* 122(8):1341-1349, Aug. 22, 2013. (9 pages).
Tsuta et al., "Comparison of Different Clones (WT49 Versus 6F-H2) of WT-1 Antibodies for Immunohistochemical Diagnosis of Malignant Pleural Mesothelioma," *Appl. Immunohistochem. Mol. Morphol.* 17(2):126-130, Mar. 2009. (5 pages).
Viola et al., "T Cell Activation Determined by T Cell Receptor Number and Tunable Thresholds," *Science* 273:104-106, Jul. 5, 1996. (3 pages).
Walseng et al., "A TCR-based Chimeric Antigen Receptor," *Nature Scientific Reports* 7:10713, Sep. 6, 2017. (10 pages).
Wang et al., "A transgene-encoded cell surface polypeptide for selection, in vivo tracking, and ablation of engineered cells," *Blood* 118(5):1255-1263, Aug. 4, 2011. (9 pages).
Wang et al., "Optimizing Adoptive Polyclonal T Cell Immunotherapy of Lymphomas, Using a Chimeric T Cell Receptor Possessing CD28 and CD137 Costimulatory Domains," *Human Gene Therapy* 18:712-725, Aug. 2007. (16 pages).
Warren et al., "Exhaustive T-cell repertoire sequencing of human peripheral blood samples reveals signatures of antigen selection and a directly measured repertoire size of at least 1 million clonotypes," *Genome Research* 21:790-797, 2011. (8 pages).
Wolfe et al., "Analysis of Zinc Fingers Optimized via Phage Display: Evaluating the Utility of a Recognition Code," *J. Mol. Biol.* 285:1917-1934, 1999. (18 pages).
Xie et al., "sgRNAcas9: A Software Package for Designing CRISPR sgRNA and Evaluating Potential Off-Target Cleavage Sites," *PLoS One* 9(6):e100448, Jun. 23, 2014. (9 pages).
Zhou et al., "Improving the Safety of T Cell Therapies using an Inducible Caspase-9 Gene," *Exp Hematol* 44(11):1013-1019, Nov. 2016. (HHS Public Access, Author Manuscript, available in PMC Nov. 1, 2017) (14 pages).
Ashouri et al., "Endogenous Nur77 Is a Specific Indicator of Antigen Receptor Signaling in Human T and B Cells," *The Journal of Immunology* 198(2):657-668, Jan. 15, 2017. (13 pages).
Chapuis et al., "T Cell Receptor Gene Therapy Targeting WTI Prevents Acute Myeloid Leukemia Relapse Post-Transplant," *Nature Medicine* 25(7):1064-1072, Jul. 2019 (HHS Public Access Author Manuscript, available in PMC Jan. 25, 2020). (36 pages).
Cohen et al., "Enhanced Antitumor Activity of T Cells Engineered to Express T-Cell Receptors with a Second Disulfide Bond," *Cancer Research* 67(8):3898-3903, Apr. 15, 2007. (6 pages).
Cole et al., "The molecular determinants of CD8 co-receptor function," *Immunology* 137:139-148, Jul. 18, 2012. (10 pages).
Dunbar et al., "ANARCI: antigen receptor numbering and receptor classification," *Bioinformatics* 32(2):298-300, 2016 [Advance Access published Sep. 30, 2015]. (3 pages).
Engels et al., "Retroviral Vectors for High-Level Transgene Expression in T Lymphocytes," *Human Gene Therapy* 14:1155-1168, Aug. 10, 2003 [Published online Jun. 25, 2003]. (14 pages).
Frecha et al., "Advances in the Field of Lentivector-based Transduction of T and B Lymphocytes for Gene Therapy," *Molecular Therapy* 18(10):1748-1757, Oct. 2010 [Published online Aug. 24, 2010]. (10 pages).
Gaiger et al., "WT1-specific Serum Antibodies in Patients with Leukemia," *Clinical Cancer Research* 7 (Suppl.):761s-765s, Mar. 2001. (5 pages).
Hu et al., "Immune Signature of Enhanced Functional Avidity CD8+ T Cells in vivo Induced by Vaccinia Vectored Vaccine," *Scientific Reports* 7(41558), Feb. 3, 2017. (12 pages).
IMGT, "IMGT Repertoire (IG and TR)," retrieved at URL=imgt.org/IMGTrepertoire/LocusGenes/listIG_TR/TR/human/Hu_TRgroup.html, last updated Sep. 22, 2023. (1 page).
Inoue et al., "WTI as a New Prognostic Factor and a New Marker for the Detection of Minimal Residual Disease in Acute Leukemia," *Blood* 84(9):3071-3079, Nov. 1, 1994. (9 pages).
International Search Report, dated Feb. 3, 2021, for International Patent Application No. PCT/US2020/047071. (8 pages).
Kennedy et al., "Multiple roles for CD4+ T cells in anti-tumor immune responses," *Immunological Reviews* 222: 129-144, Apr. 2008. (16 pages).
Krisky et al., "Development of herpes simplex virus replicationdefective multigene vectors for combination gene therapy applications," *Gene Therapy* 5:1517-1530, Nov. 1998. (14 pages).
Liebl et al., "Transfer of *Brevibacterium divaricatum* DSM 20297T, "*Brevibacterium flavum*" DSM 20411, "*Brevibacterium lactofermentum*" DSM 20412 and DSM 1412, and *Corynebacterium lilium* DSM 20137T to *Corynebacterium glutamicum* and Their Distinction by rRNA Gene Restriction Patterns," *International Journal of Systematic Bacteriology* 41(2):255-260, Apr. 1991. (6 pages).
Nakanishi et al., "CTL mobilization to virus-infected tissue requires CD4+ T cell help," *Nature* 462(7272):510-513, Nov. 26, 2009 (HHS Public Access Author Manuscript, available in PMC May 26, 2010). (12 pages).
Ogawa et al., "The usefulness of monitoring WT1 gene transcripts for the prediction and management of relapse following allogeneic stem cell transplantation in acute type leukemia," *Blood* 101(5):1698-1704, Mar. 1, 2003. (7 pages).
Richman et al., "Display, engineering, and applications of antigen-specific T cell receptors," *Biomolecular Engineering* 24:361-373, Oct. 2007. (13 pages).
Scatchard et al., "The Attractions of Proteins for Small Molecules and Ions," *Annals of the New York Academy of Sciences* 51(4):660-672, May 1949. (13 pages).
Seeliger et al., "Boosting antibody developability through rational sequence optimization," *mAbs* 7(3):505-515, May 1, 2015. (12 pages).
Udyavar et al., "Subtle Affinity-Enhancing Mutations in a Myelin Oligodendrocyte Glycoprotein-Specific TCR Alter Specificity and Generate New Self-Reactivity," *The Journal of Immunology* 182(7):4439-4447, Apr. 1, 2009. (10 pages).
Verhoeyen et al., "Chapter 8: Lentiviral Vector Gene Transfer into Human T Cells," *Methods in Molecular Biology, Methods and Protocols* 506:97-114, 2009. (18 pages).
Viganò et al., "Functional Avidity: A Measure to Predict the Efficacy of Effector T Cells?," *Clinical and Developmental Immunology* 2012(153863), Nov. 20, 2012. (14 pages).
Wälchli et al., "A Practical Approach to T-Cell Receptor Cloning and Expression," *PLoS One* 6(11):e27930, Nov. 21, 2011. (11 pages).
Walseng et al., "Soluble T-Cell Receptors Produced in Human Cells for Targeted Delivery," *PLoS One* 10(4):e0119559, Apr. 13, 2015. (15 pages).
Wilson, "Analyzing Biomolecular Interactions," *Science* 295(5562):2103-2105, Mar. 15, 2002. (3 pages).
Wolff et al., "Monoclonal Antibody Homodimers: Enhanced Antitumor Activity in Nude Mice," *Cancer Research* 53:2560-2565, Jun. 1, 1993. (6 pages).
Zhao et al., "High-Affinity TCRs Generated by Phage Display Provide CD4+ T Cells with the Ability to Recognize and Kill Tumor Cell Lines," *The Journal of Immunology* 179(9):5845-5854, Nov. 1, 2007. (11 pages).
Zhao et al., "Primary Human Lymphocytes Transduced with NY-ESO-1 Antigen-Specific TCR Genes Recognize and Kill Diverse

(56) References Cited

OTHER PUBLICATIONS

Human Tumor Cell Lines," *The Journal of Immunology* 174(7):4415-4423, Apr. 1, 2005. (10 pages).

* cited by examiner

HIGH AVIDITY WT1 T CELL RECEPTORS AND USES THEREOF

STATEMENT OF GOVERNMENT INTEREST

This invention was made with government support under CA018029 awarded by the National Institutes of Health. The government has certain rights in the invention.

STATEMENT REGARDING SEQUENCE LISTING

The contents of the electronic sequence listing (360056_466USPC_SL_V2.xml; Size: 23,117,687 bytes; and Date of Creation: Dec. 6, 2024) is herein incorporated by reference in its entirety.

BACKGROUND

Adoptive T cell immunotherapy with genetically engineered T cells has shown promise in multiple trials in which an antigen receptor of sufficient affinity was used to target a tumor—associated antigen, including antibody-based chimeric receptors[1-3] and high affinity TCRs[4-8]. While the natural process of diversity generation in the thymus employs RAG-mediated TCR gene rearrangements to generate highly diverse CDR3s varying in length as well as amino acid composition, isolating an effective high affinity TCR within the affinity limits imposed by central tolerance remains a substantive roadblock to implementing adoptive T cell immunotherapy for the diversity of malignancies in which candidate intracellular self/tumor antigens have been identified[9,10]. In addition, TCR adoptive immunotherapy has the ability to detect intracellular antigens that are presented on the cell surface by MEW Class I.

The WT1 protein is an attractive target for clinical development due to its immune characteristics (Cheever et al., *Clin. Cancer Res.* 15:5323, 2009), and its expression in many aggressive tumor-types that have associated poor prognoses. WT1 is involved in the regulation of gene expression that promotes proliferation and oncogenicity (Oji et al., *Jpn. J. Cancer Res.* 90:194, 1999), is over-expressed in most high-risk leukemias (Menssen et al., *Leukemia* 9:1060, 1995), up to 80% of NSCLCs (Oji et al., *Int. J Cancer* 100:297, 2002), 100% of mesotheliomas (Tsuta et al., *App. Immunohistochem. Mol. Morphol.* 17:126, 2009), and ≥80% of gynecological malignancies (Coosemans and Van Gool, *Expert Rev. Clin. Immunol.* 10:705, 2014). Several peptides of the WT1 protein are known to be tumor-associated antigen peptides that are HLA-A*0201-restricted antigens.

There is a clear need for alternative highly WT1 antigen-specific TCR immunotherapies directed against various cancers, such as leukemia and tumors. Presently disclosed embodiments address these needs and provide other related advantages.

DETAILED DESCRIPTION

Figure 1A:
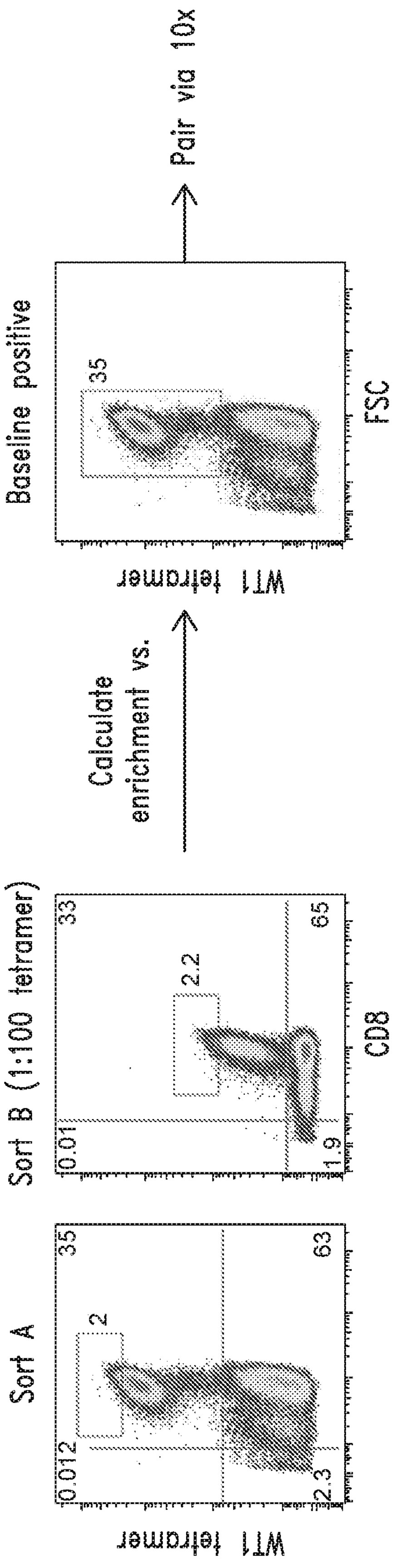
FIGS. 1A and 1B show how $WT1_{37}$-specific TCRs were identified by a high-throughput sequencing-based strategy. (A) Schematic of initial sequencing-based strategy for identifying TCR clonotypes associated with high $WT1_{37-45}$ peptide/MHC tetramer-binding. (B) Enrichment in sort populations versus percentage of total population is shown, with selected TCR highlighted. All TCRs indicated by black circles were synthesized and evaluated for antigen-specificity (27 total).

The present disclosure provides T cell receptors (TCRs) having high functional avidity for antigenic peptide from WT1 comprised of amino acids 37-45 (also referred to as $WT1_{37-45}$ peptide or p37 peptide antigen; e.g., VLDFAPPGA, SEQ ID NO:59) that is associated with a major histocompatibility complex (MHC) (e.g., human leukocyte antigen, HLA). Such p37 peptide antigen specific TCRs are useful for, for example, adoptive immunotherapy to treat cancer, such as cancers that overexpress WT1.

By way of background, most tumor targets for T cell-based immunotherapies are self-antigens since tumors arise from previously normal tissue. For example, such tumor-associated antigens (TAAs) may be expressed at high levels in a cancer cell, but may not be expressed or may be minimally expressed in other cells. During T cell development in the thymus, T cells that bind weakly to self-antigens are allowed to survive in the thymus, and can undergo further development and maturation, while T cells that bind strongly to self-antigens are eliminated by the immune system since such cells would mount an undesirable autoimmune response. Hence, T cells are sorted by their relative ability to bind to antigens to prepare the immune system to respond against a foreign invader (i.e., recognition of non-self-antigen) while at the same time preventing an autoimmune response (i.e., recognition of self-antigen). This tolerance mechanism limits naturally occurring T cells that can recognize tumor (self) antigens with high affinity and, therefore, eliminates the T cells that would effectively eliminate tumor cells. Consequently, isolating T cells having high affinity TCRs specific for tumor antigens is difficult because most such cells are essentially eliminated by the immune system.

In the instant disclosure, a high throughput sequencing-based approach was applied to immune cells from about 15 healthy donors to identify TCRs having high functional avidity for a p37:MHC complex. This strategy also allows for selection of TCRs even if when expressed at low levels of TCRs on the T cell surface. Enrichment of sort populations versus percentage of the total population was used to select high affinity and high functional avidity (i.e., those with the greatest anti-tumor efficacy) TCRs specific for p37 and compositions thereof the present disclosure. Such high functional avidity TCRs specific for p37 were identified in T cells that: (a) bound p37 peptide/MHC tetramers independent of CD8, (b) underwent less in vitro peptide-driven expansion, and (c) in some cases expressed such TCRs at relatively low levels on the T cell surface as compared to other TCRs in T cells not having such characteristics. A total of 27 TCRs were synthesized and evaluated for p37 antigen-specificity (see FIG. 1B).

In certain embodiments, a T cell receptor (TCR) specific for a WT1 peptide comprises a TCR α-chain and a TCR β-chain, wherein the TCR α-chain comprises a $V_\alpha$ domain comprising the amino acid sequence set forth in any one of SEQ ID NOS: 253-263 and 34-44 and an α-chain constant domain having the amino acid sequence of SEQ ID NO:47, and the TCR β-chain comprises a $V_\beta$ domain comprising the amino acid sequence set forth in any one of SEQ ID NOS: 253-263 and 23-33, and a β-chain constant domain having the amino acid sequence of SEQ ID NO:45 or 46, and such TCRs specifically bind to a VLDFAPPGA (SEQ ID NO:59): human leukocyte antigen (HLA) complex on a T cell surface and promote IFNγ production with a $pEC_{50}$ of 8.5 or higher. In certain embodiments, selected TCRs specifically bind to a VLDFAPPGA (SEQ ID NO:59):human leukocyte antigen (HLA) complex with a $K_D$ of less than or equal to about $10^{-8}$M, or wherein the high affinity TCR dissociates from a VLDFAPPGA (SEQ ID NO:59):HLA complex at a reduced $k_{off}$ rate as compared to a TCR disclosed by Schmitt et al., *Nat. Biotechnol.* 35:1188, 2017.

The compositions and methods described herein will in certain embodiments have therapeutic utility for the treatment of diseases and conditions associated with WT1 expression or overexpression (e.g., detectable WT1 expression at a level that is greater in magnitude, in a statistically significant manner, than the level of WT1 expression that is detectable in a normal or disease-free cell). Such diseases include various forms of hyperproliferative disorders or proliferative disorders, such as hematological malignancies and solid cancers. Non-limiting examples of these and related uses are described herein and include in vitro, ex vivo and in vivo stimulation of WT1 antigen-specific T cell responses, such as by the use of recombinant T cells expressing an enhanced affinity TCR specific for a WT1 peptide (e.g., VLDFAPPGA, SEQ ID NO:59, also known as $WT1_{37-45}$ peptide or p37 peptide).

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±10% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure.

The term "consisting essentially of" is not equivalent to "comprising" and refers to the specified materials or steps of a claim, or to those that do not materially affect the basic characteristics of the claimed subject matter. For example, a protein domain, region, or module (e.g., a binding domain, hinge region, linker module) or a protein (which may have one or more domains, regions, or modules) "consists essentially of" a particular amino acid sequence when the amino acid sequence of a domain, region, module, or protein includes extensions, deletions, mutations, or a combination thereof (e.g., amino acids at the amino- or carboxy-terminus or between domains) that, in combination, contribute to at most 20% (e.g., at most 15%, 10%, 8%, 6%, 5%, 4%, 3%, 2% or 1%) of the length of a domain, region, module, or protein and do not substantially affect (i.e., do not reduce the activity by more than 50%, such as no more than 40%, 30%, 25%, 20%, 15%, 10%, 5%, or 1%) the activity of the domain(s), region(s), module(s), or protein (e.g., the target binding affinity of a binding protein).

As used herein, an "immune system cell" in some aspects means any cell of the immune system that originates from a hematopoietic stem cell in the bone marrow, which gives rise to two major lineages, a myeloid progenitor cell (which give rise to myeloid cells such as monocytes, macrophages, dendritic cells, meagakaryocytes and granulocytes) and a lymphoid progenitor cell (which give rise to lymphoid cells such as T cells, B cells and natural killer (NK) cells). Exemplary immune system cells include a CD4+ T cell, a CD8+ T cell, a CD4− CD8− double negative T cell, a γδ T cell, a regulatory T cell, a stem cell memory T cell, a natural killer cell (e.g., a NK cell or a NK-T cell), a B cell, and a dendritic cell. Macrophages and dendritic cells may be referred to as "antigen presenting cells" or "APCs," which are specialized cells that can activate T cells when a major histocompatibility complex (MHC) receptor on the surface of the APC complexed with a peptide interacts with a TCR on the surface of a T cell.

"Major histocompatibility complex" (MHC) in some aspects can refer to glycoproteins that deliver peptide antigens to a cell surface. MHC class I molecules are heterodimers having a membrane spanning α chain (with three α domains) and a non-covalently associated β2 microglobulin. MHC class II molecules are composed of two transmembrane glycoproteins, α and β, both of which span the membrane. Each chain has two domains. MHC class I molecules deliver peptides originating in the cytosol to the cell surface, where a peptide:MHC complex is recognized by $CD8^+$ T cells. MHC class II molecules deliver peptides originating in the vesicular system to the cell surface, where they are recognized by $CD4^+$ T cells. Human MHC is referred to as human leukocyte antigen (HLA).

A "T cell" or "T lymphocyte" is an immune system cell that matures in the thymus and produces T cell receptors (TCRs). T cells can exhibit phenotypes or markers associated with naïve T cells (e.g., not exposed to antigen; increased expression of CD62L, CCR7, CD28, CD3, CD127, and CD45RA, and decreased expression of CD45RO as compared to $T_{CM}$), memory T cells ($T_M$) (e.g., antigen-experienced and long-lived), and effector cells (antigen-experienced, cytotoxic). $T_M$ can be further divided into subsets exhibiting phenotypes or markers associated with of central memory T cells ($T_{CM}$, e.g., increased expression of CD62L, CCR7, CD28, CD127, CD45RO, and CD95, and decreased expression of CD54RA as compared to naïve T cells) and effector memory T cells (TEM, e.g., decreased expression of CD62L, CCR7, CD28, CD45RA, and increased expression of CD127 as compared to naïve T cells or $T_{CM}$). Effector T cells (TE) can refer to antigen-experienced $CD8^+$ cytotoxic T lymphocytes that has decreased expression of CD62L, CCR7, CD28, and are positive for granzyme and perforin as compared to $T_{CM}$. Helper T cells ($T_H$) can include $CD4^+$ cells that influence the activity of other immune cells by releasing cytokines. $CD4^+$ T cells can activate and suppress an adaptive immune response, and which of those two functions is induced will depend on presence of other cells and signals. T cells can be collected using known techniques, and the various subpopulations or combinations thereof can be enriched or depleted by known techniques, such as by affinity binding to antibodies, flow cytometry, or immunomagnetic selection. Other exemplary T cells include regulatory T cells, such as CD4+CD25+ (Foxp3+) regulatory T cells and Treg17 cells, as well as Tr1, Th3, CD8+CD28−, and Qa-1 restricted T cells.

"T cell receptor" (TCR) in some aspects refers to an immunoglobulin superfamily member (having a variable binding domain, a constant domain, a transmembrane region, and a short cytoplasmic tail; see, e.g., Janeway et al., *Immunobiology: The Immune System in Health and Disease,* 3rd Ed., Current Biology Publications, p. 4:33, 1997) capable of specifically binding to an antigen peptide bound to a MHC receptor. In some aspects, a TCR refers to a binding protein comprising two TCR variable domains (a Vα and a Vβ) of the present disclosure. In some aspects, a TCR comprises a single-chain TCR (i.e., a single-chain fusion protein comprising TCR variable domains of the present disclosure, or a CAR comprising TCR variable domains of the present disclosure (discussed herein). In some aspects, a TCR can be found on the surface of a cell or in soluble form and generally is comprised of a heterodimer having α and β chains (also known as TCRα and TCRβ, respectively), or γ and δ chains (also known as TCRγ and TCRδ, respectively).

Like immunoglobulins, the extracellular portion of TCR chains (e.g., α-chain, β-chain) contain two immunoglobulin domains, a variable domain (e.g., α-chain variable domain or $V_\alpha$, β-chain variable domain or $V_\beta$; typically amino acids 1 to 116 based on Kabat numbering Kabat et al., "Sequences of Proteins of Immunological Interest, US Dept. Health and Human Services, Public Health Service National Institutes of Health, 1991, 5th ed.) at the N-terminus, and one constant domain (e.g., α-chain constant domain or $C_\alpha$, typically amino acids 81 to 259 based on Kabat, β-chain constant domain or $C_\beta$, typically amino acids 81 to 295 based on Kabat) adjacent to the cell membrane. Also like immunoglobulins, the variable domains contain complementary determining regions (CDRs) separated by framework regions (FRs) (see, e.g., Jores et al., *Proc. Nat'l Acad. Sci. U.S.A.* 87:9138, 1990; Chothia et al., *EMBO J.* 7:3745, 1988; see also Lefranc et al., *Dev. Comp. Immunol.* 27:55, 2003). In certain embodiments, a TCR is found on the surface of T cells (or T lymphocytes) and associates with the CD3 complex. The source of a TCR as used in the present disclosure may be from various animal species, such as a human, mouse, rat, rabbit or other mammal.

The term "variable region" or "variable domain" refers to the domain of an immunoglobulin superfamily binding protein (e.g., a TCR α-chain or β-chain (or γ chain and δ chain for γδ TCRs)) that is involved in binding of the immunoglobulin superfamily binding protein (e.g., TCR) to antigen. The variable domains of the α-chain and β-chain (Vα and Vβ, respectively) of a native TCR generally have similar structures, with each domain comprising four generally conserved framework regions (FRs) and three CDRs. The Vα domain is encoded by two separate DNA segments, the variable gene segment and the joining gene segment (V-J); the Vβ domain is encoded by three separate DNA segments, the variable gene segment, the diversity gene segment, and the joining gene segment (V-D-J). A single Vα or Vβ domain may be sufficient to confer antigen-binding specificity. Furthermore, TCRs that bind a particular antigen may be isolated using a Vα or Vβ domain from a TCR that binds the antigen to screen a library of complementary Vα or Vβ domains, respectively.

The terms "complementarity determining region," and "CDR," are synonymous with "hypervariable region" or "HVR," and are known in the art to refer to sequences of amino acids within immunoglobulin (e.g., TCR) variable regions, which confer antigen specificity and/or binding affinity and are separated from one another in primary amino acid sequence by framework regions. In general, there are three CDRs in each TCR α-chain variable region (αCDR1, αCDR2, αCDR3) and three CDRs in each TCR β-chain variable region (βCDR1, βCDR2, βCDR3). In TCRs, CDR3 is thought to be the main CDR responsible for recognizing processed antigen. In general, CDR1 and CDR2 interact mainly or exclusively with the MHC.

CDR1 and CDR2 are encoded within the variable gene segment of a TCR variable region-coding sequence, whereas CDR3 is encoded by the region spanning the variable and joining segments for Vα, or the region spanning variable, diversity, and joining segments for Vβ. Thus, if the identity of the variable gene segment of a Vα or Vβ is known, the sequences of their corresponding CDR1 and CDR2 can be deduced; e.g., according to a numbering scheme as described herein. Compared with CDR1 and CDR2, CDR3 is typically significantly more diverse due to the addition and loss of nucleotides during the recombination process.

TCR variable domain sequences can be aligned to a numbering scheme (e.g., Kabat, Chothia, EU, IMGT, Enhanced Chothia, and Aho), allowing equivalent residue positions to be annotated and for different molecules to be compared using, for example, ANARCI software tool (2016, Bioinformatics 15:298-300). A numbering scheme provides a standardized delineation of framework regions and CDRs in the TCR variable domains. In certain embodiments, a CDR of the present disclosure is identified according to the IMGT numbering scheme (Lefranc et al., *Dev. Comp. Immunol.* 27:55, 2003; imgt.org/IMGTindex/V-QUEST.php). In certain embodiments, a CDR3 amino acid sequence of the present disclosure comprises one or more junction amino acid; e.g., such as may arise during (RAG)-mediated rearrangement, discussed herein.

As used herein, the term "CD8 co-receptor" or "CD8" means the cell surface glycoprotein CD8, either as an alpha-alpha homodimer or an alpha-beta heterodimer. The CD8 co-receptor assists in the function of cytotoxic T cells (CD8+) and functions through signaling via its cytoplasmic tyrosine phosphorylation pathway (Gao and Jakobsen, *Immunol. Today* 21:630-636, 2000; Cole and Gao, *Cell. Mol. Immunol.* 1:81-88, 2004). There are five (5) known human CD8 beta chain isoforms (see UniProtKB identifier P10966) and a single known human CD8 alpha chain isoform (see UniProtKB identifier P01732).

"CD4" is an immunoglobulin co-receptor glycoprotein that assists the TCR in communicating with antigen-presenting cells (see, Campbell & Reece, *Biology* 909 (Benjamin Cummings, Sixth Ed., 2002); UniProtKB identifier P01730). CD4 is found on the surface of immune cells such as T helper cells, monocytes, macrophages, and dendritic cells, and includes four immunoglobulin domains (D1 to D4) that are expressed at the cell surface. During antigen presentation, CD4 is recruited, along with the TCR complex, to bind to different regions of the MHCII molecule (CD4 binds MHCII β2, while the TCR complex binds MHCII α1/β1). Without wishing to be bound by theory, it is believed that close proximity to the TCR complex allows CD4-associated kinase molecules to phosphorylate the immunoreceptor tyrosine activation motifs (ITAMs) present on the cytoplasmic domains of CD3. This activity is thought to amplify the signal generated by the activated TCR in order to produce or recruit various types immune system cells, including T helper cells, and immune responses.

As used herein, "D/N/P region" in some aspects refers to nucleotides, or amino acids encoded by the nucleotides, predicted to be located within diversity (D) gene segment, which can include non-templated (N) nucleotides and palindromic (P) nucleotides that are inserted (or deleted) during the V(D)J recombination process that leads to diversity of T cell receptors. Recombination activating gene (RAG)-mediated rearrangement of variable (V), diversity (D) and joining (J) gene segments is an inaccurate process that results in the variable addition or subtraction of nucleotides (referred to as palindromic or P nucleotides), which is followed by terminal deoxynucleotidyl transferase (TdT) activity that adds further adds random non-templated (N) nucleotides. Finally, exonucleases remove unpaired nucleotides and gaps are filled by DNA synthesis and repair enzymes. Such a trim and repair mechanism leads to the junctional diversity that underpins the efficient and specific recognition of different antigens by different TCRs. D gene segments can be identified using the annotation system from the international ImMunoGeneTics information system (IMGT; at imgt.org).

In some aspects, "CD3" is a multi-protein complex of six chains (see, Abbas and Lichtman, 2003; Janeway et al., p172 and 178, 1999). In mammals, the complex comprises a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged regions of T cell receptor chains. The intracellular tails of the CD3γ, CD3δ, and CD3ε chains each contain a single conserved motif known as an immunoreceptor tyrosine-based activation motif or ITAM, whereas each CD3 chain has three. Without wishing to be bound by theory, it is believed the ITAMs are important for the signaling capacity of a TCR complex. CD3 as used in the present disclosure may be from various animal species, including human, mouse, rat, or other mammals.

As used herein, "TCR complex" in some aspects refers to a complex formed by the association of CD3 with TCR. For example, a TCR complex can be composed of a CD3γ chain, a CD3δ chain, two CD3ε chains, a homodimer of CD3ζ chains, a TCRα chain, and a TCRβ chain. Alternatively, a TCR complex can be composed of a CD3γ chain, a CD3δ chain, two CD3ε chains, a homodimer of CD3ζ chains, a TCRγ chain, and a TCR chain.

In some aspects, a "component of a TCR complex," as used herein, refers to a TCR chain (i.e., TCRα, TCRβ, TCRγ or TCRδ), a CD3 chain (i.e., CD3γ, CD3δ, CD3ε or CD3ζ), or a complex formed by two or more TCR chains or CD3 chains (e.g., a complex of TCRα and TCRβ, a complex of TCRγ and TCRδ, a complex of CD3ε and CD3δ, a complex of CD3γ and CD3ε, or a sub-TCR complex of TCRα, TCRβ, CD3γ, CD3δ, and two CD3ε chains).

"Antigen" or "Ag" as used herein refers to an immunogenic molecule that provokes an immune response. This immune response may involve antibody production, activation of specific immunologically competent cells (e.g., T cells), or both. An antigen (immunogenic molecule) may be, for example, a peptide, glycopeptide, polypeptide, glycopolypeptide, polynucleotide, polysaccharide, lipid or the like. It is readily apparent that an antigen can be synthesized, produced recombinantly, or derived from a biological sample. Exemplary biological samples that can contain one or more antigens include tissue samples, tumor samples, cells, biological fluids, or combinations thereof. Antigens can be produced by cells that have been modified or genetically engineered to express an antigen, or that endogenously (e.g., without modification or genetic engineering by human intervention) express a mutation or polymorphism that is immunogenic.

A "neoantigen," as used herein, refers to a host cellular product containing a structural change, alteration, or mutation that creates a new antigen or antigenic epitope that has not previously been observed in the subject's genome (i.e., in a sample of healthy tissue from the subject) or been "seen" or recognized by the host's immune system, which: (a) is processed by the cell's antigen-processing and transport mechanisms and presented on the cell surface in association with an MHC (e.g., HLA) molecule; and (b) elicits an immune response (e.g., a cellular (T cell) response). Neoantigens may originate, for example, from coding polynucleotides having alterations (substitution, addition, deletion) that result in an altered or mutated product, or from the insertion of an exogenous nucleic acid molecule or protein into a cell, or from exposure to environmental factors (e.g., chemical, radiological) resulting in a genetic change. Neoantigens may arise separately from a tumor antigen, or may arise from or be associated with a tumor antigen. "Tumor neoantigen" (or "tumor-specific neoantigen") refers to a protein comprising a neoantigenic determinant associated with, arising from, or arising within a tumor cell or plurality of cells within a tumor. Tumor neoantigenic determinants are found on, for example, antigenic tumor proteins or peptides that contain one or more somatic mutations or chromosomal rearrangements encoded by the DNA of tumor cells (e.g., pancreas cancer, lung cancer, colorectal cancers), as well as proteins or peptides from viral open reading frames associated with virus-associated tumors.

The term "epitope" or "antigenic epitope" includes any molecule, structure, amino acid sequence or protein determinant that is recognized and specifically bound by a cognate binding molecule, such as an immunoglobulin, T cell receptor (TCR), chimeric antigen receptor, or other binding molecule, domain or protein. Epitopic determinants generally contain chemically active surface groupings of molecules, such as amino acids or sugar side chains, and can have specific three dimensional structural characteristics, as well as specific charge characteristics.

As used herein, "specifically binds" or "specific for" in some aspects refers to an association or union of a T cell receptor (TCR) or a binding domain thereof (e.g., scTCR or a fusion protein thereof) to a target molecule with an apparent affinity or $K_A$ (i.e., an equilibrium association constant of a particular binding interaction with units of 1/M) equal to or greater than $10^9$ $M^{-1}$ (which equals the ratio of the on-rate [$k_{on}$] to the off-rate [$k_{off}$] for this association reaction), or a functional avidity or $EC_{50}$ equal to or greater than $10^{-9}$ M, while not significantly associating or uniting with any other molecules or components in a sample. TCRs may be classified as "high affinity" binding proteins or binding domains (or fusion proteins thereof) or as "low affinity" binding proteins or binding domains (or fusion proteins thereof). "High affinity" TCRs or binding domains refer to those TCRs or binding domains thereof having a $K_A$ of at least $10^9$ $M^{-1}$, at least $10^{10}$ $M^{-1}$, at least $10^{11}$ $M^{-1}$, at least $10^{12}$ $M^{-1}$, or at least $10^{13}$ $M^{-1}$. "Low affinity" binding proteins or binding domains refer to those binding proteins or binding domains having a $K_A$ of up to $10^7$ $M^{-1}$, up to $10^6$ $M^{-1}$, up to $10^5$ $M^{-1}$. Alternatively, affinity may be defined as an equilibrium dissociation constant ($K_D$) of a particular binding interaction with units of M (e.g., $10^{-9}$ M to $10^{-13}$ M or less).

The term "functional avidity" refers to a biological measure or activation threshold of an in vitro T cell response to a given concentration of a ligand, wherein the biological measures can include cytokine production (e.g., IFNγ production, IL-2 production, etc.), cytotoxic activity, and proliferation. For example, T cells that biologically (immunologically) respond in vitro to a very low antigen dose by producing cytokines, being cytotoxic, or proliferating are considered to have high functional avidity, while T cells having lower functional avidity require higher amounts of antigen before an immune response, similar to the high-avidity T cells, is elicited. It will be understood that functional avidity is different from affinity and avidity. Affinity refers to the strength of any given bond between a binding protein and its antigen/ligand. Some binding proteins are multivalent and bind to multiple antigens—in this case, the strength of the overall connection is the avidity.

As used herein, "functional avidity" refers to a quantitative determinant of the activation threshold of a TCR expressed by a T cell. In vivo, T cells are exposed to similar antigen doses regardless of the TCR avidity (high or low), but numerous correlations exist between the functional avidity and the effectiveness of an immune response. Some ex vivo studies have shown that distinct T cell functions (e.g., proliferation, cytokines production, etc.) can be triggered at different thresholds (see, e.g., Betts et al., *J. Immunol.* 172:6407, 2004; Langenkamp et al., *Eur. J. Immunol.* 32:2046, 2002). Factors that affect functional avidity include (a) the affinity of a TCR for the pMHC-complex, that is, the strength of the interaction between the TCR and pMHC (Cawthon et al., *J. Immunol.* 167:2577, 2001), (b) expression levels of the TCR and the CD4 or CD8 co-receptors, and (c) the distribution and composition of signaling molecules (Viola and Lanzavecchia, *Science* 273: 104, 1996), as well as expression levels of molecules that attenuate T cell function and TCR signaling.

The concentration of antigen needed to induce a half-maximum response between the baseline and maximum response after a specified exposure time is referred to as the "half maximal effective concentration" or "$EC_{50}$". The $EC_{50}$ value is generally presented as a molar (moles/liter) amount, but it is often converted into a logarithmic value as follows—$\log_{10}(EC_{50})$—which provides a sigmoidal graph (see, e.g., FIG. 5A). For example, if the $EC_{50}$ equals 1 μM ($10^{-6}$ M), the $\log_{10}(EC_{50})$ value is −6. Another value used is $pEC_{50}$, which is defined as the negative logarithm of the $EC_{50}$ ($-\log_{10}(EC_{50})$). In the above example, the $EC_{50}$ equaling 1 μM has a $pEC_{50}$ value of 6. In certain embodiments, the functional avidity of the TCRs of this disclosure will be a measure of its ability to promote IFNγ production by T cells, which can be measured using assays described herein. "High functional avidity" TCRs or binding domains thereof refer to those TCRs or binding domains thereof having a $EC_{50}$ of at least $10^{-9}$ M, at least about $10^{-10}$ at least about $10^{-11}$ M, at least about $10^{-12}$ M, or at least about $10^{-13}$ M. In some embodiments, the response comprises IFN-γ production; e.g., the production of IFN-γ by an immune cell (such as a T cell, NK cell, or NK-T cell) expressing the TCR in response to antigen.

In some aspects, "$WT1_{37-45}$ antigen" or "$WT1_{37-45}$ peptide" or "$WT1_{37-45}$ peptide antigen" or "p37 peptide" or "p37 antigen" or "p37 peptide antigen" each refer to a naturally or synthetically produced portion of a WT1 protein ranging in length from about 9 amino acids to about 15 amino acids and comprising the amino acid sequence of VLDFAPPGA (SEQ ID NO:59), which can form a complex with a MHC (e.g., HLA) molecule and such a complex can bind with a TCR specific for a WT1 peptide:MHC (e.g., HLA) complex. Since WT1 is an internal host protein, WT1 antigen peptides will be presented in the context of class I MHC. In particular embodiments, WT1 peptide VLDFAPPGA (SEQ ID NO:59) is capable of associating with human class I HLA allele HLA-A*201.

In some aspects, the phrases "$WT1_{37-45}$ peptide-specific binding protein" or "$WT1_{37-45}$ peptide-specific TCR" or "$WT1_{37-45}$ antigen-specific TCR," or "$WT1_{37-45}$ peptide antigen-specific TCR" or "WT1 p37 peptide-specific binding protein" or "WT1 p37 peptide-specific TCR" or "WT1 p37 antigen-specific TCR," or "WT1 p37 peptide antigen-specific TCR," which are interchangeable herein, refer to a protein or polypeptide that specifically binds to a WT1 p37 peptide complexed with an MHC or HLA molecule, e.g., on a cell surface, with about, or at least about, a particular affinity or functional avidity, preferably a high functional avidity, as defined herein. Such a binding protein or polypeptide comprises TCR variable domains as provided herein. In certain embodiments, a WT1-specific binding protein binds a WT1-derived peptide:HLA complex (or WT1-derived peptide:MHC complex) have a functional avidity log[$EC_{50}$] ranging from about −2.5 μM to about −3.75 μM (which is equivalent to −8.5M to about −9.8M). The $EC_{50}$ range for these values range from about $3.16\times10^{-9}$ M to about $1.58\times10^{-10}$ M as measured, for example, by the assay described in the following paragraphs and in Example 1 herein.

Assays for assessing affinity, apparent affinity, relative affinity, or functional avidity are known. As described herein, apparent affinity or functional avidity of a TCR of this disclosure is measured by assessing binding to various concentrations of tetramers associated with p37 peptide, for example, by flow cytometry using labeled tetramers. In some examples, apparent $K_D$ or $EC_{50}$ of a TCR is measured using 2-fold dilutions of labeled tetramers at a range of concentrations, followed by determination of binding curves by non-linear regression. For example, apparent $K_D$ is determined as the concentration of ligand that yields half-maximal binding, whereas an $EC_{50}$ is determined as the concentration of ligand that yields half-maximal production of, for example, a cytokine (e.g., IFNγ, IL-2).

"MHC-peptide tetramer staining" in some aspects refers to an assay used to detect antigen-specific T cells, which features a tetramer of MHC molecules, each comprising an identical peptide having an amino acid sequence that is cognate (e.g., identical or related to) at least one antigen (e.g., WT1), wherein the complex is capable of binding T cell receptors specific for the cognate antigen. Each of the MHC molecules may be tagged with a biotin molecule. Biotinylated MHC/peptides are tetramerized by the addition of streptavidin, which can be fluorescently labeled. The tetramer may be detected by flow cytometry via the fluorescent label. In certain embodiments, an MHC-peptide tetramer assay is used to detect or select high affinity or high functional avidity TCRs of the instant disclosure.

Levels of cytokines may be determined according to methods described herein and practiced in the art, including for example, ELISA, ELISPOT, intracellular cytokine staining, and flow cytometry and combinations thereof (e.g., intracellular cytokine staining and flow cytometry). Immune cell proliferation and clonal expansion resulting from an antigen-specific elicitation or stimulation of an immune response may be determined by isolating lymphocytes, such as circulating lymphocytes in samples of peripheral blood cells or cells from lymph nodes, stimulating the cells with antigen, and measuring cytokine production, cell proliferation and/or cell viability, such as by incorporation of tritiated thymidine or non-radioactive assays, such as MTT assays and the like. The effect of an immunogen described herein on the balance between a Th1 immune response and a Th2 immune response may be examined, for example, by determining levels of Th1 cytokines, such as IFN-γ, IL-12, IL-2, and TNF-β, and Type 2 cytokines, such as IL-4, IL-5, IL-9, IL-10, and IL-13.

In some aspects, the term "WT1 p37-specific binding domain" or "$WT1_{37-45}$-specific binding domain" or "WT1 p37-specific binding fragment" or "$WT1_{37-45}$-specific binding fragment" refer to a domain or portion of a WT1-specific TCR responsible for specific binding to WT1 p37 antigen complexed with an MHC or HLA molecule. A WT1 p37 antigen-specific binding domain from a TCR alone (i.e., without any other portion of a WT1-specific TCR) can be soluble and can bind to a WT1 p37 peptide:MHC complex with a $K_D$ of less than $10^{-9}$M, less than about $10^{-10}$ M, less than about $10^{-11}$M, less than about $10^{-12}$M, or less than about $10^{-13}$M. In other embodiments, a WT1 p37 peptide-specific TCR has high functional avidity and specifically binds to a VLDFAPPGA (SEQ ID NO:59):human leukocyte antigen (HLA) complex on a T cell surface and promotes IFNγ production at a $pEC_{50}$ of 8.5 or higher (e.g., up to about 9, up to about 9.5, up to about 10, about 10.5, about 11, about 11.5, about 12, about 12.5, or about 13). Exemplary WT1 p37 peptide-specific binding domains include WT1 p37 peptide-specific scTCR (e.g., single chain αβTCR proteins such as Vα-L-Vβ, Vβ-L-Vα, Vα-Cα-L-Vα, or Vα-L-Vβ-Cβ, wherein Vα and Vβ are TCRα and β variable domains respectively, Cα and Cβ are TCRα and β constant domains, respectively, and L is a linker), which are or can be derived from an anti-WT1 p37 peptide TCR of this disclosure.

Principles of antigen processing by antigen presenting cells (APC) (such as dendritic cells, macrophages, lymphocytes or other cell types), and of antigen presentation by APC to T cells, including major histocompatibility complex (MHC)-restricted presentation between immunocompatible (e.g., sharing at least one allelic form of an WIC gene that is relevant for antigen presentation) APC and T cells, are well established (see, e.g., Murphy, Janeway's Immunobiology ($8^{th}$ Ed.) 2011 Garland Science, NY; chapters 6, 9 and 16). For example, processed antigen peptides originating in the cytosol (e.g., tumor antigen, intracellular pathogen) are generally from about 7 amino acids to about 11 amino acids in length and will associate with class I WIC molecules, whereas peptides processed in the vesicular system (e.g., bacterial, viral) will vary in length from about 10 amino acids to about 25 amino acids and associate with class II MHC molecules.

A "transmembrane domain," as used herein, means any amino acid sequence having a three-dimensional structure that is thermodynamically stable in a cell membrane, and generally ranges in length from about 15 amino acids to about 30 amino acids. The structure of a hydrophobic transmembrane domain may comprise an alpha helix, a beta barrel, a beta sheet, a beta helix, or any combination thereof. Exemplary transmembrane domains are transmembrane domains from CD4, CD8, CD28, or CD27.

As used herein, an "immune effector domain" is an intracellular portion of a scTCR or CAR fusion protein that can directly or indirectly promote an immunological response in a cell when receiving the appropriate signal. In certain embodiments, an immune effector domain is part of a protein or protein complex that receives a signal when bound, or it binds directly to a target molecule, which triggers a signal from the immune effector domain. An immune effector domain may directly promote a immune cell response when it contains one or more signaling domains or motifs, such as an immunoreceptor tyrosine-based activation motif (ITAM). In other embodiments, an effector domain will indirectly promote a cellular response by associating with one or more other proteins that directly promote a cellular response. Exemplary immune effector domains include intracellular signaling domains from 4-1BB, CD3ε, CD3δ, CD3ζ, CD27, CD28, CD79A, CD79B, CARD11, DAP10, FcRα, FcRβ, FcRγ, Fyn, HVEM, ICOS, Lck, LAG3, LAT, LRP, NOTCH1, Wnt, NKG2D, OX40, ROR2, Ryk, SLAMF1, Slp76, pTα, TCRα, TCRβ, TRIM, Zap70, PTCH2, or any combination of two or three of such domains.

A "linker" in some aspects refers to an amino acid sequence that connects two proteins, polypeptides, peptides, domains, regions, or motifs. An exemplary linker is a "variable domain linker," which specifically refers to a five to about 35 amino acid sequence that connects T cell receptor $V_{\alpha/\beta}$ and $C_{\alpha/\beta}$ chains (e.g., $V_\alpha$-$C_\alpha$, $V_\beta$-$C_\beta$, $V_\alpha$-$V_\beta$) or connects each $V_\alpha$-$C_\alpha$, $V_\beta$-$C_\beta$, $V_\alpha$-$V_\beta$ pair to a hinge or transmembrane domain, which provides a spacer function and flexibility sufficient for interaction of the two sub-binding domains so that the resulting single chain polypeptide retains a specific binding affinity or functional avidity to the same target molecule as a T cell receptor. In certain embodiments, a variable domain linker comprises from about ten to about 30 amino acids or from about 15 to about 25 amino acids. In particular embodiments, a variable domain linker peptide comprises from one to ten repeats of $Gly_xSer_y$, wherein x and y are independently an integer from 0 to 10 provided that x and y are not both 0 (e.g., $Gly_4Ser$ (SEQ ID NO:171), $Gly_3Ser$ (SEQ ID NO:172), $Gly_2Ser$, or $(Gly_3Ser)_n(Gly_4Ser)_l$ (SEQ ID NO:173), $(Gly_3Ser)_n(Gly_2Ser)_n$, (SEQ ID NO:174) $(Gly_3Ser)_n(Gly_4Ser)_n$ (SEQ ID NO:175), or $(Gly_4Ser)_n$(SEQ ID NO:171), wherein n is an integer of 1, 2, 3, 4, 5, 6, 7, 8, 9 or 10) and wherein linked variable domains form a functional binding domain (e.g., scTCR).

In some aspects, "junction amino acids" or "junction amino acid residues" refer to one or more (e.g., about 2-10) amino acid residues between two adjacent motifs, regions or domains of a polypeptide, such as between a binding domain and an adjacent constant domain or between a TCR chain and an adjacent self-cleaving peptide. Junction amino acids may result from the construct design of a fusion protein (e.g., amino acid residues resulting from the use of a restriction enzyme site during the construction of a nucleic acid molecule encoding a fusion protein), or in the process of a genetic recombination or rearrangement event (e.g., RAG-mediated rearrangement).

In some aspects, an "altered domain" or "altered protein" refers to a motif, region, domain, peptide, polypeptide, or protein with a non-identical sequence identity to a wild type motif, region, domain, peptide, polypeptide, or protein (e.g., a wild type TCRα chain, TCRβ chain, TCRα constant domain, TCRβ constant domain) of at least 85% (e.g., 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%), preferably wherein or wherein the CDR3 from each of the TCR α and β variable domains are not altered.

In any of the presently disclosed embodiments, a TCR constant domain can be modified to enhance pairing of desired TCR chains. For example, enhanced pairing in a host T cell between a heterologous TCR α-chain and a heterologous TCR β-chain due to a modification results in the preferential assembly of a TCR comprising two heterologous chains over an undesired mispairing of a heterologous TCR chain with an endogenous TCR chain (see, e.g., Govers et al., *Trends Mol. Med.* 16(2):77 (2010), the TCR modifications of which are herein incorporated by reference). Exemplary modifications to enhance pairing of heterologous TCR chains include the introduction of complementary cysteine residues in each of the heterologous TCR α-chain and β-chain. In some embodiments, a polynucleotide encoding a heterologous TCR α-chain encodes a cysteine at amino acid position 48 (corresponding to the full-length, mature human TCR α-chain sequence) and a polynucleotide encoding a heterologous TCR β-chain encodes a cysteine at amino acid position 57 (corresponding to the full-length mature human TCR β-chain sequence).

"Chimeric antigen receptor" (CAR) refers to a fusion protein that is engineered to contain two or more naturally occurring amino acid sequences, domains, or motifs, linked together in a way that does not occur naturally or does not occur naturally in a host cell, which fusion protein can function as a receptor when present on a surface of a cell. CARs can include an extracellular portion comprising an antigen-binding domain (e.g., obtained or derived from an immunoglobulin or immunoglobulin-like molecule, such as a TCR binding domain derived or obtained from a TCR specific for a cancer antigen, a scFv derived or obtained from an antibody, or an antigen-binding domain derived or obtained from a killer immunoreceptor from an NK cell) linked to a transmembrane domain and one or more intracellular signaling domains (optionally containing co-stimulatory domain(s)) (see, e.g., Sadelain et al., *Cancer Discov.,* 3(4):388 (2013); see also Harris and Kranz, Trends *Pharmacol. Sci.,* 37(3):220 (2016), Stone et al., *Cancer Immunol. Immunother.,* 63(11):1163 (2014), and Walseng et al., *Scientific Reports* 7:10713 (2017), which CAR constructs and methods of making the same are incorporated by reference herein). CARs of the present disclosure that specifically bind to a WT1 antigen (e.g., in the context of a peptide:HLA complex) comprise a TCR Vα domain and a Vβ domain.

As used herein, "nucleic acid" or "nucleic acid molecule" or "polynucleotide" in some aspects refer to any of deoxyribonucleic acid (DNA), ribonucleic acid (RNA), oligonucleotides, fragments generated, for example, by the polymerase chain reaction (PCR) or by in vitro translation, and fragments generated by any of ligation, scission, endonuclease action, or exonuclease action. In certain embodiments, the nucleic acids of the present disclosure are produced by PCR. Nucleic acids may be composed of monomers that are naturally occurring nucleotides (such as deoxyribonucleotides and ribonucleotides), analogs of naturally occurring nucleotides (e.g., α-enantiomeric forms of naturally-occurring nucleotides), or a combination of both. Modified nucleotides can have modifications in or replacement of sugar moieties, or pyrimidine or purine base moieties. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. Nucleic acid molecules can be either single stranded or double stranded.

In some aspects, the term "isolated" means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such nucleic acid could be part of a vector and/or such nucleic acid or polypeptide could be part of a composition (e.g., a cell lysate), and still be isolated in that such vector or composition is not part of the natural environment for the nucleic acid or polypeptide. The term "gene" means the segment of DNA involved in producing a polypeptide chain; it includes regions preceding and following the coding region "leader and trailer" as well as intervening sequences (introns) between individual coding segments (exons).

As used herein, the term "recombinant" in some aspects refers to a cell, microorganism, nucleic acid molecule, or vector that has been genetically engineered by human intervention—that is, modified by introduction of an exogenous or heterologous nucleic acid molecule, or refers to a cell or microorganism that has been altered such that expression of an endogenous nucleic acid molecule or gene is controlled, deregulated or constitutive. Human generated genetic alterations may include, for example, modifications that introduce nucleic acid molecules (which may include an expression control element, such as a promoter) that encode one or more proteins or enzymes, or other nucleic acid molecule additions, deletions, substitutions, or other functional disruption of or addition to a cell's genetic material. Exemplary modifications include those in coding regions or functional fragments thereof of heterologous or homologous polypeptides from a reference or parent molecule.

As used herein, "mutation" or "mutated" in some aspects refers to a change in the sequence of a nucleic acid molecule or polypeptide molecule as compared to a reference or wild-type nucleic acid molecule or polypeptide molecule, respectively. A mutation can result in several different types of change in sequence, including substitution, insertion or deletion of nucleotide(s) or amino acid(s). In certain embodiments, a mutation is a substitution of one or three codons or amino acids, a deletion of one to about 5 codons or amino acids, or a combination thereof.

A "conservative substitution" in some aspects is recognized in the art as a substitution of one amino acid for another amino acid that has similar properties. Exemplary conservative substitutions are well known in the art (see, e.g., WO 97/09433 at page 10; Lehninger, Biochemistry, $2^{nd}$ Edition; Worth Publishers, Inc. NY, NY, pp. 71-77, 1975; Lewin, Genes IV, Oxford University Press, NY and Cell Press, Cambridge, Mass., p. 8, 1990).

The term "construct" in some aspects refers to any polynucleotide that contains a recombinant nucleic acid molecule. A construct may be present in a vector (e.g., a bacterial vector, a viral vector) or may be integrated into a genome. A "vector" is a nucleic acid molecule that is capable of transporting another nucleic acid molecule. Vectors may be, for example, plasmids, cosmids, viruses, a RNA vector or a linear or circular DNA or RNA molecule that may include chromosomal, non-chromosomal, semi-synthetic or synthetic nucleic acid molecules. Exemplary vectors are those capable of autonomous replication (episomal vector) or expression of nucleic acid molecules to which they are linked (expression vectors).

Exemplary viral vectors include retrovirus, adenovirus, parvovirus (e.g., adeno-associated viruses), coronavirus, negative strand RNA viruses such as ortho-myxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomega-lovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields et al., Eds., Lippincott-Raven Publishers, Philadelphia, 1996).

In some aspects, "lentiviral vector," as used herein, means HIV-based lentiviral vectors for gene delivery, which can be integrative or non-integrative, have relatively large packaging capacity, and can transduce a range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration into the DNA of infected cells.

The term "operably-linked" in some aspects refers to the association of two or more nucleic acid molecules on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). "Unlinked" means that the associated genetic elements are not closely associated with one another and the function of one does not affect the other.

As used herein, "expression vector" in some aspects refers to a DNA construct containing a nucleic acid molecule that is operably-linked to a suitable control sequence capable of effecting the expression of the nucleic acid molecule in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, a virus, or simply a potential genomic insert. Once transformed into a suitable host, the vector may replicate and function independently of the host genome, or may, in some instances, integrate into the genome itself. In the present specification, "plasmid," "expression plasmid," "virus" and "vector" are often used interchangeably.

The term "expression", as used herein, in some aspects refers to the process by which a polypeptide is produced based on the encoding sequence of a nucleic acid molecule, such as a gene. The process may include transcription, post-transcriptional control, post-transcriptional modification, translation, post-translational control, post-translational modification, or any combination thereof.

The term "introduced" in the context of inserting a nucleic acid molecule into a cell, in some aspects means "transfection", or 'transformation" or "transduction" and includes reference to the incorporation of a nucleic acid molecule into a eukaryotic or prokaryotic cell wherein the nucleic acid molecule may be incorporated into the genome of a cell (e.g., chromosome, plasmid, plastid, or mitochondrial DNA), converted into an autonomous replicon, or transiently expressed (e.g., transfected mRNA).

As used herein, "heterologous" or "exogenous" nucleic acid molecule, construct or sequence in some aspects refers to a nucleic acid molecule or portion of a nucleic acid molecule that is not native to a host cell, but may be homologous to a nucleic acid molecule or portion of a nucleic acid molecule from the host cell. The source of the heterologous or exogenous nucleic acid molecule, construct or sequence may be from a different genus or species. In certain embodiments, a heterologous or exogenous nucleic acid molecule is added (i.e., not endogenous or native) to a host cell or host genome by, for example, conjugation, transformation, transfection, electroporation, or the like, wherein the added molecule may integrate into the host genome or exist as extra-chromosomal genetic material (e.g., as a plasmid or other form of self-replicating vector), and may be present in multiple copies. In addition, "heterologous" refers to a non-native enzyme, protein or other activity encoded by an exogenous nucleic acid molecule introduced into the host cell, even if the host cell encodes a homologous protein or activity. Moreover, a cell comprising a "modification" or a "heterologous" polynucleotide or binding protein includes progeny of that cell, regardless of whether the progeny were themselves transduced, transfected, or otherwise manipulated or changed.

As described herein, more than one heterologous or exogenous nucleic acid molecule can be introduced into a host cell as separate nucleic acid molecules, as a plurality of individually controlled genes, as a polycistronic nucleic acid molecule, as a single nucleic acid molecule encoding a fusion protein, or any combination thereof. For example, as disclosed herein, a host cell can be modified to express two or more heterologous or exogenous nucleic acid molecules encoding desired TCR specific for a WT1 antigen peptide (e.g., TCRα and TCRβ). When two or more exogenous nucleic acid molecules are introduced into a host cell, it is understood that the two or more exogenous nucleic acid molecules can be introduced as a single nucleic acid molecule (e.g., on a single vector), on separate vectors, integrated into the host chromosome at a single site or multiple sites, or any combination thereof. The number of referenced heterologous nucleic acid molecules or protein activities refers to the number of encoding nucleic acid molecules or the number of protein activities, not the number of separate nucleic acid molecules introduced into a host cell.

As used herein, the term "endogenous" or "native" in some aspects refers to a gene, protein, or activity that is normally present in a host cell. Moreover, a gene, protein or activity that is mutated, overexpressed, shuffled, duplicated or otherwise altered as compared to a parent gene, protein or activity is still considered to be endogenous or native to that particular host cell. For example, an endogenous control sequence from a first gene (e.g., promoter, translational attenuation sequences) may be used to alter or regulate expression of a second native gene or nucleic acid molecule, wherein the expression or regulation of the second native gene or nucleic acid molecule differs from normal expression or regulation in a parent cell.

In some aspects, the term "homologous" or "homolog" refers to a molecule or activity found in or derived from a host cell, species or strain. For example, a heterologous or exogenous nucleic acid molecule may be homologous to a native host cell gene, and may optionally have an altered expression level, a different sequence, an altered activity, or any combination thereof.

In some aspects, "sequence identity," as used herein, refers to the percentage of amino acid residues in one sequence that are identical with the amino acid residues in another reference polypeptide sequence after aligning the sequences and introducing gaps, if necessary, to achieve the maximum percent sequence identity, and not considering any conservative substitutions as part of the sequence identity. The percentage sequence identity values can be generated using the NCBI BLAST2.0 software as defined by Altschul et al. (1997) "Gapped BLAST and PSI-BLAST: a new generation of protein database search programs", Nucleic Acids Res. 25:3389-3402, with the parameters set to default values.

As used herein, a "hematopoietic progenitor cell" in some aspects can be a cell that can be derived from hematopoietic stem cells or fetal tissue and is capable of further differentiation into mature cells types (e.g., immune system cells). Exemplary hematopoietic progenitor cells include those with a $CD24^{Lo}$ $Lin^{-}$ $CD81^{+}$ phenotype or those found in the thymus (referred to as progenitor thymocytes).

As used herein, the term "host" in some aspects refers to a cell (e.g., T cell) or microorganism targeted for genetic modification with a heterologous or exogenous nucleic acid molecule to produce a polypeptide of interest (e.g., high or enhanced affinity anti-WT1 TCR). In certain embodiments, a host cell may optionally already possess or be modified to include other genetic modifications that confer desired properties related or unrelated to biosynthesis of the heterologous or exogenous protein (e.g., inclusion of a detectable marker; deleted, altered or truncated endogenous TCR; increased co-stimulatory factor expression). In some embodiments, host cells are genetically modified to express a protein or fusion protein that modulates immune signaling in a host cell to, for example, promote survival and/or expansion advantage to the modified cell (e.g., see immunomodulatory fusion proteins of WO 2016/141357, which are herein incorporated by reference in their entirety). In other embodiments, host cells are genetically modified to introduce a TCR as provided herein, or to knock-down or minimize immunosuppressive signals in a cell (e.g., a checkpoint inhibitor), which modifications may be made using, for example, a CRISPR/Cas system (see, e.g., US 2014/0068797, U.S. Pat. No. 8,697,359; WO 2015/071474). In certain embodiments, a host cell is a human hematopoietic progenitor cell transduced with a heterologous or exogenous nucleic acid molecule encoding a TCRα chain specific for a WT1 antigen peptide.

As used herein, "hyperproliferative disorder" in some aspects refers to excessive growth or proliferation as compared to a normal or undiseased cell. Exemplary hyperproliferative disorders include tumors, cancers, neoplastic tissue, carcinoma, sarcoma, malignant cells, pre-malignant cells, as well as non-neoplastic or non-malignant hyperproliferative disorders (e.g., adenoma, fibroma, lipoma, leiomyoma, hemangioma, fibrosis, restenosis, as well as autoimmune diseases such as rheumatoid arthritis, osteoarthritis, psoriasis, inflammatory bowel disease, or the like). Certain diseases that involve abnormal or excessive growth that occurs more slowly than in the context of a hyperproliferative disease can be referred to as "proliferative diseases", and include certain tumors, cancers, neoplastic tissue, carcinoma, sarcoma, malignant cells, pre malignant cells, as well as non-neoplastic or non-malignant disorders.

Furthermore, "cancer" may refer to any accelerated proliferation of cells, including solid tumors, ascites tumors, blood or lymph or other malignancies; connective tissue malignancies; metastatic disease; minimal residual disease following transplantation of organs or stem cells; multi-drug resistant cancers, primary or secondary malignancies, angiogenesis related to malignancy, or other forms of cancer.

TCRs Specific for WT1 p37 Antigen Peptides

In certain aspects, the instant disclosure provides a WT1 p37 peptide-specific T cell receptor (TCR) comprising (a) a T cell receptor (TCR) α-chain variable ($V_\alpha$) domain, and a TCR β-chain variable ($V_\beta$) having the CDR3 amino acid sequence shown in any one of SEQ ID NOS:1-11, 181, 187, 193, 199, 205, 211, 217, 223, 229, 235, and 241; (b) a TCR $V_\alpha$ domain having the CDR3 amino acid sequence shown in any one of SEQ ID NOS:12-22, 178, 184, 190, 196, 202, 208, 214, 220, 226, 232, and 238, and a TCR $V_\beta$ domain; or (c) a TCR $V_\alpha$ domain having the CDR3 amino acid sequence shown in any one of SEQ ID NOS:12-22, 178, 184, 190, 196, 202, 208, 214, 220, 226, 232, and 238, and a TCR $V_\beta$ domain having the CDR3 amino acid sequence shown in any one of SEQ ID NOS:1-11, 181, 187, 193, 199, 205, 211, 217, 223, 229, 235, and 241. For example, any of the TCRs, or binding domains thereof, of this disclosure can specifically bind to a WT1 p37 peptide:HLA complex on a cell (e.g., T cell) surface and/or can promote IFNγ production $pEC_{50}$ of 8.5 or higher (e.g., up to about 8.6, up to about 8.65, up to about 8.7, up to about 8.72, up to about 8.75, up to about 8.8, up to about 9, up to about 9.1, up to about 9.2, up to up to about 9.3, up to about 9.4, about 9.5, up to about 9.6, up to about 9.68 up to about 9.7, up to about 9.75, up to about 10, up to about 10.5, up to about 11, up to about 11.5, up to about 12, up to about 12.5, or up to about 13). In certain embodiments, a TCR of the present disclosure can specifically bind to a VLDFAPPGA (SEQ ID NO:59):human leukocyte antigen (HLA) complex with an IFNγ production $pEC_{50}$ of 9.0 or higher, or with an IFNγ production $pEC_{50}$ of 9.0 or higher. In certain embodiments, a TCR, or a binding domain thereof (e.g., scTCR or a fusion protein thereof), of this disclosure can specifically bind to a WT1 p37 peptide:HLA complex and promote IFNγ production at a $pEC_{50}$ ranging from 8.5 to about 9.9, or from 8.6 to about 9.8, or from 8.7 to about 9.7, or from 8.75 to about 9.65, or the like. The $EC_{50}$ can range from about $1.1\times10^{-9}$M to about $3.0\times10^{-10}$ M, or any value in between. In further examples, any of the TCRs of this disclosure can specifically bind to a WT1 peptide:HLA complex on a cell surface independent of CD8 or in the absence of CD8. In further embodiments, a TCR specifically binds to a VLDFAPPGA (SEQ ID NO:59):human leukocyte antigen (HLA) complex with a $K_D$ of less than or equal to about $10^{-9}$M. In certain embodiments, the HLA comprises HLA-A*201. The peptide antigen VLDFAPPGA (SEQ ID NO:59) is a WT1 peptide antigen and corresponds to amino acids 37-45 of the WT1 protein.

In any of the embodiments described herein, the present disclosure provides a T cell receptor (TCR) comprising an α-chain and a β-chain, wherein the TCR binds to a WT1: HLA-A*201 complex on a T cell surface and promotes (a) an IFNγ production $pEC_{50}$ of 8.5 or higher (e.g., up to about 9, up to about 9.5, up to about 10, about 10.5, about 11, about 11.5, about 12, about 12.5, or about 13); or (b) binds a cell surface independent or in the absence of CD8.

In certain embodiments, a Vβ domain comprises or is derived from a TRBV7-6*01/TRBJ2-7*01, TRBV20-1*02/TRBJ2-7*01, TRBV15*02/TRBJ1-5*01, TRBV13*01/TRBJ2-5*01, TRAJ50*01/TRBJ2-7*01, TRBV11-3*01/TRBJ1-1*01, TRBV19*01/TRBJ1-6*02, TRBV27*01/TRBJ2-7*01, TRBV13*01/TRBJ2-7*01, TRBV11-1*01/TRBJ1 4*01, or TRBV4-3*01/TRBJ1-3*01. In further embodiments, a $V_\alpha$ domain comprises or is derived from a TRAV21*02/TRAJ58*01, TRAV38-1*01/TRAJ40*01, TRAV29/DV5*01/TRAJ6*01, TRAV29/DV5*01/TRAJ20*01, TRAV41*01/TRAJ50*01, TRAV12-2*01/TRAJ11*01, TRAV1-2*01/TRAJ20*01, TRAV20*02/TRAJ8*01, TRAV26-1*02/TRAJ26*01, TRAV24*01/TRAJ48*01, or TRAV20*02/TRAJ37*02. In particular embodiments, a TCR comprises (a) a $V_\beta$ domain comprising or derived from TRBV7-6*01/TRBJ2-7*01 and a $V_\alpha$ domain comprises or is derived from a TRAV21*02/TRAJ58*01; (b) a $V_\beta$ domain comprises or is derived from a TRBV27*01/TRBJ2-7*01 and a $V_\alpha$ domain comprises or is derived from a TRAV20*02/TRAJ8*01; or (c) a $V_\beta$ domain comprises or is derived from a TRBV13*01/TRBJ2-5*01 and a $V_\alpha$ domain comprises or is derived from a TRAV29/DV5*01/TRAJ20*01.

In certain embodiments, a TCR of the present disclosure further comprises: (i) the CDR1α amino acid sequence set forth in any one of SEQ ID NOs.:194, 176, 182, 188, 200, 206, 212, 218, 224, 230, and 236, or a variant thereof comprising one or two amino acid substitutions, wherein, optionally, the one or two amino acid substitutions comprise a conservative amino acid substitution; and/or (ii) the CDR2α amino acid sequence set forth in any one of SEQ ID NOs.:195, 177, 183, 189, 201, 207, 213, 219, 225, 231, and 237, or a variant thereof comprising one or two amino acid substitutions, wherein, optionally, the one or two amino acid substitutions comprise a conservative amino acid substitution.

In certain embodiments, a TCR of the present disclosure further comprises: (i) the CDR1β amino acid sequence set forth in any one of SEQ ID NOs.: 197, 179, 185, 191, 197, 203, 209, 215, 221, 227, 233, and 239, or a variant thereof comprising one or two amino acid substitutions, wherein, optionally, the one or two amino acid substitutions comprise a conservative amino acid substitution; and/or (ii) the CDR2β amino acid sequence set forth in any one of SEQ ID NOs.:198, 180, 186, 192, 204, 210, 216, 222, 228, 234, and 240, or a variant thereof comprising one or two amino acid substitutions, wherein, optionally, the one or two amino acid substitutions comprise a conservative amino acid substitution.

In certain embodiments, a TCR of the present disclosure comprises the CDR1α, CDR2α, CDR3α, CDR1β, CDR2β, and CDR3β amino acid sequences set forth in: (i) SEQ ID NOs. 194, 195, 196 or 12, 197, 198, and 199 or 1, respectively; (ii) SEQ ID NOs.: 176, 177, 178 or 18, 179, 180, and 181 or 7, respectively; (iii) SEQ ID NOs.: 182, 183, 184 or 20, 185, 186, and 187 or 9, respectively; (iv) SEQ ID NOs.: 188, 189, 190 or 21, 191, 192, and 193 or 10, respectively; (v) SEQ ID NOs.: 200, 201, 202 or 13, 203, 204, and 205 or 2, respectively; (vi) SEQ ID NOs.: 206, 207, 208 or 14, 209, 210, and 211 or 3, respectively; (vii) SEQ ID NOs.: 212, 213, 214 or 15, 215, 216, and 217 or 4, respectively; (viii) SEQ ID NOs.: 218, 219, 220 or 17, 221, 222, and 223 or 6, respectively; (ix) SEQ ID NOs.: 224, 225, 226 or 19, 227, 228, and 229 or 8, respectively; (x) SEQ ID NOs.: 230, 231, 232 or 22, 233, 234, and 235 or 11, respectively; or (xi) SEQ ID NOs.: 236, 237, 238 or 16, 238, 240, and 241 or 5, respectively.

Any polypeptide of this disclosure can, as encoded by a polynucleotide sequence, comprise a "signal peptide" (also known as a leader sequence, leader peptide, or transit peptide). Signal peptides target newly synthesized polypeptides to their appropriate location inside or outside the cell.

A signal peptide may be removed from the polypeptide during or once localization or secretion is completed. Polypeptides that have a signal peptide are referred to herein as a "pre-protein" and polypeptides having their signal peptide removed are referred to herein as "mature" proteins or polypeptides. In any of the herein disclosed embodiments, a binding protein or fusion protein comprises, or is, a mature protein, or is or comprises a pre-protein.

In certain embodiments, amino acid residues 1-19 of SEQ ID NO.:23 are or comprise a signal peptide. In some embodiments, a TCR Vβ domain is a mature TCR Vβ domain and comprises or consists of the amino acid sequence of SEQ ID NO.:23 with amino acid residues 1-19 of SEQ ID NO.:23 removed (i.e., the TCR Vβ domain comprises or consists of the amino acid sequence set forth in SEQ ID NO.:242).

In certain embodiments, amino acid residues 1-15 of SEQ ID NO.:24 are or comprise a signal peptide. In some embodiments, a TCR Vβ domain is a mature TCR Vβ domain and comprises or consists of the amino acid sequence of SEQ ID NO.:23 with amino acid residues 1-15 of SEQ ID NO.:24 removed (i.e., the TCR Vβ domain comprises or consists of the amino acid sequence set forth in SEQ ID NO.:243).

In certain embodiments, amino acid residues 1-19 of SEQ ID NO.:25 are or comprise a signal peptide. In some embodiments, a TCR Vβ domain is a mature TCR Vβ domain and comprises or consists of the amino acid sequence of SEQ ID NO.:25 with amino acid residues 1-15 of SEQ ID NO.:25 removed (i.e., the TCR Vβ domain comprises or consists of the amino acid sequence set forth in SEQ ID NO.:244).

In certain embodiments, amino acid residues 1-29 of SEQ ID NO.:26 are or comprise a signal peptide. In some embodiments, a TCR Vβ domain is a mature TCR Vβ domain and comprises or consists of the amino acid sequence of SEQ ID NO.:26 with amino acid residues 1-29 of SEQ ID NO.:26 removed (i.e., the TCR Vβ domain comprises or consists of the amino acid sequence set forth in SEQ ID NO.:245).

In certain embodiments, amino acid residues 1-19 of SEQ ID NO.:27 are or comprise a signal peptide. In some embodiments, a TCR Vβ domain is a mature TCR Vβ domain and comprises or consists of the amino acid sequence of SEQ ID NO.:27 with amino acid residues 1-19 of SEQ ID NO.:27 removed (i.e., the TCR Vβ domain comprises or consists of the amino acid sequence set forth in SEQ ID NO.:246).

In certain embodiments, amino acid residues 1-19 of SEQ ID NO.:28 are or comprise a signal peptide. In some embodiments, a TCR Vβ domain is a mature TCR Vβ domain and comprises or consists of the amino acid sequence of SEQ ID NO.:28 with amino acid residues 1-19 of SEQ ID NO.:28 removed (i.e., the TCR Vβ domain comprises or consists of the amino acid sequence set forth in SEQ ID NO.:247).

In certain embodiments, amino acid residues 1-19 of SEQ ID NO.:29 are or comprise a signal peptide. In some embodiments, a TCR Vβ domain is a mature TCR Vβ domain and comprises or consists of the amino acid sequence of SEQ ID NO.:29 with amino acid residues 1-19 of SEQ ID NO.:29 removed (i.e., the TCR Vβ domain comprises or consists of the amino acid sequence set forth in SEQ ID NO.:248).

In certain embodiments, amino acid residues 1-19 of SEQ ID NO.:30 are or comprise a signal peptide. In some embodiments, a TCR Vβ domain is a mature TCR Vβ domain and comprises or consists of the amino acid sequence of SEQ ID NO.:30 with amino acid residues 1-19 of SEQ ID NO.:30 removed (i.e., the TCR Vβ domain comprises or consists of the amino acid sequence set forth in SEQ ID NO.:249).

In certain embodiments, amino acid residues 1-29 of SEQ ID NO.:31 are or comprise a signal peptide. In some embodiments, a TCR Vβ domain is a mature TCR Vβ domain and comprises or consists of the amino acid sequence of SEQ ID NO.:31 with amino acid residues 1-29 of SEQ ID NO.:31 removed (i.e., the TCR Vβ domain comprises or consists of the amino acid sequence set forth in SEQ ID NO.:250).

In certain embodiments, amino acid residues 1-19 of SEQ ID NO.:32 are or comprise a signal peptide. In some embodiments, a TCR Vβ domain is a mature TCR Vβ domain and comprises or consists of the amino acid sequence of SEQ ID NO.:32 with amino acid residues 1-19 of SEQ ID NO.:32 removed (i.e., the TCR Vβ domain comprises or consists of the amino acid sequence set forth in SEQ ID NO.:251).

In certain embodiments, amino acid residues 1-19 of SEQ ID NO.:33 are or comprise a signal peptide. In some embodiments, a TCR Vβ domain is a mature TCR Vβ domain and comprises or consists of the amino acid sequence of SEQ ID NO.:33 with amino acid residues 1-19 of SEQ ID NO.:33 removed (i.e., the TCR Vβ domain comprises or consists of the amino acid sequence set forth in SEQ ID NO.:252).

In certain embodiments, amino acid residues 1-19 of SEQ ID NO.:34 are or comprise a signal peptide. In some embodiments, a TCR Vα domain is a mature TCR Vα domain and comprises or consists of the amino acid sequence of SEQ ID NO.:34 with amino acid residues 1-19 of SEQ ID NO.:34 removed (i.e., the TCR Vα domain comprises or consists of the amino acid sequence set forth in SEQ ID NO.:253).

In certain embodiments, amino acid residues 1-20 of SEQ ID NO.:35 are or comprise a signal peptide. In some embodiments, a TCR Vα domain is a mature TCR Vα domain and comprises or consists of the amino acid sequence of SEQ ID NO.:35 with amino acid residues 1-20 of SEQ ID NO.:35 removed (i.e., the TCR Vα domain comprises or consists of the amino acid sequence set forth in SEQ ID NO.:254).

In certain embodiments, amino acid residues 1-26 of SEQ ID NO.:36 are or comprise a signal peptide. In some embodiments, a TCR Vα domain is a mature TCR Vα domain and comprises or consists of the amino acid sequence of SEQ ID NO.:36 with amino acid residues 1-26 of SEQ ID NO.:36 removed (i.e., the TCR Vα domain comprises or consists of the amino acid sequence set forth in SEQ ID NO.:255).

In certain embodiments, amino acid residues 1-26 of SEQ ID NO.:37 are or comprise a signal peptide. In some embodiments, a TCR Vα domain is a mature TCR Vα domain and comprises or consists of the amino acid sequence of SEQ ID NO.:37 with amino acid residues 1-26 of SEQ ID NO.:37 removed (i.e., the TCR Vα domain comprises or consists of the amino acid sequence set forth in SEQ ID NO.:256).

In certain embodiments, amino acid residues 1-22 of SEQ ID NO.:38 are or comprise a signal peptide. In some embodiments, a TCR Vα domain is a mature TCR Vα domain and comprises or consists of the amino acid sequence of SEQ ID NO.:38 with amino acid residues 1-22 of SEQ ID NO.:38 removed (i.e., the TCR Vα domain comprises or consists of the amino acid sequence set forth in SEQ ID NO.:257).

In certain embodiments, amino acid residues 1-21 of SEQ ID NO.:39 are or comprise a signal peptide. In some embodiments, a TCR Vα domain is a mature TCR Vα domain and comprises or consists of the amino acid sequence of SEQ ID NO.:39 with amino acid residues 1-21 of SEQ ID NO.:39 removed (i.e., the TCR Vα domain comprises or consists of the amino acid sequence set forth in SEQ ID NO.:258).

In certain embodiments, amino acid residues 1-17 of SEQ ID NO.:40 are or comprise a signal peptide. In some embodiments, a TCR Vα domain is a mature TCR Vα domain and comprises or consists of the amino acid sequence of SEQ ID NO.:40 with amino acid residues 1-17 of SEQ ID NO.:40 removed (i.e., the TCR Vα domain comprises or consists of the amino acid sequence set forth in SEQ ID NO.:259).

In certain embodiments, amino acid residues 1-21 of SEQ ID NO.:41 are or comprise a signal peptide. In some embodiments, a TCR Vα domain is a mature TCR Vα domain and comprises or consists of the amino acid sequence of SEQ ID NO.:41 with amino acid residues 1-21 of SEQ ID NO.:41 removed (i.e., the TCR Vα domain comprises or consists of the amino acid sequence set forth in SEQ ID NO.:260).

In certain embodiments, amino acid residues 1-17 of SEQ ID NO.:42 are or comprise a signal peptide. In some embodiments, a TCR Vα domain is a mature TCR Vα domain and comprises or consists of the amino acid sequence of SEQ ID NO.:42 with amino acid residues 1-17 of SEQ ID NO.:42 removed (i.e., the TCR Vα domain comprises or consists of the amino acid sequence set forth in SEQ ID NO.:261).

In certain embodiments, amino acid residues 1-22 of SEQ ID NO.:43 are or comprise a signal peptide. In some embodiments, a TCR Vα domain is a mature TCR Vα domain and comprises or consists of the amino acid sequence of SEQ ID NO.:43 with amino acid residues 1-22 of SEQ ID NO.:43 removed (i.e., the TCR Vα domain comprises or consists of the amino acid sequence set forth in SEQ ID NO.:262).

In certain embodiments, amino acid residues 1-21 of SEQ ID NO.:44 are or comprise a signal peptide. In some embodiments, a TCR Vα domain is a mature TCR Vα domain and comprises or consists of the amino acid sequence of SEQ ID NO.:44 with amino acid residues 1-21 of SEQ ID NO.:44 removed (i.e., the TCR Vα domain comprises or consists of the amino acid sequence set forth in SEQ ID NO.:263).

In certain embodiments, a T cell receptor (TCR) specific for a WT1 peptide:HLA complex has a $V_\alpha$ domain that comprises or consists of the amino acid sequence as set forth in any one of SEQ ID NOS:253-263 and 34-33, has a $V_\beta$ domain that comprises or consists of the amino acid sequence as set forth in any one of SEQ ID NOS:242-252 and 23-33, or any combination thereof. In particular embodiments, a $V_\alpha$ domain comprises or consists of the amino acid sequence of SEQ ID NO:34 and a $V_\beta$ domain comprises or consists of the amino acid sequence of SEQ ID NO:23. In further particular embodiments, (a) a $V_\alpha$ domain comprises or consists of the amino acid sequence of SEQ ID NO:41 and a $V_\beta$ domain comprises or consists of the amino acid sequence of SEQ ID NO:30; (b) a $V_\alpha$ domain comprises or consists of the amino acid sequence of SEQ ID NO:37 and a $V_\beta$ domain comprises or consists of the amino acid sequence of SEQ ID NO:26; or (c) a $V_\alpha$ domain comprises or consists of the amino acid sequence of SEQ ID NO:42 and a $V_\beta$ domain comprises or consists of the amino acid sequence of SEQ ID NO:31. In further particular embodiments, a $V_\alpha$ domain comprises or consists of the amino acid sequence of SEQ ID NO:24 and a $V_\beta$ domain comprises or consists of the amino acid sequence of SEQ ID NO:35.

In some embodiments, the Vα domain and the Vβ domain comprise or consist of the amino acid sequences set forth in SEQ ID NOs.: (i) 253 and 242, respectively; (ii) 259 and 248, respectively; (iii) 261 and 250, respectively; (iv) 262 and 251, respectively; (v) 257 and 246, respectively; (vi) 254 and 243, respectively; (vii) 255 and 244, respectively; (viii) 256 and 245, respectively; (ix) 258 and 247, respectively; (x) 260 and 249, respectively; (xi) 263 and 252, respectively; (xii) 34 and 23, respectively; (xiii) 40 and 29, respectively; (xiv) 42 and 31, respectively; (xv) 43 and 32, respectively; (xvi) 35 and 24, respectively; (xvii) 36 and 25, respectively; (xviii) 37 and 26, respectively; (xix) 39 and 28, respectively; (xx) 41 and 30, respectively; (xxi) 44 and 33, respectively; or (xxii) 38 and 27, respectively.

In certain embodiments, a high functional avidity recombinant TCR specific for WT1 p37 peptide as described herein includes variant polypeptide species that have one or more amino acid substitutions, insertions, or deletions in the amino acid sequence relative to the amino acid sequences of any one or more of SEQ ID NOS:48-58, as presented herein, provided that the CDR3s are not changed and the TCR retains or substantially retains its specific WT1 p37 binding function.

Conservative substitutions of amino acids are well known and may occur naturally or may be introduced when the TCR is recombinantly produced. Amino acid substitutions, deletions, and additions may be introduced into a protein using mutagenesis methods known in the art (see, e.g., Sambrook et al., *Molecular Cloning: A Laboratory Manual,* 3d ed., Cold Spring Harbor Laboratory Press, N Y, 2001). Oligonucleotide-directed site-specific (or segment specific) mutagenesis procedures may be employed to provide an altered polynucleotide that has particular codons altered according to the substitution, deletion, or insertion desired. Alternatively, random or saturation mutagenesis techniques, such as alanine scanning mutagenesis, error prone polymerase chain reaction mutagenesis, and oligonucleotide-directed mutagenesis may be used to prepare immunogen polypeptide variants (see, e.g., Sambrook et al., supra).

A variety of criteria known to persons skilled in the art indicate whether an amino acid that is substituted at a particular position in a peptide or polypeptide is conservative (or similar). For example, a similar amino acid or a conservative amino acid substitution is one in which an amino acid residue is replaced with an amino acid residue having a similar side chain. Similar amino acids may be included in the following categories: amino acids with basic side chains (e.g., lysine, arginine, histidine); amino acids with acidic side chains (e.g., aspartic acid, glutamic acid); amino acids with uncharged polar side chains (e.g., glycine, asparagine, glutamine, serine, threonine, tyrosine, cysteine, histidine); amino acids with nonpolar side chains (e.g., alanine, valine, leucine, isoleucine, proline, phenylalanine, methionine, tryptophan); amino acids with beta-branched side chains (e.g., threonine, valine, isoleucine), and amino acids with aromatic side chains (e.g., tyrosine, phenylalanine, tryptophan). Proline, which is considered more difficult to classify, shares properties with amino acids that have aliphatic side chains (e.g., leucine, valine, isoleucine, and alanine). In certain circumstances, substitution of glutamine for glutamic acid or asparagine for aspartic acid may be considered a similar substitution in that glutamine and asparagine are amide derivatives of glutamic acid and aspartic acid, respectively. As understood in the art "similarity" between two polypeptides is determined by comparing the amino acid sequence and conserved amino acid substitutes thereto of the polypeptide to the sequence of a second polypeptide (e.g., using GENEWORKS, Align, the BLAST algorithm, or other algorithms described herein and practiced in the art).

Variants of a wild-type TCR, or a binding domain thereof, specific for WT1 p37 antigen:MHC complex may include a TCR that has at least about 85%, 86%, 87%, 88%, 89%, 90%, 91%, 92%, 93%, 94%, 95%, 96%, 97%, 98%, 99%, 99.9%, or 100% amino acid sequence identity to any of the exemplary amino acid sequences disclosed herein (e.g., SEQ ID NOS:23-58), provided that neither the CDR3 of the $V_\beta$ domain nor the CDR3 of the $V_\alpha$ domain contain an alteration, and the alterations to the other portions do not reduce the functional avidity (or relative affinity) any more than 10%, 15%, or 20% as compared to the wild-type TCR. In some optional embodiments, a variant TCR further comprises no change in amino acid sequence of the $V_\alpha$ domain CDR1, the $V_\alpha$ domain CDR2, the $V_\beta$ domain CDR1, the $V_\beta$ domain CDR2, or any combination thereof, as set forth in any one of SEQ ID NOS:34-44 (parental $V_\alpha$ domain) or as set forth in any one of SEQ ID NOS:23-33 (parental $V_\beta$ domain). In each of these embodiments, the TCR retains its ability to specifically induce IFNγ production at a $pEC_{50}$ of 8.5, 8.6, 8.7, 8.8, 8.9 or higher, or the TCR retains its ability to specifically bind to a peptide antigen:HLA complex (e.g., VLDFAPPGA (SEQ ID NO:59):HLA complex) with a $K_D$ of less than or equal to about $10^{-9}$M, and specifically binds 1.5-fold, 2-fold, 2.5-fold, 3-fold, 3.3-fold, 3.5-fold, up to 5-fold better than the wild-type TCR consisting of any one of SEQ ID NOS:48-58.

In further embodiments, the present disclosure provides a p37-specific TCR, or a binding domain thereof, comprising (a) a TCR α-chain variable ($V_\alpha$) domain having at least 90% sequence identity to the amino acid sequence set forth in any one of SEQ ID NOS:34-35 and 38-44, and a TCR β-chain variable ($V_\beta$) domain having at least 90% sequence identity to the amino acid sequence set forth in any one of SEQ ID NOS:23-25, 27, 28, 30, 32, and 33; (b) a TCR $V_\alpha$ domain has at least 92% sequence identity to the amino acid sequence of SEQ ID NO:36 or 37, and a TCR $V_\beta$ domain having at least 90% e.g., 90%, 91%, 92%, 93%, 94%, 95%, 96%, 97%, 98%, 99%, or 100%) sequence identity to the amino acid sequence as set forth in any one of SEQ ID NOS:23-25, 27, 28, 30, 32, and 33; or (c) a TCR $V_\alpha$ domain comprising or consisting of an amino acid sequence of SEQ ID NOS:34-44, and a TCR $V_\beta$ domain having at least 90% sequence identity to the amino acid sequence as set forth in any one of SEQ ID NOS:23-25, 27, 28, 30, 32, and 33.

In still further embodiments, the present disclosure provides a p37-specific TCR, or a binding domain thereof, comprising (a) a TCR $V_\alpha$ domain having at least 90% sequence identity to the amino acid sequence set forth in any one of SEQ ID NOS:34-35 and 38-44, and a $V_\beta$ domain having at least 92% (e.g., 92%, 93%, 94%, 95%, 96%, 97%, 98%, 99%, or 100%) sequence identity to the amino acid sequence of SEQ ID NO:29; (b) a TCR $V_\alpha$ domain has at least 92% sequence identity to the amino acid sequence of SEQ ID NO:36 or 37, and a TCR $V_\beta$ domain having at least 92% sequence identity to the amino acid sequence of SEQ ID NO:29; or (c) a TCR $V_\alpha$ domain comprising or consisting of an amino acid sequence of SEQ ID NOS:34-44, and a TCR $V_\beta$ domain having at least 92% sequence identity to the amino acid sequence of SEQ ID NO:29.

In yet further embodiments, the present disclosure provides a p37-specific TCR, or a binding domain thereof, comprising (a) a TCR $V_\alpha$ domain having at least 90% sequence identity to the amino acid sequence set forth in any one of SEQ ID NOS:34-35 and 38-44, and a $V_\beta$ domain having at least 93% sequence identity to the amino acid sequence of SEQ ID NO:31; (b) a TCR $V_\alpha$ domain has at least 92% sequence identity to the amino acid sequence of SEQ ID NO:36 or 37, and a TCR $V_\beta$ domain having at least 93% sequence identity to the amino acid sequence of SEQ ID NO:31; or (c) a TCR $V_\alpha$ domain comprising or consisting of an amino acid sequence of SEQ ID NOS:34-44, and a TCR $V_\beta$ domain having at least 93% sequence identity to the amino acid sequence of SEQ ID NO:31.

In more embodiments, the present disclosure provides a p37-specific TCR, or a binding domain thereof, comprising (a) a TCR $V_\alpha$ domain having at least 90% sequence identity to the amino acid sequence set forth in any one of SEQ ID NOS:34-35 and 38-44, and a $V_\beta$ domain having at least 95% sequence identity to the amino acid sequence of SEQ ID NO:26; (b) a TCR $V_\alpha$ domain has at least 92% sequence identity to the amino acid sequence of SEQ ID NO:36 or 37, and a TCR $V_\beta$ domain having at least 95% sequence identity to the amino acid sequence of SEQ ID NO:26; or (c) a TCR $V_\alpha$ domain comprising or consisting of an amino acid sequence of SEQ ID NOS:34-44, and a TCR $V_\beta$ domain having at least 95% sequence identity to the amino acid sequence of SEQ ID NO:26.

In still more embodiments, the present disclosure provides a p37-specific TCR, or a binding domain thereof, comprising (a) a TCR $V_\alpha$ domain having at least 90% sequence identity to the amino acid sequence set forth in any one of SEQ ID NOS:34-35 and 38-44, and a $V_\beta$ domain comprising or consisting of the amino acid sequence set forth in any one of SEQ ID NOS:23-33; (b) a TCR $V_\alpha$ domain has at least 92% sequence identity to the amino acid sequence of SEQ ID NO:36 or 37, and a TCR $V_\beta$ domain comprising or consisting of the amino acid sequence set forth in any one of SEQ ID NOS:23-33; or (c) a TCR $V_\alpha$ domain comprising or consisting of an amino acid sequence of SEQ ID NOS:34-44, and a TCR $V_\beta$ domain comprising or consisting of the amino acid sequence set forth in any one of SEQ ID NOS:23-33.

In any of the aforementioned embodiments, the TCR has the ability to bind to a cell (e.g., T cell) surface WT1 p37 peptide VLDFAPPGA (SEQ ID NO:59):HLA complex and specifically induce IFNγ production at a $pEC_{50}$ of 8.5, 8.6, 8.7, 8.8, 8.9, or higher, and/or the TCR is capable of specifically binding to a WT1 peptide VLDFAPPGA (SEQ ID NO:59):HLA cell surface complex independent, or in the absence, of CD8. In any of the aforementioned embodiments, the $V_\beta$ domain comprises no change in the amino acid sequence of CDR1 and/or CDR2 as compared to the CDR1 and/or CDR2, respectively, present in any one of SEQ ID NOS:23-33.

In certain embodiments, any of the aforementioned WT1 p37 peptide-specific T cell receptors (TCRs) can be an antigen-binding fragment of a TCR. In further embodiments, an antigen-binding fragment of the TCR comprises a single chain TCR (scTCR), which can be contained in a chimeric antigen receptor (CAR). In some embodiments, a WT1 p37 peptide-specific TCR is a multi-chain binding protein, for example, comprising a TCR α-chain comprising a $V_\alpha$ domain and an α-chain constant domain, wherein the TCR α-chain constant domain has at least about 90% sequence identity (e.g., 90%, 91%, 92%, 93%, 94%, 95%, 96%, 97%, 98%, 99%, or 100%) to the amino acid sequence of SEQ ID NO:47; and a TCR β-chain comprising a $V_\beta$ domain and a β-chain constant domain, wherein the TCR β-chain constant domain has at least 90% (e.g., 90%, 91%, 92%, 93%, 94%, 95%, 96%, 97%, 98%, 99%, or 100%) sequence identity to the amino acid sequence of SEQ ID NO:45 or 46. In further embodiments, the present disclosure provides a WT1 p37 peptide-specific TCR comprising or consisting of an α-chain constant domain having the amino acid sequence of SEQ ID NO:47, and/or comprising or consisting of a β-chain constant domain having the amino acid sequence of SEQ ID NO:45 or 46.

In further embodiments, the present disclosure provides a WT1 p37 peptide-specific TCR comprising a TCR α-chain comprising a $V_\alpha$ domain and an α-chain constant domain, wherein: (a) the $V_\alpha$ domain has at least 90% sequence identity (e.g., 90%, 91%, 92%, 93%, 94%, 95%, 96%, 97%, 98%, 99%, or 100%) to the amino acid sequence set forth in any one of SEQ ID NOS:34-35 and 38-44, and the α-chain constant domain has at least about 98% sequence identity to the amino acid sequence of SEQ ID NO:47; or (b) the $V_\alpha$ domain has at least 92% sequence identity to the amino acid sequence of SEQ ID NO:36 or 37, and the α-chain constant domain has at least 98% sequence identity to the amino acid sequence of SEQ ID NO:47.

In some embodiments, the TCR comprises a TCR α-chain comprising a $V_\alpha$ domain and an α-chain constant domain, wherein: (a) the $V_\alpha$ domain comprises the amino acid sequence set forth in any one of SEQ ID NOS: 242-252 and 34-44, and the α-chain constant domain comprises the amino acid sequence of SEQ ID NO:47; or (b) the $V_\alpha$ domain consists of the amino acid sequence set forth in any one of SEQ ID NOS: 242-252 and 34-44, and the α-chain constant domain has at least 90% identity (e.g., 90%, 91%, 92%, 93%, 94%, 95%, 96%, 97%, 98%, 99%, or 100%) to, comprises, or consists of the amino acid sequence of SEQ ID NO:47.

In some embodiments, the α-chain constant domain is present and the Vα domain and the α-chain constant domain together form a TCR α-chain. In some embodiments, the β-chain constant domain is present and the Vβ domain and the β-chain constant domain together form a TCR β-chain.

In some embodiments, the TCR comprises a scTCR, or an scTCR is provided which is derived from a presently disclosed TCR. In some embodiments, the TCR comprises a CAR, or a CAR is provided which is derived from (e.g., includes one or more variable domains from) a presently disclosed TCR.

In more embodiments, there is provided a composition comprising a WT1-specific high functional avidity recombinant TCR, or binding domain thereof, according to any one of the aforementioned embodiments and a pharmaceutically acceptable carrier, diluent, or excipient.

Methods useful for isolating and purifying recombinantly produced soluble TCR, by way of example, may include obtaining supernatants from suitable host cell/vector systems that secrete a recombinant soluble TCR into culture media and then concentrating the media using a commercially available filter. Following concentration, the concentrate may be applied to a single suitable purification matrix or to a series of suitable matrices, such as an affinity matrix or an ion exchange resin. One or more reverse phase HPLC steps may be employed to further purify a recombinant polypeptide. These purification methods may also be employed when isolating an immunogen from its natural environment. Methods for large scale production of one or more of the isolated/recombinant soluble TCR described herein include batch cell culture, which is monitored and controlled to maintain appropriate culture conditions. Purification of the soluble TCR may be performed according to methods described herein and known in the art and that comport with laws and guidelines of domestic and foreign regulatory agencies.

In certain embodiments, nucleic acid molecules encoding high affinity or high functional avidity TCR specific for WT1 p37 peptide complexed with MEW were used to transfect/transduce a host cell (e.g., T cells) for use in adoptive transfer therapy. Advances in TCR sequencing have been described (e.g., Robins et al., *Blood* 114:4099, 2009; Robins et al., *Sci. Translat. Med.* 2:47ra64, 2010; Robins et al., (September 10) *J. Imm. Meth.* Epub ahead of print, 2011; Warren et al., *Genome Res.* 21:790, 2011) and may be employed in the course of practicing the embodiments according to the present disclosure. Similarly, methods for transfecting/transducing T cells with desired nucleic acids have been described (e.g., U.S. Patent Application Pub. No. US 2004/0087025) as have adoptive transfer procedures using T-cells of desired antigen-specificity (e.g., Schmitt et al., *Hum. Gen.* 20:1240, 2009; Dossett et al., *Mol. Ther.* 17:742, 2009; Till et al., *Blood* 112:2261, 2008; Wang et al., *Hum. Gene Ther.* 18:712, 2007; Kuball et al., *Blood* 109:2331, 2007; US 2011/0243972; US 2011/0189141; Leen et al., *Ann. Rev. Immunol.* 25:243, 2007), such that adaptation of these methodologies to the presently disclosed embodiments is contemplated, based on the teachings herein, including those directed to high affinity TCRs specific for WT1 peptide antigens complexed with an HLA receptor.

The WT1-specific TCRs, or binding domains thereof, as described herein (e.g., SEQ ID NOS:23-58, and non-CDR3 variants thereof), may be functionally characterized according to any of a large number of art accepted methodologies for assaying T cell activity, including determination of T cell binding, activation or induction and also including determination of T cell responses that are antigen-specific. Examples include determination of T cell proliferation, T cell cytokine release, antigen-specific T cell stimulation, MEW restricted T cell stimulation, cytotoxic T lymphocyte (CTL) activity (e.g., by detecting $^{51}Cr$ release from preloaded target cells), changes in T cell phenotypic marker expression, and other measures of T cell functions. Procedures for performing these and similar assays are may be found, for example, in Lefkovits (*Immunology Methods Manual: The Comprehensive Sourcebook of Techniques,* 1998). See, also, *Current Protocols in Immunology*; Weir, *Handbook of Experimental Immunology*, Blackwell Scientific, Boston, Mass. (1986); Mishell and Shigii (eds.) *Selected Methods in Cellular Immunology*, Freeman Publishing, San Francisco, Calif. (1979); Green and Reed, *Science* 281:1309 (1998) and references cited therein.

Polynucleotides Encoding TCRs Specific for WT1 p37 Antigen Peptides

Heterologous, isolated or recombinant nucleic acid molecules encoding a high affinity or high functional avidity recombinant T cell receptor (TCR), or binding domain thereof (e.g., scTCR or fusion protein thereof) specific for WT1 p37 peptide as described herein may be produced and prepared according to various methods and techniques described herein (see Examples). Construction of an expression vector that is used for recombinantly producing a high affinity or high functional avidity engineered TCR or binding domain thereof specific for a WT1 p37 peptide of interest can be accomplished by using any suitable molecular biology engineering techniques known in the art, including the use of restriction endonuclease digestion, ligation, transformation, plasmid purification, and DNA sequencing as described in, for example, Sambrook et al. (1989 and 2001 editions; *Molecular Cloning: A Laboratory Manual*, Cold Spring Harbor Laboratory Press, NY) and Ausubel et al. (Current Protocols in Molecular Biology, 2003). To obtain efficient transcription and translation, a polynucleotide in each recombinant expression construct includes at least one appropriate expression control sequence (also called a regulatory sequence), such as a leader sequence and particularly a promoter operably (i.e., operatively) linked to the nucleotide sequence encoding the immunogen.

Certain embodiments relate to nucleic acids that encode the polypeptides contemplated herein, for instance, high affinity or high functional avidity engineered TCRs or binding domain thereof specific for WT1 p37 peptide::MHC complex. As one of skill in the art will recognize, a nucleic acid may refer to a single- or a double-stranded DNA, cDNA or RNA in any form, and may include a positive and a negative strand of the nucleic acid which complement each other, including anti-sense DNA, cDNA and RNA. Also included are siRNA, microRNA, RNA-DNA hybrids, ribozymes, and other various naturally occurring or synthetic forms of DNA or RNA.

In certain embodiments, provided herein are isolated polynucleotides that encode an engineered (e.g., codon optimized) high functional avidity TCR or binding domain thereof of this disclosure specific for a WT1 p37 peptide, wherein a $V_\alpha$ domain can be encoded by a polynucleotide that is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, or 100% identical to the nucleotide sequence set forth in any one of SEQ ID NOS:97, 98, and 101-107. In particular embodiments, a polynucleotide encodes a $V_\alpha$ domain that comprises or consists of the nucleotide sequence set forth in any one of SEQ ID NO:97-107. In further embodiments, provided herein are polynucleotides that encode a high functional avidity engineered TCR or binding domain thereof of this disclosure specific for a WT1 p37 peptide, wherein a $V_\beta$ domain is encoded by a polynucleotide that is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, or 100% identical to the nucleotide sequence set forth in any one of SEQ ID NOS: 75-77, 79, 82, 84, and 85. In particular embodiments, a $V_\beta$ domain is encoded by a polynucleotide that comprises or consists of the nucleotide sequence as set forth in any one of SEQ ID NOS:75-85.

In some embodiments, a TCR, or a binding domain thereof, provided herein comprises a $V_\alpha$ domain encoded by a polynucleotide that has at least 75% (75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, or 100%) sequence identity to the polynucleotide sequence set forth in any one of SEQ ID NOS:97, 98, and 101-107, or a $V_\alpha$ domain encoded by a polynucleotide that has at least 94% sequence identity to the polynucleotide sequence of SEQ ID NO:99 or 100, or a $V_\alpha$ domain encoded by a polynucleotide that comprises or consists of a sequence set forth in any one of SEQ ID NOS:97-107; and a $V_\beta$ domain encoded by a polynucleotide that has at least 75% sequence identity to the polynucleotide sequence set forth in any one of SEQ ID NOS:75-77, 79, 82, 84 and 85, or a $V_\beta$ domain encoded by a polynucleotide that has at least 95% sequence identity to the polynucleotide sequence set forth in any one of SEQ ID NOS:78, 80, 81 and 83, or a $V_\beta$ domain encoded by the polynucleotide that comprises or consists of the nucleotide sequence as set forth in any one of SEQ ID NOS:75-85.

In any of the aforementioned embodiments, a polynucleotide encoding a $V_\alpha$ domain, $V_\beta$ domain, or both, may further encode an α-chain constant domain or a β-chain constant domain, respectively. In certain embodiments, a TCR of this disclosure comprises a TCR α-chain constant domain, wherein the α-chain constant domain is encoded by a polynucleotide comprising at least 98% to 100% sequence identity to SEQ ID NO:110. In particular embodiments, an α-chain constant domain is encoded by a polynucleotide that comprises or consists of the nucleotide sequence of SEQ ID NO:110. In further embodiments, provided herein a β-chain constant domain encoded by a polynucleotide at least 99.9% to 100% sequence identity to SEQ ID NO:108 or 109. In particular embodiments, a β-chain constant domain is encoded by a polynucleotide that comprises or consists of the nucleotide sequence of SEQ ID NO:108 or 109.

In any of the aforementioned embodiments, a polynucleotide encoding a TCR comprises a TCR α-chain, a TCR β-chain, or both. In certain embodiments, a TCR of this disclosure is encoded by a polynucleotide comprising a nucleotide sequence encoding a self-cleaving peptide disposed between the polynucleotide sequence encoding the TCR α-chain and the polynucleotide sequence encoding the TCR β-chain. Exemplary self-cleaving peptides comprise an amino acid sequence of any one of SEQ ID NOS:60-63; or consist of an amino acid sequence of any one of SEQ ID NOS:60-63. Such self-cleaving peptides can be encoded by a polynucleotide comprising a polynucleotide sequence of any one of SEQ ID NOS:166-170; or encoded by a polynucleotide consisting of a polynucleotide sequence of any one of SEQ ID NOS:166-170.

In certain embodiments, a TCR α-chain, self-cleaving peptide, and TCR β-chain are encoded by a polynucleotide comprising at least 95% (e.g., 95%, 96%, 97%, 98%, 99%, or 100%) identity to any one of SEQ ID NOS:155-165. In further embodiments, a TCR α-chain, self-cleaving peptide, and TCR β-chain are encoded by a polynucleotide comprising a polynucleotide sequence of any one of SEQ ID NOS:155-165; or encoded by a polynucleotide consisting of a sequence of any one of the polynucleotides of SEQ ID NOS:155-165. In still further embodiments, the encoded TCR α-chain, self-cleaving peptide, and TCR β-chain comprise an amino acid sequence having at least 95% (e.g., 95%, 96%, 97%, 98%, 99%, or 100%) identity to any one of the polypeptides of SEQ ID NOS: 48-58, or the encoded TCR α-chain, self-cleaving peptide, and TCR β-chain comprise or consist of an amino acid sequence of any one of SEQ ID NOS: 48-58. In any of the presently disclosed embodiments, a polynucleotide encoding a binding protein can further comprise: (i) a polynucleotide encoding a polypeptide that comprises an extracellular portion of a CD8 co-receptor a chain, wherein, optionally, the encoded polypeptide is or comprises a CD8 co-receptor a chain; (ii) a polynucleotide encoding a polypeptide that comprises an extracellular portion of a CD8 co-receptor β chain, wherein, optionally, the encoded polypeptide is or comprises a CD8 co-receptor β chain; or (iii) a polynucleotide of (i) and a polynucleotide of (ii). Without being bound by theory, in certain embodiments, co-expression or concurrent expression of a binding protein and a CD8 co-receptor protein or portion thereof functional to bind to an HLA molecule may improve one or more desired activity of a host cell (e.g., immune cell, such as a T cell, optionally a $CD4^+$ T cell) as compared to expression of the binding protein alone. It will be understood that the binding protein-encoding polynucleotide and the CD8 co-receptor polypeptide-encoding polynucleotide may be present on a single nucleic acid molecule (e.g., in a same expression vector), or may be present on separate nucleic acid molecules in a host cell.

In certain further embodiments, a polynucleotide comprises: (a) the polynucleotide encoding a polypeptide comprising an extracellular portion of a CD8 co-receptor α chain; (b) the polynucleotide encoding a polypeptide comprising an extracellular portion of a CD8 co-receptor β chain; and (c) a polynucleotide encoding a self-cleaving peptide disposed between the polynucleotide of (a) and the polynucleotide of (b). In further embodiments, a polynucleotide comprises a polynucleotide that encodes a self-cleaving peptide and is disposed between: (1) the polynucleotide encoding a binding protein (e.g., TCR of the present disclosure) and the polynucleotide encoding a polypeptide comprising an extracellular portion of a CD8 co-receptor α chain; and/or (2) the polynucleotide encoding a binding protein and the polynucleotide encoding a polypeptide comprising an extracellular portion of a CD8 co-receptor β chain.

In still further embodiments, a polynucleotide can comprise, operably linked in-frame: (i) (pnCD8α)-(pnSCP1)-(pnCD8β)-(pnSCP2)-(pnTCR); (ii) (pnCD8β)-(pnSCP1)-(pnCD8α)-(pnSCP2)-(pnTCR); (iii) (pnTCR)-(pnSCP1)-(pnCD8α)-(pnSCP2)-(pnCD8β); (iv) (pnTCR)-(pnSCP1)-(pnCD8β)-(pnSCP2)-(pnCD8α); (v) (pnCD8α)-(pnSCP1)-(pnTCR)-(pnSCP2)-(pnCD8β); or (vi) (pnCD8β)-(pnSCP1)-(pnTCR)-(pnSCP2)-(pnCD8α), wherein pnCD8α is the polynucleotide encoding a polypeptide that comprises an extracellular portion of a CD8 co-receptor α chain, wherein pnCD8β is the polynucleotide encoding a polypeptide that comprises an extracellular portion of a CD8 co-receptor α chain, wherein pnTCR is the polynucleotide encoding a TCR, and wherein pnSCP1 and pnSCP2 are each independently a polynucleotide encoding a self-cleaving peptide, wherein the polynucleotides and/or the encoded self-cleaving peptides are optionally the same or different (e.g., P2A, T2A, F2A, E2A).

In some embodiments, the encoded TCR comprises a TCRα chain and a TCRβ chain, wherein the polynucleotide comprises a polynucleotide encoding a self-cleaving peptide disposed between the polynucleotide encoding a TCRα chain and the polynucleotide encoding a TCRβ chain. In some embodiments, the polynucleotide comprises, operably linked in-frame: (i) (pnCD8α)-(pnSCP1)-(pnCD8β)-(pnSCP2)-(pnTCRβ)-(pnSCP$_3$)-(pnTCRα); (ii) (pnCD8β)-(pnSCP$_1$)-(pnCD8α)-(pnSCP$_2$)-(pnTCRβ)-(pnSCP$_3$)-(pnTCRα); (iii) (pnCD8α)-(pnSCP$_1$)-(pnCD8β)-(pnSCP$_2$)-(pnTCRα)-(pnSCP$_3$)-(pnTCRβ); (iv) (pnCD8β)-(pnSCP$_1$)-(pnCD8α)-(pnSCP$_2$)-(pnTCRα)-(pnSCP$_3$)-(pnTCRβ); (v) (pnTCRβ)-(pnSCP$_1$)-(pnTCRα)-(pnSCP$_2$)-(pnCD8α)-(pnSCP$_3$)-(pnCD8β); (vi) (pnTCRβ)-(pnSCP$_1$)-(pnTCRα)-(pnSCP$_2$)-(pnCD8β)-(pnSCP$_3$)-(pnCD8α); (vii) (pnTCRα)-(pnSCP$_1$)-(pnTCRβ)-(pnSCP$_2$)-(pnCD8α)-(pnSCP$_3$)-(pnCD8β); or (viii) (pnTCRα)-(pnSCP$_1$)-(pnTCRβ)-(pnSCP$_2$)-(pnCD8β)-(pnSCP$_3$)-(pnCD8α), wherein pnCD8α is the polynucleotide encoding a polypeptide that comprises an extracellular portion of a CD8 co-receptor α chain, wherein pnCD8β is the polynucleotide encoding a polypeptide that comprises an extracellular portion of a CD8 co-receptor α chain, wherein pnTCRα is the polynucleotide encoding a TCR α chain, wherein pnTCRβ is the polynucleotide encoding a TCR β chain, and wherein pnSCP$_1$, pnSCP$_2$, and pnSCP$_3$ are each independently a polynucleotide encoding a self-cleaving peptide, wherein the polynucleotides and/or the encoded self-cleaving peptides are optionally the same or different.

In further embodiments, a binding protein is expressed as part of a transgene construct that encodes, and/or a host cell of the present disclosure can encode: one or more additional accessory protein, such as a safety switch protein; a tag, a selection marker; a CD8 co-receptor β-chain; a CD8 co-receptor α-chain or both; or any combination thereof. Polynucleotides and transgene constructs useful for encoding and expressing binding proteins and accessory components (e.g., one or more of a safety switch protein, a selection marker, CD8 co-receptor β-chain, or a CD8 co-receptor α-chain) are described in PCT application PCT/US2017/053112, the polynucleotides, transgene constructs, and accessory components, including the nucleotide and amino acid sequences, of which are hereby incorporated by reference. It will be understood that any or all of a binding protein of the present disclosure, a safety switch protein, a tag, a selection marker, a CD8 co-receptor β-chain, or a CD8 co-receptor α-chain may be encoded by a single nucleic acid molecule or may be encoded by polynucleotide sequences that are, or are present on, separate nucleic acid molecules.

Exemplary safety switch proteins include, for example, a truncated EGF receptor polypeptide (huEGFRt) that is devoid of extracellular N-terminal ligand binding domains and intracellular receptor tyrosine kinase activity, but that retains its native amino acid sequence, has type I transmembrane cell surface localization, and has a conformationally intact binding epitope for pharmaceutical-grade anti-EGFR monoclonal antibody, cetuximab (Erbitux) tEGF receptor (tEGFr; Wang et al., *Blood* 118:1255-1263, 2011); a caspase polypeptide (e.g., iCasp9; Straathof et al., *Blood* 105:4247-4254, 2005; Di Stasi et al., *N. Engl. J. Med.* 365:1673-1683, 2011; Zhou and Brenner, *Exp. Hematol.* pii: S0301-472X(16)30513-6. doi:10.1016/j.exphem.2016.07.011), RQR8 (Philip et al., *Blood* 124:1277-1287, 2014); a 10-amino-acid tag derived from the human c-myc protein (Myc) (Kieback et al., *Proc. Natl. Acad. Sci. USA* 105:623-628, 2008); and a marker/safety switch polypeptide, such as RQR (CD20+CD34; Philip et al., 2014).

Other accessory components useful for modified host cells of the present disclosure comprise a tag or selection marker that allows the cells to be identified, sorted, isolated, enriched, or tracked. For example, marked host cells having desired characteristics (e.g., an antigen-specific TCR and a safety switch protein) can be sorted away from unmarked cells in a sample and more efficiently activated and expanded for inclusion in a product of desired purity.

As used herein, the term "selection marker" comprises a nucleic acid construct (and the encoded gene product) that confers an identifiable change to a cell permitting detection and positive selection of immune cells transduced with a polynucleotide comprising a selection marker. RQR is a selection marker that comprises a major extracellular loop of CD20 and two minimal CD34 binding sites. In some embodiments, an RQR-encoding polynucleotide comprises a polynucleotide that encodes the 16-amino-acid CD34 minimal epitope. In some embodiments, the CD34 minimal epitope is incorporated at the amino terminal position of a CD8 co-receptor stalk domain (Q8). In further embodiments, the CD34 minimal binding site sequence can be combined with a target epitope for CD20 to form a compact marker/suicide gene for T cells (RQR8) (Philip et al., 2014, incorporated by reference herein). This construct allows for the selection of host cells expressing the construct, with for example, CD34 specific antibody bound to magnetic beads (Miltenyi) and that utilizes clinically accepted pharmaceutical antibody, rituximab, that allows for the selective deletion of a transgene expressing engineered T cell (Philip et al., 2014).

Further exemplary selection markers also include several truncated type I transmembrane proteins normally not expressed on T cells: the truncated low-affinity nerve growth factor, truncated CD19, and truncated CD34 (see for example, Di Stasi et al., *N. Engl. J. Med.* 365:1673-1683, 2011; Mavilio et al., *Blood* 83:1988-1997, 1994; Fehse et al., *Mol. Ther.* 1:448-456, 2000; each incorporated herein in their entirety). A useful feature of CD19 and CD34 is the availability of the off-the-shelf Miltenyi CliniMACs™ selection system that can target these markers for clinical-grade sorting. However, CD19 and CD34 are relatively large surface proteins that may tax the vector packaging capacity and transcriptional efficiency of an integrating vector. Surface markers containing the extracellular, non-signaling domains or various proteins (e.g., CD19, CD34, LNGFR) also can be employed. Any selection marker may be employed and should be acceptable for Good Manufacturing Practices. In certain embodiments, selection markers are expressed with a polynucleotide that encodes a gene product of interest (e.g., a binding protein of the present disclosure, such as a TCR or CAR). Further examples of selection markers include, for example, reporters such as GFP, EGFP, β-gal or chloramphenicol acetyltransferase (CAT). In certain embodiments, a selection marker, such as, for example, CD34 is expressed by a cell and the CD34 can be used to select enrich for, or isolate (e.g., by immunomagnetic selection) the transduced cells of interest for use in the methods described herein. As used herein, a CD34 marker is distinguished from an anti-CD34 antibody, or, for example, a scFv, TCR, or other antigen recognition moiety that binds to CD34.

In certain embodiments, a selection marker comprises an RQR polypeptide, a truncated low-affinity nerve growth factor (tNGFR), a truncated CD19 (tCD19), a truncated CD34 (tCD34), or any combination thereof.

Regarding RQR polypeptides, without wishing to be bound by theory, distance of an epitope or target sequence from the host cell surface may be important for RQR polypeptides to function as selection markers/safety switches (Philip et al., 2010 (supra)). In some embodiments, the encoded RQR polypeptide is contained in a β-chain, an α-chain, or both, or a fragment or variant of either or both, of the encoded CD8 co-receptor. In specific embodiments, a modified host cell comprises a heterologous polynucleotide encoding iCasp9 and a heterologous polynucleotide encoding a recombinant CD8 co-receptor protein that comprises a β-chain containing a RQR polypeptide and further comprises a CD8 α-chain.

In any of the aforementioned embodiments, a polynucleotide encoding, e.g., a TCR, or a binding domain thereof, or a CD8 co-receptor or extracellular portion thereof, of the instant disclosure is codon optimized for efficient expression in a target host cell. In some embodiments, the host cell comprises a human immune system cell, such as a T cell, a NK cell, or a NK-T cell (Scholten et al., *Clin. Immunol.* 119:135, 2006). Codon optimization can be performed using known techniques and tools, e.g., using the GenScript® OptimumGene™ tool, or GeneArt (Life Technologies). Codon-optimized sequences include sequences that are partially codon-optimized (i.e., one or more of the codons, but less than all of the codons, is optimized for expression in the host cell) and those that are fully codon-optimized. It will be appreciated that in embodiments wherein a polynucleotide encodes more than one polypeptide (e.g., a TCR α chain, a TCR β chain, a CD8 co-receptor α chain, a CD8 co-receptor β chain, and one or more self-cleaving peptides), each polypeptide can independently fully codon optimized, partially codon optimized, or not codon optimized.

In certain embodiments, the present disclosure provides a host cell comprising a heterologous polynucleotide encoding any one or more of the TCRs, or binding domains thereof, of this disclosure, wherein the modified or recombinant host cell expresses on its cell surface the TCR, or binding domain thereof, encoded by the heterologous polynucleotide.

Various techniques may be used for recombinant (i.e., engineered) DNA, peptide and oligonucleotide synthesis, immunoassays and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well-known in the art and as described in various general and more specific references in microbiology, molecular biology, biochemistry, molecular genetics, cell biology, virology and immunology techniques that are cited and discussed throughout the present specification. See, e.g., Sambrook et al., *Molecular Cloning: A Laboratory Manual,* 3d ed., Cold Spring Harbor Laboratory Press, Cold Spring Harbor, N.Y.; *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, NY); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); *Next-Generation Genome Sequencing* (Janitz, 2008 Wiley-VCH); *PCR Protocols* (Methods *in Molecular Biology*) (Park, Ed., 3rd Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir and C C Blackwell, eds., 1986); Roitt, *Essential Immunology,* 6th Edition, (Blackwell Scientific Publications, Oxford, 1988); *Embryonic Stem Cells: Methods and Protocols* (Methods in Molecular Biology) (Kurstad Turksen, Ed., 2002); *Embryonic Stem Cell Protocols: Volume I: Isolation and Characterization* (Methods in Molecular Biology) (Kurstad Turksen, Ed., 2006); *Embryonic Stem Cell Protocols: Vol-*

*ume II: Differentiation Models* (Methods in Molecular Biology) (Kurstad Turksen, Ed., 2006); *Human Embryonic Stem Cell Protocols* (Methods in Molecular Biology) (Kursad Turksen Ed., 2006); *Mesenchymal Stem Cells: Methods and Protocols* (Methods in Molecular Biology) (Darwin J. Prockop, Donald G. Phinney, and Bruce A. Bunnell Eds., 2008); *Hematopoietic Stem Cell Protocols* (Methods in Molecular Medicine) (Christopher A. Klug, and Craig T. Jordan Eds., 2001); *Hematopoietic Stem Cell Protocols* (Methods in Molecular Biology) (Kevin D. Bunting Ed., 2008) *Neural Stem Cells: Methods and Protocols* (Methods in Molecular Biology) (Leslie P. Weiner Ed., 2008).

In any of the aforementioned embodiments, polynucleotides of this disclosure are contained in a host cell or, in certain embodiments, are contained in a vector and the vector containing the polynucleotide may be in a host cell. Accordingly, vectors are provided that comprise a polynucleotide as provided herein. In some embodiments, the polynucleotide is operably linked to an expression control sequence. Suitable vectors for use with certain embodiments disclosed herein are known and can be selected for a particular purpose or cell. An exemplary vector may comprise a nucleic acid molecule capable of transporting another nucleic acid molecule to which it has been linked, or which is capable of replication in a host organism. Some examples of vectors include plasmids, viral vectors, cosmids, and others. Some vectors may be capable of autonomous replication in a host cell into which they are introduced (e.g. bacterial vectors having a bacterial origin of replication and episomal mammalian vectors), whereas other vectors may be integrated into the genome of a host cell or promote integration of the polynucleotide insert upon introduction into the host cell and thereby replicate along with the host genome (e.g., lentiviral vector)). Additionally, some vectors are capable of directing the expression of genes to which they are operatively linked (these vectors may be referred to as "expression vectors"). According to related embodiments, it is further understood that, if one or more agents (e.g., polynucleotides encoding high affinity or high functional avidity recombinant TCRs, or a binding domain thereof, specific for WT1 p37, as described herein) is co-administered to a subject, that each agent may reside in separate or the same vectors, and multiple vectors (each containing a different agent the same agent) may be introduced to a cell or cell population or administered to a subject.

In certain embodiments, a polynucleotide encoding a high affinity or high functional avidity recombinant TCR, or a binding domain thereof, specific for WT1 p37 peptide::MHC of this disclosure may be operatively linked to certain expression control elements of a vector. For example, polynucleotide sequences that are needed to effect the expression and processing of coding sequences to which they are ligated may be operatively linked. Expression control sequences may include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequences); sequences that enhance protein stability; and possibly sequences that enhance protein secretion. Expression control sequences may be operatively linked if they are contiguous with the gene of interest and expression control sequences that act in trans or at a distance to control the gene of interest. In certain embodiments, polynucleotides encoding TCRs, or binding domains thereof, of the instant disclosure are contained in an expression vector that is a viral vector, such as a lentiviral vector or a γ-retroviral vector or an adenoviral vector.

In particular embodiments, the recombinant expression vector is delivered to an appropriate cell, for example, a T cell or an antigen-presenting cell, i.e., a cell that displays a peptide/MHC complex on its cell surface (e.g., a dendritic cell) and lacks CD8. In certain embodiments, the host cell is a hematopoietic progenitor cell or a human immune system cell. For example, the immune system cell can be a CD4+ T cell, a CD8+ T cell, a CD4− CD8− double negative T cell, a γδ T cell, a natural killer cell, a dendritic cell, or any combination thereof, wherein, optionally, the combination if present comprises a CD4+ T cell and a CD8+ T cell. In certain embodiments, wherein a T cell is the host, the T cell can be naïve, a central memory T cell, an effector memory T cell, or any combination thereof. The recombinant expression vectors may therefore also include, for example, lymphoid tissue-specific transcriptional regulatory elements (TREs), such as a B lymphocyte, T lymphocyte, or dendritic cell specific TREs. Lymphoid tissue specific TREs are known in the art (see, e.g., Thompson et al., *Mol. Cell. Biol.* 12:1043, 1992); Todd et al., *J. Exp. Med.* 177:1663, 1993); Penix et al., *J. Exp. Med.* 178:1483, 1993).

In addition to vectors, certain embodiments relate to host cells that comprise a heterologous polynucleotide or vector as presently disclosed. In certain embodiments, the host cell expresses on its cell surface the TCR encoded by the polynucleotide, and wherein the polynucleotide is heterologous to the host cell. One of skill in the art readily understands that many suitable host cells are available in the art. A host cell may include any individual cell or cell culture which may receive a vector or the incorporation of nucleic acids and/or proteins, as well as any progeny cells. The term also encompasses progeny of the host cell, whether genetically or phenotypically the same or different. Suitable host cells may depend on the vector and may include mammalian cells, animal cells, human cells, simian cells, insect cells, yeast cells, and bacterial cells. These cells may be induced to incorporate the vector or other material by use of a viral vector, transformation via calcium phosphate precipitation, DEAE-dextran, electroporation, microinjection, or other methods. See, for example, Sambrook et al., *Molecular Cloning: A Laboratory Manual* 2d ed. (Cold Spring Harbor Laboratory, 1989).

In certain embodiments, the $V_\alpha$ domain of the TCR expressed by the host cell is encoded by a polynucleotide comprising at least 75% (e.g., 75%, 80%, 85%, 90%, 95%, 97%, 99%, or 100%) sequence identity to any one of the polynucleotides of SEQ ID NOS:97, 98, and 101-107, or at least 94% sequence identity to SEQ ID NO:99 or 100. In certain embodiments, the $V_\alpha$ domain is encoded by a polynucleotide: (a) comprising the sequence of any one of the polynucleotides of SEQ ID NOS:97-107; or (b) consisting of the sequence of any one of the polynucleotides of SEQ ID NOS:97-107.

In certain embodiments, the $V_\beta$ domain of the host cell is encoded by a polynucleotide comprising at least 75% sequence identity to any one of the polynucleotides of SEQ ID NOS:75-77, 79, 82, 84 and 85, or at least 95% sequence identity to any one of the polynucleotides to SEQ ID NOS:78, 80, 81, and 83. In certain embodiments, $V_\beta$ domain is encoded by a polynucleotide: (a) comprising the sequence of any one of the polynucleotides of SEQ ID NOS:75-85; or (b) consisting of the sequence of any one of the polynucleotides of SEQ ID NOS:75-85.

In certain embodiments, the TCR α-chain comprises an α-chain constant domain encoded by a polynucleotide comprising at least 98% identity to SEQ ID NO:110. In certain embodiments, the TCR α-chain comprises an α-chain constant domain encoded by a polynucleotide: (a) comprising the polynucleotide sequence of SEQ ID NO:110; or (b) consisting of the polynucleotide sequence of SEQ ID NO:110. In certain embodiments, the TCR β-chain comprises a β-chain constant domain is encoded by a polynucleotide comprising at least 99.9% sequence identity to SEQ ID NO:108 or 109. In some embodiments, the TCR β-chain comprises a β-chain constant domain encoded by a polynucleotide: (a) comprising the polynucleotide sequence of SEQ ID NO:108 or 109; or (b) consisting of the polynucleotide sequence of SEQ ID NO:108 or 109.

In some embodiments, wherein the polynucleotide comprises a nucleotide sequence encoding a self-cleaving peptide disposed between the polynucleotide sequence encoding the TCR α-chain and the polynucleotide sequence encoding the TCR β-chain.

In some embodiments, the encoded self-cleaving peptide: (a) comprises the amino acid sequence of any one of the polypeptides of SEQ ID NOS:60-63; or (b) consists of the sequence of any one of the polypeptides of SEQ ID NOS: 60-63.

In some embodiments, the polynucleotide encoding the self-cleaving peptide: (a) comprises the sequence of any one of the polynucleotides of SEQ ID NOS:166-170; or (b) consists of the sequence of any one of the polynucleotides of SEQ ID NOS:166-170.

In some embodiments, the TCR α-chain, self-cleaving peptide, and TCR β-chain are encoded by a polynucleotide comprising at least 95% identity to any one of SEQ ID NOS:155-165.

In some embodiments, the TCR α-chain, self-cleaving peptide, and TCR β-chain are encoded by a polynucleotide that: (a) comprises the sequence of any one of the polynucleotides of SEQ ID NOS:155-165; or (b) consists of the sequence of any one of the polynucleotides of SEQ ID NOS:155-165.

In some embodiments, the encoded TCR α-chain, self-cleaving peptide, and TCR β-chain comprise the amino acid sequence having at least 95%, 96%, 97%, 98%, 99%, 99.1%, 99.5%, 99,9%, or 100% identity to any one of the polypeptides of SEQ ID NOS: 48-58. In some embodiments, the encoded TCR α-chain, self-cleaving peptide, and TCR β-chain: (a) comprise the amino acid sequence of any one of the polypeptides of SEQ ID NOS:48-58; or (b) consist of the amino acid sequence of any one of the polypeptides of SEQ ID NOS: 48-58.

In some embodiments, host cell is a hematopoietic progenitor cell or a human immune system cell. In some embodiments, the immune system cell is a CD4+ T cell, a CD8+ T cell, a CD4− CD8− double negative T cell, a γδ T cell, a natural killer cell, a natural killer T cell, a dendritic cell, or any combination thereof, wherein, optionally, the combination comprises a CD4+ T cell and a CD8+ T cell.

In some embodiments, wherein the host immune system cell is a T cell. In some embodiments, the T cell is a naïve T cell, a central memory T cell, an effector memory T cell, or any combination thereof.

In certain embodiments, the TCR has higher surface expression on a T cell as compared to an endogenous TCR (e.g., when the endogenous TCR is not artificially inhibited or prevented from expression).

In certain embodiments, the host cell further comprises: (i) a heterologous polynucleotide encoding a polypeptide that comprises an extracellular portion of a CD8 co-receptor α chain, wherein, optionally, the encoded polypeptide is or comprises a CD8 co-receptor α chain; (ii) a heterologous polynucleotide encoding a polypeptide that comprises an extracellular portion of a CD8 co-receptor β chain, wherein, optionally, the encoded polypeptide is or comprises a CD8 co-receptor β chain; or (iii) the polynucleotide of (i) and the polynucleotide of (ii), wherein, optionally, the host cell comprises a CD4+ T cell.

In some embodiments, the host cell comprises: (a) the heterologous polynucleotide encoding a polypeptide comprising an extracellular portion of a CD8 co-receptor α chain; (b) the heterologous polynucleotide encoding a polypeptide comprising an extracellular portion of a CD8 co-receptor β chain; and (c) a polynucleotide encoding a self-cleaving peptide disposed between the polynucleotide of (a) and the polynucleotide of (b).

In any of the presently disclosed embodiments, the host cell (e.g., immune cell, such as a human T cell) is capable of killing: (i) a tumor cell of breast cancer cell line MDA-MB-468; (ii) a tumor cell of pancreatic adenocarcinoma cell line PANC-1; (iii) a tumor cell of breast cancer cell line MDA-MB-231; (iv) a tumor cell of myelogenous leukemia cell line K562 expressing an HLA-A2, wherein, optionally, the HLA-A2 comprises HLA-A*201; (v) a tumor cell of colon carcinoma cell line RKO expressing an HLA-A2, wherein, optionally, the HLA-A2 comprises HLA-A*201; or (vi) any combination of tumor cells of (i)-(v), when the host cell and the tumor cell are both present in a sample. In some embodiments, In particular embodiments, the host cell is capable of killing the tumor cell when the host cell and the tumor cell are present in the sample at a ratio of 32:1 host cell:tumor cell, 16:1, 8:1, 4:1, 2:1, or 1.5:1. Killing of a target cell can be determined, for example, the Incucyte® bioimaging platform (Essen Bioscience). In certain embodiments, this platform uses activated caspase and labelled (e.g., RapidRed or NucRed) tumor cell signals, wherein overlap is measured and increased overlap area equals tumor cell death by apoptosis. Killing can also be determined using a 4-hour assay in which target cells are loaded with labeled chromium ($^{51}$Cr), and $^{51}$Cr in the supernatant is measured following 4-hour co-incubation with an immune cell expressing a binding protein of the present disclosure.

In any of the foregoing embodiments, a host cell (e.g., an immune cell) may modified to reduce or eliminate expression of one or more endogenous genes that encode a polypeptide involved in immune signaling or other related activities. Exemplary gene knockouts include those that encode PD-1, LAG-3, CTLA4, TIM3, TIGIT, FasL, an HLA molecule, a TCR molecule, or the like. Without wishing to be bound by theory, certain endogenously expressed immune cell proteins may be recognized as foreign by an allogeneic host receiving the modified immune cells, which may result in elimination of the modified immune cells (e.g., an HLA allele), or may downregulate the immune activity of the modified immune cells (e.g., PD-1, LAG-3, CTLA4, FasL, TIGIT, TIM3), or may interfere with the binding activity of a heterologously expressed binding protein of the present disclosure (e.g., an endogenous TCR of a modified T cell that binds a non-Ras antigen and thereby interferes with the modified immune cell binding a cell that expresses a Ras antigen).

Accordingly, decreasing or eliminating expression or activity of such endogenous genes or proteins can improve the activity, tolerance, or persistence of the modified cells in an autologous or allogeneic host setting, and may allow for universal administration of the cells (e.g., to any recipient regardless of HLA type). In certain embodiments, a modified cell is a donor cell (e.g., allogeneic) or an autologous cell. In certain embodiments, a host cell of this disclosure comprises a chromosomal gene knockout of one or more of a gene that encodes PD-1, LAG-3, CTLA4, TIM3, TIGIT, FasL, an HLA component (e.g., a gene that encodes an α1 macroglobulin, an α2 macroglobulin, an α3 macroglobulin, a β1 microglobulin, or a β2 microglobulin), or a TCR component (e.g., a gene that encodes a TCR variable region or a TCR constant region) (see, e.g., Torikai et al., *Nature Sci. Rep.* 6:21757 (2016); Torikai et al., *Blood* 119(24):5697 (2012); and Torikai et al., *Blood* 122(8):1341 (2013), the gene-editing techniques, compositions, and adoptive cell therapies of which are herein incorporated by reference in their entirety).

As used herein, the term "chromosomal gene knockout" refers to a genetic alteration or introduced inhibitory agent in a host cell that prevents (e.g., reduces, delays, suppresses, or abrogates) production, by the host cell, of a functionally active endogenous polypeptide product. Alterations resulting in a chromosomal gene knockout can include, for example, introduced nonsense mutations (including the formation of premature stop codons), missense mutations, gene deletion, and strand breaks, as well as the heterologous expression of inhibitory nucleic acid molecules that inhibit endogenous gene expression in the host cell.

In certain embodiments, a chromosomal gene knock-out or gene knock-in is made by chromosomal editing of a host cell. Chromosomal editing can be performed using, for example, endonucleases. As used herein "endonuclease" refers to an enzyme capable of catalyzing cleavage of a phosphodiester bond within a polynucleotide chain. In certain embodiments, an endonuclease is capable of cleaving a targeted gene thereby inactivating or "knocking out" the targeted gene. An endonuclease may be a naturally occurring, recombinant, genetically modified, or fusion endonuclease. The nucleic acid strand breaks caused by the endonuclease are commonly repaired through the distinct mechanisms of homologous recombination or non-homologous end joining (NHEJ). During homologous recombination, a donor nucleic acid molecule may be used for a donor gene "knock-in", for target gene "knock-out", and optionally to inactivate a target gene through a donor gene knock in or target gene knock out event. NHEJ is an error-prone repair process that often results in changes to the DNA sequence at the site of the cleavage, e.g., a substitution, deletion, or addition of at least one nucleotide. NHEJ may be used to "knock-out" a target gene. Examples of endonucleases include zinc finger nucleases, TALE-nucleases, CRISPR-Cas nucleases, meganucleases, and megaTALs.

As used herein, a "zinc finger nuclease" (ZFN) refers to a fusion protein comprising a zinc finger DNA-binding domain fused to a non-specific DNA cleavage domain, such as a FokI endonuclease. Each zinc finger motif of about 30 amino acids binds to about 3 base pairs of DNA, and amino acids at certain residues can be changed to alter triplet sequence specificity (see, e.g., Desjarlais et al., *Proc. Natl. Acad. Sci.* 90:2256-2260, 1993; Wolfe et al., *J. Mol. Biol.* 285:1917-1934, 1999). Multiple zinc finger motifs can be linked in tandem to create binding specificity to desired DNA sequences, such as regions having a length ranging from about 9 to about 18 base pairs. By way of background, ZFNs mediate genome editing by catalyzing the formation of a site-specific DNA double strand break (DSB) in the genome, and targeted integration of a transgene comprising flanking sequences homologous to the genome at the site of DSB is facilitated by homology directed repair. Alternatively, a DSB generated by a ZFN can result in knock out of target gene via repair by non-homologous end joining (NHEJ), which is an error-prone cellular repair pathway that results in the insertion or deletion of nucleotides at the cleavage site. In certain embodiments, a gene knockout comprises an insertion, a deletion, a mutation or a combination thereof, made using a ZFN molecule.

As used herein, a "transcription activator-like effector nuclease" (TALEN) refers to a fusion protein comprising a TALE DNA-binding domain and a DNA cleavage domain, such as a FokI endonuclease. A "TALE DNA binding domain" or "TALE" is composed of one or more TALE repeat domains/units, each generally having a highly conserved 33-35 amino acid sequence with divergent 12th and 13th amino acids. The TALE repeat domains are involved in binding of the TALE to a target DNA sequence. The divergent amino acid residues, referred to as the Repeat Variable Diresidue (RVD), correlate with specific nucleotide recognition. The natural (canonical) code for DNA recognition of these TALEs has been determined such that an HD (histine-aspartic acid) sequence at positions 12 and 13 of the TALE leads to the TALE binding to cytosine (C), NG (asparagine-glycine) binds to a T nucleotide, NI (asparagine-isoleucine) to A, NN (asparagine-asparagine) binds to a G or A nucleotide, and NG (asparagine-glycine) binds to a T nucleotide. Non-canonical (atypical) RVDs are also known (see, e.g., U.S. Patent Publication No. US 2011/0301073, which atypical RVDs are incorporated by reference herein in their entirety). TALENs can be used to direct site-specific double-strand breaks (DSB) in the genome of T cells. Non-homologous end joining (NHEJ) ligates DNA from both sides of a double-strand break in which there is little or no sequence overlap for annealing, thereby introducing errors that knock out gene expression. Alternatively, homology directed repair can introduce a transgene at the site of DSB providing homologous flanking sequences are present in the transgene. In certain embodiments, a gene knockout comprises an insertion, a deletion, a mutation or a combination thereof, and made using a TALEN molecule.

As used herein, a "clustered regularly interspaced short palindromic repeats/Cas" (CRISPR/Cas) nuclease system refers to a system that employs a CRISPR RNA (crRNA)-guided Cas nuclease to recognize target sites within a genome (known as protospacers) via base-pairing complementarity and then to cleave the DNA if a short, conserved protospacer associated motif (PAM) immediately follows 3' of the complementary target sequence. CRISPR/Cas systems are classified into three types (i.e., type I, type II, and type III) based on the sequence and structure of the Cas nucleases. The crRNA-guided surveillance complexes in types I and III need multiple Cas subunits. Type II system, the most studied, comprises at least three components: an RNA-guided Cas9 nuclease, a crRNA, and a trans-acting crRNA (tracrRNA). The tracrRNA comprises a duplex forming region. A crRNA and a tracrRNA form a duplex that is capable of interacting with a Cas9 nuclease and guiding the Cas9/crRNA:tracrRNA complex to a specific site on the target DNA via Watson-Crick base-pairing between the spacer on the crRNA and the protospacer on the target DNA upstream from a PAM. Cas9 nuclease cleaves a double-stranded break within a region defined by the crRNA spacer. Repair by NHEJ results in insertions and/or deletions which disrupt expression of the targeted locus. Alternatively, a transgene with homologous flanking sequences can be introduced at the site of DSB via homology directed repair. The crRNA and tracrRNA can be engineered into a single guide RNA (sgRNA or gRNA) (see, e.g., Jinek et al., *Science* 337:816-21, 2012). Further, the region of the guide RNA complementary to the target site can be altered or programed to target a desired sequence (Xie et al., *PLOS One* 9:e100448, 2014; U.S. Pat. Appl. Pub. No. US 2014/0068797, U.S. Pat. Appl. Pub. No. US 2014/0186843; U.S. Pat. No. 8,697,359, and PCT Publication No. WO 2015/071474; each of which is incorporated by reference). In certain embodiments, a gene knockout comprises an insertion, a deletion, a mutation or a combination thereof, and made using a CRISPR/Cas nuclease system. Exemplary gRNA sequences and methods of using the same to knock out endogenous genes that encode immune cell proteins include those described in Ren et al., *Clin. Cancer Res.* 23(9):2255-2266 (2017), the gRNAs, CAS9 DNAs, vectors, and gene knockout techniques of which are hereby incorporated by reference in their entirety.

As used herein, a "meganuclease," also referred to as a "homing endonuclease," refers to an endodeoxyribonuclease characterized by a large recognition site (double stranded DNA sequences of about 12 to about 40 base pairs). Meganucleases can be divided into five families based on sequence and structure motifs: LAGLIDADG, GIY-YIG, HNH, His-Cys box and PD-(D/E)XK. Exemplary meganucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII, whose recognition sequences are known (see, e.g., U.S. Pat. Nos. 5,420,032 and 6,833,252; Belfort et al., *Nucleic Acids Res.* 25:3379-3388, 1997; Dujon et al., *Gene* 82:115-118, 1989; Perler et al., *Nucleic Acids Res.* 22:1125-1127, 1994; Jasin, *Trends Genet.* 12:224-228, 1996; Gimble et al., *J. Mol. Biol.* 263:163-180, 1996; Argast et al., *J. Mol. Biol.* 280:345-353, 1998).

In certain embodiments, naturally occurring meganucleases may be used to promote site-specific genome modification of a target selected from PD-1, LAG3, TIM3, CTLA4, TIGIT, FasL, an HLA-encoding gene, or a TCR component-encoding gene. In other embodiments, an engineered meganuclease having a novel binding specificity for a target gene is used for site-specific genome modification (see, e.g., Porteus et al., *Nat. Biotechnol.* 23:967-73, 2005; Sussman et al., *J. Mol. Biol.* 342:31-41, 2004; Epinat et al., *Nucleic Acids Res.* 31:2952-62, 2003; Chevalier et al., *Molec. Cell* 10:895-905, 2002; Ashworth et al., *Nature* 441:656-659, 2006; Paques et al., *Curr. Gene Ther.* 7:49-66, 2007; U.S. Patent Publication Nos. US 2007/0117128; US 2006/0206949; US 2006/0153826; US 2006/0078552; and US 2004/0002092). In further embodiments, a chromosomal gene knockout is generated using a homing endonuclease that has been modified with modular DNA binding domains of TALENs to make a fusion protein known as a megaTAL. MegaTALs can be utilized to not only knock-out one or more target genes, but to also introduce (knock in) heterologous or exogenous polynucleotides when used in combination with an exogenous donor template encoding a polypeptide of interest.

In certain embodiments, a chromosomal gene knockout comprises an inhibitory nucleic acid molecule that is introduced into a host cell (e.g., an immune cell) comprising a heterologous polynucleotide encoding an antigen-specific receptor that specifically binds to a tumor associated antigen, wherein the inhibitory nucleic acid molecule encodes a target-specific inhibitor and wherein the encoded target-specific inhibitor inhibits endogenous gene expression (e.g., of PD-1, TIM3, LAG3, CTLA4, TIGIT, FasL, an HLA component, or a TCR component, or any combination thereof) in the host cell.

A chromosomal gene knockout can be confirmed directly by DNA sequencing of the host immune cell following use of the knockout procedure or agent. Chromosomal gene knockouts can also be inferred from the absence of gene expression (e.g., the absence of an mRNA or polypeptide product encoded by the gene) following the knockout.

In certain embodiments, a chromosomal gene knockout comprises a knockout of an HLA component gene selected from an α1 macroglobulin gene, an α2 macroglobulin gene, an α3 macroglobulin gene, a β1 microglobulin gene, or a β2 microglobulin gene.

In certain embodiments, a chromosomal gene knockout comprises a knockout of a TCR component gene selected from a TCR α variable region gene, a TCR β variable region gene, a TCR constant region gene, or a combination thereof.

Moreover, it will be appreciated that any of the presently disclosed gene editing techniques and tools may be used to introduce a TCR-encoding and/or CD8 co-receptor-encoding polynucleotide of the present disclosure into a host cell genome.

In another aspect, compositions and unit doses are provided herein that comprise a modified host cell of the present disclosure and a pharmaceutically acceptable carrier, diluent, or excipient.

In certain embodiments, a host cell composition or unit dose comprises (i) a composition comprising at least about 30%, at least about 40%, at least about 50%, at least about 60%, at least about 70%, at least about 80%, at least about 85%, at least about 90%, or at least about 95% modified CD4+ T cells, combined with (ii) a composition comprising at least about 30%, at least about 40%, at least about 50%, at least about 60%, at least about 70%, at least about 80%, at least about 85%, at least about 90%, or at least about 95% modified CD8+ T cells, in about a 1:1 ratio, wherein the unit dose contains a reduced amount or substantially no naïve T cells (i.e., has less than about 50%, less than about 40%, less than about 30%, less then about 20%, less than about 10%, less than about 5%, or less then about 1% the population of naïve T cells present in a unit dose as compared to a patient sample having a comparable number of PBMCs).

In some embodiments, a host cell composition or unit dose comprises (i) a composition comprising at least about 50% modified CD4+ T cells, combined with (ii) a composition comprising at least about 50% modified CD8+ T cells, in about a 1:1 ratio, wherein the host cell composition or unit dose contains a reduced amount or substantially no naïve T cells. In further embodiments, a host cell composition or unit dose comprises (i) a composition comprising at least about 60% modified CD4+ T cells, combined with (ii) a composition comprising at least about 60% modified CD8+ T cells, in about a 1:1 ratio, wherein the unit dose contains a reduced amount or substantially no naïve T cells. In still further embodiments, a host cell composition or unit dose comprises (i) a composition comprising at least about 70% engineered CD4+ T cells, combined with (ii) a composition comprising at least about 70% engineered CD8+ T cells, in about a 1:1 ratio, wherein the unit dose contains a reduced amount or substantially no naïve T cells. In some embodiments, a host cell composition or unit dose comprises (i) a composition comprising at least about 80% modified CD4+ T cells, combined with (ii) a composition comprising at least about 80% modified CD8+ T cells, in about a 1:1 ratio, wherein the host cell composition or unit dose contains a reduced amount or substantially no naïve T cells. In some embodiments, a host cell composition or unit dose comprises (i) a composition comprising at least about 85% modified CD4+ T cells, combined with (ii) a composition comprising at least about 85% modified CD8+ T cells, in about a 1:1 ratio, wherein the host cell composition or unit dose contains a reduced amount or substantially no naïve T cells. In some embodiments, a host cell composition or unit dose comprises (i) a composition comprising at least about 90% modified CD4+ T cells, combined with (ii) a composition comprising at least about 90% modified CD8+ T cells, in about a 1:1 ratio, wherein the host cell composition or unit dose contains a reduced amount or substantially no naïve T cells.

It will be appreciated that a host cell composition or unit dose of the present disclosure may comprise any host cell as described herein, or any combination of host cells. In certain embodiments, for example, a host cell composition or unit dose comprises modified CD8+ T cells, modified CD4+ T cells, or both, wherein these T cells are modified to encode a binding protein specific for a Ras peptide:HLA-A*02:01 complex, and further comprises modified CD8+ T cells, modified CD4+ T cells, or both, wherein these T cells are modified to encode a binding protein specific for a WT1 peptide:HLA-A*02:01 complex. In addition or alternatively, a host cell composition or unit dose of the present disclosure can comprise any host cell or combination of host cells as described herein, and can further comprise a modified cell (e.g., immune cell, such as a T cell) expressing a binding protein specific for a different antigen (e.g., a different WT1 antigen, or an antigen from a different protein or target, such as, for example, BCMA, CD3, CEACAM6, c-Met, EGFR, EGFRvIII, ErbB2, ErbB3, ErbB4, EphA2, IGF1R, GD2, O-acetyl GD2, O-acetyl GD3, GHRHR, GHR, FLT1, KDR, FLT4, CD44v6, CD151, CA125, CEA, CTLA-4, GITR, BTLA, TGFBR2, TGFBR1, IL6R, gp130, Lewis A, Lewis Y, TNFR1, TNFR2, PD1, PD-L1, PD-L2, HVEM, MAGE-A (e.g., including MAGE-A1, MAGE-A3, and MAGE-A4), mesothelin, NY-ESO-1, PSMA, RANK, ROR1, TNFRSF4, CD40, CD137, TWEAK-R, HLA, tumor- or pathogen-associated peptide bound to HLA, hTERT peptide bound to HLA, tyrosinase peptide bound to HLA, WT-1 peptide bound to HLA, LTβR, LIFRβ, LRP5, MUC1, OSMRβ, TCRα, TCRβ, CD19, CD20, CD22, CD25, CD28, CD30, CD33, CD52, CD56, CD79a, CD79b, CD80, CD81, CD86, CD123, CD171, CD276, B7H4, TLR7, TLR9, PTCH1, WT-1, HA1-H, Robo1, α-fetoprotein (AFP), Frizzled, OX40, PRAME, and SSX-2. or the like). For example, a unit dose can comprise modified CD8+ T cells expressing a binding protein that specifically binds to a WT1-HLA complex and modified CD4+ T cells (and/or modified CD8+ T cells) expressing a binding protein (e.g., a CAR) that specifically binds to a HER2 antigen. It will also be appreciated that any of the host cells disclosed herein may be administered in a combination therapy.

In any of the embodiments described herein, a host cell composition or unit dose comprises equal, or approximately equal numbers of engineered CD45RA− CD3+CD8+ and modified CD45RA− CD3+CD4+TM cells.

Uses and Methods of Treatment

In certain aspects, the instant disclosure is directed to methods for treating a hyperproliferative or proliferative disorder or a condition characterized by Wilms tumor protein 1 (WT1) expression or overexpression by administering to human subject in need thereof a composition comprising a high affinity or high functional avidity recombinant TCR, or a binding domain thereof, specific for human WT1 according to any of the aforementioned TCRs or any binding domains described herein, or a host cell, such as a T cell, engineered to express the same, or compositions comprising any of the TCRs, or a binding domain thereof, or host cells described herein. In some embodiments, the TCR is expressed by a host cell, such as a hematopoietic progenitor cell or a human immune system cell. In some embodiments, the immune system cell is a CD4+ T cell, a CD8+ T cell, a CD4− CD8− double negative T cell, a γδ T cell, a natural killer cell, a natural killer T cell, a dendritic cell, or any combination thereof.

The presence of a hyperproliferative disorder or proliferative disorder or malignant condition in a subject refers to the presence of dysplastic, cancerous and/or transformed cells in the subject, including, for example neoplastic, tumor, non-contact inhibited or oncogenically transformed cells, or the like (e.g., solid cancers; hematologic cancers including lymphomas and leukemias, such as acute myeloid leukemia, chronic myeloid leukemia, etc.), which are known in the art and for which criteria for diagnosis and classification are established (e.g., Hanahan and Weinberg, *Cell* 144:646, 2011; Hanahan and Weinberg, Cell 100:57, 2000; Cavallo et al., *Canc. Immunol. Immunother.* 60:319, 2011; Kyrigideis et al., *J. Carcinog.* 9:3, 2010). In certain embodiments, such cancer cells may be cells of acute myeloid leukemia, B-cell lymphoblastic leukemia, T-cell lymphoblastic leukemia, or myeloma, including cancer stem cells that are capable of initiating and serially transplanting any of these types of cancer (see, e.g., Park et al., *Molec. Therap.* 17:219, 2009).

In certain embodiments, there are provided methods for treating a hyperproliferative or proliferative disorder, such as a hematological malignancy or a solid cancer (see, e.g., Nakatsuka et al., *Modern* Pathology 19:804-714 (2006)). Exemplary hematological malignancies include acute lymphoblastic leukemia (ALL), acute myeloid leukemia (AML), chronic myelogenous leukemia (CIVIL), chronic eosinophilic leukemia (CEL), myelodysplastic syndrome (MDS), non-Hodgkin's lymphoma (NHL), or multiple myeloma (MM).

In further embodiments, there are provided methods for treating a hyperproliferative or proliferative disorder, such as a solid cancer is selected from biliary cancer, bladder cancer, bone and soft tissue carcinoma, brain tumor, breast cancer, cervical cancer, colon cancer, colorectal adenocarcinoma, colorectal cancer, desmoid tumor, embryonal cancer, endometrial cancer, esophageal cancer, gastric cancer, gastric adenocarcinoma, glioblastoma multiforme, gynecological tumor, head and neck squamous cell carcinoma, hepatic cancer, lung cancer, mesothelioma, malignant melanoma, osteosarcoma, ovarian cancer (see, e.g., Hylander et al., *Gynecologic Oncology* 101:12-17 (2006), pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, testicular germ-cell tumor, urothelial cancer, uterine sarcoma, or uterine cancer.

In some embodiments, the TCR is capable of promoting an antigen-specific T cell response against a human WT1 in a class I HLA-restricted manner. In some embodiments, the class I HLA-restricted response is transporter-associated with antigen processing (TAP) independent. In some embodiments, the antigen-specific T cell response comprises at least one of a CD4+ helper T lymphocyte (Th) response and a CD8+ cytotoxic T lymphocyte (CTL) response. In some embodiments, the CTL response is directed against a WT1-overexpressing cell.

Also provided herein are any of the TCRs, polynucleotides, compositions, vectors, and host cells (including in any combination) for use in a method of treating a proliferative or hyperproliferative disorder associated with Wilms tumor protein 1 (WT1) expression or overexpression.

Also provided herein are any of the TCRs, polynucleotides, compositions, vectors, and host cells (including in any combination) for use in a method of manufacturing a medicament for the treatment of a proliferative or hyperproliferative disorder associated with Wilms tumor protein 1 (WT1) expression or overexpression.

As understood by a person skilled in the medical art, the terms, "treat" and "treatment," refer to medical management of a disease, disorder, or condition of a subject (i.e., patient, host, who may be a human or non-human animal) (see, e.g., Stedman's Medical Dictionary). In general, an appropriate dose and treatment regimen provide one or more of a high functional avidity recombinant TCR, or a binding domain thereof, specific for human WT1 (e.g., SEQ ID NOS:23-58, and variants thereof provided herein) or a host cell expressing the same, and optionally an adjunctive therapy (e.g., a cytokine such as IL-2, IL-15, IL-21 or any combination thereof), in an amount sufficient to provide therapeutic or prophylactic benefit. Therapeutic or prophylactic benefit resulting from therapeutic treatment or prophylactic or preventative methods include, for example an improved clinical outcome, wherein the object is to prevent or retard or otherwise reduce (e.g., decrease in a statistically significant manner relative to an untreated control) an undesired physiological change or disorder, or to prevent, retard or otherwise reduce the expansion or severity of such a disease or disorder. Beneficial or desired clinical results from treating a subject include abatement, lessening, or alleviation of symptoms that result from or are associated the disease or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; or overall survival.

"Treatment" can also mean prolonging survival when compared to expected survival if a subject were not receiving treatment. Subjects in need of the methods and compositions described herein include those who already have the disease or disorder, as well as subjects prone to have or at risk of developing the disease or disorder. Subjects in need of prophylactic treatment include subjects in whom the disease, condition, or disorder is to be prevented (i.e., decreasing the likelihood of occurrence or recurrence of the disease or disorder). The clinical benefit provided by the compositions (and preparations comprising the compositions) and methods described herein can be evaluated by design and execution of in vitro assays, preclinical studies, and clinical studies in subjects to whom administration of the compositions is intended to benefit, as described in the examples.

In another aspect, the instant disclosure is directed to methods for treating a hyperproliferative disorder or proliferative disorder or a condition characterized by Wilms tumor protein 1 (WT1) overexpression or expression by administering to human subject in need thereof a composition comprising an isolated polynucleotide encoding a high affinity or high functional avidity recombinant TCR, or a binding domain thereof, specific for human WT1 according to any the aforementioned encoded TCRs, or a binding domain thereof, or a host cell, such as a T cell, comprising the same, or a composition comprising any of the TCRs, or a binding domain thereof, or host cells described herein. In certain embodiments, the polynucleotide encoding a TCR, or a binding domain thereof, specific for human WT1 p37 peptide::MHC is codon optimized for a host cell of interest. In further embodiments, any of the aforementioned polynucleotides are operably linked to an expression control sequence and is optionally contained in an expression vector, such as a viral vector. Exemplary viral vectors include lentiviral vectors and γ-retroviral vectors. In related embodiments, the vector is capable of delivering the polynucleotide to a host cell, such as a hematopoietic progenitor cell or an immune system cell (e.g., human hematopoietic progenitor cell or a human immune system cell). Exemplary immune system cells include a CD4+ T cell, a CD8+ T cell, a CD4− CD8− double negative T cell, a γδ T cell, a natural killer cell, a dendritic cell, or any combination thereof (e.g., human). In certain embodiments, the immune system cell is a T cell, such as a naïve T cell, a central memory T cell, an effector memory T cell, or any combination thereof, all of which are optionally human.

In still another aspect, the instant disclosure is directed to methods for treating a hyperproliferative disorder or proliferative disorder or a condition characterized by Wilms tumor protein 1 (WT1) overexpression by administering to human subject in need thereof an effective amount of a host cell comprising a heterologous polynucleotide or an expression vector according to any of the aforementioned embodiments, or any described herein, wherein the engineered or recombinant host cell expresses on its cell surface the TCR encoded by the heterologous polynucleotide that is specific for human WT1 p37::MHC. In certain embodiments, the instant disclosure is directed to methods for treating a hyperproliferative disorder or a proliferative disorder or a condition characterized by Wilms tumor protein 1 (WT1) p37 peptide production or the presence of WT1 p37 peptide::MHC complex by administering to human subject in need thereof an effective amount of a host cell comprising a heterologous polynucleotide or an expression vector according to any of the aforementioned embodiments, or any described herein, wherein the engineered or recombinant host cell expresses on its cell surface the TCR encoded by the heterologous polynucleotide that is specific for human WT1 p37::MHC.

Also provided is an adoptive immunotherapy method for treating a condition characterized by WT1 overexpression in cells of a subject having a hyperproliferative or proliferative disorder, comprising administering to the subject an effective amount of a host cell or composition of the present disclosure.

In some embodiments, the host cell is modified ex vivo. In some embodiments, the host cell is an allogeneic cell, a syngeneic cell, or an autologous cell to the subject. In some embodiments, the host cell is a hematopoietic progenitor cell or a human immune system cell. In some embodiments, the immune system cell is a CD4+ T cell, a CD8+ T cell, a CD4− CD8− double negative T cell, a γδ T cell, a natural killer cell, a dendritic cell, or any combination thereof.

In some embodiments, the T cell is a naïve T cell, a central memory T cell, an effector memory T cell, or any combination thereof.

In some embodiments, the hyperproliferative or proliferative disorder is a hematological malignancy or a solid cancer.

In some embodiments, the hematological malignancy is selected from acute myeloid leukemia (AML), acute lymphoblastic leukemia (ALL), chronic myelogenous leukemia (CIVIL), chronic eosinophilic leukemia (CEL), myelodysplastic syndrome (MDS), non-Hodgkin's lymphoma (NHL), or multiple myeloma (MM).

In some embodiments, the solid cancer is selected from breast cancer, ovarian cancer, lung cancer, biliary cancer, bladder cancer, bone and soft tissue carcinoma, brain tumor, cervical cancer, colon cancer, colorectal adenocarcinoma, colorectal cancer, desmoid tumor, embryonal cancer, endometrial cancer, esophageal cancer, gastric cancer, gastric adenocarcinoma, glioblastoma multiforme, gynecological tumor, head and neck squamous cell carcinoma, hepatic cancer, mesothelioma, malignant melanoma, osteosarcoma, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, testicular germ-cell tumor, urothelial cancer, uterine sarcoma, or uterine cancer.

In some embodiments, the host cell is administered parenterally.

In some embodiments, the method comprises administering a plurality of doses of the host cell to the subject. In some embodiments, the plurality of doses are administered at intervals between administrations of about two to about four weeks.

Cells expressing the recombinant TCR (e.g., high affinity or high functional avidity), or a binding domain thereof, specific for human WT1 p37 peptide as described herein may be administered to a subject in a pharmaceutically or physiologically acceptable or suitable excipient or carrier. Pharmaceutically acceptable excipients are biologically compatible vehicles, e.g., physiological saline, which are described in greater detail herein, that are suitable for administration to a human or other non-human mammalian subject.

A therapeutically effective dose is an amount of host cells (expressing a high affinity or high functional avidity recombinant TCR, or a binding domain thereof, specific for human WT1 p37 peptide::MHC) used in adoptive transfer that is capable of producing a clinically desirable result (i.e., a sufficient amount to induce or enhance a specific T cell immune response against cells overexpressing WT1 or producing a WT1 p37 peptide (e.g., a cytotoxic T cell response) in a statistically significant manner) in a treated human or non-human mammal. As is well known in the medical arts, the dosage for any one patient depends upon many factors, including the patient's size, weight, body surface area, age, the particular therapy to be administered, sex, time and route of administration, general health, and other drugs being administered concurrently. Doses will vary, but a preferred dose for administration of a host cell comprising a recombinant expression vector as described herein is about $10^4$ cells/$m^2$, about $5\times10^4$ cells/$m^2$, about $10^5$ cells/$m^2$, about $5\times10^5$ cells/$m^2$, about $10^6$ cells/$m^2$, about $5\times10^6$ cells/$m^2$, about $10^7$ cells/$m^2$, about $5\times10^7$ cells/$m^2$, about $10^8$ cells/$m^2$, about $5\times10^8$ cells/$m^2$, about $10^9$ cells/$m^2$, about $5\times10^9$ cells/$m^2$, about $10^{10}$ cells/$m^2$, about $5\times10^{10}$ cells/$m^2$, or about $10^{11}$ cells/$m^2$. In some embodiments, a dose comprises about $10^7$ cells/$m^2$, about $5\times10^7$ cells/$m^2$, about $10^8$ cells/$m^2$, about $5\times10^8$ cells/$m^2$, about $10^9$ cells/$m^2$, about $5\times10^9$ cells/$m^2$, about $10^{10}$ cells/$m^2$, about $5\times10^{10}$ cells/$m^2$, or about $10^{11}$ cells/$m^2$.

Pharmaceutical compositions may be administered in a manner appropriate to the disease or condition to be treated (or prevented) as determined by persons skilled in the medical art. An appropriate dose and a suitable duration and frequency of administration of the compositions will be determined by such factors as the health condition of the patient, size of the patient (i.e., weight, mass, or body area), the type and severity of the patient's disease, the particular form of the active ingredient, and the method of administration. In general, an appropriate dose and treatment regimen provide the composition(s) in an amount sufficient to provide therapeutic and/or prophylactic benefit (such as described herein, including an improved clinical outcome, such as more frequent complete or partial remissions, or longer disease-free and/or overall survival, or a lessening of symptom severity). For prophylactic use, a dose should be sufficient to prevent, delay the onset of, or diminish the severity of a disease associated with disease or disorder. Prophylactic benefit of the immunogenic compositions administered according to the methods described herein can be determined by performing pre-clinical (including in vitro and in vivo animal studies) and clinical studies and analyzing data obtained therefrom by appropriate statistical, biological, and clinical methods and techniques, all of which can readily be practiced by a person skilled in the art.

A condition associated with WT1 overexpression (or, in some embodiments, expression) includes any disorder or condition in which underactivity, over-activity or improper activity of a WT1 cellular or molecular event is present, and typically results from unusually high (with statistical significance) levels of WT1 expression in afflicted cells (e.g., leukemic cells), relative to normal cells. A subject having such a disorder or condition would benefit from treatment with a composition or method of the presently described embodiments. Some conditions associated with WT1 overexpression thus may include acute as well as chronic disorders and diseases, such as those pathological conditions that predispose the subject to a particular disorder.

Some examples of conditions associated with WT1 overexpression include hyperproliferative disorders, which in some aspects refer to states of activated and/or proliferating cells (which may also be transcriptionally overactive) in a subject including tumors, neoplasms, cancer, malignancy, etc. In addition to activated or proliferating cells, the hyperproliferative disorder may also include an aberration or dysregulation of cell death processes, whether by necrosis or apoptosis. Such aberration of cell death processes may be associated with a variety of conditions, including cancer (including primary, secondary malignancies as well as metastasis), or other conditions.

According to certain embodiments, virtually any type of cancer that is characterized by WT1 overexpression may be treated through the use of compositions and methods disclosed herein, including hematological cancers (e.g., leukemia including acute myeloid leukemia (AML), T or B cell lymphomas, myeloma, and others). Furthermore, "cancer" may refer to any accelerated proliferation of cells, including solid tumors, ascites tumors, blood or lymph or other malignancies; connective tissue malignancies; metastatic disease; minimal residual disease following transplantation of organs or stem cells; multi-drug resistant cancers, primary or secondary malignancies, angiogenesis related to malignancy, or other forms of cancer. Also contemplated within the presently disclosed embodiments are specific embodiments wherein only one of the above types of disease is included, or where specific conditions may be excluded regardless of whether or not they are characterized by WT1 overexpression.

Certain methods of treatment or prevention contemplated herein include administering a host cell (which may be autologous, allogeneic or syngeneic) comprising a desired nucleic acid molecule as described herein that is stably integrated into the chromosome of the cell. For example, such a cellular composition may be generated ex vivo using autologous, allogeneic or syngeneic immune system cells (e.g., T cells, antigen-presenting cells, natural killer cells) in order to administer a desired, WT1-targeted T-cell composition to a subject as an adoptive immunotherapy.

As used herein, administration of a composition or therapy in some aspects refers to delivering the same to a subject, regardless of the route or mode of delivery. Administration may be effected continuously or intermittently, and parenterally. Administration may be for treating a subject already confirmed as having a recognized condition, disease or disease state, or for treating a subject susceptible to or at risk of developing such a condition, disease or disease state. Co-administration with an adjunctive therapy may include simultaneous and/or sequential delivery of multiple agents in any order and on any dosing schedule (e.g., WT1 specific modified (i.e., recombinant or engineered) host cells with one or more cytokines; immunosuppressive therapy such as calcineurin inhibitors, corticosteroids, microtubule inhibitors, low dose of a mycophenolic acid prodrug, or any combination thereof). For example, a therapy of this disclosure can be combined with specific inhibitors or modulators of immunosuppression components, such as inhibitors or modulators of immune checkpoint molecules (e.g., anti-PD-1, anti-PD-L1, or anti-CTLA-4 antibodies; see, e.g., Pardol, *Nature Rev. Cancer* 12:252, 2012; Chen and Mellman, *Immunity* 39:1, 2013).

In some embodiments, the host cell is administered to the subject at a dose of about $10^7$ cells/m$^2$ to about $10^{11}$ cells/m$^2$. In some embodiments, the method further comprises administering a cytokine. In some embodiments, the cytokine is IL-2, IL-15, IL-21 or any combination thereof. In some embodiments, the cytokine is IL-2 and is administered concurrently or sequentially with the host cell. In some embodiments, the cytokine is administered sequentially, provided that the subject was administered the host cell at least three or four times before cytokine administration.

In some embodiments, the cytokine is IL-2 and is administered subcutaneously.

In some embodiments, the subject is further receiving immunosuppressive therapy.

In some embodiments, the immunosuppressive therapy is selected from calcineurin inhibitors, corticosteroids, microtubule inhibitors, low dose of a mycophenolic acid prodrug, or any combination thereof.

In some embodiments, the subject has received a non-myeloablative or a myeloablative hematopoietic cell transplant.

In some embodiments, the subject is administered the host cell at least three months after the non-myeloablative hematopoietic cell transplant.

In some embodiments, the subject is administered the host cell at least two months after the myeloablative hematopoietic cell transplant. Techniques and regimens for performing HCT are known in the art and can comprise transplantation of any suitable donor cell, such as a cell derived from umbilical cord blood, bone marrow, or peripheral blood, a hematopoietic stem cell, a mobilized stem cell, or a cell from amniotic fluid. Accordingly, in certain embodiments, a modified immune cell of the present disclosure can be administered with or shortly after hematopoietic stem cells in a modified HCT therapy. In some embodiments, the HCT comprises a donor hematopoieitic cell comprising a chromosomal knockout of a gene that encodes an HLA component, a chromosomal knockout of a gene that encodes a TCR component, or both.

In further embodiments, the subject had previously received lymphodepleting chemotherapy prior to receiving the composition or HCT. In certain embodiments, a lymphodepleting chemotherapy comprises a conditioning regimen comprising cyclophosphamide, fludarabine, anti-thymocyte globulin, or a combination thereof.

In certain embodiments, a plurality of doses of a recombinant host cell as described herein is administered to the subject, which may be administered at intervals between administrations of about two to about four weeks. In further embodiments, a cytokine is administered sequentially, provided that the subject was administered the recombinant host cell at least three or four times before cytokine administration. In certain embodiments, the cytokine is administered subcutaneously (e.g., IL-2, IL-15, IL-21).

In still further embodiments, the subject being treated is further receiving immunosuppressive therapy, such as an antibody specific for PD-1 (e.g., pidilizumab, nivolumab, or pembrolizumab), an antibody specific for PD-L1 (e.g., MDX-1105, BMS-936559, MEDI4736, MPDL3280A, or MSB0010718C), an antibody specific for CTLA4 (e.g., tremelimumab or ipilimumab), calcineurin inhibitors, corticosteroids, microtubule inhibitors, low dose of a mycophenolic acid prodrug, or any combination thereof. In yet further embodiments, the subject being treated has received a non-myeloablative or a myeloablative hematopoietic cell transplant, wherein the treatment may be administered at least two to at least three months after the non-myeloablative hematopoietic cell transplant.

An effective amount of a therapeutic or pharmaceutical composition in some aspects refers to an amount sufficient, at dosages and for periods of time needed, to achieve the desired clinical results or beneficial treatment, as described herein. An effective amount may be delivered in one or more administrations. If the administration is to a subject already known or confirmed to have a disease or disease-state, the term "therapeutic amount" may be used in reference to treatment, whereas "prophylactically effective amount" may be used to describe administrating an effective amount to a subject that is susceptible or at risk of developing a disease or disease-state (e.g., recurrence) as a preventative course.

The level of a cytotoxic T lymphocyte (CTL) immune response may be determined by any one of numerous immunological methods described herein and routinely practiced in the art. The level of a CTL immune response may be determined prior to and following administration of any one of the herein described WT1-specific TCRs expressed by, for example, a T cell. Cytotoxicity assays for determining CTL activity may be performed using any one of several techniques and methods routinely practiced in the art (see, e.g., Henkart et al., "Cytotoxic T-Lymphocytes" in *Fundamental Immunology*, Paul (ed.) (2003 Lippincott Williams & Wilkins, Philadelphia, Pa.), pages 1127-50, and references cited therein).

Antigen-specific T cell responses are typically determined by comparisons of observed T cell responses according to any of the herein described T cell functional parameters (e.g., proliferation, cytokine release, CTL activity, altered cell surface marker phenotype, etc.) that may be made between T cells that are exposed to a cognate antigen in an appropriate context (e.g., the antigen used to prime or activate the T cells, when presented by immunocompatible antigen-presenting cells) and T cells from the same source population that are exposed instead to a structurally distinct or irrelevant control antigen. A response to the cognate antigen that is greater, with statistical significance, than the response to the control antigen signifies antigen-specificity.

A biological sample may be obtained from a subject for determining the presence and level of an immune response to a WT1-derived antigen peptide as described herein. A "biological sample" as used herein may be a blood sample (from which serum or plasma may be prepared), biopsy specimen, body fluids (e.g., lung lavage, ascites, mucosal washings, synovial fluid), bone marrow, lymph nodes, tissue explant, organ culture, or any other tissue or cell preparation from the subject or a biological source. Biological samples may also be obtained from the subject prior to receiving any immunogenic composition, which biological sample is useful as a control for establishing baseline (i.e., pre-immunization) data.

The pharmaceutical compositions described herein may be presented in unit-dose or multi-dose containers, such as sealed ampoules or vials. Such containers may be frozen to preserve the stability of the formulation until. In certain embodiments, a unit dose comprises a recombinant host cell as described herein at a dose of about $10^7$ cells/$m^2$ to about $10^{11}$ cells/$m^2$. The development of suitable dosing and treatment regimens for using the particular compositions described herein in a variety of treatment regimens, including e.g., parenteral or intravenous administration or formulation.

If the subject composition is administered parenterally, the composition may also include sterile aqueous or oleaginous solution or suspension. Suitable non-toxic parenterally acceptable diluents or solvents include water, Ringer's solution, isotonic salt solution, 1,3-butanediol, ethanol, propylene glycol or polythethylene glycols in mixtures with water. Aqueous solutions or suspensions may further comprise one or more buffering agents, such as sodium acetate, sodium citrate, sodium borate or sodium tartrate. Of course, any material used in preparing any dosage unit formulation should be pharmaceutically pure and substantially non-toxic in the amounts employed. In addition, the active compounds may be incorporated into sustained-release preparation and formulations. Dosage unit form, as used herein, refers to physically discrete units suited as unitary dosages for the subject to be treated; each unit may contain a predetermined quantity of recombinant cells or active compound calculated to produce the desired therapeutic effect in association with an appropriate pharmaceutical carrier.

In general, an appropriate dosage and treatment regimen provides the active molecules or cells in an amount sufficient to provide therapeutic or prophylactic benefit. Such a response can be monitored by establishing an improved clinical outcome (e.g., more frequent remissions, complete or partial, or longer disease-free survival) in treated subjects as compared to non-treated subjects. Increases in preexisting immune responses to a tumor protein generally correlate with an improved clinical outcome. Such immune responses may generally be evaluated using standard proliferation, cytotoxicity or cytokine assays, which are routine in the art and may be performed using samples obtained from a subject before and after treatment.

Methods according to this disclosure may further include administering one or more additional agents to treat the disease or disorder in a combination therapy. For example, in certain embodiments, a combination therapy comprises administering a composition of the present disclosure with (concurrently, simultaneously, or sequentially) an immune checkpoint inhibitor. In some embodiments, a combination therapy comprises administering a composition of the present disclosure (e.g., TCR, polynucleotide, vector, or host cell, or combination thereof) with an agonist of a stimulatory immune checkpoint agent. In further embodiments, a combination therapy comprises administering a composition of the present disclosure with a secondary therapy, such as chemotherapeutic agent, a radiation therapy, a surgery, an antibody, or any combination thereof.

As used herein, the term "immune suppression agent" or "immunosuppression agent" refers to one or more cells, proteins, molecules, compounds or complexes providing inhibitory signals to assist in controlling or suppressing an immune response. For example, immune suppression agents include those molecules that partially or totally block immune stimulation; decrease, prevent or delay immune activation; or increase, activate, or up regulate immune suppression. Exemplary immunosuppression agents to target (e.g., with an immune checkpoint inhibitor) include PD-1, PD-L1, PD-L2, LAG3, CTLA4, B7-H3, B7-H4, CD244/2B4, HVEM, BTLA, CD160, TIM3, GALS, KIR, PVR1G (CD112R), PVRL2, adenosine, A2aR, immunosuppressive cytokines (e.g., IL-10, IL-4, IL-IRA, IL-35), IDO, arginase, VISTA, TIGIT, LAIR1, CEACAM-1, CEACAM-3, CEACAM-5, Treg cells, or any combination thereof.

Techniques and regimens for performing HCT are known in the art and can comprise transplantation of any suitable donor cell, such as a cell derived from umbilical cord blood, bone marrow, or peripheral blood, a hematopoietic stem cell, a mobilized stem cell, or a cell from amniotic fluid. Accordingly, in certain embodiments, a modified immune cell of the present disclosure can be administered with or shortly after hematopoietic stem cells in a modified HCT therapy. In some embodiments, the HCT comprises a donor hematopoieitic cell comprising a chromosomal knockout of a gene that encodes an HLA component, a chromosomal knockout of a gene that encodes a TCR component, or both.

In further embodiments, the subject had previously received lymphodepleting chemotherapy prior to receiving the composition or HCT. In certain embodiments, a lymphodepleting chemotherapy comprises a conditioning regimen comprising cyclophosphamide, fludarabine, anti-thymocyte globulin, or a combination thereof.

Methods according to this disclosure may further include administering one or more additional agents to treat the disease or disorder in a combination therapy. For example, in certain embodiments, a combination therapy comprises administering a composition of the present disclosure with (concurrently, simultaneously, or sequentially) an immune checkpoint inhibitor. In some embodiments, a combination therapy comprises administering a composition of the present disclosure with an agonist of a stimulatory immune checkpoint agent. In further embodiments, a combination therapy comprises administering a composition of the present disclosure with a secondary therapy, such as chemotherapeutic agent, a radiation therapy, a surgery, an antibody, or any combination thereof.

As used herein, the term "immune suppression agent" or "immunosuppression agent" refers to one or more cells, proteins, molecules, compounds or complexes providing inhibitory signals to assist in controlling or suppressing an immune response. For example, immune suppression agents include those molecules that partially or totally block immune stimulation; decrease, prevent or delay immune activation; or increase, activate, or up regulate immune suppression. Exemplary immunosuppression agents to target (e.g., with an immune checkpoint inhibitor) include PD-1, PD-L1, PD-L2, LAG3, CTLA4, B7-H3, B7-H4, CD244/2B4, HVEM, BTLA, CD160, TIM3, GALS, KIR, PVR1G (CD112R), PVRL2, adenosine, A2aR, immunosuppressive cytokines (e.g., IL-10, IL-4, IL-IRA, IL-35), IDO, arginase, VISTA, TIGIT, LAIR1, CEACAM-1, CEACAM-3, CEACAM-5, Treg cells, or any combination thereof.

An immune suppression agent inhibitor (also referred to as an immune checkpoint inhibitor) may be a compound, an antibody, an antibody fragment or fusion polypeptide (e.g., Fc fusion, such as CTLA4-Fc or LAG3-Fc), an antisense molecule, a ribozyme or RNAi molecule, or a low molecular weight organic molecule. In any of the embodiments disclosed herein, a method may comprise a composition of the present disclosure with one or more inhibitor of any one of the following immune suppression components, singly or in any combination.

In certain embodiments, a composition of the present disclosure is used in combination with a PD-1 inhibitor, for example a PD-1-specific antibody or binding fragment thereof, such as pidilizumab, nivolumab, pembrolizumab, MEDI0680 (formerly AMP-514), AMP-224, BMS-936558 or any combination thereof. In further embodiments, a composition of the present disclosure is used in combination with a PD-L1 specific antibody or binding fragment thereof, such as BMS-936559, durvalumab (MEDI4736), atezolizumab (RG7446), avelumab (MSB0010718C), MPDL3280A, or any combination thereof. Also contemplated are cemiplimab; IBI-308; nivolumab+relatlimab; BCD-100; camrelizumab; JS-001; spartalizumab; tislelizumab; AGEN-2034; BGBA-333+tislelizumab; CBT-501; dostarlimab; durvalumab+MEDI-0680; JNJ-3283; pazopanib hydrochloride+pembrolizumab; pidilizumab; REGN-1979+cemiplimab; ABBV-181; ADUS-100+spartalizumab; AK-104; AK-105; AMP-224; BAT-1306; BI-754091; CC-90006; cemiplimab+REGN-3767; CS-1003; GLS-010; LZM-009; MEDI-5752; MGD-013; PF-06801591; Sym-021; tislelizumab+pamiparib; XmAb-20717; AK-112; ALPN-202; AM-0001; an antibody to antagonize PD-1 for Alzheimer's disease; BH-2922; BH-2941; BH-2950; BH-2954; a biologic to antagonize CTLA-4 and PD-1 for solid tumor; a bispecific monoclonal antibody to target PD-1 and LAG-3 for oncology; BLSM-101; CB-201; CB-213; CBT-103; CBT-107; a cellular immunotherapy+PD-1 inhibitor; CX-188; HAB-21; HEIS-COIII-003; IKT-202; JTX-4014; MCLA-134; MD-402; mDX-400; MGD-019; a monoclonal antibody to antagonize PDCD1 for oncology; a monoclonal antibody to antagonize PD-1 for oncology; an oncolytic virus to inhibit PD-1 for oncology; OT-2; PD-1 antagonist+ropeginterferon alfa-2b; PEGMP-7; PRS-332; RXI-762; STIA-1110; TSR-075; a vaccine to target HER2 and PD-1 for oncology; a vaccine to target PD-1 for oncology and autoimmune disorders; XmAb-23104; an antisense oligonucleotide to inhibit PD-1 for oncology; AT-16201; a bispecific monoclonal antibody to inhibit PD-1 for oncology; IMM-1802; monoclonal antibodies to antagonize PD-1 and CTLA-4 for solid tumor and hematological tumor; nivolumab biosimilar; a recombinant protein to agonize CD278 and CD28 and antagonize PD-1 for oncology; a recombinant protein to agonize PD-1 for autoimmune disorders and inflammatory disorders; SNA-01; SSI-361; YBL-006; AK-103; JY-034; AUR-012; BGB-108; drug to inhibit PD-1, Gal-9, and TIM-3 for solid tumor; ENUM-244C8; ENUM-388D4; MEDI-0680; monoclonal antibodies to antagonize PD-1 for metastatic melanoma and metastatic lung cancer; a monoclonal antibody to inhibit PD-1 for oncology; monoclonal antibodies to target CTLA-4 and PD-1 for oncology; a monoclonal antibody to antagonize PD-1 for NSCLC; monoclonal antibodies to inhibit PD-1 and TIM-3 for oncology; a monoclonal antibody to inhibit PD-1 for oncology; a recombinant protein to inhibit PD-1 and VEGF-A for hematological malignancies and solid tumor; a small molecule to antagonize PD-1 for oncology; Sym-016; inebilizumab+MEDI-0680; a vaccine to target PDL-1 and IDO for metastatic melanoma; an anti-PD-1 monoclonal antibody plus a cellular immunotherapy for glioblastoma; an antibody to antagonize PD-1 for oncology; monoclonal antibodies to inhibit PD-1/PD-L1 for hematological malignancies and bacterial infections; a monoclonal antibody to inhibit PD-1 for HIV; or a small molecule to inhibit PD-1 for solid tumor.

In certain embodiments, a composition of the present disclosure of the present disclosure is used in combination with a LAG3 inhibitor, such as LAG525, IMP321, IMP701, 9H12, BMS-986016, or any combination thereof.

In certain embodiments, a composition of the present disclosure is used in combination with an inhibitor of CTLA4. In particular embodiments, a composition of the present disclosure is used in combination with a CTLA4 specific antibody or binding fragment thereof, such as ipilimumab, tremelimumab, CTLA4-Ig fusion proteins (e.g., abatacept, belatacept), or any combination thereof.

In certain embodiments, a composition of the present disclosure is used in combination with a B7-H3 specific antibody or binding fragment thereof, such as enoblituzumab (MGA271), 376.96, or both. A B7-H4 antibody binding fragment may be a scFv or fusion protein thereof, as described in, for example, Dangaj et al., *Cancer Res.* 73:4820, 2013, as well as those described in U.S. Pat. No. 9,574,000 and PCT Patent Publication Nos. WO/201640724A1 and WO 2013/025779A1.

In certain embodiments, a composition of the present disclosure is used in combination with an inhibitor of CD244.

In certain embodiments, a composition of the present disclosure is used in combination with an inhibitor of BLTA, HVEM, CD160, or any combination thereof. Anti CD-160 antibodies are described in, for example, PCT Publication No. WO 2010/084158.

In certain embodiments, a composition of the present disclosure cell is used in combination with an inhibitor of TIM3.

In certain embodiments, a composition of the present disclosure is used in combination with an inhibitor of Gal9.

In certain embodiments, a composition of the present disclosure is used in combination with an inhibitor of adenosine signaling, such as a decoy adenosine receptor.

In certain embodiments, a composition of the present disclosure is used in combination with an inhibitor of A2aR.

In certain embodiments, a composition of the present disclosure is used in combination with an inhibitor of KIR, such as lirilumab (BMS-986015).

In certain embodiments, a composition of the present disclosure is used in combination with an inhibitor of an inhibitory cytokine (typically, a cytokine other than TGFβ) or Treg development or activity.

In certain embodiments, a composition of the present disclosure is used in combination with an IDO inhibitor, such as levo-1-methyl tryptophan, epacadostat (INCB024360; Liu et al., *Blood* 115:3520-30, 2010), ebselen (Terentis et al., *Biochem.* 49:591-600, 2010), indoximod, NLG919 (Mautino et al., American Association for Cancer Research 104th Annual Meeting 2013; Apr. 6-10, 2013), 1-methyl-tryptophan (1-MT)-tira-pazamine, or any combination thereof.

In certain embodiments, a composition of the present disclosure is used in combination with an arginase inhibitor, such as N(omega)-Nitro-L-arginine methyl ester (L-NAME), N-omega-hydroxy-nor-1-arginine (nor-NOHA), L-NOHA, 2(S)-amino-6-boronohexanoic acid (ABH), S-(2-boronoethyl)-L-cysteine (BEC), or any combination thereof.

In certain embodiments, a composition of the present disclosure is used in combination with an inhibitor of VISTA, such as CA-170 (Curis, Lexington, Mass.).

In certain embodiments, a composition of the present disclosure is used in combination with an inhibitor of TIGIT such as, for example, COM902 (Compugen, Toronto, Ontario Canada), an inhibitor of CD155, such as, for example, COM701 (Compugen), or both.

In certain embodiments, a composition of the present disclosure is used in combination with an inhibitor of PVRIG, PVRL2, or both. Anti-PVRIG antibodies are described in, for example, PCT Publication No. WO 2016/134333. Anti-PVRL2 antibodies are described in, for example, PCT Publication No. WO 2017/021526.

In certain embodiments, a composition of the present disclosure is used in combination with a LAIR1 inhibitor.

In certain embodiments, a composition of the present disclosure is used in combination with an inhibitor of CEACAM-1, CEACAM-3, CEACAM-5, or any combination thereof.

In certain embodiments, a composition of the present disclosure is used in combination with an agent that increases the activity (i.e., is an agonist) of a stimulatory immune checkpoint molecule. For example a composition of the present disclosure can be used in combination with a CD137 (4-1BB) agonist (such as, for example, urelumab), a CD134 (OX-40) agonist (such as, for example, MEDI6469, MEDI6383, or MEDI0562), lenalidomide, pomalidomide, a CD27 agonist (such as, for example, CDX-1127), a CD28 agonist (such as, for example, TGN1412, CD80, or CD86), a CD40 agonist (such as, for example, CP-870,893, rhuCD40L, or SGN-40), a CD122 agonist (such as, for example, IL-2) an agonist of GITR (such as, for example, humanized monoclonal antibodies described in PCT Patent Publication No. WO 2016/054638), an agonist of ICOS (CD278) (such as, for example, GSK3359609, mAb 88.2, JTX-2011, Icos 145-1, Icos 314-8, or any combination thereof). In any of the embodiments disclosed herein, a method may comprise administering a composition of the present disclosure with one or more agonist of a stimulatory immune checkpoint molecule, including any of the foregoing, singly or in any combination.

In certain embodiments, a combination therapy comprises a composition of the present disclosure and a secondary therapy comprising one or more of: an antibody or antigen binding-fragment thereof that is specific for a cancer antigen expressed by the non-inflamed solid tumor, a radiation treatment, a surgery, a chemotherapeutic agent, a cytokine, RNAi, or any combination thereof.

In certain embodiments, a combination therapy method comprises administering a composition of the present disclosure and further administering a radiation treatment or a surgery. Radiation therapy is well-known in the art and includes X-ray therapies, such as gamma-irradiation, and radiopharmaceutical therapies. Surgeries and surgical techniques appropriate to treating a given cancer in a subject are well-known to those of ordinary skill in the art.

In certain embodiments, a combination therapy method comprises administering a composition of the present disclosure and further administering a chemotherapeutic agent. A chemotherapeutic agent includes, but is not limited to, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor.

Illustrative chemotherapeutic agents include, without limitation, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, Cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, temozolamide, teniposide, triethylenethiophosphoramide and etoposide (VP 16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes—dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); chimeric antigen receptors; cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin, *Pseudomonas* exotoxin, *Bordetella pertussis* adenylate cyclase toxin, or diphtheria toxin, and caspase activators; and chromatin disruptors.

Cytokines may be used to manipulate host immune response towards anticancer activity. See, e.g., Floros & Tarhini, *Semin. Oncol.* 42(4):539-548, 2015. Cytokines useful for promoting immune anticancer or antitumor response include, for example, IFN-α, IL-2, IL-3, IL-4, IL-10, IL-12, IL-13, IL-15, IL-16, IL-17, IL-18, IL-21, IL-24, and GM-CSF, singly or in any combination with a composition of the present disclosure.

Also provided herein are methods for modulating an adoptive immunotherapy, wherein the methods comprise administering, to a subject who has previously received a modified host cell of the present disclosure that comprises a heterologous polynucleotide encoding a safety switch protein, a cognate compound of the safety switch protein in an amount effective to ablate in the subject the previously administered modified host cell.

In certain embodiments, the safety switch protein comprises tEGFR and the cognate compound is cetuximab, or the safety switch protein comprises iCasp9 and the cognate compound is AP1903 (e.g., dimerized AP1903), or the safety switch protein comprises a RQR polypeptide and the cognate compound is rituximab, or the safety switch protein comprises a myc binding domain and the cognate compound is an antibody specific for the myc binding domain.

In still further aspects, methods are provided for manufacturing a composition, or a unit dose of the present disclosure. In certain embodiments, the methods comprise combining (i) an aliquot of a host cell transduced with a vector of the present disclosure with (ii) a pharmaceutically acceptable carrier. In certain embodiments, vectors of the present disclosure are used to transfect/transduce a host cell (e.g., a T cell) for use in adoptive transfer therapy (e.g., targeting a cancer antigen).

In some embodiments, the methods further comprise, prior to the aliquotting, culturing the transduced host cell and selecting the transduced cell as having incorporated (i.e., expressing) the vector. In further embodiments, the methods comprise, following the culturing and selection and prior to the aliquotting, expanding the transduced host cell. In any of the embodiments of the instant methods, the manufactured composition or unit dose may be frozen for later use. Any appropriate host cell can be used for manufacturing a composition or unit dose according to the instant methods, including, for example, a hematopoietic stem cell, a T cell, a primary T cell, a T cell line, a NK cell, or a NK-T cell. In specific embodiments, the methods comprise a host cell which is a $CD8^+$ T cell, a $CD4^+$ T cell, or both.

In certain embodiments, a composition of the present disclosure of the present disclosure is used in combination with a LAG3 inhibitor, such as LAG525, IMP321, IMP701, 9H12, BMS-986016, or any combination thereof.

In certain embodiments, a composition of the present disclosure is used in combination with an inhibitor of CTLA4. In particular embodiments, a composition of the present disclosure is used in combination with a CTLA4 specific antibody or binding fragment thereof, such as ipilimumab, tremelimumab, CTLA4-Ig fusion proteins (e.g., abatacept, belatacept), or any combination thereof.

In certain embodiments, a composition of the present disclosure is used in combination with a B7-H3 specific antibody or binding fragment thereof, such as enoblituzumab (MGA271), 376.96, or both. A B7-H4 antibody binding fragment may be a scFv or fusion protein thereof, as described in, for example, Dangaj et al., *Cancer Res.* 73:4820, 2013, as well as those described in U.S. Pat. No. 9,574,000 and PCT Patent Publication Nos. WO/201640724A1 and WO 2013/025779A1.

In certain embodiments, a composition of the present disclosure is used in combination with an inhibitor of CD244.

In certain embodiments, a composition of the present disclosure is used in combination with an inhibitor of BLTA, HVEM, CD160, or any combination thereof. Anti CD-160 antibodies are described in, for example, PCT Publication No. WO 2010/084158.

In certain embodiments, a composition of the present disclosure cell is used in combination with an inhibitor of TIM3.

In certain embodiments, a composition of the present disclosure is used in combination with an inhibitor of Gal9.

In certain embodiments, a composition of the present disclosure is used in combination with an inhibitor of adenosine signaling, such as a decoy adenosine receptor.

In certain embodiments, a composition of the present disclosure is used in combination with an inhibitor of A2aR.

In certain embodiments, a composition of the present disclosure is used in combination with an inhibitor of KIR, such as lirilumab (BMS-986015).

In certain embodiments, a composition of the present disclosure is used in combination with an inhibitor of an inhibitory cytokine (typically, a cytokine other than TGFβ) or Treg development or activity.

In certain embodiments, a composition of the present disclosure is used in combination with an IDO inhibitor, such as levo-1-methyl tryptophan, epacadostat (INCB024360; Liu et al., Blood 115:3520-30, 2010), ebselen (Terentis et al., *Biochem.* 49:591-600, 2010), indoximod, NLG919 (Mautino et al., American Association for Cancer Research 104th Annual Meeting 2013; Apr. 6-10, 2013), 1-methyl-tryptophan (1-MT)-tira-pazamine, or any combination thereof.

In certain embodiments, a composition of the present disclosure is used in combination with an arginase inhibitor, such as N(omega)-Nitro-L-arginine methyl ester (L-NAME), N-omega-hydroxy-nor-1-arginine (nor-NOHA), L-NOHA, 2(S)-amino-6-boronohexanoic acid (ABH), S-(2-boronoethyl)-L-cysteine (BEC), or any combination thereof.

In certain embodiments, a composition of the present disclosure is used in combination with an inhibitor of VISTA, such as CA-170 (Curis, Lexington, Mass.).

In certain embodiments, a composition of the present disclosure is used in combination with an inhibitor of TIGIT such as, for example, COM902 (Compugen, Toronto, Ontario Canada), an inhibitor of CD155, such as, for example, COM701 (Compugen), or both.

In certain embodiments, a composition of the present disclosure is used in combination with an inhibitor of PVRIG, PVRL2, or both. Anti-PVRIG antibodies are described in, for example, PCT Publication No. WO 2016/134333. Anti-PVRL2 antibodies are described in, for example, PCT Publication No. WO 2017/021526.

In certain embodiments, a composition of the present disclosure is used in combination with a LAIR1 inhibitor.

In certain embodiments, a composition of the present disclosure is used in combination with an inhibitor of CEACAM-1, CEACAM-3, CEACAM-5, or any combination thereof.

In certain embodiments, a composition of the present disclosure is used in combination with an agent that increases the activity (i.e., is an agonist) of a stimulatory immune checkpoint molecule. For example a composition of the present disclosure can be used in combination with a CD137 (4-1BB) agonist (such as, for example, urelumab), a CD134 (OX-40) agonist (such as, for example, MEDI6469, MEDI6383, or MEDI0562), lenalidomide, pomalidomide, a CD27 agonist (such as, for example, CDX-1127), a CD28 agonist (such as, for example, TGN1412, CD80, or CD86), a CD40 agonist (such as, for example, CP-870,893, rhuCD40L, or SGN-40), a CD122 agonist (such as, for example, IL-2) an agonist of GITR (such as, for example, humanized monoclonal antibodies described in PCT Patent Publication No. WO 2016/054638), an agonist of ICOS (CD278) (such as, for example, GSK3359609, mAb 88.2, JTX-2011, Icos 145-1, Icos 314-8, or any combination thereof). In any of the embodiments disclosed herein, a method may comprise administering a composition of the present disclosure with one or more agonist of a stimulatory immune checkpoint molecule, including any of the foregoing, singly or in any combination.

In certain embodiments, a combination therapy comprises a composition of the present disclosure and a secondary therapy comprising one or more of: an antibody or antigen binding-fragment thereof that is specific for a cancer antigen expressed by the non-inflamed solid tumor, a radiation treatment, a surgery, a chemotherapeutic agent, a cytokine, RNAi, or any combination thereof.

In certain embodiments, a combination therapy method comprises administering a composition of the present disclosure and further administering a radiation treatment or a surgery. Radiation therapy is well-known in the art and includes X-ray therapies, such as gamma-irradiation, and radiopharmaceutical therapies. Surgeries and surgical techniques appropriate to treating a given cancer in a subject are well-known to those of ordinary skill in the art.

In certain embodiments, a combination therapy method comprises administering a composition of the present disclosure and further administering a chemotherapeutic agent. A chemotherapeutic agent includes, but is not limited to, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor. Illustrative chemotherapeutic agents include, without limitation, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, Cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, temozolamide, teniposide, triethylenethiophosphoramide and etoposide (VP 16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes—dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); chimeric antigen receptors; cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin, *Pseudomonas* exotoxin, *Bordetella pertussis* adenylate cyclase toxin, or diphtheria toxin, and caspase activators; and chromatin disruptors.

Cytokines may be used to manipulate host immune response towards anticancer activity. See, e.g., Floros & Tarhini, *Semin. Oncol.* 42(4):539-548, 2015. Cytokines useful for promoting immune anticancer or antitumor response include, for example, IFN-α, IL-2, IL-3, IL-4, IL-10, IL-12, IL-13, IL-15, IL-16, IL-17, IL-18, IL-21, IL-24, and GM-CSF, singly or in any combination with a composition of the present disclosure.

Also provided herein are methods for modulating an adoptive immunotherapy, wherein the methods comprise administering, to a subject who has previously received a modified host cell of the present disclosure that comprises a heterologous polynucleotide encoding a safety switch protein, a cognate compound of the safety switch protein in an amount effective to ablate in the subject the previously administered modified host cell.

In certain embodiments, the safety switch protein comprises tEGFR and the cognate compound is cetuximab, or the safety switch protein comprises iCasp9 and the cognate compound is AP1903 (e.g., dimerized AP1903), or the safety switch protein comprises a RQR polypeptide and the cognate compound is rituximab, or the safety switch protein comprises a myc binding domain and the cognate compound is an antibody specific for the myc binding domain.

In still further aspects, methods are provided for manufacturing a composition, or a unit dose of the present disclosure. In certain embodiments, the methods comprise combining (i) an aliquot of a host cell transduced with a vector of the present disclosure with (ii) a pharmaceutically acceptable carrier. In certain embodiments, vectors of the present disclosure are used to transfect/transduce a host cell (e.g., a T cell) for use in adoptive transfer therapy (e.g., targeting a cancer antigen).

In some embodiments, the methods further comprise, prior to the aliquotting, culturing the transduced host cell and selecting the transduced cell as having incorporated (i.e., expressing) the vector. In further embodiments, the methods comprise, following the culturing and selection and prior to the aliquotting, expanding the transduced host cell. In any of the embodiments of the instant methods, the manufactured composition or unit dose may be frozen for later use. Any appropriate host cell can be used for manufacturing a composition or unit dose according to the instant methods, including, for example, a hematopoietic stem cell, a T cell, a primary T cell, a T cell line, a NK cell, or a NK-T cell. In specific embodiments, the methods comprise a host cell which is a $CD8^+$ T cell, a $CD4^+$ T cell, or both.

EXAMPLES

Example 1

Methods

Cell Lines

T2 is a TAP-deficient T cell leukemia/B-LCL hybrid cell line expressing only HLA A*02:01[11], and 293T/17 is a highly-transfectable cell line purchased from ATCC. Jurkat76 cells are a TCRα/TCRβ deficient derivative of the parental Jurkat cell line, and do not naturally express CD8[12]. Jurkat76 cells were previously transduced to express CD8αβ Jurkat-CD8). Cell lines were maintained in RPMI 1640 medium with HEPES (Invitrogen, GIBCO) supplemented with 10% heat-inactivated FBS (Hyclone, GE Healthcare Life Sciences), 100 U/mL penicillin and 100 μg/mL streptomycin.

Human T Cell Culture:

Leukapheresis samples were collected from healthy donors at the Seattle Cancer Care Alliance after written informed consent in accordance with the Declaration of Helsinki and with approval of the institutional review board under protocol 868.01. PBMCs were isolated from HLA-typed donors and 10 HLA-A*02:01-restricted T cell lines were generated per donor specific for peptide $WT1_{37-45}$, VLDFAPPGA, (10 donors total) as previously described[13, 14]. Briefly, $CD8^+$ T cells were purified using the EasySep™ Human $CD8^+$ T cell isolation kit (StemCell Technologies) and DC were generated from autologous PBMC by adhesion to plastic and culture with 1000 U/ml IL-4 and 800 U/ml GMCSF for 2 days with the addition of a maturation cytokine cocktail for the last day before harvest. DC were loaded with 1 μg/ml peptide for 90 minutes and then washed to remove excess peptide and irradiated at 4000 Rad. Approximately $5\times10^6$ $CD8^+$ T cells were co-cultured at a 2.5:1 ratio with peptide-pulsed DC plus 30 ng/ml IL-21. T cells were maintained in RPMI 1640 medium with HEPES (Invitrogen, GIBCO) supplemented with 5% heat-inactivated pooled human serum (Bloodworks Northwest), 100 U/mL penicillin, 100 μg/mL streptomycin and 55 μM 2-β-mercaptoethanol. Cultures were fed every 2-3 days by exchanging half of the medium and adding 12.5 U/ml IL-2, 2250 U/ml IL-7 and IL-15. T cells were re-stimulated every 10 days by culturing at a 1:2 ratio with irradiated, peptide-pulsed, autologous PBMCs.

Flow Cytometry-Based Cell Sorting

T cell lines from all donors were combined on ice at the end of the antigen-specific expansion. The pooled sample was divided and stained with peptide/HLA-A2 tetramer under 3 conditions: (1) a wild type tetramer concentration empirically determined to give maximal separation of positive and negative populations as described in the 'Tetramer binding and affinity measurements' section; (2) a 100-fold dilution of the optimal tetramer dose; and 3) a separate modified tetramer made by mutating the HLA-A2 molecule at positions D227K and T228A of the α3-domain), which interact with CD8[15]. This tetramer has been shown to selectively bind high affinity CD8-independent TCRs[16, hu 17] For each tetramer-stained sample, cells with the highest levels of tetramer binding (top ~2% of labelled cells) were flow cytometrically sorted. The sorted populations were analyzed by Adaptive Biotechnologies immunoseq assay to quantitate the relative abundance of each clonotype. An additional sample containing the entire tetramer positive population was also sorted from the optimal tetramer stained sample and TCRαβ pairing information determined by Adaptive Biotechnologies pairSeq Assay[18].

Data Analysis

Enrichment Calculations

The enrichment score for each clonotype was calculated as: (frequency in the sorted tetramer$^+$ population)/(frequency in the unsorted pooled sample). Clonotypes that were not detected in the pooled sample were assigned a frequency in the pooled sample corresponding to 1 cell for enrichment calculations.

TCR Sequencing and Alpha/Beta Pairing:

TCR repertoire analysis was performed by Adaptive Biotechnologies ImmunoSeq assay. Single cell V(D)J analysis (TCR alpha/beta pairing) was performed using Chromium Single Cell Immune Profiling by 10× genomics.

TCR Transduction

Codon-optimized TCR constructs in a TCRβ-p2a-TCRα orientation were synthesized on the BioXp™ 3200 (SGI-DNA) and cloned into the pRRLSIN.cPPT.MSCV.WPRE lentiviral expression plasmid (gift from Dr. Richard Morgan, NCI) by Gibson Assembly. The expression vector was then packaged in 293T cells using a 3$^{rd}$ generation lentiviral packaging system. Lentiviral supernatant was harvested after 48 hr and filtered to remove cell debris. Approximately $5\times10^5$ Jurkat76 cells were combined with 2 ml of lentiviral supernatant plus 5 ug/ml polybrene. Cells were centrifuged at 1000 g for 90 min at 30° C. to facilitate transduction. For TCR-transduction of primary $CD8^+$ T cells, HLA-A2$^+$ PBMC were enriched for $CD8^+$ T cells using the EasySep™ Human $CD8^+$ T cell isolation kit (StemCell Technologies) and activated for 4 hours with Dynabeads™ Human T-Expander CD3/CD28 (Gibco). Approximately $2\times10^6$ $CD8^+$ T cells were combined with 2 ml of lentiviral supernatant plus 5 μg/ml protamine sulphate and 50 U/ml IL-2. Transgenic TCR$^+$ cells were FACSorted using peptide/HLA-A*02:01 tetramers to obtain pure antigen-specific cell populations for downstream assays.

TCR Binding Data

Assessment of Correct TCR Pairing

Jurkat76 cells, were transduced with each TCR construct and analyzed for tetramer binding relative to CD3 surface expression, which reflects total transgenic TCR surface expression in these cells lacking an endogenous TCR.

Tetramer Binding and Affinity Measurements

The optimal tetramer dose was determined by performing a tetramer titration on a positive T cell population and selecting the concentration, which best separated the positive and negative populations without increasing the background staining of the negative population.

TCR Functional Data

IFN-γ Production

Primary $CD8^+$ T cells were lentivirally transduced with each TCR expression construct and sorted to yield a uniformly tetramer positive cell population, then mixed at a 1:1 ratio with T2 target cells pulsed with decreasing doses of peptide ($1\text{-}10^{-5}$ μM). Autologous PBMC were alternatively used as APC where indicated. After 4 hours of incubation in the presence of golgi-inhibitors (BD GolgiPlug and GolgiStop), cells were surface-stained with anti-CD8 and then fixed (BD Cytofix/Cytoperm) before intracellular labelling with anti-IFN-γ in BD Perm/Wash buffer. The cells were analyzed by flow cytometry to determine the percentage of IFN-$\gamma^+$ cells for each sample. These data were fit to a dose-response curve by non-linear regression using Graphpad Prism (four parameter-variable slope, with the bottom and top of the curve constrained to 0 and 100, respectively).

Figure 1B:
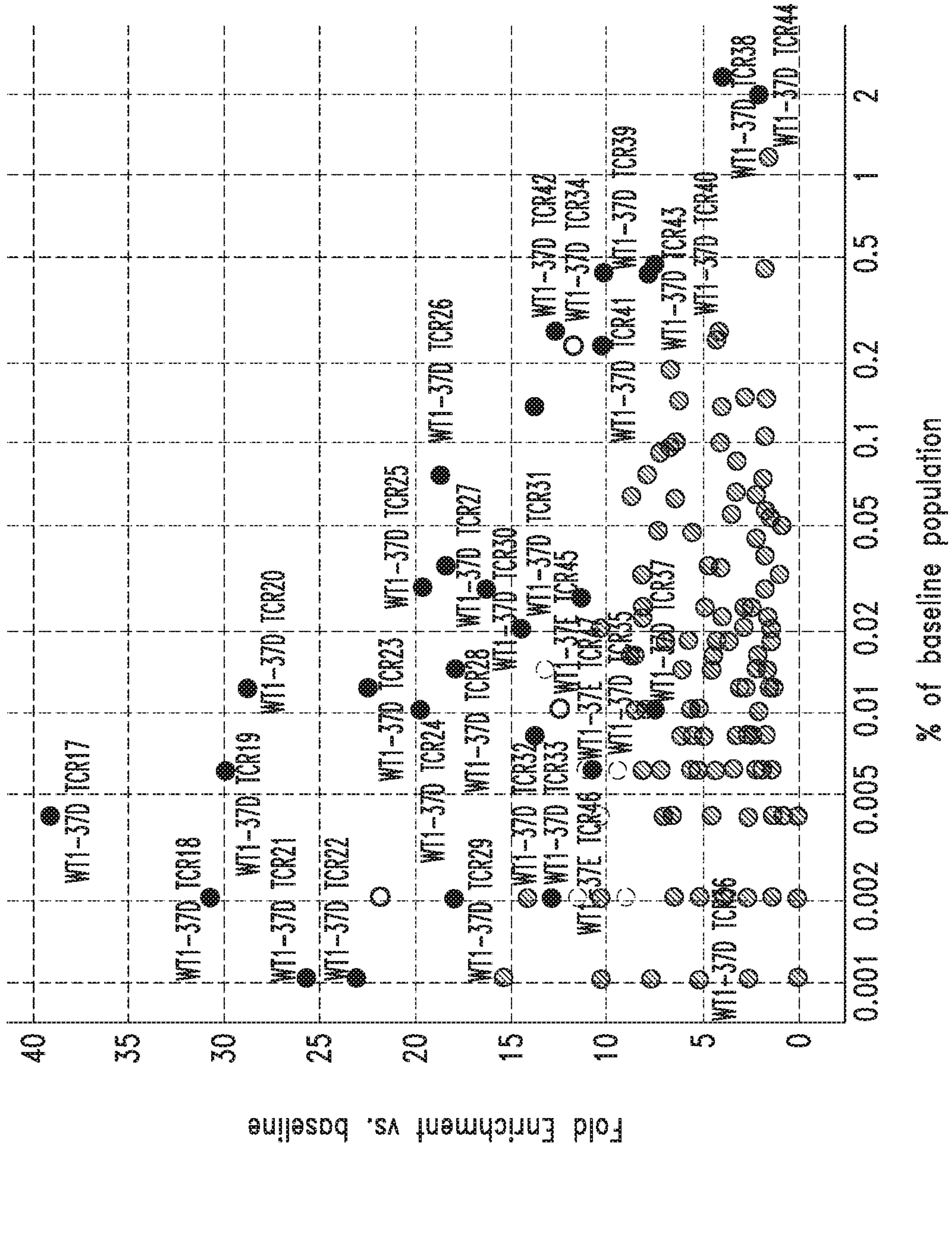

FIGS. 1(A) and 1(B) show how $WT1_{37-45}$ peptide-specific TCRs were identified by high-throughput sequencing-based strategy. TCR clonotypes that were enriched in the high tetramer-binding sort compared to the total tetramer-positive population were identified as likely to have a high affinity or high functional avidity for the peptide/HLA-A2 ligand. (A) Schematic of initial sequencing-based strategy for identifying TCR clonotypes associated with high $WT1_{37-45}$ peptide/WIC tetramer-binding. (B) Enrichment in sort populations versus percentage of total population is shown, with selected TCR highlighted. All TCRs indicated by black circles were synthesized and evaluated for antigen-specificity (27 total).

Figure 2:
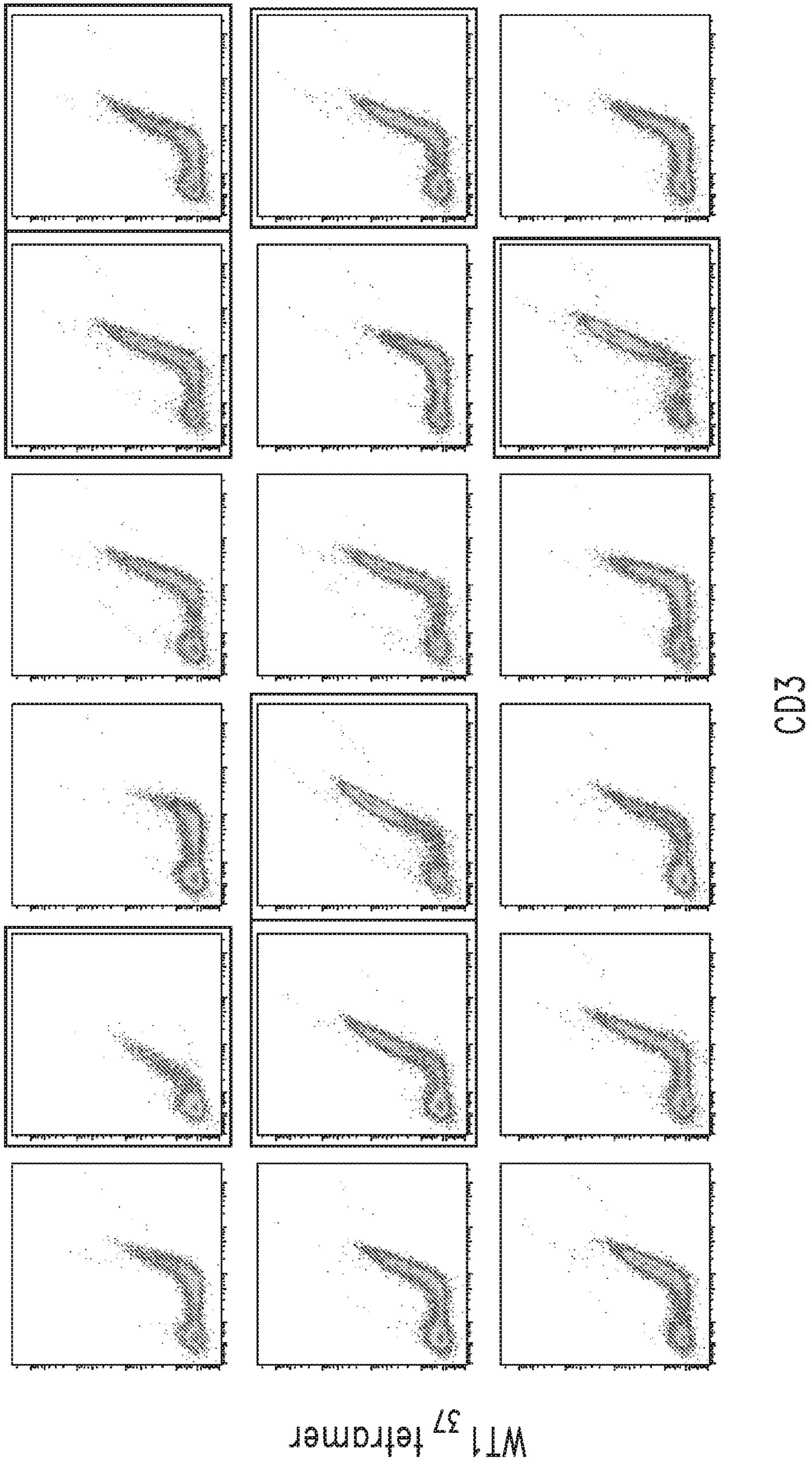
FIG. 2 shows results of functional evaluation of TCRs that bind high levels of CD8 independent (CD8i) tetramer. TCR constructs were expressed in Jurkat cells that lack endogenous TCRα/β chains. Tetramer staining versus CD3 expression for each TCR is shown (CD3 expression directly correlates with transgenic TCR surface expression).

FIG. 2 shows results of tetramer-binding studies evaluating the specificity and relative tetramer binding affinity of the selected TCRs. TCR constructs were expressed in Jurkat cells that lack endogenous TCRα/β chains. Tetramer staining versus CD3 expression for each TCR is shown (CD3 expression directly correlates with transgenic TCR surface expression).

Example 2

Identification of High Functional Avidity TCRs

Figure 3A:
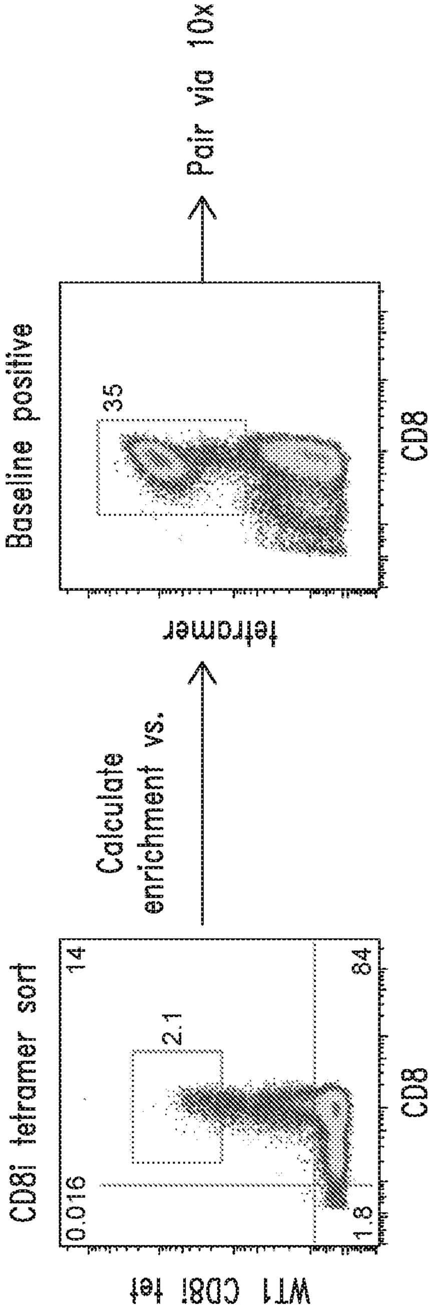
FIGS. 3A-3C show additional $WT1_{37}$-specific TCRs were identified by a modified high-throughput sequencing-based strategy using a CD8 independent (CD8i) tetramer. (A) Schematic of modified sequencing-based strategy for identifying TCR clonotypes associated with high CD8-independent $WT1_{37}$ peptide/MHC tetramer-binding. (B) Enrichment in original sort populations versus percentage of total population as compared with (C) a similar analysis when CD8i tetramer is used is shown. An additional 14 TCRs were selected based on decreased surface CD3 levels and CD8i tetramer binding. All TCRs indicated by shaded (diagonal line pattern) circles were synthesized and evaluated for antigen-specificity.
Figure 3B:
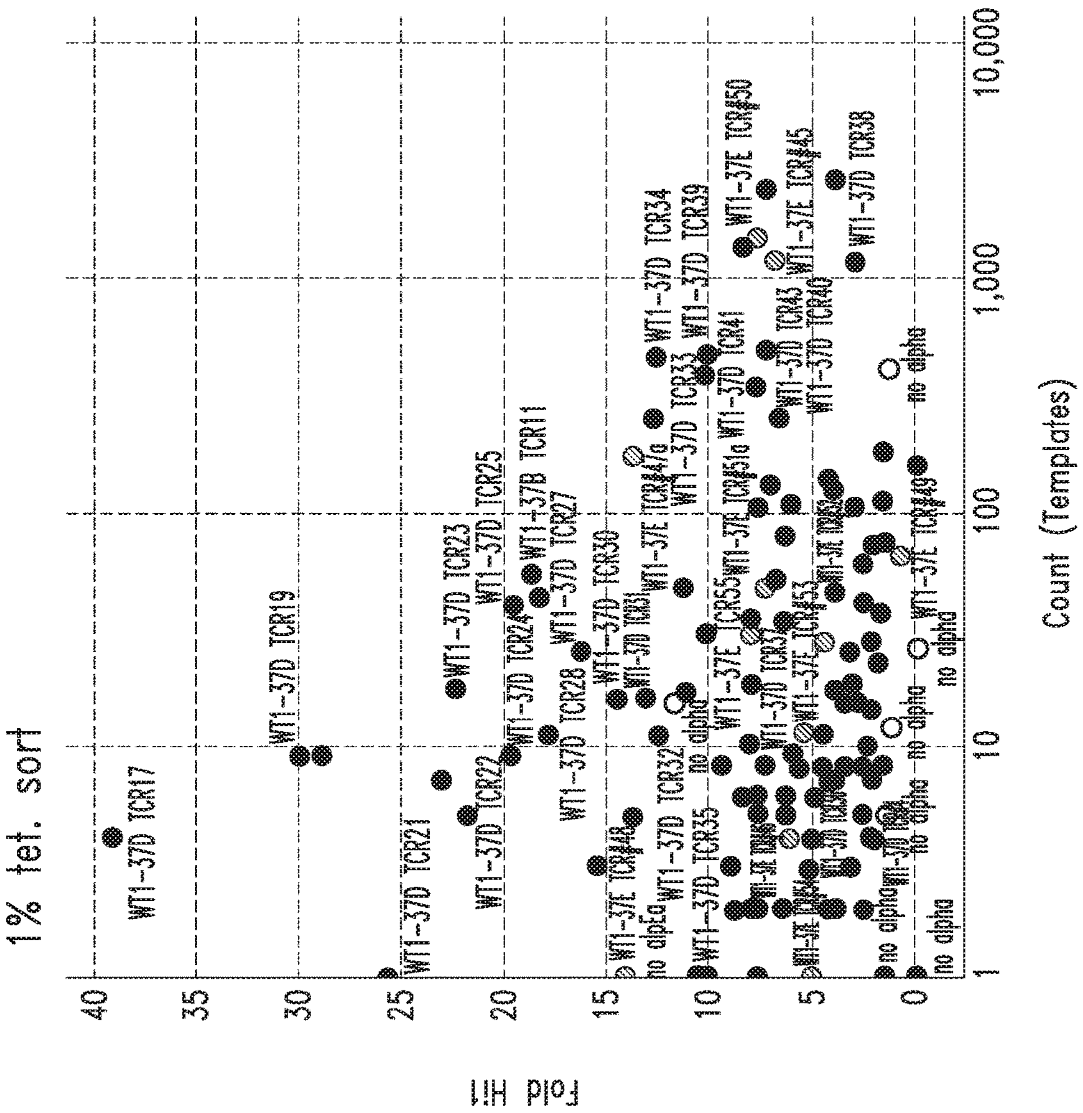
Figure 3C:
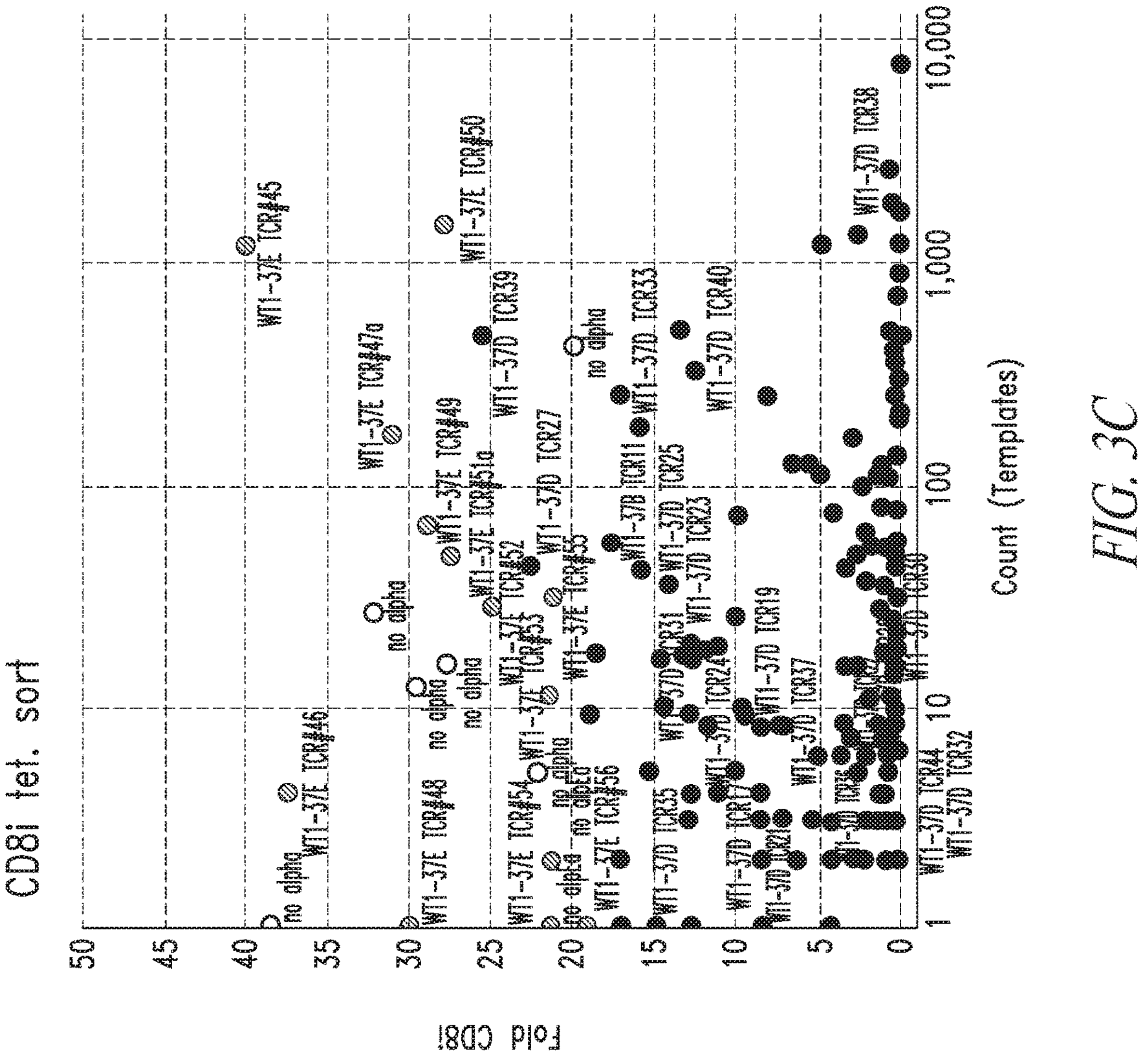

Since some high affinity TCRs have been shown to bind tetramer independent of CD8, a second experiment was performed to identify additional TCRs that are specifically enriched in the high tetramer binding sort population when a CD8 independent (CD8i) tetramer was used. FIGS. 3A-3C show how additional $WT1_{37-45}$ peptide-specific TCRs were identified by a modified high-throughput sequencing-based strategy using a CD8 independent (CD8i) tetramer. A schematic of a modified sequencing-based strategy for identifying TCR clonotypes associated with high CD8 independent $WT1_{37}$ peptide/MHC tetramer-binding is shown in FIG. 3A. Enrichment in original sort populations versus percentage of total population as compared with a similar analysis when CD8i tetramer used is shown in FIGS. 3B and 3C. An additional 14 TCRs were selected based on surface CD3 levels and CD8i tetramer binding. All named TCR clonotypes in FIGS. 3B and 3C were synthesized and evaluated for antigen-specificity. All TCRs indicated by shaded (diagonal line pattern) circles in FIG. 3C represent additional TCRs identified using CD8i tetramer.

Example 3

Tetramer Staining Versus CD3 Expression

Figure 4:
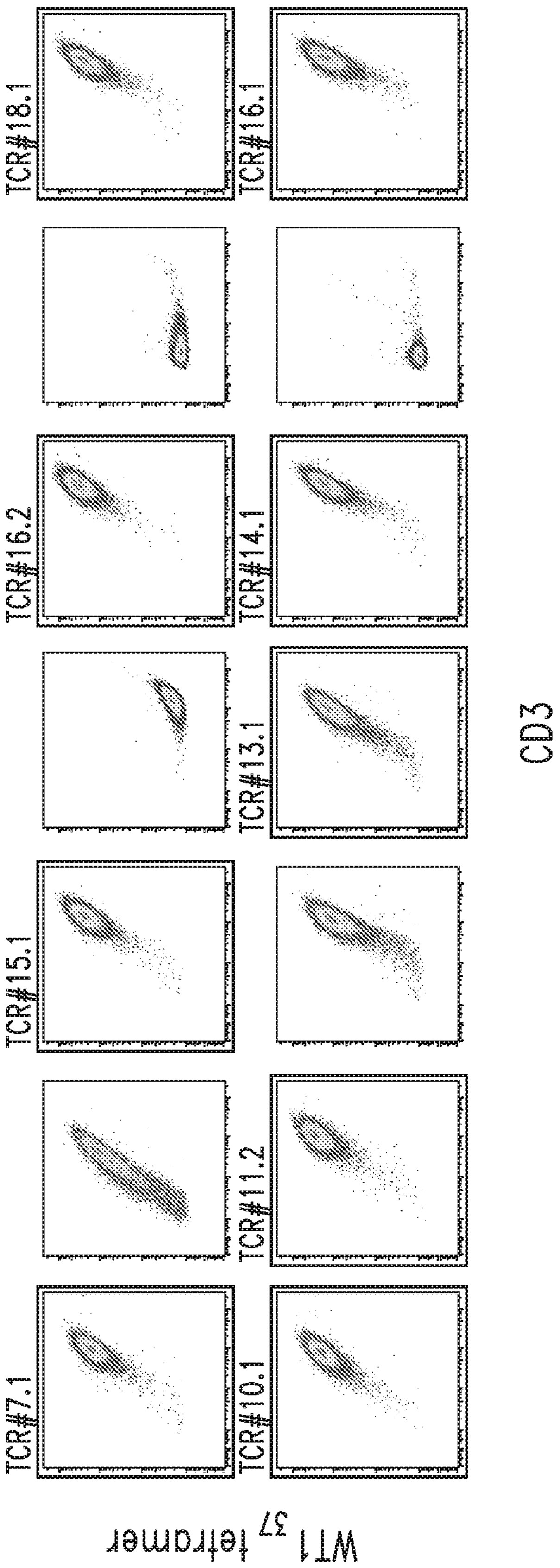
FIG. 4 shows CD8i tetramer binding of selected $WT1_{37}$ TCRs. TCR constructs were expressed in Jurkat cells that lack endogenous TCRα/β chains. Tetramer staining versus CD3 expression for each TCR is shown (CD3 expression directly correlates with transgenic TCR surface expression).

CD8i tetramer binding of additional CD8i tetramer-selected $WT1_{37-45}$ peptide-specific TCRs is shown in FIG. 4. TCR constructs were expressed in Jurkat cells that lack endogenous TCRα/β chains (as well as lacking CD8 expression). Tetramer staining versus CD3 expression for each TCR is shown in FIG. 4 (CD3 expression directly correlates with transgenic TCR surface expression). TCRs that bound most strongly to tetramer, resulting in high levels of tetramer staining relative to anti-CD3 staining, were selected for further analysis.

Example 4

IFNγ Assay to Measure Functional Avidity ($EC_{50}$)

Figure 5A:
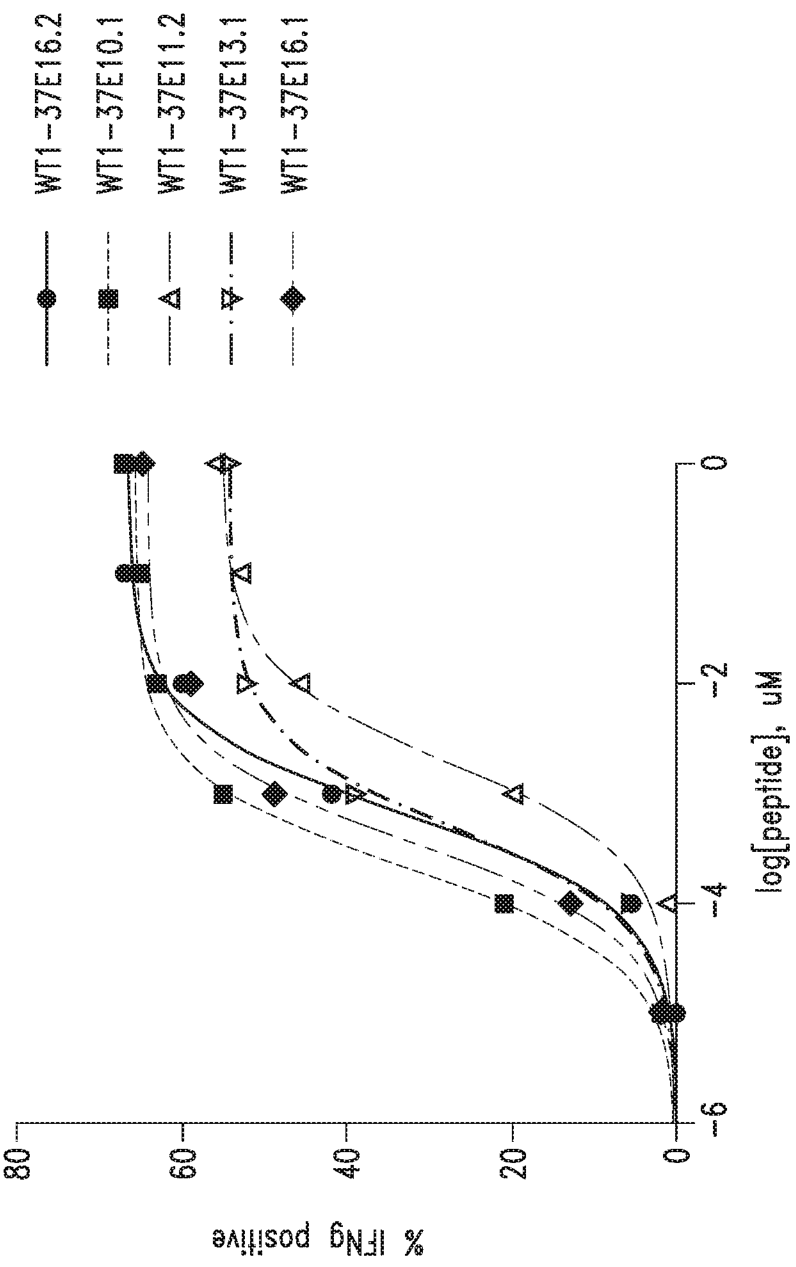
FIGS. 5A and 5B show calculation of peptide $EC_{50}$ for selected TCRs in IFNγ assay when transduced into primary $CD8^+$ PBMCs. (A) Selected TCRs were transduced into $CD8^+$ T cells isolated from donor PMBCs. After 1 week, cells were sorted for $tetramer^+$ $CD8^+$ T cells and expanded. Expanded antigen-specific cells were cultured for 4-6 hours with peptide-pulsed T2 target cells and IFNγ production was determined by flow cytometry. (B) Percentage of IFNγ-producing cells was fit to dose-response curves by nonlinear regression to calculate peptide $EC_{50}$ for each TCR.
Figure 5B:
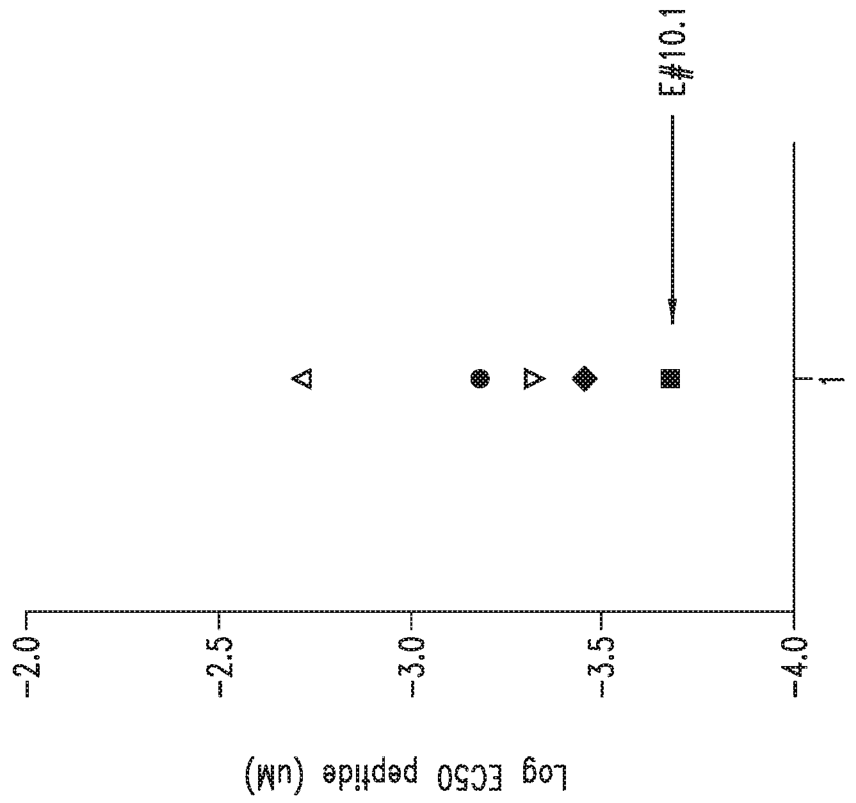

The ability of a TCR to signal T cell activation at limiting concentrations of antigen was measured by the peptide $EC_{50}$, which is the amount of peptide that target cells need to be pulsed with to elicit a T cell response (e.g., IFNγ production) from 50% of the present TCR-transduced T cells. This value directly correlates with the ability of T cells expressing a given TCR to kill antigen-expressing target cells. To determine the peptide $EC_{50}$ for the selected TCRs, each TCR was transduced into $CD8^+$ T cells isolated from donor PMBCs (FIG. 5A). After 1 week, cells were sorted for $tetramer^+$ $CD8^+$ T cells and expanded. Expanded antigen-specific cells were cultured for 4-6 hours with peptide-pulsed T2 target cells and IFNγ production was determined by flow cytometry (FIG. 5A). The percentage of IFNγ-producing cells was fit to dose-response curves by non-linear regression to calculate peptide $EC_{50}$ for each TCR (FIG. 5B).

Example 5

Figure 6:
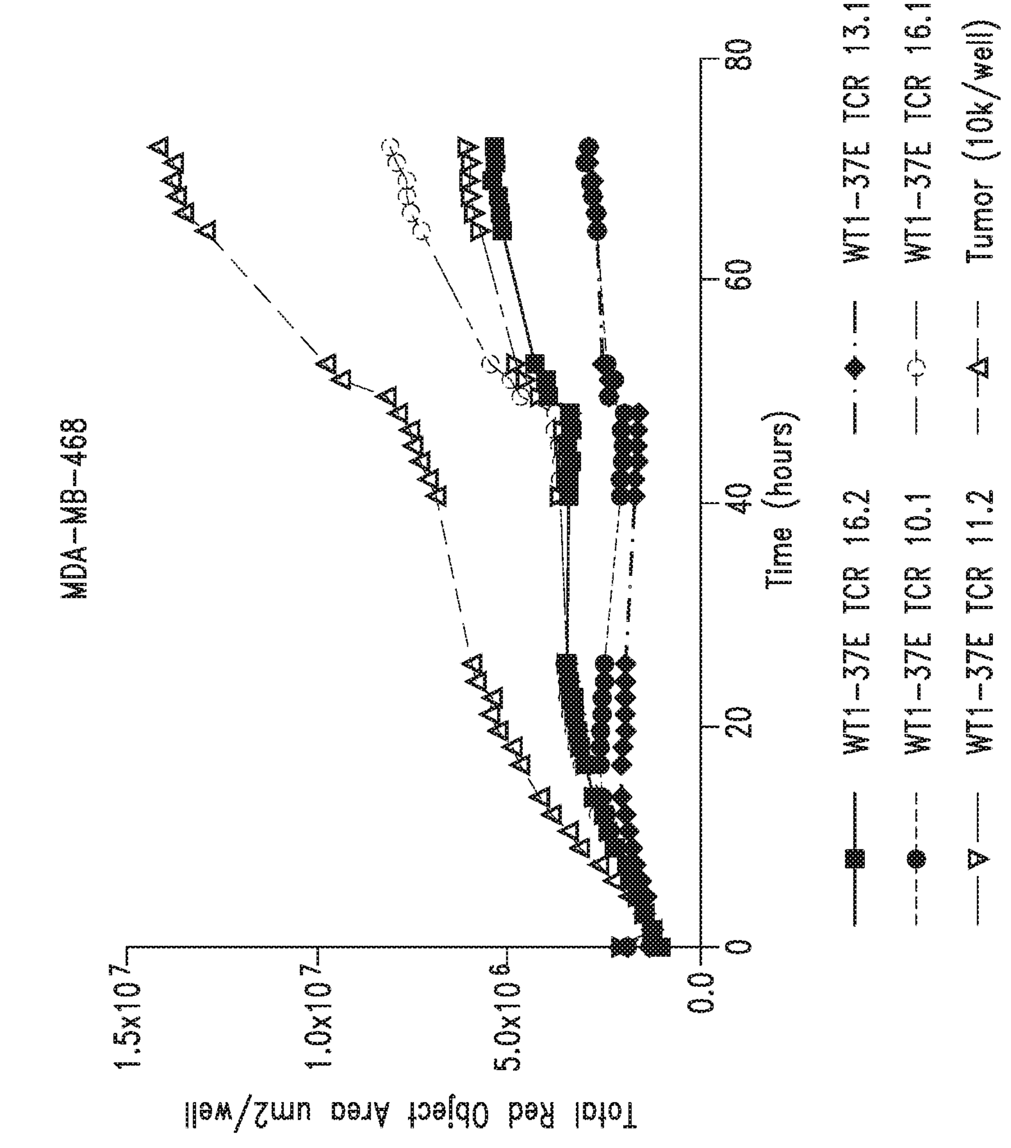
FIG. 6 shows that primary $CD8^+$ T cells expressing $WT1_{37}$-specific TCRs efficiently kill the $WT1^+$ $HLA\text{-}A2^+$ breast cancer cell line MDA-MB-468. Sort-purified for high tetramer binding, CD8+ primary T cells were transduced with TCR and mixed at an 8:1 ratio (in triplicate) with the breast cancer cell line MDA-MB-468, which had been stained with CytoLight® Rapid Red dye. Total red object area (which correlates with the total number of live target cells) was calculated at the time points indicated for each TCR-transduced T cell population over a 72 hour period. In order to assess ongoing responsiveness of TCR-transduced T cells to persistent antigen, additional MDA-MB-468 cells were added at 48 hours.

In Vitro Killing of $HLA-A2^+WT1^+$MDA-MB-468 Cells by Primary CD8+ T Cells Expressing $WT1_{37-45}$ Peptide-Specific TCRs In order to directly assess TCR-transduced $CD8^+$ T cell-mediated lysis of tumor cells that naturally express and present WT1 p37 antigen on HLA-A2, donor-derived $CD8^+$ T cells were transduced with one of each of the selected TCRs and sort-purified for high tetramer binding. TCR-transduced T cells were then mixed at an 8:1 ratio (in triplicate) with the breast cancer cell line MDA-MB-468, which had been stained with CytoLight® Rapid Red dye. Total red object area (which correlates with the total number of live target cells) was calculated at the time points indicated for each TCR-transduced T cell population over a 72 hour period. The most potent tumor-reactive T cells would remain responsive to tumor antigens for long periods after in vivo transfer into patients. Therefore, in order to assess ongoing responsiveness of TCR-transduced T cells to persistent antigen, additional MDA-MB-468 cells were added at 48 hours. See FIG. 6.

Example 6

Figure 7:
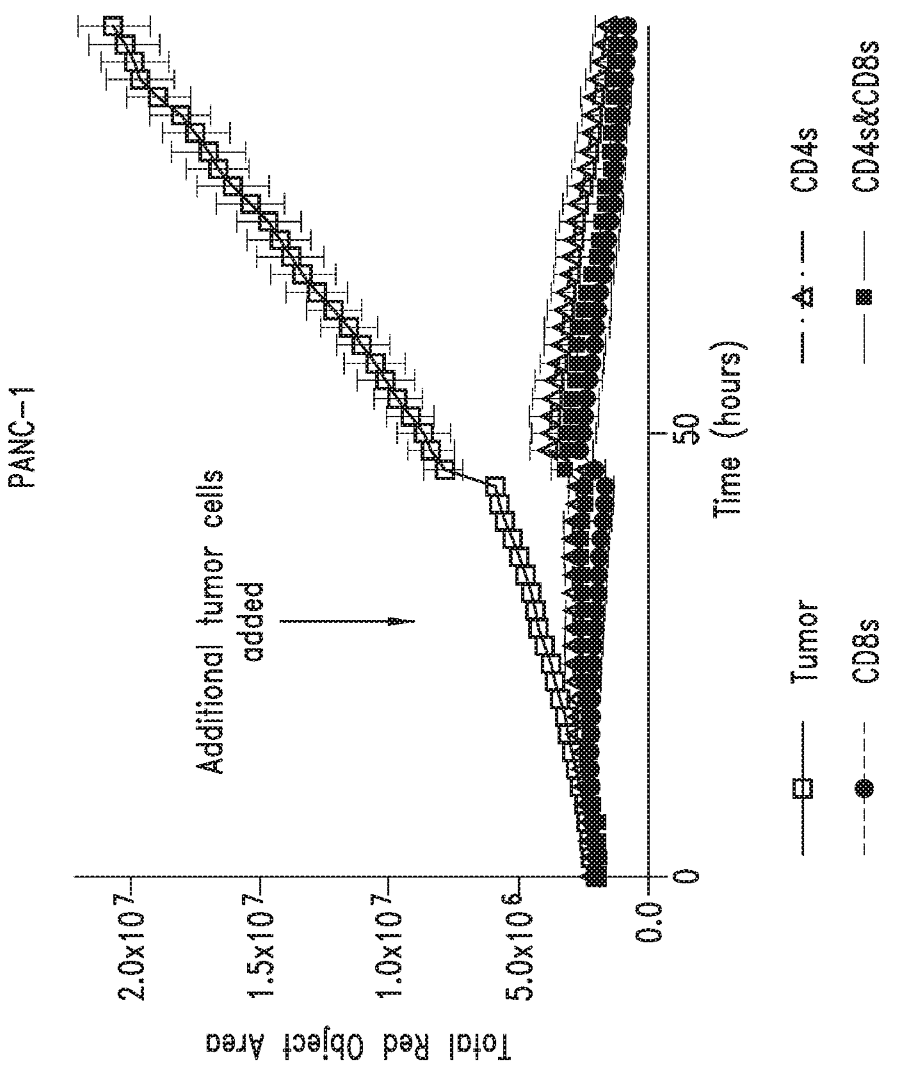
FIG. 7 shows that both $CD4^+$ and $CD8^+$ T cells expressing TCR 10.1 can eliminate the $WT1^+$ $A2^+$ pancreatic adenocarcinoma cell line PANC-1 after repeat challenge in vitro. Both $CD4^+$ and $CD8^+$ T cells were transduced to express the $WT1_{37}$ TCR 10.1. $CD4^+$ T cells were further transduced to express CD8α and CD8β genes. After 8 days, transduced cells were sorted to purify $CD8^+$ $tetramer^+$ and $CD4^+/CD8^+$ $tetramer^+$ T cells. Antigen-specific cells that were either CD4+/CD8+, CD8+, or a mixture of these two populations (CD4 and CD8) were mixed 8:1 (in triplicate) with the pancreatic adenocarcinoma cell line PANC-1, which had been previously transduced to express NucLight® Red dye. Total red object area (which correlates with the total number of live target cells) was calculated at the time points indicated for each TCR-transduced T cell population. In order to assess ongoing responsiveness of TCR-transduced T cells to persistent antigen, additional PANC-1 cells were added at 48 hours.
Figure 8A:
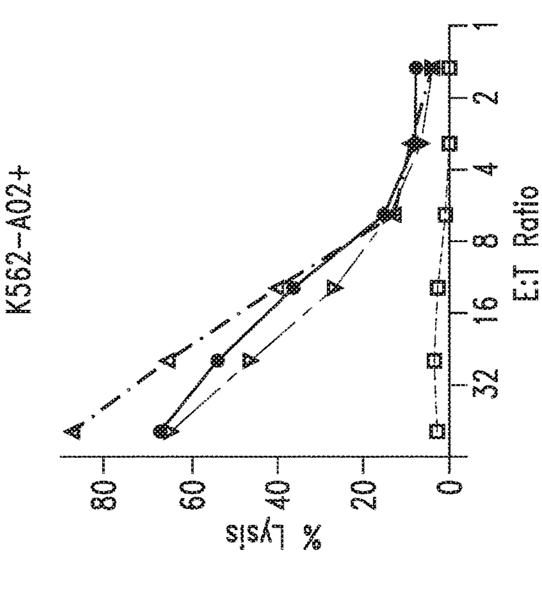
FIGS. 8A-8D show a comparison of tumor cell line killing by T cells transduced with WT1 p126 peptide-specific C4 TCR from Schmitt et al. (*Nat. Biotechnol.* 35:1188, 2017) as compared to killing by T cells transduced with WT1 p37 peptide-specific TCR of the present disclosure ($WT1_{37-45}$ TCR15.1). Note that the C4 TCR has a lower affinity for its peptide::MHC complex as compared to the WT1 p37 peptide-specific TCRs of this disclosure.
Figure 8B:
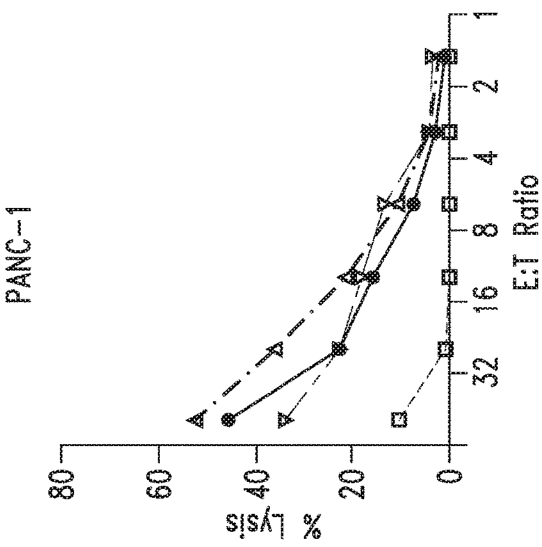
Figure 8B:
Figure 8C:
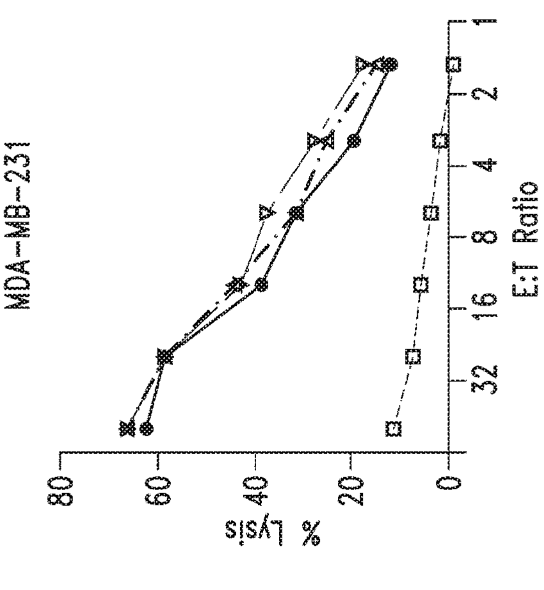
Figure 8D:
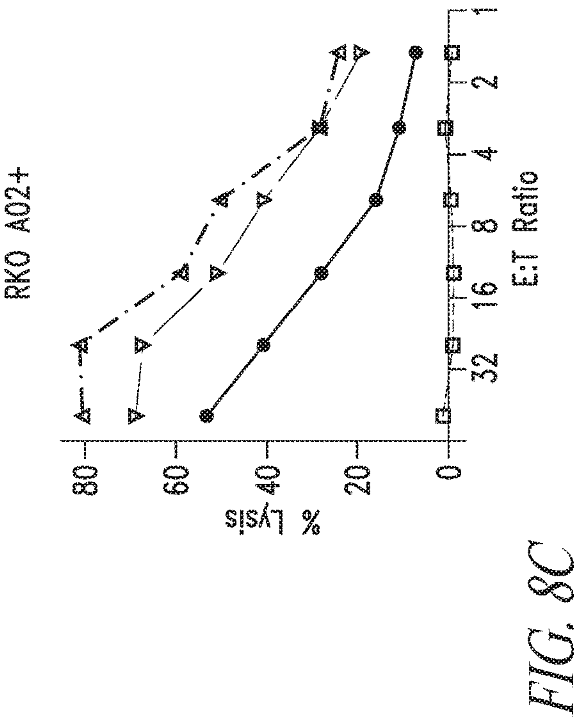

In Vitro Killing of $HLA-A2^+WT1^+$Panc-1 Cells by Primary $CD4^+$ and $CD8^+$ T Cells Expressing $WT1_{37-45}$ Peptide-Specific TCRs Both $CD4^+$ and $CD8^+$ T cells can play a role in tumor clearance in vivo. Therefore, an MEW class I-restricted TCR that can also signal an antigen-specific response in $CD4^+$ T cells is preferable to a TCR that can only activate $CD8^+$ T cells. The ability of MEW class I-restricted TCRs to function in $CD4^+$ T cells appears to be, in part, dependent on the affinity of the TCR for peptide MHC. In many cases, transduction of the CD4+ T cells with genes encoding CD8α and CD8β helps to efficiently elicit an antigen-specific response. Therefore, to assess the ability CD4 (transduced with CD8α/CD8β) versus CD8 T cells that express TCR10.1 to target HLA-A2$^+$WT1$^+$ tumor cells, both CD4$^+$ and CD8$^+$ T cells were transduced to express the $WT1_{37-45}$ TCR10.1. CD4$^+$ T cells were further transduced to express CD8α and CD8β genes. After 8 days, transduced cells were sorted to purify CD8$^+$ tetramer$^+$ and CD4$^+$/CD8$^+$ tetramer$^+$ T cells. Antigen-specific cells that were either CD4$^+$, CD8$^+$, or a mixture of these two populations (CD4 and CD8) were mixed 8:1 (in triplicate) with the pancreatic adenocarcinoma cell line PANC-1, which had been previously transduced to express NucLight® Red dye. Total red object area (which correlates with the total number of live target cells) was calculated at the time points indicated for each TCR-transduced T cell population. In order to assess ongoing responsiveness of TCR-transduced T cells to persistent antigen, additional PANC-1 cells were added at 48 hours. FIG. 7 shows that both CD4$^+$ and CD8$^+$ T cells expressing $WT1_{37-45}$ TCR10.1 can eliminate the WT1$^+$ A2$^+$ pancreatic adenocarcinoma cell line PANC-1 after repeat challenge in vitro.

The WT1 p126 epitope is not always processed/presented efficiently by cells expressing WT1 and HLA-A2 (Jaigirdar et al., J. Immunother. 39:105, 2017). In particular, several solid tumor-derived cell lines that express WT1 and HLA-A2 are not efficiently targeted by WT1-p126-specific TCRs, with or without pre-culture with IFNγ to up-regulate immunoproteasome expression. In some aspects, the present disclosure relates, in part, to the finding that the WT1-p37 epitope is more broadly processed and presented by a wide variety of tumor types as compared to the WT1-p126 epitope. FIGS. 8A-8D shows the lysis of various WT1+A2+ tumor cell lines by a WT1-p126 peptide-specific TCR as compared to a WT1 p37 peptide-specific TCR. These data highlight the fact that WT1 p-37 peptide-specific TCRs appear to be generally more reliably able to target a broad set of WT1+A2+ tumors.

The various embodiments described herein can be combined to provide further embodiments. All of the patents, patent application publications, patent applications, and non-patent publications referred to in this specification and/or listed in the Application Data Sheet, including but not limited to U.S. Patent Application No. 62/816,746, filed Mar. 11, 2019, are incorporated herein by reference in their entirety. In general, terms used in the following claims should not be construed as limited to specific embodiments disclosed herein, but should be construed to include all possible embodiments along with the full scope of equivalents to which such claims are entitled.

REFERENCES

1. Kalos, M. et al. T cells with chimeric antigen receptors have potent antitumor effects and can establish memory in patients with advanced Leukemia. *Sci. Transl. Med.* 3, 95ra73-95ra73 (2011).
2. Porter, D. L., Levine, B. L., Kalos, M., Bagg, A. & June, C. H. Chimeric antigen receptor-modified T cells in chronic lymphoid leukemia. *N Engl J Med* 365, 725-733 (2011).
3. Kochenderfer, J. N. et al. Eradication of B-lineage cells and regression of lymphoma in a patient treated with autologous T cells genetically engineered to recognize CD19. *Blood* 116, 4099-4102 (2010).
4. Chapuis, A. G. et al. Transferred WT1-reactive CD8+ T cells can mediate antileukemic activity and persist in post-transplant patients. *Sci Transl Med* 5, 174ra27 (2013).
5. Chapuis, A. G. et al. Transferred melanoma-specific CD8+ T cells persist, mediate tumor regression, and acquire central memory phenotype. *Proc Natl Acad Sci USA* (2012). doi:10.1073/pnas.1113748109
6. Morgan, R. et al. Cancer Regression in Patients After Transfer of Genetically Engineered Lymphocytes. *Science* 314, 126-129 (2006).
7. Dudley, M. et al. Adoptive cell therapy for patients with metastatic melanoma: evaluation of intensive myeloablative chemoradiation preparative regimens. *J Clin Oncol* 26, 5233-5239 (2008).
8. Robbins, P. F. et al. Tumor regression in patients with metastatic synovial cell sarcoma and melanoma using genetically engineered lymphocytes reactive with NY-ESO-1. *Journal of Clinical Oncology* 29, 917-924 (2011).
9. Stromnes, I. M. et al. Abrogation of SRC homology region 2 domain-containing phosphatase 1 in tumor-specific T cells improves efficacy of adoptive immunotherapy by enhancing the effector function and accumulation of short-lived effector T cells in vivo. *The Journal of Immunology* 189, 1812-1825 (2012).
10. Schmitt, T. M., Ragnarsson, G. B. & Greenberg, P. D. T Cell Receptor Gene Therapy for Cancer. *Hum Gene Ther* 20, 1240-1248 (2009).
11. Salter, R. D. & Cresswell, P. Impaired assembly and transport of HLA-A and -B antigens in a mutant T×B cell hybrid. *EMBO. J.* 5, 943-949 (1986).
12. Heemskerk, M. H. et al. Redirection of antileukemic reactivity of peripheral T lymphocytes using gene transfer of minor histocompatibility antigen HA-2-specific T-cell receptor complexes expressing a conserved alpha joining region. *Blood* 102, 3530-3540 (2003).
13. Ho, W. Y., Nguyen, H. N., Wolfl, M., Kuball, J. & Greenberg, P. D. In vitro methods for generating CD8+ T-cell clones for immunotherapy from the naive repertoire. *J Immunol Methods* 310, 40-52 (2006).
14. Chapuis, A. G. et al. Transferred WT1-reactive CD8+ T cells can mediate antileukemic activity and persist in post-transplant patients. *Sci Transl Med* 5, 174ra127 (2013).
15. Luescher, I. F. et al. CD8 modulation of T-cell antigen receptor-ligand interactions on living cytotoxic T lymphocytes. *Nature* 373, 353-356 (1995).
16. Stone, J. D. & Kranz, D. M. Role of T cell receptor affinity in the efficacy and specificity of adoptive T cell therapies. *Front Immunol* 4, 244 (2013).
17. Pittet, M. J. et al. α3 Domain Mutants of Peptide/WIC Class I Multimers Allow the Selective Isolation of High Avidity Tumor-Reactive CD8 T Cells. *The Journal of Immunology* 171, 1844-1849 (2003).
18. Howie, B. et al. High-throughput pairing of T cell receptor alpha and beta sequences. *Sci Transl Med* 7, 301ra131 (2015).

What is claimed is:

1. A host cell comprising a heterologous polynucleotide encoding a T cell receptor (TCR), wherein the TCR comprises:

(a) a TCR α-chain variable (Vα) domain comprising the CDR1α amino acid sequence set forth in SEQ ID NO:194, the CDR2a amino acid sequence set forth in SEQ ID NO:195, and the CDR3a amino acid sequence set forth in SEQ ID NO:196 or 12; and (b) a TCR β-chain variable (VB) domain comprising the CDR1β amino acid sequence set forth in SEQ ID NO:197, the CDR2β amino acid sequence set forth in SEQ ID NO:198, and the CDR3β amino acid sequence set forth in SEQ ID NO:199 or 1, wherein the TCR binds to a VLDFAPPGA (SEQ ID NO:59): human leukocyte antigen (HLA) complex, wherein the HLA comprises HLA-A*201.

2. The host cell of claim 1, wherein the TCR specifically binds to the VLDFAPPGA (SEQ ID NO:59): HLA complex.

3. The host cell of claim 1, wherein the TCR further binds to the VLDFAPPGA (SEQ ID NO:59): human leukocyte antigen (HLA) complex on a cell surface independent of CD8 or in the absence of CD8.

4. The host cell of claim 1, wherein:

(a) the Vα domain of the TCR comprises an amino acid sequence that has at least 90% sequence identity to the amino acid sequence set forth in SEQ ID NO:253; and/or;

(b) the Vβ domain of the TCR comprises an amino acid sequence that has at least 90% sequence identity to the amino acid sequence set forth in SEQ ID NO:242.

5. The host cell of claim 1, wherein the Vα domain of the TCR comprises the amino acid sequence set forth in SEQ ID NO:253, and/or wherein the Vβ domain of the TCR comprises the amino acid sequence set forth in SEQ ID NO:242.

6. The host cell of claim 1, wherein:

(i) the Vα domain of the TCR consists of the amino acid sequence set forth in SEQ ID NO:253; and/or (ii) the VB domain of the TCR consists of the amino acid sequence set forth in SEQ ID NO:242.

7. The host cell of claim 1, wherein the TCR further comprises:

(i) a TCR α-chain constant domain having at least 90% sequence identity to the amino acid sequence of SEQ ID NO:47; and/or (ii) a TCR β-chain constant domain having at least 90% sequence identity to the amino acid sequence of SEQ ID NO:45 or 46.

8. The host cell of claim 7, wherein the TCR α-chain constant domain and the TCR β-chain constant domain comprise a non-native cysteine.

9. The host cell of claim 1, wherein the TCR comprises a TCR α-chain comprising the Vα domain and an α-chain constant domain, wherein the Vα domain comprises the amino acid sequence set forth in SEQ ID NO: 253, and the α-chain constant domain comprises the amino acid sequence of SEQ ID NO:47.

10. The host cell of claim 1, wherein the TCR comprises a TCR β-chain comprising the Vβ domain and a β-chain constant domain, wherein the Vβ domain comprises the amino acid sequence set forth in SEQ ID NO:242, and the β-chain constant domain comprises the amino acid sequence of SEQ ID NO:45 or 46.

11. The host cell of claim 1, wherein the TCR comprises a TCR β-chain comprising the Vβ domain and a β-chain constant domain, wherein:

the Vβ domain consists of the amino acid sequence set forth in SEQ ID NO:242, and the β-chain constant domain consists of the amino acid sequence of SEQ ID NO:45 or 46.

12. The host cell of claim 1, wherein:

the Vα domain and the Vβ domain of the TCR comprise the amino acid sequences set forth in SEQ ID NOs:253 and 242, respectively.

13. The host cell of claim 12, wherein the TCR further comprises an α-chain constant domain and/or a β-chain constant domain, wherein the α-chain constant domain comprises the amino acid sequence set forth in SEQ ID NO:47, and wherein the β-chain constant domain comprises the amino acid sequence set forth SEQ ID NO:46.

14. The host cell of claim 1, wherein the TCR comprises a single-chain TCR (scTCR) or a CAR.

15. The host cell of claim 1, wherein the heterologous polynucleotide encoding the TCR:

(i) is codon optimized for the host cell;

(ii) has at least 75% identity to or comprises the nucleotide sequence set forth in any one of SEQ ID NOs:64, 75, 86, 97, 108, 109, 110, 111, 122, 133, and 144;

(iii) has at least 95% identity to or comprises the polynucleotide sequence set forth in SEQ ID NO:155; or (iv) encodes an amino acid sequence having at least 95% identity to or comprising the amino acid sequence set forth in SEQ ID NO:48.

16. The host cell of claim 1, wherein the heterologous polynucleotide encoding the TCR further comprises:

(i) a polynucleotide encoding a polypeptide that comprises an extracellular portion of a CD8 co-receptor α chain;

ii a polynucleotide encoding a polypeptide that comprises an extracellular portion of a CD8 co-receptor β chain; and/or (iii) the polynucleotide of (i) and the polynucleotide of (ii); and/or (iv) the polynucleotide of (i) and the polynucleotide of (ii), and further comprises a polynucleotide encoding a self-cleaving peptide disposed between the polynucleotide of (i) and the polynucleotide of (ii); and/or (v) the polynucleotide of (i) and the polynucleotide of (ii), and further comprises a polynucleotide encoding a self-cleaving peptide disposed between the polynucleotide encoding the TCR and the polynucleotide of (i) and/or between the polynucleotide encoding the TCR and the polynucleotide of (ii); and/or (vi) a polynucleotide encoding a self-cleaving peptide disposed between a polynucleotide encoding a TCRα chain of the TCR and a polynucleotide encoding a TCRβ chain of the TCR.

17. The host cell of claim 16, wherein the heterologous polynucleotide comprises, operably linked in-frame:

(i) (pnCD8α)-(pnSCP$_1$)-(pnCD8β)-(pnSCP$_2$)-(pnTCR);

(ii) (pnCD8β)-(pnSCP$_1$)-(pnCD8α)-(pnSCP$_2$)-(pnTCR);

iii) (pnTCR)-(pnSCP$_1$)-(pnCD8α)-(pnSCP$_2$)-(pnCD8β);

(iv) (pnTCR)-(pnSCP$_1$)-(pnCD8β)-(pnSCP$_2$)-(pnCD8α);

(v) (pnCD8α)-(pnSCP$_1$)-(pnTCR)-(pnSCP$_2$)-(pnCD8β); or (vi) (pnCD8β)-(pnSCP$_1$)-(pnTCR)-(pnSCP$_2$)-(pnCD8α), wherein pnCD8a is the polynucleotide encoding the polypeptide that comprises the extracellular portion of the CD8 co-receptor a chain, wherein pnCD8β is the polynucleotide encoding the polypeptide that comprises the extracellular portion of the CD8 co-receptor chain, wherein pnTCR is the polynucleotide encoding the TCR, and wherein $pnSCP_1$ and $pnSCP_2$ are each independently a polynucleotide encoding a self-cleaving peptide, wherein the polynucleotides and/or the encoded self-cleaving peptides are the same or different.

18. The host cell of claim 17, wherein the heterologous polynucleotide comprises, operably linked in-frame:

(i) (pnCD8α)-($pnSCP_1$)-(pnCD8β)-($pnSCP_2$)-(pnTCRβ)-($pnSCP_3$)-(pnTCRα);

(ii) (pnCD8β)-($pnSCP_1$)-(pnCD8α)-($pnSCP_2$)-(pnTCRβ)-($pnSCP_3$)-(pnTCRα);

(iii) (pnCD8α)-($pnSCP_1$)-(pnCD8β)-($pnSCP_2$)-(pnTCRα)-($pnSCP_3$)-(pnTCRβ);

(iv) (pnCD8β)-($pnSCP_1$)-(pnCD8α)-($pnSCP_2$)-(pnTCRα)-($pnSCP_3$)-(pnTCRβ);

(v) (pnTCRβ)-($pnSCP_1$)-(pnTCRα)-($pnSCP_2$)-(pnCD8α)-($pnSCP_3$)-(pnCD8β);

(vi) (pnTCRβ)-($pnSCP_1$)-(pnTCRα)-($pnSCP_2$)-(pnCD8β)-($pnSCP_3$)-(pnCD8α);

(vii) (pnTCRα)-($pnSCP_1$)-(pnTCRβ)-($pnSCP_2$)-(pnCD8α)-($pnSCP_3$)-(pnCD8β); or (viii) (pnTCRα)-($pnSCP_1$)-(pnTCRβ)-($pnSCP_2$)-(pnCD8β)-($pnSCP_3$)-(pnCD8α), wherein pnCD8α is the polynucleotide encoding the polypeptide that comprises the extracellular portion of the CD8 co-receptor a chain, wherein pnCD8β is the polynucleotide encoding the polypeptide that comprises the extracellular portion of the CD8 co-receptor chain, wherein pnTCRα is the polynucleotide encoding the TCR α chain, wherein pnTCRβ is the polynucleotide encoding the TCR β chain, and wherein $pnSCP_1$, $pnSCP_2$, and $pnSCP_3$ are each independently a polynucleotide encoding a self-cleaving peptide, wherein the polynucleotides and/or the encoded self-cleaving peptides are the same or different.

19. The host cell of claim 18, wherein the encoded TCR α-chain, self-cleaving peptide, and TCR β-chain comprise an amino acid sequence having at least 95% identity to SEQ ID NO:48.

20. The host cell of claim 1, wherein the host cell is a hematopoietic progenitor cell or a human immune system cell.

21. The host cell of claim 20, wherein:

(i) the immune system cell is a CD4+T cell, a CD8+T cell, a CD4-CD8-double negative T cell, a y& T cell, a natural killer cell, a natural killer T cell, dendritic cell, or any combination thereof, wherein, optionally, the combination, if present, comprises a CD4+T cell and a CD8+T cell; or (ii) the immune system cell is a T cell, wherein the T cell is a naïve T cell, a central memory T cell, an effector memory T cell, or any combination thereof.

22. A method for alleviating symptoms or prolonging survival of a human subject having a hyperproliferative or proliferative disorder characterized by WT1 overexpression, comprising administering to the human subject an effective amount of the host cell of claim 20.

23. The method of claim 22, wherein the TCR is expressed on the surface of the host cell and wherein the host cell is a hematopoietic progenitor cell or a human immune system cell selected from a CD4+T cell, a CD8+T cell, a CD4-CD8-double negative T cell, a γδ T cell, a natural killer cell, a natural killer T cell, a dendritic cell, or any combination thereof.

24. The method of claim 23, wherein the host cell is a CD4+cell, a CD8+T cell, or both.

25. The method of claim 24, wherein the host cell is a CD8+T cell.

26. The method of claim 22, wherein the hyperproliferative or proliferative disorder is a hematological malignancy or a solid cancer.

27. The method of claim 26, wherein:

(i) the hematological malignancy is selected from acute myeloid leukemia (AML), acute lymphoblastic leukemia (ALL), chronic myelogenous leukemia (CML), chronic eosinophilic leukemia (CEL), myelodysplastic syndrome (MDS), non-Hodgkin's lymphoma (NHL), or multiple myeloma (MM); and/or (ii) the solid cancer is selected from breast cancer, ovarian cancer, lung cancer, biliary cancer, bladder cancer, bone and soft tissue carcinoma, brain tumor, cervical cancer, colon cancer, colorectal adenocarcinoma, colorectal cancer, desmoid tumor, embryonal cancer, endometrial cancer, esophageal cancer, gastric cancer, gastric adenocarcinoma, glioblastoma multiforme, gynecological tumor, head and neck squamous cell carcinoma, hepatic cancer, mesothelioma, malignant melanoma, osteosarcoma, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, testicular germ-cell tumor, urothelial cancer, uterine sarcoma, or uterine cancer.

28. An adoptive immunotherapy method for alleviating symptoms or prolonging survival of a subject having a hyperproliferative or proliferative disorder characterized by WT1 overexpression, comprising administering to the subject an effective amount of the host cell of claim 20, wherein:

(a) the subject is human; and/or (b) the host cell was modified ex vivo to comprise the heterologous polynucleotide encoding the TCR, wherein, optionally, the recombinant host cell is an allogeneic cell, a syngeneic cell, or an autologous cell to the subject; and/or (c) the host cell is formulated for parenteral administration, wherein, optionally, the host cell is formulated for administration to the subject at a dose of about $10^7$ cells/$m^2$ to about $10^{11}$ cells/$m^2$; and/or (d) the host cell is formulated for administering a plurality of doses of the host cell to the subject, wherein, optionally, the plurality of doses are formulated for administration at intervals between administrations of about two to about four weeks; and/or (e) the subject is further receiving immunosuppressive therapy, wherein, optionally, the immunosuppressive therapy is selected from calcineurin inhibitors, corticosteroids, microtubule inhibitors, low dose of a mycophenolic acid prodrug, or any combination thereof; and/or (f) the subject has received a non-myeloablative or a myeloablative hematopoietic cell transplant; wherein, optionally, the subject is administered the host cell at least three months after the non-myeloablative hematopoietic cell transplant; wherein, further optionally, the subject is administered the host cell at least two months after the myeloablative hematopoietic cell transplant; and/or (g) the subject has received or is receiving an immune checkpoint inhibitor and/or an agonist of a stimulatory immune checkpoint agent.

29. The host cell of claim 1, wherein the host cell is a T cell.

30. The host cell of claim 1, wherein the host cell is capable of killing:

(i) a tumor cell of breast cancer cell line MDA-MB-468;

(ii) a tumor cell of pancreatic adenocarcinoma cell line PANC-1;

(iii) a tumor cell of breast cancer cell line MDA-MB-231;

(iv) a tumor cell of myelogenous leukemia cell line K562 expressing an HLA-A2, wherein, optionally, the HLA-A2 comprises HLA-A*201;

(v) a tumor cell of colon carcinoma cell line RKO expressing an HLA-A2, wherein, optionally, the HLA-A2 comprises HLA-A*201; or (vi) any combination of tumor cells of (i)-(v), when the host cell and the tumor cell are both present in a sample.

31. A composition, comprising the host cell of claim 1 and a pharmaceutically acceptable carrier, diluent, or excipient.

32. The composition of claim 31, wherein the composition comprises a host CD4+T cell and/or a host CD8+T cell.

33. A unit dose form comprising the host cell of claim 1, wherein the host cell is at a dose of about $10^7$ cells/$m^2$ to about $10^{11}$ cells/$m^2$.

34. The host cell of claim 1, wherein:

(i) the Vα domain of the TCR consists of the amino acid sequence set forth in SEQ ID NO.: 253; and (ii) the Vβ domain of the TCR consists of the amino acid sequence set forth in SEQ ID NO.: 242.

35. The host cell of claim 1, wherein the TCR comprises a TCR α-chain comprising the Vα domain and an α-chain constant domain, wherein the Vα domain consists of the amino acid sequence set forth in SEQ ID NO:253, and the α-chain constant domain consists of the amino acid sequence of SEQ ID NO:47.

36. The host cell of claim 1, wherein the Vα domain and the Vβ domain of the TCR consist of the amino acid sequences set forth in SEQ ID NOs:253 and 242, respectively, and wherein the TCR comprises a TCR α-chain constant domain and a TCR β-chain constant domain, and wherein the TCR α-chain constant domain and the TCR β-chain constant domain comprise a non-native cysteine.

37. The host cell of claim 1, wherein the polynucleotide encoding the TCR comprises (a) a sequence encoding the amino acid sequence set forth in SEQ ID NO:34, and/or (b) a sequence encoding the amino acid sequence set forth in SEQ ID NO:23.

38. The host cell of claim 1, wherein the polynucleotide encoding the TCR comprises (a) a sequence encoding an amino acid sequence having at least 90% sequence identity to the amino acid sequence set forth in SEQ ID NO.: 34, and (b) a sequence encoding an amino acid sequence having at least 98% sequence identity to the amino acid sequence of SEQ ID NO:47.

39. The host cell of claim 1, wherein the polynucleotide encoding the TCR comprises (a) a sequence encoding an amino acid sequence having at least 90% sequence identity to the amino acid sequence set forth in SEQ ID NO.: 23, and (b) a sequence encoding the amino acid sequence of SEQ ID NO:45 or a sequence encoding an amino acid sequence having at least 95% sequence identity to the amino acid sequence of SEQ ID NO:46.

40. The host cell of claim 1, wherein the polynucleotide encoding the TCR comprises a sequence encoding the amino acid sequence set forth in SEQ ID NO.: 23, and a sequence encoding the amino acid sequence of SEQ ID NO:46.

41. The host cell of claim 1, wherein the TCR comprises a TCR a chain and a TCR β-chain.

42. A recombinant expression vector comprising a heterologous polynucleotide encoding a T cell receptor (TCR) operably linked to an expression control sequence, wherein the TCR comprises:

(a) a TCR α-chain variable (Vα) domain comprising the CDR1α amino acid sequence set forth in SEQ ID NO:194, the CDR2a amino acid sequence set forth in SEQ ID NO:195, and the CDR3a amino acid sequence set forth in SEQ ID NO:196 or 12; and (b) a TCR β-chain variable (VB) domain comprising the CDR1β amino acid sequence set forth in SEQ ID NO:197, the CDR2β amino acid sequence set forth in SEQ ID NO:198, and the CDR3β amino acid sequence set forth in SEQ ID NO:199 or 1, wherein the TCR binds to a VLDFAPPGA (SEQ ID NO:59): human leukocyte antigen (HLA) complex, wherein the HLA comprises HLA-A*201.

43. The recombinant expression vector of claim 42, wherein:

(i) the Vα domain comprises the amino acid sequence set forth in SEQ ID NO: 253 and/or (ii) the Vβ domain comprises the amino acid sequence set forth in SEQ ID NO: 242.

44. The recombinant expression vector of claim 42, wherein the TCR comprises a TCR α-chain constant domain and a TCR β-chain constant domain, and wherein the TCR α-chain constant domain and the TCR β-chain constant domain comprise a non-native cysteine.

45. The recombinant expression vector of claim 44, wherein the α-chain constant domain comprises the amino acid sequence set forth in SEQ ID NO:47, and wherein the β chain constant domain comprises the amino acid sequence set forth SEQ ID NO:46.

46. The recombinant expression vector of claim 42, wherein the vector is a viral vector selected from an adenoviral vector, a lentiviral vector, or a y-retroviral vector.

47. The recombinant expression vector of claim 42, wherein the polynucleotide encoding the TCR comprises:

(i) a sequence encoding the amino acid sequence set forth in SEQ ID NO:34 and/or (ii) a sequence encoding the amino acid sequence set forth in SEQ ID NO:23.

48. A T cell receptor (TCR) comprising a TCR α-chain and a TCR β-chain, wherein:

(i) the TCR α-chain comprises the CDR1a amino acid sequence set forth in SEQ ID NO:194, the CDR2a amino acid sequence set forth in SEQ ID NO:195, and the CDR3a amino acid sequence set forth in SEQ ID NO:196 or 12;

(ii) the TCR β-chain comprises the CDR1β amino acid sequence set forth in SEQ ID NO:197, the CDR2β amino acid sequence set forth in SEQ ID NO:198, and the CDR3β amino acid sequence set forth in SEQ ID NO:199 or 1; and (iii) the TCR α-chain, the TCR β-chain, or both, comprise a non-native cysteine in a respective TCR constant domain.

49. The TCR of claim 48, wherein the TCR α-chain comprises the amino acid sequence set forth in SEQ ID NO:47, and wherein the TCR β-chain comprises the amino acid sequence set forth SEQ ID NO:46.

* * * * *

SEQUENCE LISTING

```
<160> NUMBER OF SEQ ID NOS: 263

<210> SEQ ID NO 1
<211> LENGTH: 13
<212> TYPE: PRT
```

<213> ORGANISM: Artificial Sequence
<220> FEATURE:
<223> OTHER INFORMATION: Synthetic sequence WT137-45 TCR10.1 - beta CDR3
(IMGT junction)

<400> SEQUENCE: 1

Cys Ala Ser Ser Leu Thr Gly Ser Tyr Glu Gln Tyr Phe
1 5 10

<210> SEQ ID NO 2
<211> LENGTH: 15
<212> TYPE: PRT
<213> ORGANISM: Artificial Sequence
<220> FEATURE:
<223> OTHER INFORMATION: Synthetic sequence WT137-45 TCR11.2 - beta CDR3
(IMGT junction)

<400> SEQUENCE: 2

Cys Ser Ala Thr Pro Glu Ala Ser Ser Pro Tyr Glu Gln Tyr Phe
1 5 10 15

<210> SEQ ID NO 3
<211> LENGTH: 14
<212> TYPE: PRT
<213> ORGANISM: Artificial Sequence
<220> FEATURE:
<223> OTHER INFORMATION: Synthetic sequence WT137-45 TCR12.1 - beta CDR3
(IMGT junction)

<400> SEQUENCE: 3

Cys Ala Thr Ser Asn Leu Gln Gly Arg Gln Pro Gln His Phe
1 5 10

<210> SEQ ID NO 4
<211> LENGTH: 14
<212> TYPE: PRT
<213> ORGANISM: Artificial Sequence
<220> FEATURE:
<223> OTHER INFORMATION: Synthetic sequence WT137-45 TCR13.1 - beta CDR3
(IMGT junction)

<400> SEQUENCE: 4

Cys Ala Ser Ser Leu Arg Leu Gly Arg Glu Thr Gln Tyr Phe
1 5 10

<210> SEQ ID NO 5
<211> LENGTH: 13
<212> TYPE: PRT
<213> ORGANISM: Artificial Sequence
<220> FEATURE:
<223> OTHER INFORMATION: Synthetic sequence WT137-45 TCR13.2 - beta CDR3
(IMGT junction)

<400> SEQUENCE: 5

Cys Ala Ser Ser Leu Gly Gln Ala Tyr Glu Gln Tyr Phe
1 5 10

<210> SEQ ID NO 6
<211> LENGTH: 13
<212> TYPE: PRT
<213> ORGANISM: Artificial Sequence
<220> FEATURE:
<223> OTHER INFORMATION: Synthetic sequence WT137-45 TCR14.1 - beta CDR3
(IMGT junction)

<400> SEQUENCE: 6

Cys Ala Ser Ser Leu Thr Arg Gly Ala Glu Ala Phe Phe
1 5 10

<210> SEQ ID NO 7
<211> LENGTH: 15
<212> TYPE: PRT
<213> ORGANISM: Artificial Sequence
<220> FEATURE:
<223> OTHER INFORMATION: Synthetic sequence WT137-45 TCR15.1 - beta
CDR3 (IMGT junction)

<400> SEQUENCE: 7

```
Cys Ala Ser Ser Arg Asp Arg Glu Gln Glu Ser Pro Leu His Phe
1               5                   10                  15
```

<210> SEQ ID NO 8
<211> LENGTH: 14
<212> TYPE: PRT
<213> ORGANISM: Artificial Sequence
<220> FEATURE:
<223> OTHER INFORMATION: Synthetic sequence WT137-45 TCR16.1 - beta
CDR3 (IMGT junction)

<400> SEQUENCE: 8

```
Cys Ala Ser Ser Phe Ser Gly Gly Thr Tyr Glu Gln Tyr Phe
1               5                   10
```

<210> SEQ ID NO 9
<211> LENGTH: 15
<212> TYPE: PRT
<213> ORGANISM: Artificial Sequence
<220> FEATURE:
<223> OTHER INFORMATION: Synthetic sequence WT137-45 TCR16.2 - beta
CDR3 (IMGT junction)

<400> SEQUENCE: 9

```
Cys Ala Ser Ser Tyr Arg Gly Gly Ser Thr Tyr Glu Gln Tyr Phe
1               5                   10                  15
```

<210> SEQ ID NO 10
<211> LENGTH: 15
<212> TYPE: PRT
<213> ORGANISM: Artificial Sequence
<220> FEATURE:
<223> OTHER INFORMATION: Synthetic sequence WT137-45 TCR18.1 - beta
CDR3 (IMGT junction)

<400> SEQUENCE: 10

```
Cys Ala Ser Ser Gln Arg Asp Ser Pro Asn Glu Lys Leu Phe Phe
1               5                   10                  15
```

<210> SEQ ID NO 11
<211> LENGTH: 17
<212> TYPE: PRT
<213> ORGANISM: Artificial Sequence
<220> FEATURE:
<223> OTHER INFORMATION: Synthetic sequence WT137-45 TCR19.1 - beta
CDR3 (IMGT junction)

<400> SEQUENCE: 11

```
Cys Ala Ser Ser Gln Asp Pro Tyr Lys Leu Ser Gly Asn Thr Ile Tyr
1               5                   10                  15

Phe
```

<210> SEQ ID NO 12
<211> LENGTH: 13
<212> TYPE: PRT
<213> ORGANISM: Artificial Sequence
<220> FEATURE:

<223> OTHER INFORMATION: Synthetic sequence WT137-45 TCR10.1 - alpha
      CDR3 (IMGT junction)

<400> SEQUENCE: 12

Cys Ala Val Lys Glu Thr Ser Gly Ser Arg Leu Thr Phe
1               5                   10

<210> SEQ ID NO 13
<211> LENGTH: 17
<212> TYPE: PRT
<213> ORGANISM: Artificial Sequence
<220> FEATURE:
<223> OTHER INFORMATION: Synthetic sequence WT137-45 TCR11.2 - alpha
      CDR3 (IMGT junction)

<400> SEQUENCE: 13

Cys Ala Phe Ile Tyr Pro Ser Tyr Thr Ser Gly Thr Tyr Lys Tyr Ile
1               5                   10                  15

Phe

<210> SEQ ID NO 14
<211> LENGTH: 14
<212> TYPE: PRT
<213> ORGANISM: Artificial Sequence
<220> FEATURE:
<223> OTHER INFORMATION: Synthetic sequence WT137-45 TCR12.1 - alpha
      CDR3 (IMGT junction)

<400> SEQUENCE: 14

Cys Ala Ala Ser Gly Thr Gly Gly Ser Tyr Ile Pro Thr Phe
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetic sequence WT137-45 TCR13.1 - alpha
      CDR3 (IMGT junction)

<400> SEQUENCE: 15

Cys Ala Ala Ser Gly Ile Gly Asp Tyr Lys Leu Ser Phe
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic sequence WT137-45 TCR13.2 - alpha
      CDR3 (IMGT junction)

<400> SEQUENCE: 16

Cys Ala Val Arg Thr Ser Tyr Asp Lys Val Ile Phe
1               5                   10

<210> SEQ ID NO 17
<211> LENGTH: 16
<212> TYPE: PRT
<213> ORGANISM: Artificial Sequence
<220> FEATURE:
<223> OTHER INFORMATION: Synthetic sequence WT137-45 TCR14.1 - alpha
      CDR3 (IMGT junction)

<400> SEQUENCE: 17

Cys Ala Val Asn Leu Leu Gly Ala Thr Gly Tyr Ser Thr Leu Thr Phe
1               5                   10                  15

<210> SEQ ID NO 18
<211> LENGTH: 13
<212> TYPE: PRT
<213> ORGANISM: Artificial Sequence
<220> FEATURE:
<223> OTHER INFORMATION: Synthetic sequence WT137-45 TCR15.1 - alpha CDR3 (IMGT junction)

<400> SEQUENCE: 18

Cys Ala Val Arg Gly Ile Asn Asp Tyr Lys Leu Ser Phe
1 5 10

<210> SEQ ID NO 19
<211> LENGTH: 12
<212> TYPE: PRT
<213> ORGANISM: Artificial Sequence
<220> FEATURE:
<223> OTHER INFORMATION: Synthetic sequence WT137-45 TCR16.1 - alpha CDR3 (IMGT junction)

<400> SEQUENCE: 19

Cys Ala Val Ile Thr Gly Phe Gln Lys Leu Val Phe
1 5 10

<210> SEQ ID NO 20
<211> LENGTH: 13
<212> TYPE: PRT
<213> ORGANISM: Artificial Sequence
<220> FEATURE:
<223> OTHER INFORMATION: Synthetic sequence WT137-45 TCR16.2 - alpha CDR3 (IMGT junction)

<400> SEQUENCE: 20

Cys Ile Ala Gly Val Gly Arg Gly Gln Asn Phe Val Phe
1 5 10

<210> SEQ ID NO 21
<211> LENGTH: 14
<212> TYPE: PRT
<213> ORGANISM: Artificial Sequence
<220> FEATURE:
<223> OTHER INFORMATION: Synthetic sequence WT137-45 TCR18.1 - alpha CDR3 (IMGT junction)

<400> SEQUENCE: 21

Cys Ala Phe His Pro Asn Phe Gly Asn Glu Lys Leu Thr Phe
1 5 10

<210> SEQ ID NO 22
<211> LENGTH: 18
<212> TYPE: PRT
<213> ORGANISM: Artificial Sequence
<220> FEATURE:
<223> OTHER INFORMATION: Synthetic sequence WT137-45 TCR19.1 - alpha CDR3 (IMGT junction)

<400> SEQUENCE: 22

Cys Ala Val Gln Pro Arg Gly Asp Gly Ser Ser Asn Thr Gly Lys Leu
1 5 10 15

Ile Phe

<210> SEQ ID NO 23
<211> LENGTH: 133
<212> TYPE: PRT
<213> ORGANISM: Artificial Sequence
<220> FEATURE:

<223> OTHER INFORMATION: Synthetic sequence WT137-45 TCR10.1 - Vbeta

<400> SEQUENCE: 23

Met Gly Thr Ser Leu Leu Cys Trp Val Val Leu Gly Phe Leu Gly Thr
1 5 10 15

Asp His Thr Gly Ala Gly Val Ser Gln Ser Pro Arg Tyr Lys Val Thr
20 25 30

Lys Arg Gly Gln Asp Val Ala Leu Arg Cys Asp Pro Ile Ser Gly His
35 40 45

Val Ser Leu Tyr Trp Tyr Arg Gln Ala Leu Gly Gln Gly Pro Glu Phe
50 55 60

Leu Thr Tyr Phe Asn Tyr Glu Ala Gln Gln Asp Lys Ser Gly Leu Pro
65 70 75 80

Asn Asp Arg Phe Ser Ala Glu Arg Pro Glu Gly Ser Ile Ser Thr Leu
85 90 95

Thr Ile Gln Arg Thr Glu Gln Arg Asp Ser Ala Met Tyr Arg Cys Ala
100 105 110

Ser Ser Leu Thr Gly Ser Tyr Glu Gln Tyr Phe Gly Pro Gly Thr Arg
115 120 125

Leu Thr Val Thr Glu
130

<210> SEQ ID NO 24
<211> LENGTH: 133
<212> TYPE: PRT
<213> ORGANISM: Artificial Sequence
<220> FEATURE:
<223> OTHER INFORMATION: Synthetic sequence WT137-45 TCR11.2 - Vbeta

<400> SEQUENCE: 24

Met Leu Leu Leu Leu Leu Leu Leu Gly Pro Ala Gly Ser Gly Leu Gly
1 5 10 15

Ala Val Val Ser Gln His Pro Ser Trp Val Ile Cys Lys Ser Gly Thr
20 25 30

Ser Val Lys Ile Glu Cys Arg Ser Leu Asp Phe Gln Ala Thr Thr Met
35 40 45

Phe Trp Tyr Arg Gln Phe Pro Lys Gln Ser Leu Met Leu Met Ala Thr
50 55 60

Ser Asn Glu Gly Ser Lys Ala Thr Tyr Glu Gln Gly Val Glu Lys Asp
65 70 75 80

Lys Phe Leu Ile Asn His Ala Ser Leu Thr Leu Ser Thr Leu Thr Val
85 90 95

Thr Ser Ala His Pro Glu Asp Ser Ser Phe Tyr Ile Cys Ser Ala Thr
100 105 110

Pro Glu Ala Ser Ser Pro Tyr Glu Gln Tyr Phe Gly Pro Gly Thr Arg
115 120 125

Leu Thr Val Thr Glu
130

<210> SEQ ID NO 25
<211> LENGTH: 133
<212> TYPE: PRT
<213> ORGANISM: Artificial Sequence
<220> FEATURE:
<223> OTHER INFORMATION: Synthetic sequence WT137-45 TCR12.1 - Vbeta

<400> SEQUENCE: 25

Met Gly Pro Gly Leu Leu His Trp Met Ala Leu Cys Leu Leu Gly Thr

```
1               5                   10                  15

Gly His Gly Asp Ala Met Val Ile Gln Asn Pro Arg Tyr Gln Val Thr
            20                  25                  30

Gln Phe Gly Lys Pro Val Thr Leu Ser Cys Ser Gln Thr Leu Asn His
        35                  40                  45

Asn Val Met Tyr Trp Tyr Gln Gln Lys Ser Ser Gln Ala Pro Lys Leu
    50                  55                  60

Leu Phe His Tyr Tyr Asp Lys Asp Phe Asn Asn Glu Ala Asp Thr Pro
65                  70                  75                  80

Asp Asn Phe Gln Ser Arg Arg Pro Asn Thr Ser Phe Cys Phe Leu Asp
                85                  90                  95

Ile Arg Ser Pro Gly Leu Gly Asp Ala Ala Met Tyr Leu Cys Ala Thr
            100                 105                 110

Ser Asn Leu Gln Gly Arg Gln Pro Gln His Phe Gly Asp Gly Thr Arg
        115                 120                 125

Leu Ser Ile Leu Glu
    130


<210> SEQ ID NO 26
<211> LENGTH: 143
<212> TYPE: PRT
<213> ORGANISM: Artificial Sequence
<220> FEATURE:
<223> OTHER INFORMATION: Synthetic sequence WT137-45 TCR13.1 - Vbeta

<400> SEQUENCE: 26

Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
            20                  25                  30

Val Ile Gln Ser Pro Arg His Leu Ile Lys Glu Lys Arg Glu Thr Ala
        35                  40                  45

Thr Leu Lys Cys Tyr Pro Ile Pro Arg His Asp Thr Val Tyr Trp Tyr
    50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Leu Arg Leu Gly Arg
        115                 120                 125

Glu Thr Gln Tyr Phe Gly Pro Gly Thr Arg Leu Leu Val Leu Glu
    130                 135                 140


<210> SEQ ID NO 27
<211> LENGTH: 133
<212> TYPE: PRT
<213> ORGANISM: Artificial Sequence
<220> FEATURE:
<223> OTHER INFORMATION: Synthetic sequence WT137-45 TCR13.2 - Vbeta

<400> SEQUENCE: 27

Met Gly Thr Arg Leu Leu Cys Trp Val Val Leu Gly Phe Leu Gly Thr
1               5                   10                  15

Asp His Thr Gly Ala Gly Val Ser Gln Ser Pro Arg Tyr Lys Val Ala
            20                  25                  30
```

```
Lys Arg Gly Gln Asp Val Ala Leu Arg Cys Asp Pro Ile Ser Gly His
        35                  40                  45

Val Ser Leu Phe Trp Tyr Gln Gln Ala Leu Gly Gln Gly Pro Glu Phe
    50                  55                  60

Leu Thr Tyr Phe Gln Asn Glu Ala Gln Leu Asp Lys Ser Gly Leu Pro
65                  70                  75                  80

Ser Asp Arg Phe Phe Ala Glu Arg Pro Glu Gly Ser Val Ser Thr Leu
                85                  90                  95

Lys Ile Gln Arg Thr Gln Gln Glu Asp Ser Ala Val Tyr Leu Cys Ala
            100                 105                 110

Ser Ser Leu Gly Gln Ala Tyr Glu Gln Tyr Phe Gly Pro Gly Thr Arg
        115                 120                 125

Leu Thr Val Thr Glu
    130


<210> SEQ ID NO 28
<211> LENGTH: 133
<212> TYPE: PRT
<213> ORGANISM: Artificial Sequence
<220> FEATURE:
<223> OTHER INFORMATION: Synthetic sequence WT137-45 TCR14.1 - Vbeta

<400> SEQUENCE: 28

Met Gly Thr Arg Leu Leu Cys Trp Val Ala Phe Cys Leu Leu Val Glu
1               5                   10                  15

Glu Leu Ile Glu Ala Gly Val Val Gln Ser Pro Arg Tyr Lys Ile Ile
            20                  25                  30

Glu Lys Lys Gln Pro Val Ala Phe Trp Cys Asn Pro Ile Ser Gly His
        35                  40                  45

Asn Thr Leu Tyr Trp Tyr Leu Gln Asn Leu Gly Gln Gly Pro Glu Leu
    50                  55                  60

Leu Ile Arg Tyr Glu Asn Glu Glu Ala Val Asp Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Glu Leu Gly Asp Ser Ala Val Tyr Leu Cys Ala
            100                 105                 110

Ser Ser Leu Thr Arg Gly Ala Glu Ala Phe Phe Gly Gln Gly Thr Arg
        115                 120                 125

Leu Thr Val Val Glu
    130


<210> SEQ ID NO 29
<211> LENGTH: 134
<212> TYPE: PRT
<213> ORGANISM: Artificial Sequence
<220> FEATURE:
<223> OTHER INFORMATION: Synthetic sequence WT137-45 TCR15.1 - Vbeta

<400> SEQUENCE: 29

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60
```

```
Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Arg Asp Arg Glu Gln Glu Ser Pro Leu His Phe Gly Asn Gly Thr
        115                 120                 125

Arg Leu Thr Val Thr Glu
    130


<210> SEQ ID NO 30
<211> LENGTH: 133
<212> TYPE: PRT
<213> ORGANISM: Artificial Sequence
<220> FEATURE:
<223> OTHER INFORMATION: Synthetic sequence WT137-45 TCR16.1 - Vbeta

<400> SEQUENCE: 30

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Phe Ser Gly Gly Thr Tyr Glu Gln Tyr Phe Gly Pro Gly Thr Arg
        115                 120                 125

Leu Thr Val Thr Glu
    130


<210> SEQ ID NO 31
<211> LENGTH: 144
<212> TYPE: PRT
<213> ORGANISM: Artificial Sequence
<220> FEATURE:
<223> OTHER INFORMATION: Synthetic sequence WT137-45 TCR16.2 - Vbeta

<400> SEQUENCE: 31

Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
            20                  25                  30

Val Ile Gln Ser Pro Arg His Leu Ile Lys Glu Lys Arg Glu Thr Ala
        35                  40                  45

Thr Leu Lys Cys Tyr Pro Ile Pro Arg His Asp Thr Val Tyr Trp Tyr
    50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
```

```
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Tyr Arg Gly Gly Ser
        115                 120                 125

Thr Tyr Glu Gln Tyr Phe Gly Pro Gly Thr Arg Leu Thr Val Thr Glu
    130                 135                 140


<210> SEQ ID NO 32
<211> LENGTH: 135
<212> TYPE: PRT
<213> ORGANISM: Artificial Sequence
<220> FEATURE:
<223> OTHER INFORMATION: Synthetic sequence WT137-45 TCR18.1 - Vbeta

<400> SEQUENCE: 32

Met Ser Thr Arg Leu Leu Cys Trp Met Ala Leu Cys Leu Leu Gly Ala
1               5                   10                  15

Glu Leu Ser Glu Ala Glu Val Ala Gln Ser Pro Arg Tyr Lys Ile Thr
            20                  25                  30

Glu Lys Ser Gln Ala Val Ala Phe Trp Cys Asp Pro Ile Ser Gly His
        35                  40                  45

Ala Thr Leu Tyr Trp Tyr Arg Gln Ile Leu Gly Gln Gly Pro Glu Leu
    50                  55                  60

Leu Val Gln Phe Gln Asp Glu Ser Val Val Asp Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Glu Leu Gly Asp Ser Ala Met Tyr Leu Cys Ala
            100                 105                 110

Ser Ser Gln Arg Asp Ser Pro Asn Glu Lys Leu Phe Phe Gly Ser Gly
        115                 120                 125

Thr Gln Leu Ser Val Leu Glu
    130                 135


<210> SEQ ID NO 33
<211> LENGTH: 136
<212> TYPE: PRT
<213> ORGANISM: Artificial Sequence
<220> FEATURE:
<223> OTHER INFORMATION: Synthetic sequence WT137-45 TCR19.1 - Vbeta

<400> SEQUENCE: 33

Met Gly Cys Arg Leu Leu Cys Cys Ala Val Leu Cys Leu Leu Gly Ala
1               5                   10                  15

Val Pro Met Glu Thr Gly Val Thr Gln Thr Pro Arg His Leu Val Met
            20                  25                  30

Gly Met Thr Asn Lys Lys Ser Leu Lys Cys Glu Gln His Leu Gly His
        35                  40                  45

Asn Ala Met Tyr Trp Tyr Lys Gln Ser Ala Lys Lys Pro Leu Glu Leu
    50                  55                  60

Met Phe Val Tyr Ser Leu Glu Glu Arg Val Glu Asn Asn Ser Val Pro
65                  70                  75                  80

Ser Arg Phe Ser Pro Glu Cys Pro Asn Ser Ser His Leu Phe Leu His
                85                  90                  95

Leu His Thr Leu Gln Pro Glu Asp Ser Ala Leu Tyr Leu Cys Ala Ser
            100                 105                 110
```

```
Ser Gln Asp Pro Tyr Lys Leu Ser Gly Asn Thr Ile Tyr Phe Gly Glu
        115                 120                 125

Gly Ser Trp Leu Thr Val Val Glu
    130                 135


<210> SEQ ID NO 34
<211> LENGTH: 131
<212> TYPE: PRT
<213> ORGANISM: Artificial Sequence
<220> FEATURE:
<223> OTHER INFORMATION: Synthetic sequence WT137-45 TCR10.1 Valpha

<400> SEQUENCE: 34

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Lys
            100                 105                 110

Glu Thr Ser Gly Ser Arg Leu Thr Phe Gly Glu Gly Thr Gln Leu Thr
        115                 120                 125

Val Asn Pro
    130


<210> SEQ ID NO 35
<211> LENGTH: 139
<212> TYPE: PRT
<213> ORGANISM: Artificial Sequence
<220> FEATURE:
<223> OTHER INFORMATION: Synthetic sequence WT137-45 TCR11.2 Valpha

<400> SEQUENCE: 35

Met Thr Arg Val Ser Leu Leu Trp Ala Val Val Val Ser Thr Cys Leu
1               5                   10                  15

Glu Ser Gly Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Asn Asn Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Thr Ala Met Tyr Phe Cys
            100                 105                 110

Ala Phe Ile Tyr Pro Ser Tyr Thr Ser Gly Thr Tyr Lys Tyr Ile Phe
        115                 120                 125

Gly Thr Gly Thr Arg Leu Lys Val Leu Ala Asn
    130                 135
```

<210> SEQ ID NO 36
<211> LENGTH: 140
<212> TYPE: PRT
<213> ORGANISM: Artificial Sequence
<220> FEATURE:
<223> OTHER INFORMATION: Synthetic sequence WT137-45 TCR12.1 Valpha

<400> SEQUENCE: 36

```
Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
    50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Ser Gly Thr Gly Gly Ser Tyr Ile Pro Thr
        115                 120                 125

Phe Gly Arg Gly Thr Ser Leu Ile Val His Pro Tyr
    130                 135                 140
```

<210> SEQ ID NO 37
<211> LENGTH: 139
<212> TYPE: PRT
<213> ORGANISM: Artificial Sequence
<220> FEATURE:
<223> OTHER INFORMATION: Synthetic sequence WT137-45 TCR13.1 Valpha

<400> SEQUENCE: 37

```
Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
    50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Ser Gly Ile Gly Asp Tyr Lys Leu Ser Phe
        115                 120                 125

Gly Ala Gly Thr Thr Val Thr Val Arg Ala Asn
    130                 135
```

<210> SEQ ID NO 38
<211> LENGTH: 131
<212> TYPE: PRT

<213> ORGANISM: Artificial Sequence
<220> FEATURE:
<223> OTHER INFORMATION: Synthetic sequence WT137-45 TCR13.2 Valpha

<400> SEQUENCE: 38

```
Met Val Lys Ile Arg Gln Phe Leu Leu Ala Ile Leu Trp Leu Gln Leu
1               5                   10                  15

Ser Cys Val Ser Ala Ala Lys Asn Glu Val Glu Gln Ser Pro Gln Asn
            20                  25                  30

Leu Thr Ala Gln Glu Gly Glu Phe Ile Thr Ile Asn Cys Ser Tyr Ser
        35                  40                  45

Val Gly Ile Ser Ala Leu His Trp Leu Gln Gln His Pro Gly Gly Gly
    50                  55                  60

Ile Val Ser Leu Phe Met Leu Ser Ser Gly Lys Lys Lys His Gly Arg
65                  70                  75                  80

Leu Ile Ala Thr Ile Asn Ile Gln Glu Lys His Ser Ser Leu His Ile
                85                  90                  95

Thr Ala Ser His Pro Arg Asp Ser Ala Val Tyr Ile Cys Ala Val Arg
            100                 105                 110

Thr Ser Tyr Asp Lys Val Ile Phe Gly Pro Gly Thr Ser Leu Ser Val
        115                 120                 125

Ile Pro Asn
    130
```

<210> SEQ ID NO 39
<211> LENGTH: 135
<212> TYPE: PRT
<213> ORGANISM: Artificial Sequence
<220> FEATURE:
<223> OTHER INFORMATION: Synthetic sequence WT137-45 TCR14.1 Valpha

<400> SEQUENCE: 39

```
Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Asn Leu Leu Gly Ala Thr Gly Tyr Ser Thr Leu Thr Phe Gly Lys Gly
        115                 120                 125

Thr Met Leu Leu Val Ser Pro
    130                 135
```

<210> SEQ ID NO 40
<211> LENGTH: 128
<212> TYPE: PRT
<213> ORGANISM: Artificial Sequence
<220> FEATURE:
<223> OTHER INFORMATION: Synthetic sequence WT137-45 TCR15.1 Valpha

<400> SEQUENCE: 40

```
Met Trp Gly Val Phe Leu Leu Tyr Val Ser Met Lys Met Gly Gly Thr
1               5                   10                  15

Thr Gly Gln Asn Ile Asp Gln Pro Thr Glu Met Thr Ala Thr Glu Gly
            20                  25                  30

Ala Ile Val Gln Ile Asn Cys Thr Tyr Gln Thr Ser Gly Phe Asn Gly
        35                  40                  45

Leu Phe Trp Tyr Gln Gln His Ala Gly Glu Ala Pro Thr Phe Leu Ser
    50                  55                  60

Tyr Asn Val Leu Asp Gly Leu Glu Glu Lys Gly Arg Phe Ser Ser Phe
65                  70                  75                  80

Leu Ser Arg Ser Lys Gly Tyr Ser Tyr Leu Leu Leu Lys Glu Leu Gln
                85                  90                  95

Met Lys Asp Ser Ala Ser Tyr Leu Cys Ala Val Arg Gly Ile Asn Asp
            100                 105                 110

Tyr Lys Leu Ser Phe Gly Ala Gly Thr Thr Val Thr Val Arg Ala Asn
        115                 120                 125


<210> SEQ ID NO 41
<211> LENGTH: 131
<212> TYPE: PRT
<213> ORGANISM: Artificial Sequence
<220> FEATURE:
<223> OTHER INFORMATION: Synthetic sequence WT137-45 TCR16.1 Valpha

<400> SEQUENCE: 41

Met Glu Lys Met Leu Glu Cys Ala Phe Ile Val Leu Trp Leu Gln Leu
1               5                   10                  15

Gly Trp Leu Ser Gly Glu Asp Gln Val Thr Gln Ser Pro Glu Ala Leu
            20                  25                  30

Arg Leu Gln Glu Gly Glu Ser Ser Ser Leu Asn Cys Ser Tyr Thr Val
        35                  40                  45

Ser Gly Leu Arg Gly Leu Phe Trp Tyr Arg Gln Asp Pro Gly Lys Gly
    50                  55                  60

Pro Glu Phe Leu Phe Thr Leu Tyr Ser Ala Gly Glu Glu Lys Glu Lys
65                  70                  75                  80

Glu Arg Leu Lys Ala Thr Leu Thr Lys Lys Glu Ser Phe Leu His Ile
                85                  90                  95

Thr Ala Pro Lys Pro Glu Asp Ser Ala Thr Tyr Leu Cys Ala Val Ile
            100                 105                 110

Thr Gly Phe Gln Lys Leu Val Phe Gly Thr Gly Thr Arg Leu Leu Val
        115                 120                 125

Ser Pro Asn
    130


<210> SEQ ID NO 42
<211> LENGTH: 128
<212> TYPE: PRT
<213> ORGANISM: Artificial Sequence
<220> FEATURE:
<223> OTHER INFORMATION: Synthetic sequence WT137-45 TCR16.2 Valpha

<400> SEQUENCE: 42

Met Arg Leu Val Ala Arg Val Thr Val Phe Leu Thr Phe Gly Thr Ile
1               5                   10                  15

Ile Asp Ala Lys Thr Thr Gln Pro Thr Ser Met Asp Cys Ala Glu Gly
            20                  25                  30

Arg Ala Ala Asn Leu Pro Cys Asn His Ser Thr Ile Ser Gly Asn Glu
```

```
        35                  40                  45

Tyr Val Tyr Trp Tyr Arg Gln Ile His Ser Gln Gly Pro Gln Tyr Ile
    50                  55                  60

Ile His Gly Leu Lys Asn Asn Glu Thr Asn Glu Met Ala Ser Leu Ile
65                  70                  75                  80

Ile Thr Glu Asp Arg Lys Ser Ser Thr Leu Ile Leu Pro His Ala Thr
                85                  90                  95

Leu Arg Asp Thr Ala Val Tyr Tyr Cys Ile Ala Gly Val Gly Arg Gly
            100                 105                 110

Gln Asn Phe Val Phe Gly Pro Gly Thr Arg Leu Ser Val Leu Pro Tyr
        115                 120                 125


<210> SEQ ID NO 43
<211> LENGTH: 136
<212> TYPE: PRT
<213> ORGANISM: Artificial Sequence
<220> FEATURE:
<223> OTHER INFORMATION: Synthetic sequence WT137-45 TCR18.1 Valpha

<400> SEQUENCE: 43

Met Glu Lys Asn Pro Leu Ala Ala Pro Leu Leu Ile Leu Trp Phe His
1               5                   10                  15

Leu Asp Cys Val Ser Ser Ile Leu Asn Val Glu Gln Ser Pro Gln Ser
            20                  25                  30

Leu His Val Gln Glu Gly Asp Ser Thr Asn Phe Thr Cys Ser Phe Pro
        35                  40                  45

Ser Ser Asn Phe Tyr Ala Leu His Trp Tyr Arg Trp Glu Thr Ala Lys
    50                  55                  60

Ser Pro Glu Ala Leu Phe Val Met Thr Leu Asn Gly Asp Glu Lys Lys
65                  70                  75                  80

Lys Gly Arg Ile Ser Ala Thr Leu Asn Thr Lys Glu Gly Tyr Ser Tyr
                85                  90                  95

Leu Tyr Ile Lys Gly Ser Gln Pro Glu Asp Ser Ala Thr Tyr Leu Cys
            100                 105                 110

Ala Phe His Pro Asn Phe Gly Asn Glu Lys Leu Thr Phe Gly Thr Gly
        115                 120                 125

Thr Arg Leu Thr Ile Ile Pro Asn
    130                 135


<210> SEQ ID NO 44
<211> LENGTH: 136
<212> TYPE: PRT
<213> ORGANISM: Artificial Sequence
<220> FEATURE:
<223> OTHER INFORMATION: Synthetic sequence WT137-45 TCR19.1 Valpha

<400> SEQUENCE: 44

Met Glu Lys Met Leu Glu Cys Ala Phe Ile Val Leu Trp Leu Gln Leu
1               5                   10                  15

Gly Trp Leu Ser Gly Glu Asp Gln Val Thr Gln Ser Pro Glu Ala Leu
            20                  25                  30

Arg Leu Gln Glu Gly Glu Ser Ser Ser Leu Asn Cys Ser Tyr Thr Val
        35                  40                  45

Ser Gly Leu Arg Gly Leu Phe Trp Tyr Arg Gln Asp Pro Gly Lys Gly
    50                  55                  60

Pro Glu Phe Leu Phe Thr Leu Tyr Ser Ala Gly Glu Glu Lys Glu Lys
65                  70                  75                  80
```

```
Glu Arg Leu Lys Ala Thr Leu Thr Lys Lys Glu Ser Phe Leu His Ile
                85                  90                  95

Thr Ala Pro Lys Pro Glu Asp Ser Ala Thr Tyr Leu Cys Ala Val Gln
            100                 105                 110

Pro Arg Gly Asp Gly Ser Ser Asn Thr Gly Lys Leu Ile Phe Gly Gln
        115                 120                 125

Gly Thr Thr Leu Gln Val Lys Pro
    130                 135
```

<210> SEQ ID NO 45
<211> LENGTH: 176
<212> TYPE: PRT
<213> ORGANISM: Artificial Sequence
<220> FEATURE:
<223> OTHER INFORMATION: Synthetic sequence WT137-45 TCR15.1 Cbeta

<400> SEQUENCE: 45

```
Asp Leu Asn Lys Val Phe Pro Pro Glu Val Ala Val Phe Glu Pro Ser
1               5                   10                  15

Glu Ala Glu Ile Ser His Thr Gln Lys Ala Thr Leu Val Cys Leu Ala
            20                  25                  30

Thr Gly Phe Phe Pro Asp His Val Glu Leu Ser Trp Trp Val Asn Gly
        35                  40                  45

Lys Glu Val His Ser Gly Val Cys Thr Asp Pro Gln Pro Leu Lys Glu
    50                  55                  60

Gln Pro Ala Leu Asn Asp Ser Arg Tyr Cys Leu Ser Ser Arg Leu Arg
65                  70                  75                  80

Val Ser Ala Thr Phe Trp Gln Asn Pro Arg Asn His Phe Arg Cys Gln
                85                  90                  95

Val Gln Phe Tyr Gly Leu Ser Glu Asn Asp Glu Trp Thr Gln Asp Arg
            100                 105                 110

Ala Lys Pro Val Thr Gln Ile Val Ser Ala Glu Ala Trp Gly Arg Ala
        115                 120                 125

Asp Cys Gly Phe Thr Ser Val Ser Tyr Gln Gln Gly Val Leu Ser Ala
    130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Phe
                165                 170                 175
```

<210> SEQ ID NO 46
<211> LENGTH: 178
<212> TYPE: PRT
<213> ORGANISM: Artificial Sequence
<220> FEATURE:
<223> OTHER INFORMATION: Synthetic sequence WT137-45 TCR16.2 Cbeta

<400> SEQUENCE: 46

```
Asp Leu Lys Asn Val Phe Pro Pro Glu Val Ala Val Phe Glu Pro Ser
1               5                   10                  15

Glu Ala Glu Ile Ser His Thr Gln Lys Ala Thr Leu Val Cys Leu Ala
            20                  25                  30

Thr Gly Phe Tyr Pro Asp His Val Glu Leu Ser Trp Trp Val Asn Gly
        35                  40                  45

Lys Glu Val His Ser Gly Val Cys Thr Asp Pro Gln Pro Leu Lys Glu
    50                  55                  60

Gln Pro Ala Leu Asn Asp Ser Arg Tyr Cys Leu Ser Ser Arg Leu Arg
65                  70                  75                  80
```

```
Val Ser Ala Thr Phe Trp Gln Asn Pro Arg Asn His Phe Arg Cys Gln
                85                  90                  95

Val Gln Phe Tyr Gly Leu Ser Glu Asn Asp Glu Trp Thr Gln Asp Arg
            100                 105                 110

Ala Lys Pro Val Thr Gln Ile Val Ser Ala Glu Ala Trp Gly Arg Ala
        115                 120                 125

Asp Cys Gly Phe Thr Ser Glu Ser Tyr Gln Gln Gly Val Leu Ser Ala
    130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Ser
                165                 170                 175

Arg Gly


<210> SEQ ID NO 47
<211> LENGTH: 140
<212> TYPE: PRT
<213> ORGANISM: Artificial Sequence
<220> FEATURE:
<223> OTHER INFORMATION: Synthetic sequence WT137-45 TCR15.1 Calpha

<400> SEQUENCE: 47

Ile Gln Asn Pro Asp Pro Ala Val Tyr Gln Leu Arg Asp Ser Lys Ser
1               5                   10                  15

Ser Asp Lys Ser Val Cys Leu Phe Thr Asp Phe Asp Ser Gln Thr Asn
            20                  25                  30

Val Ser Gln Ser Lys Asp Ser Asp Val Tyr Ile Thr Asp Lys Cys Val
        35                  40                  45

Leu Asp Met Arg Ser Met Asp Phe Lys Ser Asn Ser Ala Val Ala Trp
    50                  55                  60

Ser Asn Lys Ser Asp Phe Ala Cys Ala Asn Ala Phe Asn Asn Ser Ile
65                  70                  75                  80

Ile Pro Glu Asp Thr Phe Phe Pro Ser Pro Glu Ser Ser Cys Asp Val
                85                  90                  95

Lys Leu Val Glu Lys Ser Phe Glu Thr Asp Thr Asn Leu Asn Phe Gln
            100                 105                 110

Asn Leu Ser Val Ile Gly Phe Arg Ile Leu Leu Leu Lys Val Ala Gly
        115                 120                 125

Phe Asn Leu Leu Met Thr Leu Arg Leu Trp Ser Ser
    130                 135                 140


<210> SEQ ID NO 48
<211> LENGTH: 605
<212> TYPE: PRT
<213> ORGANISM: Artificial Sequence
<220> FEATURE:
<223> OTHER INFORMATION: Synthetic sequence WT1 37-45 TCR10.1 TCRbeta-
      P2A-TCRalpha

<400> SEQUENCE: 48

Met Gly Thr Ser Leu Leu Cys Trp Val Val Leu Gly Phe Leu Gly Thr
1               5                   10                  15

Asp His Thr Gly Ala Gly Val Ser Gln Ser Pro Arg Tyr Lys Val Thr
            20                  25                  30

Lys Arg Gly Gln Asp Val Ala Leu Arg Cys Asp Pro Ile Ser Gly His
        35                  40                  45

Val Ser Leu Tyr Trp Tyr Arg Gln Ala Leu Gly Gln Gly Pro Glu Phe
```

-continued

```
    50                  55                  60

Leu Thr Tyr Phe Asn Tyr Glu Ala Gln Gln Asp Lys Ser Gly Leu Pro
65                  70                  75                  80

Asn Asp Arg Phe Ser Ala Glu Arg Pro Glu Gly Ser Ile Ser Thr Leu
                85                  90                  95

Thr Ile Gln Arg Thr Glu Gln Arg Asp Ser Ala Met Tyr Arg Cys Ala
            100                 105                 110

Ser Ser Leu Thr Gly Ser Tyr Glu Gln Tyr Phe Gly Pro Gly Thr Arg
        115                 120                 125

Leu Thr Val Thr Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly Gly Ser Gly Ala Thr Asn Phe Ser Leu
305                 310                 315                 320

Leu Lys Gln Ala Gly Asp Val Glu Glu Asn Pro Gly Pro Met Glu Thr
                325                 330                 335

Leu Leu Gly Leu Leu Ile Leu Trp Leu Gln Leu Gln Trp Val Ser Ser
            340                 345                 350

Lys Gln Glu Val Thr Gln Ile Pro Ala Ala Leu Ser Val Pro Glu Gly
        355                 360                 365

Glu Asn Leu Val Leu Asn Cys Ser Phe Thr Asp Ser Ala Ile Tyr Asn
    370                 375                 380

Leu Gln Trp Phe Arg Gln Asp Pro Gly Lys Gly Leu Thr Ser Leu Leu
385                 390                 395                 400

Leu Ile Gln Ser Ser Gln Arg Glu Gln Thr Ser Gly Arg Leu Asn Ala
                405                 410                 415

Ser Leu Asp Lys Ser Ser Gly Arg Ser Thr Leu Tyr Ile Ala Ala Ser
            420                 425                 430

Gln Pro Gly Asp Ser Ala Thr Tyr Leu Cys Ala Val Lys Glu Thr Ser
        435                 440                 445

Gly Ser Arg Leu Thr Phe Gly Glu Gly Thr Gln Leu Thr Val Asn Pro
    450                 455                 460

Asp Ile Gln Asn Pro Asp Pro Ala Val Tyr Gln Leu Arg Asp Ser Lys
465                 470                 475                 480
```

```
Ser Ser Asp Lys Ser Val Cys Leu Phe Thr Asp Phe Asp Ser Gln Thr
                485                 490                 495

Asn Val Ser Gln Ser Lys Asp Ser Asp Val Tyr Ile Thr Asp Lys Cys
            500                 505                 510

Val Leu Asp Met Arg Ser Met Asp Phe Lys Ser Asn Ser Ala Val Ala
        515                 520                 525

Trp Ser Asn Lys Ser Asp Phe Ala Cys Ala Asn Ala Phe Asn Asn Ser
    530                 535                 540

Ile Ile Pro Glu Asp Thr Phe Phe Pro Ser Pro Glu Ser Ser Cys Asp
545                 550                 555                 560

Val Lys Leu Val Glu Lys Ser Phe Glu Thr Asp Thr Asn Leu Asn Phe
                565                 570                 575

Gln Asn Leu Ser Val Ile Gly Phe Arg Ile Leu Leu Leu Lys Val Ala
            580                 585                 590

Gly Phe Asn Leu Leu Met Thr Leu Arg Leu Trp Ser Ser
        595                 600                 605
```

```
<210> SEQ ID NO 49
<211> LENGTH: 612
<212> TYPE: PRT
<213> ORGANISM: Artificial Sequence
<220> FEATURE:
<223> OTHER INFORMATION: Synthetic sequence WT137-45 TCR11.2 TCRbeta-
      P2A-alpha

<400> SEQUENCE: 49

Met Leu Leu Leu Leu Leu Leu Leu Gly Pro Ala Gly Ser Gly Leu Gly
1               5                   10                  15

Ala Val Val Ser Gln His Pro Ser Trp Val Ile Cys Lys Ser Gly Thr
            20                  25                  30

Ser Val Lys Ile Glu Cys Arg Ser Leu Asp Phe Gln Ala Thr Thr Met
        35                  40                  45

Phe Trp Tyr Arg Gln Phe Pro Lys Gln Ser Leu Met Leu Met Ala Thr
    50                  55                  60

Ser Asn Glu Gly Ser Lys Ala Thr Tyr Glu Gln Gly Val Glu Lys Asp
65                  70                  75                  80

Lys Phe Leu Ile Asn His Ala Ser Leu Thr Leu Ser Thr Leu Thr Val
                85                  90                  95

Thr Ser Ala His Pro Glu Asp Ser Ser Phe Tyr Ile Cys Ser Ala Thr
            100                 105                 110

Pro Glu Ala Ser Ser Pro Tyr Glu Gln Tyr Phe Gly Pro Gly Thr Arg
        115                 120                 125

Leu Thr Val Thr Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
```

```
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly Gly Ser Gly Ala Thr Asn Phe Ser Leu
305                 310                 315                 320

Leu Lys Gln Ala Gly Asp Val Glu Glu Asn Pro Gly Pro Met Thr Arg
                325                 330                 335

Val Ser Leu Leu Trp Ala Val Val Val Ser Thr Cys Leu Glu Ser Gly
            340                 345                 350

Met Ala Gln Thr Val Thr Gln Ser Gln Pro Glu Met Ser Val Gln Glu
        355                 360                 365

Ala Glu Thr Val Thr Leu Ser Cys Thr Tyr Asp Thr Ser Glu Asn Asn
    370                 375                 380

Tyr Tyr Leu Phe Trp Tyr Lys Gln Pro Pro Ser Arg Gln Met Ile Leu
385                 390                 395                 400

Val Ile Arg Gln Glu Ala Tyr Lys Gln Gln Asn Ala Thr Glu Asn Arg
                405                 410                 415

Phe Ser Val Asn Phe Gln Lys Ala Ala Lys Ser Phe Ser Leu Lys Ile
            420                 425                 430

Ser Asp Ser Gln Leu Gly Asp Thr Ala Met Tyr Phe Cys Ala Phe Ile
        435                 440                 445

Tyr Pro Ser Tyr Thr Ser Gly Thr Tyr Lys Tyr Ile Phe Gly Thr Gly
    450                 455                 460

Thr Arg Leu Lys Val Leu Ala Asn Ile Gln Asn Pro Asp Pro Ala Val
465                 470                 475                 480

Tyr Gln Leu Arg Asp Ser Lys Ser Ser Asp Lys Ser Val Cys Leu Phe
                485                 490                 495

Thr Asp Phe Asp Ser Gln Thr Asn Val Ser Gln Ser Lys Asp Ser Asp
            500                 505                 510

Val Tyr Ile Thr Asp Lys Cys Val Leu Asp Met Arg Ser Met Asp Phe
        515                 520                 525

Lys Ser Asn Ser Ala Val Ala Trp Ser Asn Lys Ser Asp Phe Ala Cys
    530                 535                 540

Ala Asn Ala Phe Asn Asn Ser Ile Ile Pro Glu Asp Thr Phe Phe Pro
545                 550                 555                 560

Ser Pro Glu Ser Ser Cys Asp Val Lys Leu Val Glu Lys Ser Phe Glu
                565                 570                 575

Thr Asp Thr Asn Leu Asn Phe Gln Asn Leu Ser Val Ile Gly Phe Arg
            580                 585                 590

Ile Leu Leu Leu Lys Val Ala Gly Phe Asn Leu Leu Met Thr Leu Arg
        595                 600                 605

Leu Trp Ser Ser
    610
```

<210> SEQ ID NO 50
<211> LENGTH: 611
<212> TYPE: PRT
<213> ORGANISM: Artificial Sequence
<220> FEATURE:
<223> OTHER INFORMATION: Synthetic sequence WT137-45 TCR12.1 TCRbeta-
P2A-alpha

<400> SEQUENCE: 50

Met Gly Pro Gly Leu Leu His Trp Met Ala Leu Cys Leu Leu Gly Thr
1 5 10 15

Gly His Gly Asp Ala Met Val Ile Gln Asn Pro Arg Tyr Gln Val Thr
20 25 30

Gln Phe Gly Lys Pro Val Thr Leu Ser Cys Ser Gln Thr Leu Asn His
35 40 45

Asn Val Met Tyr Trp Tyr Gln Gln Lys Ser Ser Gln Ala Pro Lys Leu
50 55 60

Leu Phe His Tyr Tyr Asp Lys Asp Phe Asn Asn Glu Ala Asp Thr Pro
65 70 75 80

Asp Asn Phe Gln Ser Arg Arg Pro Asn Thr Ser Phe Cys Phe Leu Asp
85 90 95

Ile Arg Ser Pro Gly Leu Gly Asp Ala Ala Met Tyr Leu Cys Ala Thr
100 105 110

Ser Asn Leu Gln Gly Arg Gln Pro Gln His Phe Gly Asp Gly Thr Arg
115 120 125

Leu Ser Ile Leu Glu Asp Leu Asn Lys Val Phe Pro Pro Glu Val Ala
130 135 140

Val Phe Glu Pro Ser Glu Ala Glu Ile Ser His Thr Gln Lys Ala Thr
145 150 155 160

Leu Val Cys Leu Ala Thr Gly Phe Phe Pro Asp His Val Glu Leu Ser
165 170 175

Trp Trp Val Asn Gly Lys Glu Val His Ser Gly Val Cys Thr Asp Pro
180 185 190

Gln Pro Leu Lys Glu Gln Pro Ala Leu Asn Asp Ser Arg Tyr Cys Leu
195 200 205

Ser Ser Arg Leu Arg Val Ser Ala Thr Phe Trp Gln Asn Pro Arg Asn
210 215 220

His Phe Arg Cys Gln Val Gln Phe Tyr Gly Leu Ser Glu Asn Asp Glu
225 230 235 240

Trp Thr Gln Asp Arg Ala Lys Pro Val Thr Gln Ile Val Ser Ala Glu
245 250 255

Ala Trp Gly Arg Ala Asp Cys Gly Phe Thr Ser Val Ser Tyr Gln Gln
260 265 270

Gly Val Leu Ser Ala Thr Ile Leu Tyr Glu Ile Leu Leu Gly Lys Ala
275 280 285

Thr Leu Tyr Ala Val Leu Val Ser Ala Leu Val Leu Met Ala Met Val
290 295 300

Lys Arg Lys Asp Phe Gly Ser Gly Ala Thr Asn Phe Ser Leu Leu Lys
305 310 315 320

Gln Ala Gly Asp Val Glu Glu Asn Pro Gly Pro Met Ala Met Leu Leu
325 330 335

Gly Ala Ser Val Leu Ile Leu Trp Leu Gln Pro Asp Trp Val Asn Ser
340 345 350

Gln Gln Lys Asn Asp Asp Gln Gln Val Lys Gln Asn Ser Pro Ser Leu
355 360 365

Ser Val Gln Glu Gly Arg Ile Ser Ile Leu Asn Cys Asp Tyr Thr Asn
370 375 380

Ser Met Phe Asp Tyr Phe Leu Trp Tyr Lys Lys Tyr Pro Ala Glu Gly 385 390 395 400

Pro Thr Phe Leu Ile Ser Ile Ser Ser Ile Lys Asp Lys Asn Glu Asp
405 410 415

Gly Arg Phe Thr Val Phe Leu Asn Lys Ser Ala Lys His Leu Ser Leu
420 425 430

His Ile Val Pro Ser Gln Pro Gly Asp Ser Ala Val Tyr Phe Cys Ala
435 440 445

Ala Ser Gly Thr Gly Gly Ser Tyr Ile Pro Thr Phe Gly Arg Gly Thr
450 455 460

Ser Leu Ile Val His Pro Tyr Ile Gln Asn Pro Asp Pro Ala Val Tyr
465 470 475 480

Gln Leu Arg Asp Ser Lys Ser Ser Asp Lys Ser Val Cys Leu Phe Thr
485 490 495

Asp Phe Asp Ser Gln Thr Asn Val Ser Gln Ser Lys Asp Ser Asp Val
500 505 510

Tyr Ile Thr Asp Lys Cys Val Leu Asp Met Arg Ser Met Asp Phe Lys
515 520 525

Ser Asn Ser Ala Val Ala Trp Ser Asn Lys Ser Asp Phe Ala Cys Ala
530 535 540

Asn Ala Phe Asn Asn Ser Ile Ile Pro Glu Asp Thr Phe Phe Pro Ser
545 550 555 560

Pro Glu Ser Ser Cys Asp Val Lys Leu Val Glu Lys Ser Phe Glu Thr
565 570 575

Asp Thr Asn Leu Asn Phe Gln Asn Leu Ser Val Ile Gly Phe Arg Ile
580 585 590

Leu Leu Leu Lys Val Ala Gly Phe Asn Leu Leu Met Thr Leu Arg Leu
595 600 605

Trp Ser Ser
610

<210> SEQ ID NO 51
<211> LENGTH: 622
<212> TYPE: PRT
<213> ORGANISM: Artificial Sequence
<220> FEATURE:
<223> OTHER INFORMATION: Synthetic sequence WT137-45 TCR13.1 TCRbeta-
P2A-TCRalpha

<400> SEQUENCE: 51

Met Leu Ser Pro Asp Leu Pro Asp Ser Ala Trp Asn Thr Arg Leu Leu
1 5 10 15

Cys His Val Met Leu Cys Leu Leu Gly Ala Val Ser Val Ala Ala Gly
20 25 30

Val Ile Gln Ser Pro Arg His Leu Ile Lys Glu Lys Arg Glu Thr Ala
35 40 45

Thr Leu Lys Cys Tyr Pro Ile Pro Arg His Asp Thr Val Tyr Trp Tyr
50 55 60

Gln Gln Gly Pro Gly Gln Asp Pro Gln Phe Leu Ile Ser Phe Tyr Glu
65 70 75 80

Lys Met Gln Ser Asp Lys Gly Ser Ile Pro Asp Arg Phe Ser Ala Gln
85 90 95

Gln Phe Ser Asp Tyr His Ser Glu Leu Asn Met Ser Ser Leu Glu Leu
100 105 110

Gly Asp Ser Ala Leu Tyr Phe Cys Ala Ser Ser Leu Arg Leu Gly Arg
115 120 125

-continued

```
Glu Thr Gln Tyr Phe Gly Pro Gly Thr Arg Leu Leu Val Leu Glu Asp
    130                 135                 140

Leu Lys Asn Val Phe Pro Pro Glu Val Ala Val Phe Glu Pro Ser Glu
145                 150                 155                 160

Ala Glu Ile Ser His Thr Gln Lys Ala Thr Leu Val Cys Leu Ala Thr
                165                 170                 175

Gly Phe Tyr Pro Asp His Val Glu Leu Ser Trp Trp Val Asn Gly Lys
            180                 185                 190

Glu Val His Ser Gly Val Cys Thr Asp Pro Gln Pro Leu Lys Glu Gln
        195                 200                 205

Pro Ala Leu Asn Asp Ser Arg Tyr Cys Leu Ser Ser Arg Leu Arg Val
    210                 215                 220

Ser Ala Thr Phe Trp Gln Asn Pro Arg Asn His Phe Arg Cys Gln Val
225                 230                 235                 240

Gln Phe Tyr Gly Leu Ser Glu Asn Asp Glu Trp Thr Gln Asp Arg Ala
                245                 250                 255

Lys Pro Val Thr Gln Ile Val Ser Ala Glu Ala Trp Gly Arg Ala Asp
            260                 265                 270

Cys Gly Phe Thr Ser Glu Ser Tyr Gln Gln Gly Val Leu Ser Ala Thr
        275                 280                 285

Ile Leu Tyr Glu Ile Leu Leu Gly Lys Ala Thr Leu Tyr Ala Val Leu
    290                 295                 300

Val Ser Ala Leu Val Leu Met Ala Met Val Lys Arg Lys Asp Ser Arg
305                 310                 315                 320

Gly Gly Ser Gly Ala Thr Asn Phe Ser Leu Leu Lys Gln Ala Gly Asp
                325                 330                 335

Val Glu Glu Asn Pro Gly Pro Met Ala Met Leu Leu Gly Ala Ser Val
            340                 345                 350

Leu Ile Leu Trp Leu Gln Pro Asp Trp Val Asn Ser Gln Gln Lys Asn
        355                 360                 365

Asp Asp Gln Gln Val Lys Gln Asn Ser Pro Ser Leu Ser Val Gln Glu
    370                 375                 380

Gly Arg Ile Ser Ile Leu Asn Cys Asp Tyr Thr Asn Ser Met Phe Asp
385                 390                 395                 400

Tyr Phe Leu Trp Tyr Lys Lys Tyr Pro Ala Glu Gly Pro Thr Phe Leu
                405                 410                 415

Ile Ser Ile Ser Ser Ile Lys Asp Lys Asn Glu Asp Gly Arg Phe Thr
            420                 425                 430

Val Phe Leu Asn Lys Ser Ala Lys His Leu Ser Leu His Ile Val Pro
        435                 440                 445

Ser Gln Pro Gly Asp Ser Ala Val Tyr Phe Cys Ala Ala Ser Gly Ile
    450                 455                 460

Gly Asp Tyr Lys Leu Ser Phe Gly Ala Gly Thr Thr Val Thr Val Arg
465                 470                 475                 480

Ala Asn Ile Gln Asn Pro Asp Pro Ala Val Tyr Gln Leu Arg Asp Ser
                485                 490                 495

Lys Ser Ser Asp Lys Ser Val Cys Leu Phe Thr Asp Phe Asp Ser Gln
            500                 505                 510

Thr Asn Val Ser Gln Ser Lys Asp Ser Asp Val Tyr Ile Thr Asp Lys
        515                 520                 525

Cys Val Leu Asp Met Arg Ser Met Asp Phe Lys Ser Asn Ser Ala Val
    530                 535                 540

Ala Trp Ser Asn Lys Ser Asp Phe Ala Cys Ala Asn Ala Phe Asn Asn
```

545 550 555 560

Ser Ile Ile Pro Glu Asp Thr Phe Phe Pro Ser Pro Glu Ser Ser Cys
565 570 575

Asp Val Lys Leu Val Glu Lys Ser Phe Glu Thr Asp Thr Asn Leu Asn
580 585 590

Phe Gln Asn Leu Ser Val Ile Gly Phe Arg Ile Leu Leu Leu Lys Val
595 600 605

Ala Gly Phe Asn Leu Leu Met Thr Leu Arg Leu Trp Ser Ser
610 615 620

<210> SEQ ID NO 52
<211> LENGTH: 604
<212> TYPE: PRT
<213> ORGANISM: Artificial Sequence
<220> FEATURE:
<223> OTHER INFORMATION: Synthetic sequence WT1-37E TCR#62 - WT137-45
TCR13.2 TCRbeta-P2A-TCRalpha

<400> SEQUENCE: 52

Met Gly Thr Arg Leu Leu Cys Trp Val Val Leu Gly Phe Leu Gly Thr
1 5 10 15

Asp His Thr Gly Ala Gly Val Ser Gln Ser Pro Arg Tyr Lys Val Ala
20 25 30

Lys Arg Gly Gln Asp Val Ala Leu Arg Cys Asp Pro Ile Ser Gly His
35 40 45

Val Ser Leu Phe Trp Tyr Gln Gln Ala Leu Gly Gln Gly Pro Glu Phe
50 55 60

Leu Thr Tyr Phe Gln Asn Glu Ala Gln Leu Asp Lys Ser Gly Leu Pro
65 70 75 80

Ser Asp Arg Phe Phe Ala Glu Arg Pro Glu Gly Ser Val Ser Thr Leu
85 90 95

Lys Ile Gln Arg Thr Gln Gln Glu Asp Ser Ala Val Tyr Leu Cys Ala
100 105 110

Ser Ser Leu Gly Gln Ala Tyr Glu Gln Tyr Phe Gly Pro Gly Thr Arg
115 120 125

Leu Thr Val Thr Glu Asp Leu Lys Asn Val Phe Pro Pro Glu Val Ala
130 135 140

Val Phe Glu Pro Ser Glu Ala Glu Ile Ser His Thr Gln Lys Ala Thr
145 150 155 160

Leu Val Cys Leu Ala Thr Gly Phe Tyr Pro Asp His Val Glu Leu Ser
165 170 175

Trp Trp Val Asn Gly Lys Glu Val His Ser Gly Val Cys Thr Asp Pro
180 185 190

Gln Pro Leu Lys Glu Gln Pro Ala Leu Asn Asp Ser Arg Tyr Cys Leu
195 200 205

Ser Ser Arg Leu Arg Val Ser Ala Thr Phe Trp Gln Asn Pro Arg Asn
210 215 220

His Phe Arg Cys Gln Val Gln Phe Tyr Gly Leu Ser Glu Asn Asp Glu
225 230 235 240

Trp Thr Gln Asp Arg Ala Lys Pro Val Thr Gln Ile Val Ser Ala Glu
245 250 255

Ala Trp Gly Arg Ala Asp Cys Gly Phe Thr Ser Glu Ser Tyr Gln Gln
260 265 270

Gly Val Leu Ser Ala Thr Ile Leu Tyr Glu Ile Leu Leu Gly Lys Ala
275 280 285

```
Thr Leu Tyr Ala Val Leu Val Ser Ala Leu Val Leu Met Ala Met Val
    290                 295                 300

Lys Arg Lys Asp Ser Arg Gly Gly Ser Gly Ala Thr Asn Phe Ser Leu
305                 310                 315                 320

Leu Lys Gln Ala Gly Asp Val Glu Glu Asn Pro Gly Pro Met Val Lys
                325                 330                 335

Ile Arg Gln Phe Leu Leu Ala Ile Leu Trp Leu Gln Leu Ser Cys Val
            340                 345                 350

Ser Ala Ala Lys Asn Glu Val Glu Gln Ser Pro Gln Asn Leu Thr Ala
        355                 360                 365

Gln Glu Gly Glu Phe Ile Thr Ile Asn Cys Ser Tyr Ser Val Gly Ile
    370                 375                 380

Ser Ala Leu His Trp Leu Gln Gln His Pro Gly Gly Gly Ile Val Ser
385                 390                 395                 400

Leu Phe Met Leu Ser Ser Gly Lys Lys Lys His Gly Arg Leu Ile Ala
                405                 410                 415

Thr Ile Asn Ile Gln Glu Lys His Ser Ser Leu His Ile Thr Ala Ser
            420                 425                 430

His Pro Arg Asp Ser Ala Val Tyr Ile Cys Ala Val Arg Thr Ser Tyr
        435                 440                 445

Asp Lys Val Ile Phe Gly Pro Gly Thr Ser Leu Ser Val Ile Pro Asn
    450                 455                 460

Ile Gln Asn Pro Asp Pro Ala Val Tyr Gln Leu Arg Asp Ser Lys Ser
465                 470                 475                 480

Ser Asp Lys Ser Val Cys Leu Phe Thr Asp Phe Asp Ser Gln Thr Asn
                485                 490                 495

Val Ser Gln Ser Lys Asp Ser Asp Val Tyr Ile Thr Asp Lys Cys Val
            500                 505                 510

Leu Asp Met Arg Ser Met Asp Phe Lys Ser Asn Ser Ala Val Ala Trp
        515                 520                 525

Ser Asn Lys Ser Asp Phe Ala Cys Ala Asn Ala Phe Asn Asn Ser Ile
    530                 535                 540

Ile Pro Glu Asp Thr Phe Phe Pro Ser Pro Glu Ser Ser Cys Asp Val
545                 550                 555                 560

Lys Leu Val Glu Lys Ser Phe Glu Thr Asp Thr Asn Leu Asn Phe Gln
                565                 570                 575

Asn Leu Ser Val Ile Gly Phe Arg Ile Leu Leu Leu Lys Val Ala Gly
            580                 585                 590

Phe Asn Leu Leu Met Thr Leu Arg Leu Trp Ser Ser
        595                 600


<210> SEQ ID NO 53
<211> LENGTH: 607
<212> TYPE: PRT
<213> ORGANISM: Artificial Sequence
<220> FEATURE:
<223> OTHER INFORMATION: Synthetic sequence WT137-45 TCR14.1 TCRbeta-
      P2A-TCRalpha

<400> SEQUENCE: 53

Met Gly Thr Arg Leu Leu Cys Trp Val Ala Phe Cys Leu Leu Val Glu
1               5                   10                  15

Glu Leu Ile Glu Ala Gly Val Val Gln Ser Pro Arg Tyr Lys Ile Ile
            20                  25                  30

Glu Lys Lys Gln Pro Val Ala Phe Trp Cys Asn Pro Ile Ser Gly His
        35                  40                  45
```

-continued

Asn Thr Leu Tyr Trp Tyr Leu Gln Asn Leu Gly Gln Gly Pro Glu Leu
    50                  55                  60

Leu Ile Arg Tyr Glu Asn Glu Glu Ala Val Asp Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Glu Leu Gly Asp Ser Ala Val Tyr Leu Cys Ala
            100                 105                 110

Ser Ser Leu Thr Arg Gly Ala Glu Ala Phe Phe Gly Gln Gly Thr Arg
        115                 120                 125

Leu Thr Val Val Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Phe Gly Ser Gly Ala Thr Asn Phe Ser Leu Leu Lys
305                 310                 315                 320

Gln Ala Gly Asp Val Glu Glu Asn Pro Gly Pro Met Lys Ser Leu Arg
                325                 330                 335

Val Leu Leu Val Ile Leu Trp Leu Gln Leu Ser Trp Val Trp Ser Gln
            340                 345                 350

Gln Lys Glu Val Glu Gln Asn Ser Gly Pro Leu Ser Val Pro Glu Gly
        355                 360                 365

Ala Ile Ala Ser Leu Asn Cys Thr Tyr Ser Asp Arg Gly Ser Gln Ser
    370                 375                 380

Phe Phe Trp Tyr Arg Gln Tyr Ser Gly Lys Ser Pro Glu Leu Ile Met
385                 390                 395                 400

Phe Ile Tyr Ser Asn Gly Asp Lys Glu Asp Gly Arg Phe Thr Ala Gln
                405                 410                 415

Leu Asn Lys Ala Ser Gln Tyr Val Ser Leu Leu Ile Arg Asp Ser Gln
            420                 425                 430

Pro Ser Asp Ser Ala Thr Tyr Leu Cys Ala Val Asn Leu Leu Gly Ala
        435                 440                 445

Thr Gly Tyr Ser Thr Leu Thr Phe Gly Lys Gly Thr Met Leu Leu Val
    450                 455                 460

```
Ser Pro Asp Ile Gln Asn Pro Asp Pro Ala Val Tyr Gln Leu Arg Asp
465                 470                 475                 480

Ser Lys Ser Ser Asp Lys Ser Val Cys Leu Phe Thr Asp Phe Asp Ser
                485                 490                 495

Gln Thr Asn Val Ser Gln Ser Lys Asp Ser Asp Val Tyr Ile Thr Asp
            500                 505                 510

Lys Cys Val Leu Asp Met Arg Ser Met Asp Phe Lys Ser Asn Ser Ala
        515                 520                 525

Val Ala Trp Ser Asn Lys Ser Asp Phe Ala Cys Ala Asn Ala Phe Asn
    530                 535                 540

Asn Ser Ile Ile Pro Glu Asp Thr Phe Phe Pro Ser Pro Glu Ser Ser
545                 550                 555                 560

Cys Asp Val Lys Leu Val Glu Lys Ser Phe Glu Thr Asp Thr Asn Leu
                565                 570                 575

Asn Phe Gln Asn Leu Ser Val Ile Gly Phe Arg Ile Leu Leu Leu Lys
            580                 585                 590

Val Ala Gly Phe Asn Leu Leu Met Thr Leu Arg Leu Trp Ser Ser
        595                 600                 605


<210> SEQ ID NO 54
<211> LENGTH: 600
<212> TYPE: PRT
<213> ORGANISM: Artificial Sequence
<220> FEATURE:
<223> OTHER INFORMATION: Synthetic sequence WT137-45 TCR15.1 TCRbeta-
      P2A-TCRalpha

<400> SEQUENCE: 54

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Arg Asp Arg Glu Gln Glu Ser Pro Leu His Phe Gly Asn Gly Thr
        115                 120                 125

Arg Leu Thr Val Thr Glu Asp Leu Asn Lys Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Cys Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220
```

```
Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Phe Gly Ser Gly Ala Thr Asn Phe Ser Leu Leu
305                 310                 315                 320

Lys Gln Ala Gly Asp Val Glu Glu Asn Pro Gly Pro Met Trp Gly Val
                325                 330                 335

Phe Leu Leu Tyr Val Ser Met Lys Met Gly Gly Thr Thr Gly Gln Asn
            340                 345                 350

Ile Asp Gln Pro Thr Glu Met Thr Ala Thr Glu Gly Ala Ile Val Gln
        355                 360                 365

Ile Asn Cys Thr Tyr Gln Thr Ser Gly Phe Asn Gly Leu Phe Trp Tyr
    370                 375                 380

Gln Gln His Ala Gly Glu Ala Pro Thr Phe Leu Ser Tyr Asn Val Leu
385                 390                 395                 400

Asp Gly Leu Glu Glu Lys Gly Arg Phe Ser Ser Phe Leu Ser Arg Ser
                405                 410                 415

Lys Gly Tyr Ser Tyr Leu Leu Leu Lys Glu Leu Gln Met Lys Asp Ser
            420                 425                 430

Ala Ser Tyr Leu Cys Ala Val Arg Gly Ile Asn Asp Tyr Lys Leu Ser
        435                 440                 445

Phe Gly Ala Gly Thr Thr Val Thr Val Arg Ala Asn Ile Gln Asn Pro
    450                 455                 460

Asp Pro Ala Val Tyr Gln Leu Arg Asp Ser Lys Ser Ser Asp Lys Ser
465                 470                 475                 480

Val Cys Leu Phe Thr Asp Phe Asp Ser Gln Thr Asn Val Ser Gln Ser
                485                 490                 495

Lys Asp Ser Asp Val Tyr Ile Thr Asp Lys Cys Val Leu Asp Met Arg
            500                 505                 510

Ser Met Asp Phe Lys Ser Asn Ser Ala Val Ala Trp Ser Asn Lys Ser
        515                 520                 525

Asp Phe Ala Cys Ala Asn Ala Phe Asn Asn Ser Ile Ile Pro Glu Asp
    530                 535                 540

Thr Phe Phe Pro Ser Pro Glu Ser Ser Cys Asp Val Lys Leu Val Glu
545                 550                 555                 560

Lys Ser Phe Glu Thr Asp Thr Asn Leu Asn Phe Gln Asn Leu Ser Val
                565                 570                 575

Ile Gly Phe Arg Ile Leu Leu Leu Lys Val Ala Gly Phe Asn Leu Leu
            580                 585                 590

Met Thr Leu Arg Leu Trp Ser Ser
        595                 600
```

<210> SEQ ID NO 55
<211> LENGTH: 604
<212> TYPE: PRT
<213> ORGANISM: Artificial Sequence
<220> FEATURE:

<223> OTHER INFORMATION: Synthetic sequence WT137-45 TCR16.1 TCRbeta-
P2A-TCRalpha

<400> SEQUENCE: 55

```
Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Phe Ser Gly Gly Thr Tyr Glu Gln Tyr Phe Gly Pro Gly Thr Arg
        115                 120                 125

Leu Thr Val Thr Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly Gly Ser Gly Ala Thr Asn Phe Ser Leu
305                 310                 315                 320

Leu Lys Gln Ala Gly Asp Val Glu Glu Asn Pro Gly Pro Met Glu Lys
                325                 330                 335

Met Leu Glu Cys Ala Phe Ile Val Leu Trp Leu Gln Leu Gly Trp Leu
            340                 345                 350

Ser Gly Glu Asp Gln Val Thr Gln Ser Pro Glu Ala Leu Arg Leu Gln
        355                 360                 365

Glu Gly Glu Ser Ser Ser Leu Asn Cys Ser Tyr Thr Val Ser Gly Leu
    370                 375                 380

Arg Gly Leu Phe Trp Tyr Arg Gln Asp Pro Gly Lys Gly Pro Glu Phe
385                 390                 395                 400
```

Leu Phe Thr Leu Tyr Ser Ala Gly Glu Glu Lys Glu Lys Glu Arg Leu
405 410 415

Lys Ala Thr Leu Thr Lys Lys Glu Ser Phe Leu His Ile Thr Ala Pro
420 425 430

Lys Pro Glu Asp Ser Ala Thr Tyr Leu Cys Ala Val Ile Thr Gly Phe
435 440 445

Gln Lys Leu Val Phe Gly Thr Gly Thr Arg Leu Leu Val Ser Pro Asn
450 455 460

Ile Gln Asn Pro Asp Pro Ala Val Tyr Gln Leu Arg Asp Ser Lys Ser
465 470 475 480

Ser Asp Lys Ser Val Cys Leu Phe Thr Asp Phe Asp Ser Gln Thr Asn
485 490 495

Val Ser Gln Ser Lys Asp Ser Asp Val Tyr Ile Thr Asp Lys Cys Val
500 505 510

Leu Asp Met Arg Ser Met Asp Phe Lys Ser Asn Ser Ala Val Ala Trp
515 520 525

Ser Asn Lys Ser Asp Phe Ala Cys Ala Asn Ala Phe Asn Asn Ser Ile
530 535 540

Ile Pro Glu Asp Thr Phe Phe Pro Ser Pro Glu Ser Ser Cys Asp Val
545 550 555 560

Lys Leu Val Glu Lys Ser Phe Glu Thr Asp Thr Asn Leu Asn Phe Gln
565 570 575

Asn Leu Ser Val Ile Gly Phe Arg Ile Leu Leu Leu Lys Val Ala Gly
580 585 590

Phe Asn Leu Leu Met Thr Leu Arg Leu Trp Ser Ser
595 600

<210> SEQ ID NO 56
<211> LENGTH: 612
<212> TYPE: PRT
<213> ORGANISM: Artificial Sequence
<220> FEATURE:
<223> OTHER INFORMATION: Synthetic sequence WT137-45 TCR16.2 TCRbeta-P2A-TCRalpha

<400> SEQUENCE: 56

Met Leu Ser Pro Asp Leu Pro Asp Ser Ala Trp Asn Thr Arg Leu Leu
1 5 10 15

Cys His Val Met Leu Cys Leu Leu Gly Ala Val Ser Val Ala Ala Gly
20 25 30

Val Ile Gln Ser Pro Arg His Leu Ile Lys Glu Lys Arg Glu Thr Ala
35 40 45

Thr Leu Lys Cys Tyr Pro Ile Pro Arg His Asp Thr Val Tyr Trp Tyr
50 55 60

Gln Gln Gly Pro Gly Gln Asp Pro Gln Phe Leu Ile Ser Phe Tyr Glu
65 70 75 80

Lys Met Gln Ser Asp Lys Gly Ser Ile Pro Asp Arg Phe Ser Ala Gln
85 90 95

Gln Phe Ser Asp Tyr His Ser Glu Leu Asn Met Ser Ser Leu Glu Leu
100 105 110

Gly Asp Ser Ala Leu Tyr Phe Cys Ala Ser Ser Tyr Arg Gly Gly Ser
115 120 125

Thr Tyr Glu Gln Tyr Phe Gly Pro Gly Thr Arg Leu Thr Val Thr Glu
130 135 140

Asp Leu Lys Asn Val Phe Pro Pro Glu Val Ala Val Phe Glu Pro Ser

-continued

```
145                 150                 155                 160

Glu Ala Glu Ile Ser His Thr Gln Lys Ala Thr Leu Val Cys Leu Ala
                165                 170                 175

Thr Gly Phe Tyr Pro Asp His Val Glu Leu Ser Trp Trp Val Asn Gly
            180                 185                 190

Lys Glu Val His Ser Gly Val Cys Thr Asp Pro Gln Pro Leu Lys Glu
        195                 200                 205

Gln Pro Ala Leu Asn Asp Ser Arg Tyr Cys Leu Ser Ser Arg Leu Arg
    210                 215                 220

Val Ser Ala Thr Phe Trp Gln Asn Pro Arg Asn His Phe Arg Cys Gln
225                 230                 235                 240

Val Gln Phe Tyr Gly Leu Ser Glu Asn Asp Glu Trp Thr Gln Asp Arg
                245                 250                 255

Ala Lys Pro Val Thr Gln Ile Val Ser Ala Glu Ala Trp Gly Arg Ala
            260                 265                 270

Asp Cys Gly Phe Thr Ser Glu Ser Tyr Gln Gln Gly Val Leu Ser Ala
        275                 280                 285

Thr Ile Leu Tyr Glu Ile Leu Leu Gly Lys Ala Thr Leu Tyr Ala Val
    290                 295                 300

Leu Val Ser Ala Leu Val Leu Met Ala Met Val Lys Arg Lys Asp Ser
305                 310                 315                 320

Arg Gly Gly Ser Gly Ala Thr Asn Phe Ser Leu Leu Lys Gln Ala Gly
                325                 330                 335

Asp Val Glu Glu Asn Pro Gly Pro Met Arg Leu Val Ala Arg Val Thr
            340                 345                 350

Val Phe Leu Thr Phe Gly Thr Ile Ile Asp Ala Lys Thr Thr Gln Pro
        355                 360                 365

Thr Ser Met Asp Cys Ala Glu Gly Arg Ala Ala Asn Leu Pro Cys Asn
    370                 375                 380

His Ser Thr Ile Ser Gly Asn Glu Tyr Val Tyr Trp Tyr Arg Gln Ile
385                 390                 395                 400

His Ser Gln Gly Pro Gln Tyr Ile Ile His Gly Leu Lys Asn Asn Glu
                405                 410                 415

Thr Asn Glu Met Ala Ser Leu Ile Ile Thr Glu Asp Arg Lys Ser Ser
            420                 425                 430

Thr Leu Ile Leu Pro His Ala Thr Leu Arg Asp Thr Ala Val Tyr Tyr
        435                 440                 445

Cys Ile Ala Gly Val Gly Arg Gly Gln Asn Phe Val Phe Gly Pro Gly
    450                 455                 460

Thr Arg Leu Ser Val Leu Pro Tyr Ile Gln Asn Pro Asp Pro Ala Val
465                 470                 475                 480

Tyr Gln Leu Arg Asp Ser Lys Ser Ser Asp Lys Ser Val Cys Leu Phe
                485                 490                 495

Thr Asp Phe Asp Ser Gln Thr Asn Val Ser Gln Ser Lys Asp Ser Asp
            500                 505                 510

Val Tyr Ile Thr Asp Lys Cys Val Leu Asp Met Arg Ser Met Asp Phe
        515                 520                 525

Lys Ser Asn Ser Ala Val Ala Trp Ser Asn Lys Ser Asp Phe Ala Cys
    530                 535                 540

Ala Asn Ala Phe Asn Asn Ser Ile Ile Pro Glu Asp Thr Phe Phe Pro
545                 550                 555                 560

Ser Pro Glu Ser Ser Cys Asp Val Lys Leu Val Glu Lys Ser Phe Glu
                565                 570                 575
```

Thr Asp Thr Asn Leu Asn Phe Gln Asn Leu Ser Val Ile Gly Phe Arg
580 585 590

Ile Leu Leu Leu Lys Val Ala Gly Phe Asn Leu Leu Met Thr Leu Arg
595 600 605

Leu Trp Ser Ser
610

<210> SEQ ID NO 57
<211> LENGTH: 609
<212> TYPE: PRT
<213> ORGANISM: Artificial Sequence
<220> FEATURE:
<223> OTHER INFORMATION: Synthetic sequence WT137-45 TCR18.1 TCRbeta-
P2A-TCRalpha

<400> SEQUENCE: 57

Met Ser Thr Arg Leu Leu Cys Trp Met Ala Leu Cys Leu Leu Gly Ala
1 5 10 15

Glu Leu Ser Glu Ala Glu Val Ala Gln Ser Pro Arg Tyr Lys Ile Thr
20 25 30

Glu Lys Ser Gln Ala Val Ala Phe Trp Cys Asp Pro Ile Ser Gly His
35 40 45

Ala Thr Leu Tyr Trp Tyr Arg Gln Ile Leu Gly Gln Gly Pro Glu Leu
50 55 60

Leu Val Gln Phe Gln Asp Glu Ser Val Val Asp Asp Ser Gln Leu Pro
65 70 75 80

Lys Asp Arg Phe Ser Ala Glu Arg Leu Lys Gly Val Asp Ser Thr Leu
85 90 95

Lys Ile Gln Pro Ala Glu Leu Gly Asp Ser Ala Met Tyr Leu Cys Ala
100 105 110

Ser Ser Gln Arg Asp Ser Pro Asn Glu Lys Leu Phe Phe Gly Ser Gly
115 120 125

Thr Gln Leu Ser Val Leu Glu Asp Leu Asn Lys Val Phe Pro Pro Glu
130 135 140

Val Ala Val Phe Glu Pro Ser Glu Ala Glu Ile Ser His Thr Gln Lys
145 150 155 160

Ala Thr Leu Val Cys Leu Ala Thr Gly Phe Phe Pro Asp His Val Glu
165 170 175

Leu Ser Trp Trp Val Asn Gly Lys Glu Val His Ser Gly Val Cys Thr
180 185 190

Asp Pro Gln Pro Leu Lys Glu Gln Pro Ala Leu Asn Asp Ser Arg Tyr
195 200 205

Cys Leu Ser Ser Arg Leu Arg Val Ser Ala Thr Phe Trp Gln Asn Pro
210 215 220

Arg Asn His Phe Arg Cys Gln Val Gln Phe Tyr Gly Leu Ser Glu Asn
225 230 235 240

Asp Glu Trp Thr Gln Asp Arg Ala Lys Pro Val Thr Gln Ile Val Ser
245 250 255

Ala Glu Ala Trp Gly Arg Ala Asp Cys Gly Phe Thr Ser Val Ser Tyr
260 265 270

Gln Gln Gly Val Leu Ser Ala Thr Ile Leu Tyr Glu Ile Leu Leu Gly
275 280 285

Lys Ala Thr Leu Tyr Ala Val Leu Val Ser Ala Leu Val Leu Met Ala
290 295 300

Met Val Lys Arg Lys Asp Phe Gly Ser Gly Ala Thr Asn Phe Ser Leu

```
305                 310                 315                 320

Leu Lys Gln Ala Gly Asp Val Glu Glu Asn Pro Gly Pro Met Glu Lys
                325                 330                 335

Asn Pro Leu Ala Ala Pro Leu Leu Ile Leu Trp Phe His Leu Asp Cys
            340                 345                 350

Val Ser Ser Ile Leu Asn Val Glu Gln Ser Pro Gln Ser Leu His Val
        355                 360                 365

Gln Glu Gly Asp Ser Thr Asn Phe Thr Cys Ser Phe Pro Ser Ser Asn
    370                 375                 380

Phe Tyr Ala Leu His Trp Tyr Arg Trp Glu Thr Ala Lys Ser Pro Glu
385                 390                 395                 400

Ala Leu Phe Val Met Thr Leu Asn Gly Asp Glu Lys Lys Lys Gly Arg
                405                 410                 415

Ile Ser Ala Thr Leu Asn Thr Lys Glu Gly Tyr Ser Tyr Leu Tyr Ile
            420                 425                 430

Lys Gly Ser Gln Pro Glu Asp Ser Ala Thr Tyr Leu Cys Ala Phe His
        435                 440                 445

Pro Asn Phe Gly Asn Glu Lys Leu Thr Phe Gly Thr Gly Thr Arg Leu
    450                 455                 460

Thr Ile Ile Pro Asn Ile Gln Asn Pro Asp Pro Ala Val Tyr Gln Leu
465                 470                 475                 480

Arg Asp Ser Lys Ser Ser Asp Lys Ser Val Cys Leu Phe Thr Asp Phe
                485                 490                 495

Asp Ser Gln Thr Asn Val Ser Gln Ser Lys Asp Ser Asp Val Tyr Ile
            500                 505                 510

Thr Asp Lys Cys Val Leu Asp Met Arg Ser Met Asp Phe Lys Ser Asn
        515                 520                 525

Ser Ala Val Ala Trp Ser Asn Lys Ser Asp Phe Ala Cys Ala Asn Ala
    530                 535                 540

Phe Asn Asn Ser Ile Ile Pro Glu Asp Thr Phe Phe Pro Ser Pro Glu
545                 550                 555                 560

Ser Ser Cys Asp Val Lys Leu Val Glu Lys Ser Phe Glu Thr Asp Thr
                565                 570                 575

Asn Leu Asn Phe Gln Asn Leu Ser Val Ile Gly Phe Arg Ile Leu Leu
            580                 585                 590

Leu Lys Val Ala Gly Phe Asn Leu Leu Met Thr Leu Arg Leu Trp Ser
        595                 600                 605

Ser


<210> SEQ ID NO 58
<211> LENGTH: 611
<212> TYPE: PRT
<213> ORGANISM: Artificial Sequence
<220> FEATURE:
<223> OTHER INFORMATION: Synthetic sequence WT137-45 TCR19.1 TCRbeta-
      P2A-TCRalpha

<400> SEQUENCE: 58

Met Gly Cys Arg Leu Leu Cys Cys Ala Val Leu Cys Leu Leu Gly Ala
1               5                   10                  15

Val Pro Met Glu Thr Gly Val Thr Gln Thr Pro Arg His Leu Val Met
            20                  25                  30

Gly Met Thr Asn Lys Lys Ser Leu Lys Cys Glu Gln His Leu Gly His
        35                  40                  45

Asn Ala Met Tyr Trp Tyr Lys Gln Ser Ala Lys Lys Pro Leu Glu Leu
```

```
    50                  55                  60

Met Phe Val Tyr Ser Leu Glu Glu Arg Val Glu Asn Asn Ser Val Pro
65                  70                  75                  80

Ser Arg Phe Ser Pro Glu Cys Pro Asn Ser Ser His Leu Phe Leu His
                85                  90                  95

Leu His Thr Leu Gln Pro Glu Asp Ser Ala Leu Tyr Leu Cys Ala Ser
            100                 105                 110

Ser Gln Asp Pro Tyr Lys Leu Ser Gly Asn Thr Ile Tyr Phe Gly Glu
        115                 120                 125

Gly Ser Trp Leu Thr Val Val Glu Asp Leu Asn Lys Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Phe Pro Asp His Val
                165                 170                 175

Glu Leu Ser Trp Trp Val Asn Gly Lys Glu Val His Ser Gly Val Cys
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Val Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Phe Gly Ser Gly Ala Thr Asn Phe Ser
305                 310                 315                 320

Leu Leu Lys Gln Ala Gly Asp Val Glu Glu Asn Pro Gly Pro Met Glu
                325                 330                 335

Lys Met Leu Glu Cys Ala Phe Ile Val Leu Trp Leu Gln Leu Gly Trp
            340                 345                 350

Leu Ser Gly Glu Asp Gln Val Thr Gln Ser Pro Glu Ala Leu Arg Leu
        355                 360                 365

Gln Glu Gly Glu Ser Ser Ser Leu Asn Cys Ser Tyr Thr Val Ser Gly
    370                 375                 380

Leu Arg Gly Leu Phe Trp Tyr Arg Gln Asp Pro Gly Lys Gly Pro Glu
385                 390                 395                 400

Phe Leu Phe Thr Leu Tyr Ser Ala Gly Glu Glu Lys Glu Lys Glu Arg
                405                 410                 415

Leu Lys Ala Thr Leu Thr Lys Lys Glu Ser Phe Leu His Ile Thr Ala
            420                 425                 430

Pro Lys Pro Glu Asp Ser Ala Thr Tyr Leu Cys Ala Val Gln Pro Arg
        435                 440                 445

Gly Asp Gly Ser Ser Asn Thr Gly Lys Leu Ile Phe Gly Gln Gly Thr
    450                 455                 460

Thr Leu Gln Val Lys Pro Asp Ile Gln Asn Pro Asp Pro Ala Val Tyr
465                 470                 475                 480
```

```
Gln Leu Arg Asp Ser Lys Ser Ser Asp Lys Ser Val Cys Leu Phe Thr
                485                 490                 495

Asp Phe Asp Ser Gln Thr Asn Val Ser Gln Ser Lys Asp Ser Asp Val
            500                 505                 510

Tyr Ile Thr Asp Lys Cys Val Leu Asp Met Arg Ser Met Asp Phe Lys
        515                 520                 525

Ser Asn Ser Ala Val Ala Trp Ser Asn Lys Ser Asp Phe Ala Cys Ala
    530                 535                 540

Asn Ala Phe Asn Asn Ser Ile Ile Pro Glu Asp Thr Phe Phe Pro Ser
545                 550                 555                 560

Pro Glu Ser Ser Cys Asp Val Lys Leu Val Glu Lys Ser Phe Glu Thr
                565                 570                 575

Asp Thr Asn Leu Asn Phe Gln Asn Leu Ser Val Ile Gly Phe Arg Ile
            580                 585                 590

Leu Leu Leu Lys Val Ala Gly Phe Asn Leu Leu Met Thr Leu Arg Leu
        595                 600                 605

Trp Ser Ser
    610


<210> SEQ ID NO 59
<211> LENGTH: 9
<212> TYPE: PRT
<213> ORGANISM: Artificial Sequence
<220> FEATURE:
<223> OTHER INFORMATION: Synthetic sequence WT1 (37-45) Peptide Antigen

<400> SEQUENCE: 59

Val Leu Asp Phe Ala Pro Pro Gly Ala
1               5


<210> SEQ ID NO 60
<211> LENGTH: 22
<212> TYPE: PRT
<213> ORGANISM: Artificial Sequence
<220> FEATURE:
<223> OTHER INFORMATION: Synthetic sequence Porcine teschovirus-1 2A
      (P2A) peptide

<400> SEQUENCE: 60

Gly Ser Gly Ala Thr Asn Phe Ser Leu Leu Lys Gln Ala Gly Asp Val
1               5                   10                  15

Glu Glu Asn Pro Gly Pro
            20


<210> SEQ ID NO 61
<211> LENGTH: 21
<212> TYPE: PRT
<213> ORGANISM: Artificial Sequence
<220> FEATURE:
<223> OTHER INFORMATION: Synthetic sequence Thoseaasigna virus 2A (T2A)
      peptide

<400> SEQUENCE: 61

Gly Ser Gly Glu Gly Arg Gly Ser Leu Leu Thr Cys Gly Asp Val Glu
1               5                   10                  15

Glu Asn Pro Gly Pro
            20


<210> SEQ ID NO 62
<211> LENGTH: 23
<212> TYPE: PRT
```

<213> ORGANISM: Artificial Sequence
<220> FEATURE:
<223> OTHER INFORMATION: Synthetic sequence Equine rhinitis A virus (ERAV) 2A (E2A) peptide

<400> SEQUENCE: 62

```
Gly Ser Gly Gln Cys Thr Asn Tyr Ala Leu Leu Lys Leu Ala Gly Asp
1               5                   10                  15

Val Glu Ser Asn Pro Gly Pro
            20
```

<210> SEQ ID NO 63
<211> LENGTH: 25
<212> TYPE: PRT
<213> ORGANISM: Artificial Sequence
<220> FEATURE:
<223> OTHER INFORMATION: Synthetic sequence Foot-and-Mouth disease virus 2A (F2A) peptide

<400> SEQUENCE: 63

```
Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25
```

<210> SEQ ID NO 64
<211> LENGTH: 440
<212> TYPE: DNA
<213> ORGANISM: Artificial Sequence
<220> FEATURE:
<223> OTHER INFORMATION: Synthetic sequence WT137-45 TCR10.1 Wild-type Vbeta

<400> SEQUENCE: 64

```
atgggcacca gtctcctatg ctgggtggtc ctgggtttcc tagggacaga tcacacaggt     60

gctggagtct cccagtctcc caggtacaaa gtcacaaaga ggggacagga tgtagctctc    120

aggtgtgatc caatttcggg tcatgtatcc ctttattggt accgacaggc cctggggcag    180

ggcccagagt ttctgactta cttcaattat gaagcccaac aagacaaatc agggctgccc    240

aatgatcggt tctctgcaga gaggcctgag ggatccatct ccactctgac gatccagcgc    300

acagagcagc gggactcggc catgtatcgc tgtgccagca gcctgacagg gtcctacgag    360

cagtacttcg ggccgggcac caggctcacg gtcacagagg acctgaaaaa cgtgttccca    420

cccgaggtcg ctgtgtttga                                                440
```

<210> SEQ ID NO 65
<211> LENGTH: 440
<212> TYPE: DNA
<213> ORGANISM: Artificial Sequence
<220> FEATURE:
<223> OTHER INFORMATION: Synthetic sequence WT137-45 TCR11.2 Wild-type Vbeta

<400> SEQUENCE: 65

```
atgctgctgc ttctgctgct tctggggcca gcaggctccg ggcttggtgc tgtcgtctct     60

caacatccga gctgggttat ctgtaagagt ggaacctctg tgaagatcga gtgccgttcc    120

ctggactttc aggccacaac tatgttttgg tatcgtcagt tcccgaaaca gagtctcatg    180

ctgatggcaa cttccaatga gggctccaag gccacatacg agcaaggcgt cgagaaggac    240

aagtttctca tcaaccatgc aagcctgacc ttgtccactc tgacagtgac cagtgcccat    300

cctgaagaca gcagcttcta catctgcagt gcaaccccgg aggctagtag cccctacgag    360
```

cagtacttcg ggccgggcac caggctcacg gtcacagagg acctgaaaaa cgtgttccca 420
cccgaggtcg ctgtgtttga 440

<210> SEQ ID NO 66
<211> LENGTH: 440
<212> TYPE: DNA
<213> ORGANISM: Artificial Sequence
<220> FEATURE:
<223> OTHER INFORMATION: Synthetic sequence WT137-45 TCR12.1 Wild-type Vbeta

<400> SEQUENCE: 66
atgggtcctg ggcttctcca ctggatggcc ctttgtctcc ttggaacagg tcatggggat 60
gccatggtca tccagaaccc aagataccag gttacccagt ttggaaagcc agtgaccctg 120
agttgttctc agactttgaa ccataacgtc atgtactggt accagcagaa gtcaagtcag 180
gccccaaagc tgctgttcca ctactatgac aaagatttta acaatgaagc agacacccct 240
gataacttcc aatccaggag gccgaacact tctttctgct ttcttgacat ccgctcacca 300
ggcctggggg acgcagccat gtacctgtgt gccaccagca accttcaggg gcgacagccc 360
cagcattttg gtgatgggac tcgactctcc atcctagagg acctgaacaa ggtgttccca 420
cccgaggtcg ctgtgtttga 440

<210> SEQ ID NO 67
<211> LENGTH: 470
<212> TYPE: DNA
<213> ORGANISM: Artificial Sequence
<220> FEATURE:
<223> OTHER INFORMATION: Synthetic sequence WT137-45 TCR13.1 Wild-type Vbeta

<400> SEQUENCE: 67
atgcttagtc ctgacctgcc tgactctgcc tggaacacca ggctcctctg ccatgtcatg 60
ctttgtctcc tgggagcagt ttcagtggct gctggagtca tccagtcccc aagacatctg 120
atcaaagaaa agagggaaac agccactctg aaatgctatc ctatccctag acacgacact 180
gtctactggt accagcaggg tccaggtcag gacccccagt tcctcatttc gttttatgaa 240
aagatgcaga gcgataaagg aagcatccct gatcgattct cagctcaaca gttcagtgac 300
tatcattctg aactgaacat gagctccttg gagctggggg actcagccct gtacttctgt 360
gccagcagcc tccggttggg gcgagagacc cagtacttcg ggccaggcac gcggctcctg 420
gtgctcgagg acctgaaaaa cgtgttccca cccgaggtcg ctgtgtttga 470

<210> SEQ ID NO 68
<211> LENGTH: 440
<212> TYPE: DNA
<213> ORGANISM: Artificial Sequence
<220> FEATURE:
<223> OTHER INFORMATION: Synthetic sequence WT137-45 TCR13.2 Wild-type Vbeta

<400> SEQUENCE: 68
atgggcacca ggctcctctg ctgggtggtc ctgggtttcc tagggacaga tcacacaggt 60
gctggagtct cccagtcccc taggtacaaa gtcgcaaaga gaggacagga tgtagctctc 120
aggtgtgatc caatttcggg tcatgtatcc cttttttggt accaacaggc cctggggcag 180
gggccagagt ttctgactta tttccagaat gaagctcaac tagacaaatc ggggctgccc 240
agtgatcgct tctttgcaga aaggcctgag ggatccgtct ccactctgaa gatccagcgc 300

```
acacagcagg aggactccgc cgtgtatctc tgtgccagca gcctgggaca ggcctacgag    360

cagtacttcg ggccgggcac caggctcacg gtcacagagg acctgaaaaa cgtgttccca    420

cccgaggtcg ctgtgtttga                                                440


<210> SEQ ID NO 69
<211> LENGTH: 440
<212> TYPE: DNA
<213> ORGANISM: Artificial Sequence
<220> FEATURE:
<223> OTHER INFORMATION: Synthetic sequence WT137-45 TCR14.1 Wild-type
      Vbeta

<400> SEQUENCE: 69

atgggtacca ggctcctctg ctgggtggcc ttctgtctcc tggtggaaga actcatagaa     60

gctggagtgg ttcagtctcc cagatataag attatagaga aaaaacagcc tgtggctttt    120

tggtgcaatc ctatttctgg ccacaatacc ctttactggt acctgcagaa cttgggacag    180

ggcccggagc ttctgattcg atatgagaat gaggaagcag tagacgattc acagttgcct    240

aaggatcgat tttctgcaga gaggctcaaa ggagtagact ccactctcaa gatccagcct    300

gcagagcttg gggactcggc cgtgtatctc tgtgccagca gcctaaccag gggggctgaa    360

gctttctttg gacaaggcac cagactcaca gttgtagagg acctgaacaa ggtgttccca    420

cccgaggtcg ctgtgtttga                                                440


<210> SEQ ID NO 70
<211> LENGTH: 443
<212> TYPE: DNA
<213> ORGANISM: Artificial Sequence
<220> FEATURE:
<223> OTHER INFORMATION: Synthetic sequence WT137-45 TCR15.1 Wild-type
      Vbeta

<400> SEQUENCE: 70

atgagcaacc aggtgctctg ctgtgtggtc ctttgtttcc tgggagcaaa caccgtggat     60

ggtggaatca ctcagtcccc aaagtacctg ttcagaaagg aaggacagaa tgtgaccctg    120

agttgtgaac agaatttgaa ccacgatgcc atgtactggt accgacagga cccagggcaa    180

gggctgagat tgatctacta ctcacagata gtaaatgact ttcagaaagg agatatagct    240

gaagggtaca gcgtctctcg ggagaagaag gaatcctttc ctctcactgt gacatcggcc    300

caaaagaacc cgacagcttt ctatctctgt gccagtagta gagacaggga gcaagaatca    360

cccctccact ttgggaacgg gaccaggctc actgtgacag aggacctgaa caaggtgttc    420

ccacccgagg tcgctgtgtt tga                                            443


<210> SEQ ID NO 71
<211> LENGTH: 440
<212> TYPE: DNA
<213> ORGANISM: Artificial Sequence
<220> FEATURE:
<223> OTHER INFORMATION: Synthetic sequence WT137-45 TCR16.1 Wild-type
      Vbeta

<400> SEQUENCE: 71

atgggccccc agctccttgg ctatgtggtc ctttgccttc taggagcagg ccccctggaa     60

gcccaagtga cccagaaccc aagatacctc atcacagtga ctggaaagaa gttaacagtg    120

acttgttctc agaatatgaa ccatgagtat atgtcctggt atcgacaaga cccagggctg    180

ggcttaaggc agatctacta ttcaatgaat gttgaggtga ctgataaggg agatgttcct    240
```

```
gaagggtaca aagtctctcg aaaagagaag aggaatttcc ccctgatcct ggagtcgccc    300

agccccaacc agacctctct gtacttctgt gccagcagtt ttagcggggg aacctacgag    360

cagtacttcg ggccgggcac caggctcacg gtcacagagg acctgaaaaa cgtgttccca    420

cccgaggtcg ctgtgtttga                                                440


<210> SEQ ID NO 72
<211> LENGTH: 473
<212> TYPE: DNA
<213> ORGANISM: Artificial Sequence
<220> FEATURE:
<223> OTHER INFORMATION: Synthetic sequence WT137-45 TCR16.2 Wild-type
      Vbeta

<400> SEQUENCE: 72

atgcttagtc ctgacctgcc tgactctgcc tggaacacca ggctcctctg ccatgtcatg     60

ctttgtctcc tgggagcagt ttcagtggct gctggagtca tccagtcccc aagacatctg    120

atcaaagaaa agagggaaac agccactctg aaatgctatc ctatccctag acacgacact    180

gtctactggt accagcaggg tccaggtcag gacccccagt tcctcatttc gttttatgaa    240

aagatgcaga gcgataaagg aagcatccct gatcgattct cagctcaaca gttcagtgac    300

tatcattctg aactgaacat gagctccttg gagctggggg actcagccct gtacttctgt    360

gccagcagct acagaggggg ctctacgtac gagcagtact tcgggccggg caccaggctc    420

acggtcacag aggacctgaa aaacgtgttc ccacccgagg tcgctgtgtt tga           473


<210> SEQ ID NO 73
<211> LENGTH: 446
<212> TYPE: DNA
<213> ORGANISM: Artificial Sequence
<220> FEATURE:
<223> OTHER INFORMATION: Synthetic sequence WT137-45 TCR18.1 Wild-type
      Vbeta

<400> SEQUENCE: 73

atgagcacca ggcttctctg ctggatggcc ctctgtctcc tgggggcaga actctcagaa     60

gctgaagttg cccagtcccc cagatataag attacagaga aaagccaggc tgtggctttt    120

tggtgtgatc ctatttctgg ccatgctacc ctttactggt accggcagat cctgggacag    180

ggcccggagc ttctggttca atttcaggat gagagtgtag tagatgattc acagttgcct    240

aaggatcgat ttctgcagag gaggctcaaa ggagtagact ccactctcaa gatccagcct    300

gcagagcttg gggactcggc catgtatctc tgtgccagca gccaacggga cagcccaaat    360

gaaaaactgt tttttggcag tggaacccag ctctctgtct tggaggacct gaacaaggtg    420

ttcccacccg aggtcgctgt gtttga                                         446


<210> SEQ ID NO 74
<211> LENGTH: 449
<212> TYPE: DNA
<213> ORGANISM: Artificial Sequence
<220> FEATURE:
<223> OTHER INFORMATION: Synthetic sequence WT137-45 TCR19.1 Wild-type
      Vbeta

<400> SEQUENCE: 74

atgggctgca ggctgctctg ctgtgcggtt ctctgtctcc tgggagcggt ccccatggaa     60

acgggagtta cgcagacacc aagacacctg gtcatgggaa tgacaaataa gaagtctttg    120

aaatgtgaac aacatctggg tcataacgct atgtattggt acaagcaaag tgctaagaag    180
```

ccactggagc tcatgtttgt ctacagtctt gaagaacggg ttgaaaacaa cagtgtgcca 240
agtcgcttct cacctgaatg ccccaacagc tctcacttat tccttcacct acacaccctg 300
cagccagaag actcggccct gtatctctgc gccagcagcc aagatccgta caagctctct 360
ggaaacacca tatattttgg agagggaagt tggctcactg ttgtagagga cctgaacaag 420
gtgttcccac ccgaggtcgc tgtgtttga 449

<210> SEQ ID NO 75
<211> LENGTH: 440
<212> TYPE: DNA
<213> ORGANISM: Artificial Sequence
<220> FEATURE:
<223> OTHER INFORMATION: Synthetic sequence WT137-45 TCR10.1 - Vbeta Codon Optimized

<400> SEQUENCE: 75
ctcaataaaa gagcccacaa cccctcactc ggcgcgccac catgggcaca tctcttctct 60
gttgggtggt tctgggcttt ctgggcacag atcatacagg agctggagtt agccagtctc 120
ctaggtataa ggtgaccaag aggggacagg atgtggctct gagatgtgac cctattagcg 180
gacatgtgag cctgtactgg tacagacaag ctctgggaca aggacccgag tttctgacct 240
acttcaacta tgaggcccag caggacaaat ctggactgcc caacgacaga ttcagcgccg 300
aaagaccaga aggctctatt agcacactga ccatccagag aacagagcag agggattctg 360
ccatgtacag atgcgccagc agcttaacag gctcttacga gcagtacttt ggacctggca 420
caagactgac agtgacagag 440

<210> SEQ ID NO 76
<211> LENGTH: 440
<212> TYPE: DNA
<213> ORGANISM: Artificial Sequence
<220> FEATURE:
<223> OTHER INFORMATION: Synthetic sequence WT137-45 TCR11.2 - Vbeta Codon Optimized

<400> SEQUENCE: 76
ctcaataaaa gagcccacaa cccctcactc ggcgcgccac catgctgctt cttctcctcc 60
ttctcggacc tgctggatct ggattaggag ctgttgtgtc tcagcaccct tcttgggtga 120
tctgtaaaag cggcacaagc gtgaagatcg agtgcagaag cctggacttt caggccacaa 180
ccatgttctg gtataggcag ttccccaagc agtctctgat gctgatggcc acctctaatg 240
agggctctaa ggccacatat gaacagggag tggagaagga caagttcctg atcaaccacg 300
cctctctgac cctgtctacc ctgacagtta catctgccca ccctgaggat agcagctttt 360
acatctgtag cgccacacct gaagcctcta gcccatatga gcagtacttt ggccctggca 420
ccagattaac agtgacagag 440

<210> SEQ ID NO 77
<211> LENGTH: 440
<212> TYPE: DNA
<213> ORGANISM: Artificial Sequence
<220> FEATURE:
<223> OTHER INFORMATION: Synthetic sequence WT137-45 TCR12.1 - Vbeta Codon Optimized

<400> SEQUENCE: 77
ctcaataaaa gagcccacaa cccctcactc ggcgcgccac catgggacct ggactgcttc 60
attggatggc tctgtgtttg ctgggaacag gacatggaga tgctatggtg atccagaacc 120
ccaggtatca ggtgacccag tttggcaaac cagtgacact gagctgttct cagaccctga 180
accacaacgt gatgtactgg taccagcaga agtcttctca ggcccctaag ctgctgttcc 240
actactacga caaggacttc aacaacgagg ccgatacccc tgacaatttc cagagcagga 300
ggcccaatac cagcttctgt ttcctggaca ttagaagccc tggactggga gatgctgcca 360
tgtacctgtg tgccaccagc aatttacagg gaagacaacc tcagcacttt ggcgatggca 420
caaggctgtc tatcctggag 440

<210> SEQ ID NO 78
<211> LENGTH: 470
<212> TYPE: DNA
<213> ORGANISM: Artificial Sequence
<220> FEATURE:
<223> OTHER INFORMATION: Synthetic sequence WT137-45 TCR13.1 - Vbeta Codon Optimized

<400> SEQUENCE: 78
ctcaataaaa gagcccacaa cccctcactc ggcgcgccac catgctgagc cctgatctcc 60
ctgattctgc ctggaatacc agactgctgt gtcatgtgat gctgtgtctg cttggagccg 120
tttctgtggc tgctggcgtg attcaatctc ctagacacct gatcaaggag aagagagaaa 180
cagccaccct gaagtgctac cccatcccca gacacgatac agtgtactgg tatcagcaag 240
gacctggaca agatccccag ttcctgatca gcttctacga gaagatgcag agcgacaaag 300
gcagcatccc agacagattt agcgcccagc agtttagcga ctatcactct gagctgaaca 360
tgagcagcct ggaactgggc gattctgctc tgtacttctg tgcctcttct ctgagactgg 420
gaagagaaac ccagtacttt ggacccggca caagactgct ggttcttgag 470

<210> SEQ ID NO 79
<211> LENGTH: 440
<212> TYPE: DNA
<213> ORGANISM: Artificial Sequence
<220> FEATURE:
<223> OTHER INFORMATION: Synthetic sequence WT137-45 TCR13.2 - Vbeta Codon Optimized

<400> SEQUENCE: 79
ctcaataaaa gagcccacaa cccctcactc ggcgcgccac catgggcaca agacttctct 60
gctgggtggt gcttggattt ctgggcacag atcatacagg agctggagtt agccagtctc 120
ctaggtacaa agtggccaag agaggacagg atgtggctct gagatgtgac cctattagcg 180
gacatgtgag cctgttttgg taccagcaag ctctgggaca aggacccgag tttctgacct 240
acttccagaa tgaagcccag ctggataaat ctggactgcc tagcgaccgg ttcttcgccg 300
aaagacctga aggatctgtt agcaccctga agattcagag aacacagcag gaggactctg 360
ccgtgtacct gtgtgcctct tctttaggac aggcctatga gcagtatttt ggacctggca 420
ccagactgac cgtgacagag 440

<210> SEQ ID NO 80
<211> LENGTH: 440
<212> TYPE: DNA
<213> ORGANISM: Artificial Sequence
<220> FEATURE:
<223> OTHER INFORMATION: Synthetic sequence WT137-45 TCR14.1 - Vbeta Codon Optimized

<400> SEQUENCE: 80
ctcaataaaa gagcccacaa cccctcactc ggcgcgccac catgggcaca agacttctct 60
gctgggtggc cttttgtctg ctggtggaag agctgattga agctggagtt gtgcagtctc 120
ctaggtacaa gatcatcgag aagaagcagc ccgtggcctt ctggtgtaat cccatttctg 180
gccacaacac cctgtactgg tatctgcaga atctgggaca gggccctgaa ctgctgatca 240
gatacgagaa cgaagaagcc gtggacgatt ctcaactgcc taaggaccgc ttttctgccg 300
agaggctgaa aggagtggat tctaccctga agatccaacc tgctgaactg ggcgattctg 360
ctgtgtacct gtgcgcttct agcctgacaa gaggagctga agccttttt ggacagggca 420 caagactgac agtggtggag 440

<210> SEQ ID NO 81
<211> LENGTH: 443
<212> TYPE: DNA
<213> ORGANISM: Artificial Sequence
<220> FEATURE:
<223> OTHER INFORMATION: Synthetic sequence WT137-45 TCR15.1 - Vbeta
Codon Optimized

<400> SEQUENCE: 81
ctcaataaaa gagcccacaa cccctcactc ggcgcgccac catgagcaac caggtcttgt 60
gctgtgtggt gctgtgcttt cttggcgcca atacagtgga tggcggcatt acacaaagcc 120
ccaagtacct gttcaggaaa gagggccaga atgtgacact gagctgtgag cagaacctga 180
atcacgacgc catgtactgg tacagacagg atccaggaca aggactgagg ctgatctact 240
actcccagat cgtgaacgac ttccagaagg gcgatattgc cgagggctat agcgtgagca 300
gagagaagaa agagagcttc ccactgacag tgacatctgc ccagaagaac cctaccgcct 360
tctacctgtg tgcctcttct agagatagag agcaggagtc tcctctgcac ttcggaaatg 420
gcaccagact gacagtgacc gag 443

<210> SEQ ID NO 82
<211> LENGTH: 440
<212> TYPE: DNA
<213> ORGANISM: Artificial Sequence
<220> FEATURE:
<223> OTHER INFORMATION: Synthetic sequence WT137-45 TCR16.1 - Vbeta
Codon Optimized

<400> SEQUENCE: 82
ctcaataaaa gagcccacaa cccctcactc ggcgcgccac catgggacct cagcttcttg 60
gatacgttgt gctgtgtctg cttggagctg gacctcttga agctcaggtt acccagaacc 120
ccagatacct gattaccgtg acaggcaaaa agctgaccgt gacatgtagc cagaacatga 180
accacgagta catgagctgg taccggcagg atcctggatt aggcctgaga cagatctact 240
acagcatgaa cgtggaggtg accgataaag gcgacgtgcc tgagggatac aaggtgagca 300
gaaaggagaa gaggaatttc cccctgatcc tggaaagccc aagccccaat cagacaagcc 360
tgtacttttg tgccagcagc ttttctggcg gcacatatga gcagtacttc ggccctggca 420
caagactgac agttacagag 440

<210> SEQ ID NO 83
<211> LENGTH: 473
<212> TYPE: DNA
<213> ORGANISM: Artificial Sequence
<220> FEATURE:
<223> OTHER INFORMATION: Synthetic sequence WT137-45 TCR16.2 - Vbeta
Codon Optimized

<400> SEQUENCE: 83
ctcaataaaa gagcccacaa cccctcactc ggcgcgccac catgctgagc cctgatctcc 60
ctgattctgc ctggaatacc agactgctgt gtcatgtgat gctgtgtctg cttggagccg 120
tttctgtggc tgctggcgtg attcaatctc ctagacacct gatcaaggag aagagagaaa 180
cagccaccct gaagtgctac cccatcccca gacacgatac agtgtactgg tatcagcaag 240
gacctggaca agatccccag ttcctgatca gcttctacga gaagatgcag agcgacaaag 300
gcagcatccc agacagattt agcgcccagc agtttagcga ctatcactct gagctgaaca 360
tgagcagcct ggaactgggc gattctgctc tgtacttctg tgccagcagc tatagaggag 420
gcagcacata tgagcagtac tttggccctg gcacaagact gacagtgaca gag 473

<210> SEQ ID NO 84
<211> LENGTH: 446
<212> TYPE: DNA
<213> ORGANISM: Artificial Sequence
<220> FEATURE:
<223> OTHER INFORMATION: Synthetic sequence WT137-45 TCR18.1 - Vbeta Codon Optimized

<400> SEQUENCE: 84
ctcaataaaa gagcccacaa cccctcactc ggcgcgccac catgagcacc agactccttt 60
gctggatggc tttgtgtctg cttggagctg agctgtctga agctgaagtt gcccagtctc 120
ccagatacaa gatcaccgag aaatctcagg ctgtggcctt ctggtgtgac cctatttctg 180
gacacgccac cctgtactgg tataggcaaa ttctgggaca aggccctgaa ctgctggtgc 240
aatttcagga tgagagcgtg gtggacgatt ctcaactgcc taaggacagg ttttctgccg 300
agcggctgaa aggagttgat agcaccctga agatccaacc tgctgaactg ggcgattctg 360
ctatgtacct gtgcgcctct tctcagagag atagccctaa cgagaagctg ttctttggct 420
ctggaaccca gctgtctgtg ctggag 446

<210> SEQ ID NO 85
<211> LENGTH: 449
<212> TYPE: DNA
<213> ORGANISM: Artificial Sequence
<220> FEATURE:
<223> OTHER INFORMATION: Synthetic sequence WT137-45 TCR19.1 - Vbeta Codon Optimized

<400> SEQUENCE: 85
ctcaataaaa gagcccacaa cccctcactc ggcgcgccac catgggctgt agactgttgt 60
gttgtgctgt gctgtgtctg ttgggagctg tgcctatgga aacaggcgtt acccagacac 120
ctagacatct ggttatgggc atgaccaaca agaagagcct gaagtgcgag cagcatctgg 180
gccataacgc catgtactgg tataagcaga gcgccaagaa accactggaa ctgatgttcg 240
tgtacagcct ggaggagagg gtggagaata atagcgtgcc cagcagattt agccctgagt 300
gcccaaattc ttctcacctg ttcctgcacc tgcacacatt acagcccgag gattctgccc 360
tgtacctgtg tgcttcttct caagaccctt acaagctgag cggcaatacc atctacttcg 420
gcgaaggctc ttggctgaca gtggttgaa 449

<210> SEQ ID NO 86
<211> LENGTH: 396
<212> TYPE: DNA
<213> ORGANISM: Artificial Sequence
<220> FEATURE:
<223> OTHER INFORMATION: Synthetic sequence WT137-45 TCR10.1 Wild-type Valpha

<400> SEQUENCE: 86
atggagaccc tcttgggcct gcttatcctt tggctgcagc tgcaatgggt gagcagcaaa 60
caggaggtga cacagattcc tgcagctctg agtgtcccag aaggagaaaa cttggttctc 120
aactgcagtt tcactgatag cgctatttac aacctccagt ggtttaggca ggaccctggg 180
aaaggtctca catctctgtt gcttattcag tcaagtcaga gagagcaaac aagtggaaga 240
cttaatgcct cgctggataa atcatcagga cgtagtactt tatacattgc agcttctcag 300
cctggtgact cagccaccta cctctgtgct gtgaaagaaa ccagtggctc taggttgacc 360
tttggggaag gaacacagct cacagtgaat cctgat 396

<210> SEQ ID NO 87
<211> LENGTH: 417
<212> TYPE: DNA
<213> ORGANISM: Artificial Sequence
<220> FEATURE:
<223> OTHER INFORMATION: Synthetic sequence WT137-45 TCR11.2 Wild-type Valpha

<400> SEQUENCE: 87
atgacacgag ttagcttgct gtgggcagtc gtggtctcca cctgtcttga atccggcatg 60
gcccagacag tcactcagtc tcaaccagag atgtctgtgc aggaggcaga gactgtgacc 120
ctgagttgca catatgacac cagtgagaat aattattatt tgttctggta caagcagcct 180
cccagcaggc agatgattct cgttattcgc caagaagctt ataagcaaca gaatgcaacg 240
gagaatcgtt tctctgtgaa cttccagaaa gcagccaaat ccttcagtct caagatctca 300
gactcacagc tgggggacac tgcgatgtat ttctgtgctt tcatctaccc atcctacacc 360
tcaggaacct acaaatacat ctttggaaca ggcaccaggc tgaaggtttt agcaaat 417

<210> SEQ ID NO 88
<211> LENGTH: 420
<212> TYPE: DNA
<213> ORGANISM: Artificial Sequence
<220> FEATURE:
<223> OTHER INFORMATION: Synthetic sequence WT137-45 TCR12.1 Wild-type Valpha

<400> SEQUENCE: 88
atggccatgc tcctgggggc atcagtgctg attctgtggc ttcagccaga ctgggtaaac 60
agtcaacaga agaatgatga ccagcaagtt aagcaaaatt caccatccct gagcgtccag 120
gaaggaagaa tttctattct gaactgtgac tatactaaca gcatgtttga ttatttccta 180
tggtacaaaa aataccctgc tgaaggtcct acattcctga tatctataag ttccattaag 240
gataaaaatg aagatggaag attcactgtc ttcttaaaca aaagtgccaa gcacctctct 300
ctgcacattg tgccctccca gcctggagac tctgcagtgt acttctgtgc agcaagcgga 360
acaggaggaa gctacatacc tacatttgga agaggaacca gccttattgt tcatccgtat 420

<210> SEQ ID NO 89
<211> LENGTH: 417
<212> TYPE: DNA
<213> ORGANISM: Artificial Sequence
<220> FEATURE:
<223> OTHER INFORMATION: Synthetic sequence WT137-45 TCR13.1 Wild-type Valpha

<400> SEQUENCE: 89
atggccatgc tcctgggggc atcagtgctg attctgtggc ttcagccaga ctgggtaaac 60
agtcaacaga agaatgatga ccagcaagtt aagcaaaatt caccatccct gagcgtccag 120
gaaggaagaa tttctattct gaactgtgac tatactaaca gcatgtttga ttatttccta 180
tggtacaaaa aataccctgc tgaaggtcct acattcctga tatctataag ttccattaag 240
gataaaaatg aagatggaag attcactgtc ttcttaaaca aaagtgccaa gcacctctct 300
ctgcacattg tgccctccca gcctggagac tctgcagtgt acttctgtgc agcaagcggt 360
ataggcgact acaagctcag ctttggagcc ggaaccacag taactgtaag agcaaat 417

<210> SEQ ID NO 90
<211> LENGTH: 393
<212> TYPE: DNA
<213> ORGANISM: Artificial Sequence
<220> FEATURE:
<223> OTHER INFORMATION: Synthetic sequence WT137-45 TCR13.2 Wild-type Valpha

<400> SEQUENCE: 90
atggtgaaga tccggcaatt tttgttggct attttgtggc ttcagctaag ctgtgtaagt 60
gccgccaaaa atgaagtgga gcagagtcct cagaacctga ctgcccagga aggagaattt 120
atcacaatca actgcagtta ctcggtagga ataagtgcct tacactggct gcaacagcat 180
ccaggaggag gcattgtttc cttgtttatg ctgagctcag ggaagaagaa gcatggaaga 240
ttaattgcca caataaacat acaggaaaag cacagctccc tgcacatcac agcctcccat 300
cccagagact ctgccgtcta catctgtgct gtcaggacct cctacgacaa ggtgatattt 360
gggccaggga caagcttatc agtcattcca aat 393

<210> SEQ ID NO 91
<211> LENGTH: 408
<212> TYPE: DNA
<213> ORGANISM: Artificial Sequence
<220> FEATURE:
<223> OTHER INFORMATION: Synthetic sequence WT137-45 TCR14.1 Wild-type Valpha

<400> SEQUENCE: 91
atgaaatcct tgagagtttt actagtgatc ctgtggcttc agttgagctg ggtttggagc 60
caacagaagg aggtggagca gaattctgga cccctcagtg ttccagaggg agccattgcc 120
tctctcaact gcacttacag tgaccgaggt tcccagtcct tcttctggta cagacaatat 180
tctgggaaaa gccctgagtt gataatgttc atatactcca atggtgacaa agaagatgga 240
aggtttacag cacagctcaa taaagccagc cagtatgttt ctctgctcat cagagactcc 300
cagcccagtg attcagccac ctacctctgt gccgtgaacc tcctaggggc tacaggatac 360
agcaccctca cctttgggaa ggggactatg cttctagtct ctccagat 408

<210> SEQ ID NO 92
<211> LENGTH: 384
<212> TYPE: DNA
<213> ORGANISM: Artificial Sequence
<220> FEATURE:
<223> OTHER INFORMATION: Synthetic sequence WT137-45 TCR15.1 Wild-type Valpha

<400> SEQUENCE: 92
atgtggggag ttttccttct ttatgtttcc atgaagatgg gaggcactac aggacaaaac 60
attgaccagc ccactgagat gacagctacg gaaggtgcca ttgtccagat caactgcacg 120
taccagacat ctgggttcaa cgggctgttc tggtaccagc aacatgctgg cgaagcaccc 180
acatttctgt cttacaatgt tctggatggt ttggaggaga aaggtcgttt ttcttcattc 240
cttagtcggt ctaaagggta cagttacctc cttttgaagg agctccagat gaaagactct 300
gcctcttacc tctgtgctgt gaggggcatt aacgactaca agctcagctt tggagccgga 360
accacagtaa ctgtaagagc aaat 384

<210> SEQ ID NO 93
<211> LENGTH: 393
<212> TYPE: DNA
<213> ORGANISM: Artificial Sequence
<220> FEATURE:
<223> OTHER INFORMATION: Synthetic sequence WT137-45 TCR16.1 Wild-type
Valpha

<400> SEQUENCE: 93
atggagaaaa tgttggagtg tgcattcata gtcttgtggc ttcagcttgg ctggttgagt 60
ggagaagacc aggtgacgca gagtcccgag gccctgagac tccaggaggg agagagtagc 120
agtctcaact gcagttacac agtcagcggt ttaagagggc tgttctggta taggcaagat 180
cctgggaaag gccctgaatt cctcttcacc ctgtattcag ctggggaaga aaaggagaaa 240
gaaaggctaa aagccacatt aacaaagaag gaaagctttc tgcacatcac agcccctaaa 300
cctgaagact cagccactta tctctgtgct gtgatcacag gctttcagaa acttgtattt 360
ggaactggca cccgacttct ggtcagtcca aat 393

<210> SEQ ID NO 94
<211> LENGTH: 384
<212> TYPE: DNA
<213> ORGANISM: Artificial Sequence
<220> FEATURE:
<223> OTHER INFORMATION: Synthetic sequence WT137-45 TCR16.2 Wild-type
Valpha

<400> SEQUENCE: 94
atgaggctgg tggcaagagt aactgtgttt ctgacctttg gaactataat tgatgctaag 60
accacccagc ccacctccat ggattgcgct gaaggaagag ctgcaaacct gccttgtaat 120
cactctacca tcagtggaaa tgagtatgtg tattggtatc gacagattca ctcccagggg 180
ccacagtata tcattcatgg tctaaaaaac aatgaaacca atgaaatggc ctctctgatc 240
atcacagaag acagaaagtc cagcaccttg atcctgcccc acgctacgct gagagacact 300
gctgtgtact attgcatcgc cggtgtcggg cggggtcaga attttgtctt tggtcccgga 360
accagattgt ccgtgctgcc ctat 384

<210> SEQ ID NO 95
<211> LENGTH: 408
<212> TYPE: DNA
<213> ORGANISM: Artificial Sequence
<220> FEATURE:
<223> OTHER INFORMATION: Synthetic sequence WT137-45 TCR18.1 Wild-type
Valpha

<400> SEQUENCE: 95
atggagaaga atcctttggc agccccatta ctaatcctct ggtttcatct tgactgcgtg 60
agcagcatac tgaacgtgga acaaagtcct cagtcactgc atgttcagga gggagacagc 120
accaatttca cctgcagctt cccttccagc aatttttatg ccttacactg gtacagatgg 180
gaaactgcaa aaagccccga ggccttgttt gtaatgactt taaatgggga tgaaaagaag 240
aaaggacgaa taagtgccac tcttaatacc aaggagggtt acagctattt gtacatcaaa 300
ggatcccagc ctgaagactc agccacatac ctctgtgcct ttcatcctaa ctttggaaat 360
gagaaattaa cctttgggac tggaacaaga ctcaccatca tacccaat 408

<210> SEQ ID NO 96
<211> LENGTH: 411
<212> TYPE: DNA
<213> ORGANISM: Artificial Sequence
<220> FEATURE:
<223> OTHER INFORMATION: Synthetic sequence WT137-45 TCR19.1 Wild-type Valpha

<400> SEQUENCE: 96
atggagaaaa tgttggagtg tgcattcata gtcttgtggc ttcagcttgg ctggttgagt 60
ggagaagacc aggtgacgca gagtcccgag gccctgagac tccaggaggg agagagtagc 120
agtctcaact gcagttacac agtcagcggt ttaagagggc tgttctggta taggcaagat 180
cctgggaaag gccctgaatt cctcttcacc ctgtattcag ctggggaaga aaaggagaaa 240
gaaaggctaa aagccacatt aacaaagaag gaaagctttc tgcacatcac agcccctaaa 300
cctgaagact cagccactta tctctgtgct gtgcagccgc ggggggatgg gtctagcaac 360
acaggcaaac taatctttgg gcaagggaca actttacaag taaaaccaga t 411

<210> SEQ ID NO 97
<211> LENGTH: 396
<212> TYPE: DNA
<213> ORGANISM: Artificial Sequence
<220> FEATURE:
<223> OTHER INFORMATION: Synthetic sequence WT137-45 TCR10.1 - Valpha Codon Optimized

<400> SEQUENCE: 97
atggagacac tgctgggact actgattctg tggctgcaac tgcaatgggt gagcagcaaa 60
caggaggtta cccagattcc tgctgctctg tctgttcctg aaggcgagaa tctggtgctg 120
aactgcagct tcacagatag cgccatctac aacctgcagt ggttcagaca ggatcctgga 180
aaaggcctga caagcctgct gctgattcag agctctcaga gagagcagac atctggaaga 240
ctgaatgcta gcctggacaa gtctagcggc agaagcaccc tgtatattgc cgcctctcaa 300
cctggagatt ctgccacata cctgtgtgct gtgaaggaga catctggctc tagactgacc 360
tttggcgagg gaacacaact gaccgtgaat cctgac 396

<210> SEQ ID NO 98
<211> LENGTH: 417
<212> TYPE: DNA
<213> ORGANISM: Artificial Sequence
<220> FEATURE:
<223> OTHER INFORMATION: Synthetic sequence WT137-45 TCR11.2 - Valpha Codon Optimized

<400> SEQUENCE: 98
atgaccagag ttagcctgtt atgggctgtg gtggtgagca catgtctgga atctggaatg 60
gcccagacag tgacacagtc tcagcctgaa atgtctgtgc aggaagccga aaccgttaca 120
ctgagctgca cctacgatac aagcgagaac aactactacc tgttctggta caagcagccc 180
ccctctaggc agatgatcct ggtgatcaga caggaggcct ataaacagca gaatgccaca 240
gagaaccggt tcagcgtgaa cttccagaaa gccgccaaga gcttcagcct gaagatctct 300
gattctcagc tgggcgatac agccatgtac ttttgcgcct tcatctaccc cagctacaca 360
agcggcacat acaagtacat cttcggcacc ggcacaagac tgaaggttct ggccaac 417

<210> SEQ ID NO 99
<211> LENGTH: 420
<212> TYPE: DNA
<213> ORGANISM: Artificial Sequence
<220> FEATURE:
<223> OTHER INFORMATION: Synthetic sequence WT137-45 TCR12.1 - Valpha
Codon Optimized

<400> SEQUENCE: 99
atggccatgt tactaggagc gagcgtgctg attctgtggt tacagcctga ttgggtgaac 60
tctcagcaga agaacgatga tcagcaggtg aagcagaaca gcccctctct gtctgtgcag 120
gaaggcagaa tcagcatcct gaattgcgat tacaccaaca gcatgttcga ctacttcctg 180
tggtacaaga agtaccccgc cgagggccct acctttctga tcagcatctc tagcatcaag 240
gacaagaacg aagatggcag attcaccgtg ttcctgaaca agagcgccaa gcacctgagc 300
ctgcacattg tgccttctca acctggagat tctgccgtgt acttttgtgc tgcctctgga 360
acaggcggaa gctatatccc cacatttgga agaggaacaa gcctgatcgt gcacccttac 420

<210> SEQ ID NO 100
<211> LENGTH: 417
<212> TYPE: DNA
<213> ORGANISM: Artificial Sequence
<220> FEATURE:
<223> OTHER INFORMATION: Synthetic sequence WT137-45 TCR13.1 - Valpha
Codon Optimized

<400> SEQUENCE: 100
atggccatgt tactaggagc gagcgtgctg attctgtggt tacagcctga ttgggtgaac 60
tctcagcaga agaacgatga tcagcaggtg aagcagaaca gcccctctct gtctgtgcag 120
gaaggcagaa tcagcatcct gaattgcgat tacaccaaca gcatgttcga ctacttcctg 180
tggtacaaga agtaccccgc cgagggccct acctttctga tcagcatctc tagcatcaag 240
gacaagaacg aagatggcag attcaccgtg ttcctgaaca agagcgccaa gcacctgagc 300
ctgcacattg tgccttctca acctggagat tctgccgtgt acttttgtgc tgcctctggc 360
attggcgact acaaactgag ctttggagcc ggcacaacag tgaccgttag agccaat 417

<210> SEQ ID NO 101
<211> LENGTH: 393
<212> TYPE: DNA
<213> ORGANISM: Artificial Sequence
<220> FEATURE:
<223> OTHER INFORMATION: Synthetic sequence WT137-45 TCR13.2 - Valpha
Codon Optimized

<400> SEQUENCE: 101
atggtgaaga tccggcagtt cctcctggct attctgtggc tgcaactgtc ttgtgtgtct 60
gctgccaaga atgaagtgga gcagtctccc cagaacctta cagcccagga aggcgagttt 120
atcaccatca actgcagcta ttctgtgggc attagcgccc tgcattggct gcagcaacac 180
cctggaggag gaattgtgtc tctgtttatg ctgtcttctg gcaagaagaa gcacggccgg 240
ctgattgcca ccatcaacat ccaggagaag cactcttctc tgcacattac agcctctcat 300
cccagggatt ctgccgtgta catctgtgcc gtgagaacca gctacgataa ggtgattttc 360
ggaccaggca cctctctgag cgtgatcccc aat 393

<210> SEQ ID NO 102
<211> LENGTH: 408

```
<212> TYPE: DNA
<213> ORGANISM: Artificial Sequence
<220> FEATURE:
<223> OTHER INFORMATION: Synthetic sequence WT137-45 TCR14.1 - Valpha
      Codon Optimized

<400> SEQUENCE: 102

atgaagagcc tgagagtcct gctggtgatt ttgtggctgc agctgtcttg ggtttggtct      60

cagcagaaag aagtggagca gaatagcggc cctctgtctg ttcctgaagg cgctattgct     120

agcctgaatt gcacatacag cgatagagga tctcagagct tcttctggta ccggcagtac     180

agcggcaaga gcccagaact gatcatgttc atctacagca atggcgacaa ggaggatggc     240

aggtttacag cccagctgaa caaggccagc cagtatgttt ctctgctgat cagagatagc     300

cagcctagcg attctgccac ctacctgtgt gccgtgaact tacttggagc tacaggatac     360

tctacactga ccttcggcaa aggcaccatg ctgctggtga gccctgat                  408


<210> SEQ ID NO 103
<211> LENGTH: 384
<212> TYPE: DNA
<213> ORGANISM: Artificial Sequence
<220> FEATURE:
<223> OTHER INFORMATION: Synthetic sequence WT137-45 TCR15.1 - Valpha
      Codon Optimized

<400> SEQUENCE: 103

atgtggggcg ttttccttct gtatgtgagc atgaagatgg gcggcacaac aggccagaac      60

atcgatcagc ctaccgagat gacagccaca gaaggagcta ttgttcagat caactgcacc     120

taccagacaa gcggcttcaa cggcctgttc tggtaccagc agcatgctgg agaagctcct     180

acatttctga gctacaatgt gctggatggc ctggaggaga aaggcaggtt tagcagcttc     240

ctgagcaggt ctaagggcta ttcttatctg ctgctgaagg agctgcagat gaaggattcc     300

gccagctacc tgtgtgccgt taggggcatc aatgattaca agctgagctt tggagccgga     360

acaacagtga ccgtgagagc caac                                            384


<210> SEQ ID NO 104
<211> LENGTH: 393
<212> TYPE: DNA
<213> ORGANISM: Artificial Sequence
<220> FEATURE:
<223> OTHER INFORMATION: Synthetic sequence WT137-45 TCR16.1 - Valpha
      Codon Optimized

<400> SEQUENCE: 104

atggagaaga tgctggagtg tgcgttcatc gttctgtggc tgcaacttgg atggctgtct      60

ggagaggatc aggttacaca gtctcctgaa gccctgagac tgcaagaagg agaaagctct     120

agcctgaact gcagctacac agtgtctgga ctgagaggcc tgttctggta cagacaggat     180

cctggaaaag gcccagagtt cctgtttacc ctgtattctg ccggcgagga gaaggagaaa     240

gagagactga aagctaccct gaccaagaag gagagcttcc tgcacattac cgcccccaaa     300

cctgaggatt ctgccacata tctgtgtgcc gtgattaccg gctttcagaa gctggtgttt     360

ggcacaggca ccagactgct ggtttctccc aat                                 393


<210> SEQ ID NO 105
<211> LENGTH: 384
<212> TYPE: DNA
<213> ORGANISM: Artificial Sequence
<220> FEATURE:
<223> OTHER INFORMATION: Synthetic sequence WT137-45 TCR16.2 - Valpha
```

Codon Optimized

<400> SEQUENCE: 105
atgagactgg tggcacgcgt aactgtgttt ctgacctttg gcaccatcat cgatgccaag 60
acaacccagc ctacaagcat ggactgtgcc gagggaagag ctgctaatct gccatgtaat 120
cacagcacaa tcagcggcaa cgagtacgtg tactggtacc ggcagatcca ctctcaagga 180
cctcagtaca tcattcatgg cctgaagaac aacgagacca acgagatggc cagcctgatc 240
atcaccgagg acaggaagtc ttctaccctg attctgcctc atgctacact gagagatacc 300
gccgtgtact actgcattgc cggagtggga agaggccaga atttcgtgtt tggacctgga 360
acaagactga gcgttctgcc ctat 384

<210> SEQ ID NO 106
<211> LENGTH: 408
<212> TYPE: DNA
<213> ORGANISM: Artificial Sequence
<220> FEATURE:
<223> OTHER INFORMATION: Synthetic sequence WT137-45 TCR18.1 - Valpha
Codon Optimized

<400> SEQUENCE: 106
atggagaaga acccccttggc agcacctctg cttattctgt ggttccacct ggattgtgtg 60
agcagcatcc tgaatgtgga gcagtctcct cagagcctgc atgtgcaaga aggcgatagc 120
accaatttca cctgcagctt tccaagcagc aacttctacg ccctgcactg gtacagatgg 180
gaaaccgcca aatctcctga agccctgttt gtgatgaccc tgaatggcga cgagaagaag 240
aagggcagaa ttagcgccac cctgaatacc aaggagggct acagctacct gtacatcaag 300
ggctctcaac ctgaggattc tgccacctac ctttgcgcct ttcaccccaa tttcggcaac 360
gagaaactga cctttggaac cggaacaagg ctgaccatca tccccaac 408

<210> SEQ ID NO 107
<211> LENGTH: 411
<212> TYPE: DNA
<213> ORGANISM: Artificial Sequence
<220> FEATURE:
<223> OTHER INFORMATION: Synthetic sequence WT137-45 TCR19.1 - Valpha
Codon Optimized

<400> SEQUENCE: 107
atggagaaga tgctggagtg tgcgttcatc gttctgtggc tgcaacttgg atggctgtct 60
ggagaggatc aggttacaca gtctcctgaa gccctgagac tgcaagaagg agaaagctct 120
agcctgaact gcagctacac agtgtctgga ctgagaggcc tgttctggta cagacaggat 180
cctggaaaag gcccagagtt cctgtttacc ctgtattctg ccggcgagga gaaggagaaa 240
gagagactga aagctaccct gaccaagaag gagagcttcc tgcacattac cgcccccaaa 300
cctgaggatt ctgccacata tctgtgtgct gttcagccta gaggagatgg ctctagcaat 360
accggcaagc tgatctttgg ccagggaaca acactgcagg tgaagcctga t 411

<210> SEQ ID NO 108
<211> LENGTH: 528
<212> TYPE: DNA
<213> ORGANISM: Artificial Sequence
<220> FEATURE:
<223> OTHER INFORMATION: Synthetic sequence WT137-45 TCR15.1 - Cbeta
Codon Optimized

<400> SEQUENCE: 108

-continued

```
gatctgaaca aggtgttccc cccagaggtg gccgtgttcg agccttctga ggccgagatc     60

tcccacaccc agaaagccac cctcgtgtgc ctggccaccg gctttttccc cgaccacgtg    120

gaactgtctt ggtgggtcaa cggcaaagag gtgcactccg gcgtgtgcac cgatccccag    180

cctctgaaag aacagcccgc cctgaacgac agccggtact gcctgagcag cagactgaga    240

gtgtccgcca ccttctggca gaacccccgg aaccacttca gatgccaggt gcagttctac    300

ggcctgagcg agaacgacga gtggacccag gacagagcca agcccgtgac acagatcgtg    360

tctgccgaag cctggggcag agccgattgc ggctttacct ccgtgtccta tcagcagggc    420

gtgctgagcg ccacaatcct gtacgagatc ctgctgggca aggccaccct gtacgccgtg    480

ctggtgtctg ccctggtgct gatggccatg gtcaagcgga aggacttc                 528
```

```
<210> SEQ ID NO 109
<211> LENGTH: 534
<212> TYPE: DNA
<213> ORGANISM: Artificial Sequence
<220> FEATURE:
<223> OTHER INFORMATION: Synthetic sequence WT137-45 TCR16.2 - Cbeta
      Codon Optimized

<400> SEQUENCE: 109

gacctgaaga acgtgttccc cccagaggtg gccgtgttcg agcctagcga ggccgagatc     60

agccacaccc agaaagccac cctcgtgtgc ctggccaccg gcttttaccc cgaccacgtg    120

gaactgtctt ggtgggtcaa cggcaaagag gtgcacagcg gcgtctgcac cgacccccag    180

cccctgaaag agcagcccgc cctgaacgac agccggtact gtctgagcag cagactgaga    240

gtgtccgcca ccttctggca gaacccccgg aaccacttca gatgccaggt gcagttctac    300

ggcctgagcg agaacgacga gtggacccag gaccgggcca agcccgtgac ccagatcgtg    360

tctgctgagg cctggggcag agccgattgc ggcttcacca gcgagagcta ccagcagggc    420

gtgctgagcg ccaccatcct gtacgagatc ctgctgggca aggccaccct gtacgccgtg    480

ctggtgtccg ccctggtgct gatggccatg gtcaagcgga aggacagccg gggc          534
```

```
<210> SEQ ID NO 110
<211> LENGTH: 423
<212> TYPE: DNA
<213> ORGANISM: Artificial Sequence
<220> FEATURE:
<223> OTHER INFORMATION: Synthetic sequence WT137-45 TCR15.1 - Calpha
      Codon Optimized

<400> SEQUENCE: 110

atccagaatc ccgatcctgc tgtgtaccag ctgcgggaca gcaagagcag cgacaagagc     60

gtgtgcctgt tcaccgactt cgacagccag accaacgtgt cccagagcaa ggacagcgac    120

gtgtacatca ccgataagtg cgtgctggac atgcggagca tggacttcaa gagcaacagc    180

gccgtggcct ggtccaacaa gagcgacttc gcctgcgcca acgccttcaa caacagcatt    240

atccccgagg acacattctt cccaagcccc gagagcagct gcgacgtgaa gctggtggaa    300

aagagcttcg agacagacac caacctgaac ttccagaacc tcagcgtgat cggcttccgg    360

atcctgctgc tgaaggtggc cggcttcaac ctgctgatga ccctgcggct gtggtccagc    420

tga                                                                  423
```

```
<210> SEQ ID NO 111
<211> LENGTH: 936
<212> TYPE: DNA
<213> ORGANISM: Artificial Sequence
```

```
<220> FEATURE:
<223> OTHER INFORMATION: Synthetic sequence WT137-45 TCR10.1 Wild-type
      beta-Chain (TCRBV7-6 01 / TCRBJ2-7 01)

<400> SEQUENCE: 111

atgggcacca gtctcctatg ctgggtggtc ctgggtttcc tagggacaga tcacacaggt     60

gctggagtct cccagtctcc caggtacaaa gtcacaaaga ggggacagga tgtagctctc    120

aggtgtgatc caatttcggg tcatgtatcc ctttattggt accgacaggc cctggggcag    180

ggcccagagt ttctgactta cttcaattat gaagcccaac aagacaaatc agggctgccc    240

aatgatcggt tctctgcaga gaggcctgag ggatccatct ccactctgac gatccagcgc    300

acagagcagc gggactcggc catgtatcgc tgtgccagca gcctgacagg gtcctacgag    360

cagtacttcg ggccgggcac caggctcacg gtcacagagg acctgaaaaa cgtgttccca    420

cccgaggtcg ctgtgtttga gccatcagaa gcagagatct cccacaccca aaaggccaca    480

ctggtgtgcc tggccacagg cttctacccc gaccacgtgg agctgagctg gtgggtgaat    540

gggaaggagg tgcacagtgg ggtcagcaca gacccgcagc ccctcaagga gcagcccgcc    600

ctcaatgact ccagatactg cctgagcagc cgcctgaggg tctcggccac cttctggcag    660

aacccccgca accacttccg ctgtcaagtc cagttctacg ggctctcgga gaatgacgag    720

tggacccagg atagggccaa acctgtcacc cagatcgtca gcgccgaggc ctggggtaga    780

gcagactgtg gcttcacctc cgagtcttac cagcaagggg tcctgtctgc caccatcctc    840

tatgagatct tgctagggaa ggccaccttg tatgccgtgc tggtcagtgc cctcgtgctg    900

atggccatgg tcaagagaaa ggattccaga ggctag                               936


<210> SEQ ID NO 112
<211> LENGTH: 936
<212> TYPE: DNA
<213> ORGANISM: Artificial Sequence
<220> FEATURE:
<223> OTHER INFORMATION: Synthetic sequence WT137-45 TCR11.2 Wild-type
      beta-Chain (TCRBV20-1 02 / TCRBJ2-7 01)

<400> SEQUENCE: 112

atgctgctgc ttctgctgct tctggggcca gcaggctccg ggcttggtgc tgtcgtctct     60

caacatccga gctgggttat ctgtaagagt ggaacctctg tgaagatcga gtgccgttcc    120

ctggactttc aggccacaac tatgttttgg tatcgtcagt tcccgaaaca gagtctcatg    180

ctgatggcaa cttccaatga gggctccaag gccacatacg agcaaggcgt cgagaaggac    240

aagtttctca tcaaccatgc aagcctgacc ttgtccactc tgacagtgac cagtgcccat    300

cctgaagaca gcagcttcta catctgcagt gcaaccccgg aggctagtag cccctacgag    360

cagtacttcg ggccgggcac caggctcacg gtcacagagg acctgaaaaa cgtgttccca    420

cccgaggtcg ctgtgtttga gccatcagaa gcagagatct cccacaccca aaaggccaca    480

ctggtgtgcc tggccacagg cttctacccc gaccacgtgg agctgagctg gtgggtgaat    540

gggaaggagg tgcacagtgg ggtcagcaca gacccgcagc ccctcaagga gcagcccgcc    600

ctcaatgact ccagatactg cctgagcagc cgcctgaggg tctcggccac cttctggcag    660

aacccccgca accacttccg ctgtcaagtc cagttctacg ggctctcgga gaatgacgag    720

tggacccagg atagggccaa acctgtcacc cagatcgtca gcgccgaggc ctggggtaga    780

gcagactgtg gcttcacctc cgagtcttac cagcaagggg tcctgtctgc caccatcctc    840

tatgagatct tgctagggaa ggccaccttg tatgccgtgc tggtcagtgc cctcgtgctg    900
```

atggccatgg tcaagagaaa ggattccaga ggctag 936

<210> SEQ ID NO 113
<211> LENGTH: 930
<212> TYPE: DNA
<213> ORGANISM: Artificial Sequence
<220> FEATURE:
<223> OTHER INFORMATION: Synthetic sequence WT137-45 TCR12.1 Wild-type beta-Chain (TCRBV15 02 / TCRBJ1-5 01)

<400> SEQUENCE: 113
atgggtcctg ggcttctcca ctggatggcc ctttgtctcc ttggaacagg tcatggggat 60
gccatggtca tccagaaccc aagataccag gttacccagt ttggaaagcc agtgaccctg 120
agttgttctc agactttgaa ccataacgtc atgtactggt accagcagaa gtcaagtcag 180
gccccaaagc tgctgttcca ctactatgac aaagatttta acaatgaagc agacacccct 240
gataacttcc aatccaggag gccgaacact tctttctgct ttcttgacat ccgctcacca 300
ggcctggggg acgcagccat gtacctgtgt gccaccagca accttcaggg gcgacagccc 360
cagcattttg gtgatgggac tcgactctcc atcctagagg acctgaacaa ggtgttccca 420
cccgaggtcg ctgtgtttga gccatcagaa gcagagatct cccacaccca aaaggccaca 480
ctggtgtgcc tggccacagg cttcttcccc gaccacgtgg agctgagctg gtgggtgaat 540
gggaaggagg tgcacagtgg ggtcagcacg gacccgcagc ccctcaagga gcagcccgcc 600
ctcaatgact ccagatactg cctgagcagc cgcctgaggg tctcggccac cttctggcag 660
aacccccgca accacttccg ctgtcaagtc cagttctacg ggctctcgga gaatgacgag 720
tggacccagg atagggccaa acccgtcacc cagatcgtca gcgccgaggc ctggggtaga 780
gcagactgtg gctttacctc ggtgtcctac cagcaagggg tcctgtctgc caccatcctc 840
tatgagatcc tgctagggaa ggccaccctg tatgctgtgc tggtcagcgc ccttgtgttg 900
atggccatgg tcaagagaaa ggatttctga 930

<210> SEQ ID NO 114
<211> LENGTH: 966
<212> TYPE: DNA
<213> ORGANISM: Artificial Sequence
<220> FEATURE:
<223> OTHER INFORMATION: Synthetic sequence WT137-45 TCR13.1 Wild-type beta-Chain (TCRBV13 01 / TCRBJ2-5 01)

<400> SEQUENCE: 114
atgcttagtc ctgacctgcc tgactctgcc tggaacacca ggctcctctg ccatgtcatg 60
ctttgtctcc tgggagcagt ttcagtggct gctggagtca tccagtcccc aagacatctg 120
atcaaagaaa agagggaaac agccactctg aaatgctatc ctatccctag acacgacact 180
gtctactggt accagcaggg tccaggtcag gacccccagt tcctcatttc gttttatgaa 240
aagatgcaga gcgataaagg aagcatccct gatcgattct cagctcaaca gttcagtgac 300
tatcattctg aactgaacat gagctccttg gagctggggg actcagccct gtacttctgt 360
gccagcagcc tccggttggg gcgagagacc cagtacttcg ggccaggcac gcggctcctg 420
gtgctcgagg acctgaaaaa cgtgttccca cccgaggtcg ctgtgtttga gccatcagaa 480
gcagagatct cccacaccca aaaggccaca ctggtgtgcc tggccacagg cttctacccc 540
gaccacgtgg agctgagctg gtgggtgaat gggaaggagg tgcacagtgg ggtcagcaca 600
gacccgcagc ccctcaagga gcagcccgcc ctcaatgact ccagatactg cctgagcagc 660
cgcctgaggg tctcggccac cttctggcag aacccccgca accacttccg ctgtcaagtc 720

```
cagttctacg ggctctcgga gaatgacgag tggacccagg atagggccaa acctgtcacc    780

cagatcgtca gcgccgaggc ctggggtaga gcagactgtg gcttcacctc cgagtcttac    840

cagcaagggg tcctgtctgc caccatcctc tatgagatct tgctagggaa ggccaccttg    900

tatgccgtgc tggtcagtgc cctcgtgctg atggccatgg tcaagagaaa ggattccaga    960

ggctag                                                               966
```

<210> SEQ ID NO 115
<211> LENGTH: 936
<212> TYPE: DNA
<213> ORGANISM: Artificial Sequence
<220> FEATURE:
<223> OTHER INFORMATION: Synthetic sequence WT137-45 TCR13.2 Wild-type beta-Chain (TRAJ50 01 / TRBJ2-7 01)

<400> SEQUENCE: 115

```
atgggcacca ggctcctctg ctgggtggtc ctgggtttcc tagggacaga tcacacaggt     60

gctggagtct cccagtcccc taggtacaaa gtcgcaaaga gaggacagga tgtagctctc    120

aggtgtgatc caatttcggg tcatgtatcc ctttttggt accaacaggc cctggggcag     180

gggccagagt ttctgactta tttccagaat gaagctcaac tagacaaatc ggggctgccc    240

agtgatcgct tctttgcaga aaggcctgag ggatccgtct ccactctgaa gatccagcgc    300

acacagcagg aggactccgc cgtgtatctc tgtgccagca gcctgggaca ggcctacgag    360

cagtacttcg ggccgggcac caggctcacg gtcacagagg acctgaaaaa cgtgttccca    420

cccgaggtcg ctgtgtttga gccatcagaa gcagagatct cccacaccca aaaggccaca    480

ctggtgtgcc tggccacagg cttctacccc gaccacgtgg agctgagctg gtgggtgaat    540

gggaaggagg tgcacagtgg ggtcagcaca gacccgcagc ccctcaagga gcagcccgcc    600

ctcaatgact ccagatactg cctgagcagc cgcctgaggg tctcggccac cttctggcag    660

aacccccgca accacttccg ctgtcaagtc cagttctacg ggctctcgga gaatgacgag    720

tggacccagg atagggccaa acctgtcacc cagatcgtca gcgccgaggc ctggggtaga    780

gcagactgtg gcttcacctc cgagtcttac cagcaagggg tcctgtctgc caccatcctc    840

tatgagatct tgctagggaa ggccaccttg tatgccgtgc tggtcagtgc cctcgtgctg    900

atggccatgg tcaagagaaa ggattccaga ggctag                              936
```

<210> SEQ ID NO 116
<211> LENGTH: 930
<212> TYPE: DNA
<213> ORGANISM: Artificial Sequence
<220> FEATURE:
<223> OTHER INFORMATION: Synthetic sequence WT137-45 TCR14.1 Wild-type beta-Chain (TCRBV11-3 01 / TCRBJ1 1 01)

<400> SEQUENCE: 116

```
atgggtacca ggctcctctg ctgggtggcc ttctgtctcc tggtggaaga actcatagaa     60

gctggagtgg ttcagtctcc cagatataag attatagaga aaaaacagcc tgtggctttt    120

tggtgcaatc ctatttctgg ccacaatacc ctttactggt acctgcagaa cttgggacag    180

ggcccggagc ttctgattcg atatgagaat gaggaagcag tagacgattc acagttgcct    240

aaggatcgat tttctgcaga gaggctcaaa ggagtagact ccactctcaa gatccagcct    300

gcagagcttg gggactcggc cgtgtatctc tgtgccagca gcctaaccag gggggctgaa    360

gctttctttg gacaaggcac cagactcaca gttgtagagg acctgaacaa ggtgttccca    420
```

```
cccgaggtcg ctgtgtttga gccatcagaa gcagagatct cccacaccca aaaggccaca    480

ctggtgtgcc tggccacagg cttcttcccc gaccacgtgg agctgagctg gtgggtgaat    540

gggaaggagg tgcacagtgg ggtcagcacg gacccgcagc ccctcaagga gcagcccgcc    600

ctcaatgact ccagatactg cctgagcagc cgcctgaggg tctcggccac cttctggcag    660

aacccccgca accacttccg ctgtcaagtc cagttctacg ggctctcgga gaatgacgag    720

tggacccagg atagggccaa acccgtcacc cagatcgtca gcgccgaggc ctggggtaga    780

gcagactgtg gctttacctc ggtgtcctac cagcaagggg tcctgtctgc caccatcctc    840

tatgagatcc tgctagggaa ggccaccctg tatgctgtgc tggtcagcgc ccttgtgttg    900

atggccatgg tcaagagaaa ggatttctga                                     930
```

<210> SEQ ID NO 117
<211> LENGTH: 933
<212> TYPE: DNA
<213> ORGANISM: Artificial Sequence
<220> FEATURE:
<223> OTHER INFORMATION: Synthetic sequence WT137-45 TCR15.1 Wild-type beta-Chain (TRBV19 01 / TRBJ1-6 02)

<400> SEQUENCE: 117

```
atgagcaacc aggtgctctg ctgtgtggtc ctttgtttcc tgggagcaaa caccgtggat     60

ggtggaatca ctcagtcccc aaagtacctg ttcagaaagg aaggacagaa tgtgaccctg    120

agttgtgaac agaatttgaa ccacgatgcc atgtactggt accgacagga cccagggcaa    180

gggctgagat tgatctacta ctcacagata gtaaatgact ttcagaaagg agatatagct    240

gaagggtaca gcgtctctcg ggagaagaag gaatcctttc ctctcactgt gacatcggcc    300

caaaagaacc cgacagcttt ctatctctgt gccagtagta gagacaggga gcaagaatca    360

cccctccact ttgggaacgg gaccaggctc actgtgacag aggacctgaa caaggtgttc    420

ccacccgagg tcgctgtgtt tgagccatca gaagcagaga tctcccacac ccaaaaggcc    480

acactggtgt gcctggccac aggcttcttc cccgaccacg tggagctgag ctggtgggtg    540

aatgggaagg aggtgcacag tggggtcagc acggacccgc agcccctcaa ggagcagccc    600

gccctcaatg actccagata ctgcctgagc agccgcctga gggtctcggc caccttctgg    660

cagaaccccc gcaaccactt ccgctgtcaa gtccagttct acgggctctc ggagaatgac    720

gagtggaccc aggatagggc caaacccgtc acccagatcg tcagcgccga ggcctggggt    780

agagcagact gtggctttac ctcggtgtcc taccagcaag gggtcctgtc tgccaccatc    840

ctctatgaga tcctgctagg gaaggccacc ctgtatgctg tgctggtcag cgcccttgtg    900

ttgatggcca tggtcaagag aaaggatttc tga                                 933
```

<210> SEQ ID NO 118
<211> LENGTH: 936
<212> TYPE: DNA
<213> ORGANISM: Artificial Sequence
<220> FEATURE:
<223> OTHER INFORMATION: Synthetic sequence WT137-45 TCR16.1 Wild-type beta-Chain (TCRBV27 01 / TCRBJ2-7 01)

<400> SEQUENCE: 118

```
atgggccccc agctccttgg ctatgtggtc ctttgccttc taggagcagg cccccctggaa    60

gcccaagtga cccagaaccc aagatacctc atcacagtga ctggaaagaa gttaacagtg    120

acttgttctc agaatatgaa ccatgagtat atgtcctggt atcgacaaga cccagggctg    180

ggcttaaggc agatctacta ttcaatgaat gttgaggtga ctgataaggg agatgttcct    240
```

```
gaagggtaca aagtctctcg aaaagagaag aggaatttcc ccctgatcct ggagtcgccc    300

agccccaacc agacctctct gtacttctgt gccagcagtt ttagcggggg aacctacgag    360

cagtacttcg ggccgggcac caggctcacg gtcacagagg acctgaaaaa cgtgttccca    420

cccgaggtcg ctgtgtttga gccatcagaa gcagagatct cccacaccca aaaggccaca    480

ctggtgtgcc tggccacagg cttctacccc gaccacgtgg agctgagctg gtgggtgaat    540

gggaaggagg tgcacagtgg ggtcagcaca gacccgcagc ccctcaagga gcagcccgcc    600

ctcaatgact ccagatactg cctgagcagc cgcctgaggg tctcggccac cttctggcag    660

aacccccgca accacttccg ctgtcaagtc cagttctacg ggctctcgga gaatgacgag    720

tggacccagg atagggccaa acctgtcacc cagatcgtca gcgccgaggc ctggggtaga    780

gcagactgtg gcttcacctc cgagtcttac cagcaagggg tcctgtctgc caccatcctc    840

tatgagatct tgctagggaa ggccaccttg tatgccgtgc tggtcagtgc cctcgtgctg    900

atggccatgg tcaagagaaa ggattccaga ggctag                              936
```

<210> SEQ ID NO 119
<211> LENGTH: 969
<212> TYPE: DNA
<213> ORGANISM: Artificial Sequence
<220> FEATURE:
<223> OTHER INFORMATION: Synthetic sequence WT137-45 TCR16.2 Wild-type beta-Chain (TRBV13 01 / TRBJ2-7 01)

<400> SEQUENCE: 119

```
atgcttagtc ctgacctgcc tgactctgcc tggaacacca ggctcctctg ccatgtcatg     60

ctttgtctcc tgggagcagt ttcagtggct gctggagtca tccagtcccc aagacatctg    120

atcaaagaaa agagggaaac agccactctg aaatgctatc ctatccctag acacgacact    180

gtctactggt accagcaggg tccaggtcag gacccccagt tcctcatttc gttttatgaa    240

aagatgcaga gcgataaagg aagcatccct gatcgattct cagctcaaca gttcagtgac    300

tatcattctg aactgaacat gagctccttg gagctggggg actcagccct gtacttctgt    360

gccagcagct acagaggggg ctctacgtac gagcagtact tcgggccggg caccaggctc    420

acggtcacag aggacctgaa aaacgtgttc ccacccgagg tcgctgtgtt tgagccatca    480

gaagcagaga tctcccacac ccaaaaggcc acactggtgt gcctggccac aggcttctac    540

cccgaccacg tggagctgag ctggtgggtg aatgggaagg aggtgcacag tggggtcagc    600

acagacccgc agcccctcaa ggagcagccc gccctcaatg actccagata ctgcctgagc    660

agccgcctga gggtctcggc caccttctgg cagaaccccc gcaaccactt ccgctgtcaa    720

gtccagttct acgggctctc ggagaatgac gagtggaccc aggatagggc caaacctgtc    780

acccagatcg tcagcgccga ggcctggggt agagcagact gtggcttcac ctccgagtct    840

taccagcaag gggtcctgtc tgccaccatc ctctatgaga tcttgctagg gaaggccacc    900

ttgtatgccg tgctggtcag tgccctcgtg ctgatggcca tggtcaagag aaaggattcc    960

agaggctag                                                            969
```

<210> SEQ ID NO 120
<211> LENGTH: 936
<212> TYPE: DNA
<213> ORGANISM: Artificial Sequence
<220> FEATURE:
<223> OTHER INFORMATION: Synthetic sequence WT137-45 TCR18.1 Wild-type beta-Chain (TCRBV11-1 01 / TCRBJ1 4 01)

<400> SEQUENCE: 120

```
atgagcacca ggcttctctg ctggatggcc ctctgtctcc tgggggcaga actctcagaa     60
gctgaagttg cccagtcccc cagatataag attacagaga aaagccaggc tgtggctttt    120
tggtgtgatc ctatttctgg ccatgctacc ctttactggt accggcagat cctgggacag    180
ggcccggagc ttctggttca atttcaggat gagagtgtag tagatgattc acagttgcct    240
aaggatcgat tttctgcaga gaggctcaaa ggagtagact ccactctcaa gatccagcct    300
gcagagcttg gggactcggc catgtatctc tgtgccagca gccaacggga cagcccaaat    360
gaaaaactgt tttttggcag tggaacccag ctctctgtct tggaggacct gaacaaggtg    420
ttcccacccg aggtcgctgt gtttgagcca tcagaagcag agatctccca cacccaaaag    480
gccacactgg tgtgcctggc cacaggcttc ttccccgacc acgtggagct gagctggtgg    540
gtgaatggga aggaggtgca cagtggggtc agcacggacc cgcagcccct caaggagcag    600
cccgccctca atgactccag atactgcctg agcagccgcc tgagggtctc ggccaccttc    660
tggcagaacc cccgcaacca cttccgctgt caagtccagt tctacgggct ctcggagaat    720
gacgagtgga cccaggatag ggccaaaccc gtcacccaga tcgtcagcgc cgaggcctgg    780
ggtagagcag actgtggctt tacctcggtg tcctaccagc aaggggtcct gtctgccacc    840
atcctctatg agatcctgct agggaaggcc accctgtatg ctgtgctggt cagcgccctt    900
gtgttgatgg ccatggtcaa gagaaaggat ttctga                              936
```

<210> SEQ ID NO 121
<211> LENGTH: 939
<212> TYPE: DNA
<213> ORGANISM: Artificial Sequence
<220> FEATURE:
<223> OTHER INFORMATION: Synthetic sequence WT137-45 TCR19.1 Wild-type beta-Chain (TCRBV4-3 01 / TCRBJ1-3 01)

<400> SEQUENCE: 121

```
atgggctgca ggctgctctg ctgtgcggtt ctctgtctcc tgggagcggt ccccatggaa     60
acgggagtta cgcagacacc aagacacctg gtcatgggaa tgacaaataa gaagtctttg    120
aaatgtgaac aacatctggg tcataacgct atgtattggt acaagcaaag tgctaagaag    180
ccactggagc tcatgtttgt ctacagtctt gaagaacggg ttgaaaacaa cagtgtgcca    240
agtcgcttct cacctgaatg ccccaacagc tctcacttat tccttcacct acacaccctg    300
cagccagaag actcggccct gtatctctgc gccagcagcc aagatccgta caagctctct    360
ggaaacacca tatattttgg agagggaagt tggctcactg ttgtagagga cctgaacaag    420
gtgttcccac ccgaggtcgc tgtgtttgag ccatcagaag cagagatctc ccacacccaa    480
aaggccacac tggtgtgcct ggccacaggc ttcttccccg accacgtgga gctgagctgg    540
tgggtgaatg ggaaggaggt gcacagtggg gtcagcacgg acccgcagcc cctcaaggag    600
cagcccgccc tcaatgactc cagatactgc ctgagcagcc gcctgagggt ctcggccacc    660
ttctggcaga acccccgcaa ccacttccgc tgtcaagtcc agttctacgg gctctcggag    720
aatgacgagt ggacccagga tagggccaaa cccgtcaccc agatcgtcag cgccgaggcc    780
tggggtagag cagactgtgg ctttacctcg gtgtcctacc agcaaggggt cctgtctgcc    840
accatcctct atgagatcct gctagggaag gccaccctgt atgctgtgct ggtcagcgcc    900
cttgtgttga tggccatggt caagagaaag gatttctga                           939
```

<210> SEQ ID NO 122

```
<211> LENGTH: 974
<212> TYPE: DNA
<213> ORGANISM: Artificial Sequence
<220> FEATURE:
<223> OTHER INFORMATION: Synthetic sequence WT137-45 TCR10.1 - Codon
      Optimized beta-Chain

<400> SEQUENCE: 122

ctcaataaaa gagcccacaa cccctcactc ggcgcgccac catgggcaca tctcttctct     60

gttgggtggt tctgggcttt ctgggcacag atcatacagg agctggagtt agccagtctc    120

ctaggtataa ggtgaccaag aggggacagg atgtggctct gagatgtgac cctattagcg    180

gacatgtgag cctgtactgg tacagacaag ctctgggaca aggacccgag tttctgacct    240

acttcaacta tgaggcccag caggacaaat ctggactgcc caacgacaga ttcagcgccg    300

aaagaccaga aggctctatt agcacactga ccatccagag aacagagcag agggattctg    360

ccatgtacag atgcgccagc agcttaacag gctcttacga gcagtacttt ggacctggca    420

caagactgac agtgacagag gacctgaaga acgtgttccc cccagaggtg gccgtgttcg    480

agcctagcga ggccgagatc agccacaccc agaaagccac cctcgtgtgc ctggccaccg    540

gcttttaccc cgaccacgtg gaactgtctt ggtgggtcaa cggcaaagag gtgcacagcg    600

gcgtctgcac cgacccccag cccctgaaag agcagcccgc cctgaacgac agccggtact    660

gtctgagcag cagactgaga gtgtccgcca ccttctggca gaacccccgg aaccacttca    720

gatgccaggt gcagttctac ggcctgagcg agaacgacga gtggacccag gaccgggcca    780

agcccgtgac ccagatcgtg tctgctgagg cctggggcag agccgattgc ggcttcacca    840

gcgagagcta ccagcagggc gtgctgagcg ccaccatcct gtacgagatc ctgctgggca    900

aggccaccct gtacgccgtg ctggtgtccg ccctggtgct gatggccatg gtcaagcgga    960

aggacagccg gggc                                                      974


<210> SEQ ID NO 123
<211> LENGTH: 974
<212> TYPE: DNA
<213> ORGANISM: Artificial Sequence
<220> FEATURE:
<223> OTHER INFORMATION: Synthetic sequence WT137-45 TCR11.2 - Codon
      Optimized beta-Chain

<400> SEQUENCE: 123

ctcaataaaa gagcccacaa cccctcactc ggcgcgccac catgctgctt cttctcctcc     60

ttctcggacc tgctggatct ggattaggag ctgttgtgtc tcagcaccct tcttgggtga    120

tctgtaaaag cggcacaagc gtgaagatcg agtgcagaag cctggacttt caggccacaa    180

ccatgttctg gtataggcag ttccccaagc agtctctgat gctgatggcc acctctaatg    240

agggctctaa ggccacatat gaacagggag tggagaagga caagttcctg atcaaccacg    300

cctctctgac cctgtctacc ctgacagtta catctgccca ccctgaggat agcagctttt    360

acatctgtag cgccacacct gaagcctcta gcccatatga gcagtacttt ggccctggca    420

ccagattaac agtgacagag gacctgaaga acgtgttccc cccagaggtg gccgtgttcg    480

agcctagcga ggccgagatc agccacaccc agaaagccac cctcgtgtgc ctggccaccg    540

gcttttaccc cgaccacgtg gaactgtctt ggtgggtcaa cggcaaagag gtgcacagcg    600

gcgtctgcac cgacccccag cccctgaaag agcagcccgc cctgaacgac agccggtact    660

gtctgagcag cagactgaga gtgtccgcca ccttctggca gaacccccgg aaccacttca    720

gatgccaggt gcagttctac ggcctgagcg agaacgacga gtggacccag gaccgggcca    780
```

agcccgtgac ccagatcgtg tctgctgagg cctggggcag agccgattgc ggcttcacca 840
gcgagagcta ccagcagggc gtgctgagcg ccaccatcct gtacgagatc ctgctgggca 900
aggccaccct gtacgccgtg ctggtgtccg ccctggtgct gatggccatg gtcaagcgga 960
aggacagccg gggc 974

<210> SEQ ID NO 124
<211> LENGTH: 968
<212> TYPE: DNA
<213> ORGANISM: Artificial Sequence
<220> FEATURE:
<223> OTHER INFORMATION: Synthetic sequence WT137-45 TCR12.1 - Codon Optimized beta-Chain

<400> SEQUENCE: 124
ctcaataaaa gagcccacaa cccctcactc ggcgcgccac catgggacct ggactgcttc 60
attggatggc tctgtgtttg ctgggaacag gacatggaga tgctatggtg atccagaacc 120
ccaggtatca ggtgacccag tttggcaaac cagtgacact gagctgttct cagaccctga 180
accacaacgt gatgtactgg taccagcaga agtcttctca ggcccctaag ctgctgttcc 240
actactacga caaggacttc aacaacgagg ccgataccc tgacaatttc cagagcagga 300
ggcccaatac cagcttctgt ttcctggaca ttagaagccc tggactggga gatgctgcca 360
tgtacctgtg tgccaccagc aatttacagg gaagacaacc tcagcacttt ggcgatggca 420
caaggctgtc tatcctggag gatctgaaca aggtgttccc cccagaggtg gccgtgttcg 480
agccttctga ggccgagatc tcccacaccc agaaagccac cctcgtgtgc ctggccaccg 540
gctttttccc cgaccacgtg gaactgtctt ggtgggtcaa cggcaaagag gtgcactccg 600
gcgtgtgcac cgatccccag cctctgaaag aacagcccgc cctgaacgac agccggtact 660
gcctgagcag cagactgaga gtgtccgcca ccttctggca gaacccccgg aaccacttca 720
gatgccaggt gcagttctac ggcctgagcg agaacgacga gtggacccag gacagagcca 780
agcccgtgac acagatcgtg tctgccgaag cctggggcag agccgattgc ggctttacct 840
ccgtgtccta tcagcagggc gtgctgagcg ccacaatcct gtacgagatc ctgctgggca 900
aggccaccct gtacgccgtg ctggtgtctg ccctggtgct gatggccatg gtcaagcgga 960
aggacttc 968

<210> SEQ ID NO 125
<211> LENGTH: 1004
<212> TYPE: DNA
<213> ORGANISM: Artificial Sequence
<220> FEATURE:
<223> OTHER INFORMATION: Synthetic sequence WT137-45 TCR13.1 - Codon Optimized beta-Chain

<400> SEQUENCE: 125
ctcaataaaa gagcccacaa cccctcactc ggcgcgccac catgctgagc cctgatctcc 60
ctgattctgc ctggaatacc agactgctgt gtcatgtgat gctgtgtctg cttggagccg 120
tttctgtggc tgctggcgtg attcaatctc ctagacacct gatcaaggag aagagagaaa 180
cagccaccct gaagtgctac ccccatcccca gacacgatac agtgtactgg tatcagcaag 240
gacctggaca agatccccag ttcctgatca gcttctacga gaagatgcag agcgacaaag 300
gcagcatccc agacagattt agcgcccagc agtttagcga ctatcactct gagctgaaca 360
tgagcagcct ggaactgggc gattctgctc tgtacttctg tgcctcttct ctgagactgg 420

```
gaagagaaac ccagtacttt ggacccggca caagactgct ggttcttgag gacctgaaga    480

acgtgttccc cccagaggtg gccgtgttcg agcctagcga ggccgagatc agccacaccc    540

agaaagccac cctcgtgtgc ctggccaccg gcttttaccc cgaccacgtg gaactgtctt    600

ggtgggtcaa cggcaaagag gtgcacagcg gcgtctgcac cgacccccag cccctgaaag    660

agcagcccgc cctgaacgac agccggtact gtctgagcag cagactgaga gtgtccgcca    720

ccttctggca gaacccccgg aaccacttca gatgccaggt gcagttctac ggcctgagcg    780

agaacgacga gtggacccag gaccgggcca agcccgtgac ccagatcgtg tctgctgagg    840

cctggggcag agccgattgc ggcttcacca gcgagagcta ccagcagggc gtgctgagcg    900

ccaccatcct gtacgagatc ctgctgggca aggccaccct gtacgccgtg ctggtgtccg    960

ccctggtgct gatggccatg gtcaagcgga aggacagccg gggc                    1004
```

<210> SEQ ID NO 126
<211> LENGTH: 974
<212> TYPE: DNA
<213> ORGANISM: Artificial Sequence
<220> FEATURE:
<223> OTHER INFORMATION: Synthetic sequence WT137-45 TCR13.2 - Codon
      Optimized beta-Chain

<400> SEQUENCE: 126

```
ctcaataaaa gagcccacaa cccctcactc ggcgcgccac catgggcaca agacttctct     60

gctgggtggt gcttggattt ctgggcacag atcatacagg agctggagtt agccagtctc    120

ctaggtacaa agtggccaag agaggacagg atgtggctct gagatgtgac cctattagcg    180

gacatgtgag cctgttttgg taccagcaag ctctgggaca aggacccgag tttctgacct    240

acttccagaa tgaagcccag ctggataaat ctggactgcc tagcgaccgg ttcttcgccg    300

aaagacctga aggatctgtt agcaccctga agattcagag aacacagcag gaggactctg    360

ccgtgtacct gtgtgcctct tctttaggac aggcctatga gcagtatttt ggacctggca    420

ccagactgac cgtgacagag gacctgaaga acgtgttccc cccagaggtg gccgtgttcg    480

agcctagcga ggccgagatc agccacaccc agaaagccac cctcgtgtgc ctggccaccg    540

gcttttaccc cgaccacgtg gaactgtctt ggtgggtcaa cggcaaagag gtgcacagcg    600

gcgtctgcac cgacccccag cccctgaaag agcagcccgc cctgaacgac agccggtact    660

gtctgagcag cagactgaga gtgtccgcca ccttctggca gaacccccgg aaccacttca    720

gatgccaggt gcagttctac ggcctgagcg agaacgacga gtggacccag gaccgggcca    780

agcccgtgac ccagatcgtg tctgctgagg cctggggcag agccgattgc ggcttcacca    840

gcgagagcta ccagcagggc gtgctgagcg ccaccatcct gtacgagatc ctgctgggca    900

aggccaccct gtacgccgtg ctggtgtccg ccctggtgct gatggccatg gtcaagcgga    960

aggacagccg gggc                                                      974
```

<210> SEQ ID NO 127
<211> LENGTH: 968
<212> TYPE: DNA
<213> ORGANISM: Artificial Sequence
<220> FEATURE:
<223> OTHER INFORMATION: Synthetic sequence WT137-45 TCR14.1 - Codon
      Optimized beta-Chain

<400> SEQUENCE: 127

```
ctcaataaaa gagcccacaa cccctcactc ggcgcgccac catgggcaca agacttctct     60

gctgggtggc cttttgtctg ctggtggaag agctgattga agctggagtt gtgcagtctc    120
```

```
ctaggtacaa gatcatcgag aagaagcagc ccgtggcctt ctggtgtaat cccatttctg    180

gccacaacac cctgtactgg tatctgcaga atctgggaca gggccctgaa ctgctgatca    240

gatacgagaa cgaagaagcc gtggacgatt ctcaactgcc taaggaccgc ttttctgccg    300

agaggctgaa aggagtggat tctaccctga agatccaacc tgctgaactg ggcgattctg    360

ctgtgtacct gtgcgcttct agcctgacaa gaggagctga agccttttt ggacagggca     420

caagactgac agtggtggag gatctgaaca aggtgttccc cccagaggtg gccgtgttcg    480

agccttctga ggccgagatc tcccacaccc agaaagccac cctcgtgtgc ctggccaccg    540

gctttttccc cgaccacgtg gaactgtctt ggtgggtcaa cggcaaagag gtgcactccg    600

gcgtgtgcac cgatccccag cctctgaaag aacagcccgc cctgaacgac agccggtact    660

gcctgagcag cagactgaga gtgtccgcca ccttctggca gaacccccgg aaccacttca    720

gatgccaggt gcagttctac ggcctgagcg agaacgacga gtggacccag gacagagcca    780

agcccgtgac acagatcgtg tctgccgaag cctggggcag agccgattgc ggctttacct    840

ccgtgtccta tcagcagggc gtgctgagcg ccacaatcct gtacgagatc ctgctgggca    900

aggccaccct gtacgccgtg ctggtgtctg ccctggtgct gatggccatg gtcaagcgga    960

aggacttc                                                             968
```

<210> SEQ ID NO 128
<211> LENGTH: 971
<212> TYPE: DNA
<213> ORGANISM: Artificial Sequence
<220> FEATURE:
<223> OTHER INFORMATION: Synthetic sequence WT137-45 TCR15.1 - Codon Optimized beta-Chain

<400> SEQUENCE: 128

```
ctcaataaaa gagcccacaa cccctcactc ggcgcgccac catgagcaac caggtcttgt     60

gctgtgtggt gctgtgcttt cttggcgcca atacagtgga tggcggcatt acacaaagcc    120

ccaagtacct gttcaggaaa gagggccaga atgtgacact gagctgtgag cagaacctga    180

atcacgacgc catgtactgg tacagacagg atccaggaca aggactgagg ctgatctact    240

actcccagat cgtgaacgac ttccagaagg gcgatattgc cgagggctat agcgtgagca    300

gagagaagaa agagagcttc ccactgacag tgacatctgc ccagaagaac cctaccgcct    360

tctacctgtg tgcctcttct agagatagag agcaggagtc tcctctgcac ttcggaaatg    420

gcaccagact gacagtgacc gaggatctga acaaggtgtt ccccccagag gtggccgtgt    480

tcgagccttc tgaggccgag atctcccaca cccagaaagc caccctcgtg tgcctggcca    540

ccggcttttt ccccgaccac gtggaactgt cttggtgggt caacggcaaa gaggtgcact    600

ccggcgtgtg caccgatccc cagcctctga aagaacagcc cgccctgaac gacagccggt    660

actgcctgag cagcagactg agagtgtccg ccaccttctg gcagaacccc cggaaccact    720

tcagatgcca ggtgcagttc tacggcctga gcgagaacga cgagtggacc caggacagag    780

ccaagcccgt gacacagatc gtgtctgccg aagcctgggg cagagccgat tgcggcttta    840

cctccgtgtc ctatcagcag ggcgtgctga gcgccacaat cctgtacgag atcctgctgg    900

gcaaggccac cctgtacgcc gtgctggtgt ctgccctggt gctgatggcc atggtcaagc    960

ggaaggactt c                                                         971
```

<210> SEQ ID NO 129
<211> LENGTH: 974

<212> TYPE: DNA
<213> ORGANISM: Artificial Sequence
<220> FEATURE:
<223> OTHER INFORMATION: Synthetic sequence WT137-45 TCR16.1 - Codon Optimized beta-Chain

<400> SEQUENCE: 129
ctcaataaaa gagcccacaa cccctcactc ggcgcgccac catgggacct cagcttcttg 60
gatacgttgt gctgtgtctg cttggagctg gacctcttga agctcaggtt acccagaacc 120
ccagatacct gattaccgtg acaggcaaaa agctgaccgt gacatgtagc cagaacatga 180
accacgagta catgagctgg taccggcagg atcctggatt aggcctgaga cagatctact 240
acagcatgaa cgtggaggtg accgataaag gcgacgtgcc tgagggatac aaggtgagca 300
gaaaggagaa gaggaatttc cccctgatcc tggaaagccc aagccccaat cagacaagcc 360
tgtacttttg tgccagcagc ttttctggcg gcacatatga gcagtacttc ggccctggca 420
caagactgac agttacagag gacctgaaga acgtgttccc cccagaggtg gccgtgttcg 480
agcctagcga ggccgagatc agccacaccc agaaagccac cctcgtgtgc ctggccaccg 540
gcttttaccc cgaccacgtg gaactgtctt ggtgggtcaa cggcaaagag gtgcacagcg 600
gcgtctgcac cgacccccag cccctgaaag agcagcccgc cctgaacgac agccggtact 660
gtctgagcag cagactgaga gtgtccgcca ccttctggca gaacccccgg aaccacttca 720
gatgccaggt gcagttctac ggcctgagcg agaacgacga gtggacccag gaccgggcca 780
agcccgtgac ccagatcgtg tctgctgagg cctggggcag agccgattgc ggcttcacca 840
gcgagagcta ccagcagggc gtgctgagcg ccaccatcct gtacgagatc ctgctgggca 900
aggccaccct gtacgccgtg ctggtgtccg ccctggtgct gatggccatg gtcaagcgga 960
aggacagccg gggc 974

<210> SEQ ID NO 130
<211> LENGTH: 1007
<212> TYPE: DNA
<213> ORGANISM: Artificial Sequence
<220> FEATURE:
<223> OTHER INFORMATION: Synthetic sequence WT137-45 TCR16.2 - Codon Optimized beta-Chain

<400> SEQUENCE: 130
ctcaataaaa gagcccacaa cccctcactc ggcgcgccac catgctgagc cctgatctcc 60
ctgattctgc ctggaatacc agactgctgt gtcatgtgat gctgtgtctg cttggagccg 120
tttctgtggc tgctggcgtg attcaatctc ctagacacct gatcaaggag aagagagaaa 180
cagccaccct gaagtgctac cccatcccca gacacgatac agtgtactgg tatcagcaag 240
gacctggaca agatccccag ttcctgatca gcttctacga gaagatgcag agcgacaaag 300
gcagcatccc agacagattt agcgcccagc agtttagcga ctatcactct gagctgaaca 360
tgagcagcct ggaactgggc gattctgctc tgtacttctg tgccagcagc tatagaggag 420
gcagcacata tgagcagtac tttggccctg gcacaagact gacagtgaca gaggacctga 480
agaacgtgtt ccccccagag gtggccgtgt tcgagcctag cgaggccgag atcagccaca 540
cccagaaagc caccctcgtg tgcctggcca ccggctttta ccccgaccac gtggaactgt 600
cttggtgggt caacggcaaa gaggtgcaca gcggcgtctg caccgacccc cagcccctga 660
aagagcagcc cgccctgaac gacagccggt actgtctgag cagcagactg agagtgtccg 720
ccaccttctg gcagaacccc cggaaccact tcagatgcca ggtgcagttc tacggcctga 780

```
gcgagaacga cgagtggacc caggaccggg ccaagcccgt gacccagatc gtgtctgctg    840

aggcctgggg cagagccgat tgcggcttca ccagcgagag ctaccagcag ggcgtgctga    900

gcgccaccat cctgtacgag atcctgctgg gcaaggccac cctgtacgcc gtgctggtgt    960

ccgccctggt gctgatggcc atggtcaagc ggaaggacag ccggggc                 1007
```

```
<210> SEQ ID NO 131
<211> LENGTH: 974
<212> TYPE: DNA
<213> ORGANISM: Artificial Sequence
<220> FEATURE:
<223> OTHER INFORMATION: Synthetic sequence WT137-45 TCR18.1 - Codon
      Optimized beta-Chain

<400> SEQUENCE: 131

ctcaataaaa gagcccacaa cccctcactc ggcgcgccac catgagcacc agactccttt     60

gctggatggc tttgtgtctg cttggagctg agctgtctga agctgaagtt gcccagtctc    120

ccagatacaa gatcaccgag aaatctcagg ctgtggcctt ctggtgtgac cctatttctg    180

gacacgccac cctgtactgg tataggcaaa ttctgggaca aggccctgaa ctgctggtgc    240

aatttcagga tgagagcgtg gtggacgatt ctcaactgcc taaggacagg ttttctgccg    300

agcggctgaa aggagttgat agcaccctga agatccaacc tgctgaactg ggcgattctg    360

ctatgtacct gtgcgcctct tctcagagag atagccctaa cgagaagctg ttctttggct    420

ctggaaccca gctgtctgtg ctggaggatc tgaacaaggt gttcccccca gaggtggccg    480

tgttcgagcc ttctgaggcc gagatctccc acacccagaa agccaccctc gtgtgcctgg    540

ccaccggctt tttccccgac cacgtggaac tgtcttggtg ggtcaacggc aaagaggtgc    600

actccggcgt gtgcaccgat ccccagcctc tgaaagaaca gcccgccctg aacgacagcc    660

ggtactgcct gagcagcaga ctgagagtgt ccgccacctt ctggcagaac ccccggaacc    720

acttcagatg ccaggtgcag ttctacggcc tgagcgagaa cgacgagtgg acccaggaca    780

gagccaagcc cgtgacacag atcgtgtctg ccgaagcctg gggcagagcc gattgcggct    840

ttacctccgt gtcctatcag cagggcgtgc tgagcgccac aatcctgtac gagatcctgc    900

tgggcaaggc caccctgtac gccgtgctgg tgtctgccct ggtgctgatg gccatggtca    960

agcggaagga cttc                                                      974
```

```
<210> SEQ ID NO 132
<211> LENGTH: 977
<212> TYPE: DNA
<213> ORGANISM: Artificial Sequence
<220> FEATURE:
<223> OTHER INFORMATION: Synthetic sequence WT137-45 TCR19.1 - Codon
      Optimized beta-Chain

<400> SEQUENCE: 132

ctcaataaaa gagcccacaa cccctcactc ggcgcgccac catgggctgt agactgttgt     60

gttgtgctgt gctgtgtctg ttgggagctg tgcctatgga aacaggcgtt acccagacac    120

ctagacatct ggttatgggc atgaccaaca agaagagcct gaagtgcgag cagcatctgg    180

gccataacgc catgtactgg tataagcaga gcgccaagaa accactggaa ctgatgttcg    240

tgtacagcct ggaggagagg gtggagaata atagcgtgcc cagcagattt agccctgagt    300

gcccaaattc ttctcacctg ttcctgcacc tgcacacatt acagcccgag gattctgccc    360

tgtacctgtg tgcttcttct caagaccctt acaagctgag cggcaatacc atctacttcg    420

gcgaaggctc ttggctgaca gtggttgaag atctgaacaa ggtgttcccc ccagaggtgg    480
```

ccgtgttcga gccttctgag gccgagatct cccacaccca gaaagccacc ctcgtgtgcc 540
tggccaccgg ctttttcccc gaccacgtgg aactgtcttg gtgggtcaac ggcaaagagg 600
tgcactccgg cgtgtgcacc gatccccagc ctctgaaaga acagcccgcc ctgaacgaca 660
gccggtactg cctgagcagc agactgagag tgtccgccac cttctggcag aacccccgga 720
accacttcag atgccaggtg cagttctacg gcctgagcga gaacgacgag tggacccagg 780
acagagccaa gcccgtgaca cagatcgtgt ctgccgaagc ctggggcaga gccgattgcg 840
gctttacctc cgtgtcctat cagcagggcg tgctgagcgc cacaatcctg tacgagatcc 900
tgctgggcaa ggccaccctg tacgccgtgc tggtgtctgc cctggtgctg atggccatgg 960
tcaagcggaa ggacttc 977

<210> SEQ ID NO 133
<211> LENGTH: 819
<212> TYPE: DNA
<213> ORGANISM: Artificial Sequence
<220> FEATURE:
<223> OTHER INFORMATION: Synthetic sequence WT137-45 TCR10.1 Wild-type alpha-Chain (TRAV21 02 / TRAJ58 01)

<400> SEQUENCE: 133
atggagaccc tcttgggcct gcttatcctt tggctgcagc tgcaatgggt gagcagcaaa 60
caggaggtga cacagattcc tgcagctctg agtgtcccag aaggagaaaa cttggttctc 120
aactgcagtt tcactgatag cgctatttac aacctccagt ggtttaggca ggaccctggg 180
aaaggtctca catctctgtt gcttattcag tcaagtcaga gagagcaaac aagtggaaga 240
cttaatgcct cgctggataa atcatcagga cgtagtactt tatacattgc agcttctcag 300
cctggtgact cagccaccta cctctgtgct gtgaaagaaa ccagtggctc taggttgacc 360
tttggggaag gaacacagct cacagtgaat cctgatatcc agaaccctga ccctgccgtg 420
taccagctga gagactctaa atccagtgac aagtctgtct gcctattcac cgattttgat 480
tctcaaacaa atgtgtcaca aagtaaggat tctgatgtgt atatcacaga caaaactgtg 540
ctagacatga ggtctatgga cttcaagagc aacagtgctg tggcctggag caacaaatct 600
gactttgcat gtgcaaacgc cttcaacaac agcattattc cagaagacac cttcttcccc 660
agcccagaaa gttcctgtga tgtcaagctg gtcgagaaaa gctttgaaac agatacgaac 720
ctaaactttc aaaacctgtc agtgattggg ttccgaatcc tcctcctgaa agtggccggg 780
tttaatctgc tcatgacgct gcggctgtgg tccagctga 819

<210> SEQ ID NO 134
<211> LENGTH: 840
<212> TYPE: DNA
<213> ORGANISM: Artificial Sequence
<220> FEATURE:
<223> OTHER INFORMATION: Synthetic sequence WT137-45 TCR11.2 Wild-type alpha-Chain (TRAV38-1 01 / TRAJ40 01)

<400> SEQUENCE: 134
atgacacgag ttagcttgct gtgggcagtc gtggtctcca cctgtcttga atccggcatg 60
gcccagacag tcactcagtc tcaaccagag atgtctgtgc aggaggcaga gactgtgacc 120
ctgagttgca catatgacac cagtgagaat aattattatt tgttctggta caagcagcct 180
cccagcaggc agatgattct cgttattcgc caagaagctt ataagcaaca gaatgcaacg 240
gagaatcgtt tctctgtgaa cttccagaaa gcagccaaat ccttcagtct caagatctca 300
gactcacagc tgggggacac tgcgatgtat ttctgtgctt tcatctaccc atcctacacc 360
tcaggaacct acaaatacat ctttggaaca ggcaccaggc tgaaggtttt agcaaatatc 420
cagaaccctg accctgccgt gtaccagctg agagactcta aatccagtga caagtctgtc 480
tgcctattca ccgattttga ttctcaaaca aatgtgtcac aaagtaagga ttctgatgtg 540
tatatcacag acaaaactgt gctagacatg aggtctatgg acttcaagag caacagtgct 600
gtggcctgga gcaacaaatc tgactttgca tgtgcaaacg ccttcaacaa cagcattatt 660
ccagaagaca ccttcttccc cagcccagaa agttcctgtg atgtcaagct ggtcgagaaa 720
agctttgaaa cagatacgaa cctaaacttt caaaacctgt cagtgattgg gttccgaatc 780
ctcctcctga aagtggccgg gtttaatctg ctcatgacgc tgcggctgtg gtccagctga 840

<210> SEQ ID NO 135
<211> LENGTH: 843
<212> TYPE: DNA
<213> ORGANISM: Artificial Sequence
<220> FEATURE:
<223> OTHER INFORMATION: Synthetic sequence WT137-45 TCR12.1 Wild-type alpha-Chain (TRAV29/DV5 01 / TRAJ6 01)

<400> SEQUENCE: 135
atggccatgc tcctgggggc atcagtgctg attctgtggc ttcagccaga ctgggtaaac 60
agtcaacaga agaatgatga ccagcaagtt aagcaaaatt caccatccct gagcgtccag 120
gaaggaagaa tttctattct gaactgtgac tatactaaca gcatgtttga ttatttccta 180
tggtacaaaa aataccctgc tgaaggtcct acattcctga tatctataag ttccattaag 240
gataaaaatg aagatggaag attcactgtc ttcttaaaca aaagtgccaa gcacctctct 300
ctgcacattg tgccctccca gcctggagac tctgcagtgt acttctgtgc agcaagcgga 360
acaggaggaa gctacatacc tacatttgga agaggaacca gccttattgt tcatccgtat 420
atccagaacc ctgaccctgc cgtgtaccag ctgagagact ctaaatccag tgacaagtct 480
gtctgcctat tcaccgattt tgattctcaa acaaatgtgt cacaaagtaa ggattctgat 540
gtgtatatca cagacaaaac tgtgctagac atgaggtcta tggacttcaa gagcaacagt 600
gctgtggcct ggagcaacaa atctgacttt gcatgtgcaa acgccttcaa caacagcatt 660
attccagaag acaccttctt ccccagccca gaaagttcct gtgatgtcaa gctggtcgag 720
aaaagctttg aaacagatac gaacctaaac tttcaaaacc tgtcagtgat tgggttccga 780
atcctcctcc tgaaagtggc cgggtttaat ctgctcatga cgctgcggct gtggtccagc 840
tga 843

<210> SEQ ID NO 136
<211> LENGTH: 840
<212> TYPE: DNA
<213> ORGANISM: Artificial Sequence
<220> FEATURE:
<223> OTHER INFORMATION: Synthetic sequence WT137-45 TCR13.1 Wild-type alpha-Chain (TRAV29/DV5 01 / TRAJ20 01)

<400> SEQUENCE: 136
atggccatgc tcctgggggc atcagtgctg attctgtggc ttcagccaga ctgggtaaac 60
agtcaacaga agaatgatga ccagcaagtt aagcaaaatt caccatccct gagcgtccag 120
gaaggaagaa tttctattct gaactgtgac tatactaaca gcatgtttga ttatttccta 180
tggtacaaaa aataccctgc tgaaggtcct acattcctga tatctataag ttccattaag 240
gataaaaatg aagatggaag attcactgtc ttcttaaaca aaagtgccaa gcacctctct 300

```
ctgcacattg tgccctccca gcctggagac tctgcagtgt acttctgtgc agcaagcggt    360

ataggcgact acaagctcag ctttggagcc ggaaccacag taactgtaag agcaaatatc    420

cagaaccctg accctgccgt gtaccagctg agagactcta aatccagtga caagtctgtc    480

tgcctattca ccgattttga ttctcaaaca aatgtgtcac aaagtaagga ttctgatgtg    540

tatatcacag acaaaactgt gctagacatg aggtctatgg acttcaagag caacagtgct    600

gtggcctgga gcaacaaatc tgactttgca tgtgcaaacg ccttcaacaa cagcattatt    660

ccagaagaca ccttcttccc cagcccagaa agttcctgtg atgtcaagct ggtcgagaaa    720

agctttgaaa cagatacgaa cctaaacttt caaaacctgt cagtgattgg gttccgaatc    780

ctcctcctga aagtggccgg gtttaatctg ctcatgacgc tgcggctgtg gtccagctga    840
```

<210> SEQ ID NO 137
<211> LENGTH: 816
<212> TYPE: DNA
<213> ORGANISM: Artificial Sequence
<220> FEATURE:
<223> OTHER INFORMATION: Synthetic sequence WT137-45 TCR13.2 Wild-type alpha-Chain (TRAV41 01 / TRAJ50 01)

<400> SEQUENCE: 137

```
atggtgaaga tccggcaatt tttgttggct attttgtggc ttcagctaag ctgtgtaagt     60

gccgccaaaa atgaagtgga gcagagtcct cagaacctga ctgcccagga aggagaattt    120

atcacaatca actgcagtta ctcggtagga ataagtgcct tacactggct gcaacagcat    180

ccaggaggag gcattgtttc cttgtttatg ctgagctcag ggaagaagaa gcatggaaga    240

ttaattgcca caataaacat acaggaaaag cacagctccc tgcacatcac agcctcccat    300

cccagagact ctgccgtcta catctgtgct gtcaggacct cctacgacaa ggtgatattt    360

gggccaggga caagcttatc agtcattcca aatatccaga accctgaccc tgccgtgtac    420

cagctgagag actctaaatc cagtgacaag tctgtctgcc tattcaccga ttttgattct    480

caaacaaatg tgtcacaaag taaggattct gatgtgtata tcacagacaa aactgtgcta    540

gacatgaggt ctatggactt caagagcaac agtgctgtgg cctggagcaa caaatctgac    600

tttgcatgtg caaacgcctt caacaacagc attattccag aagacacctt cttccccagc    660

ccagaaagtt cctgtgatgt caagctggtc gagaaaagct ttgaaacaga tacgaaccta    720

aactttcaaa acctgtcagt gattgggttc cgaatcctcc tcctgaaagt ggccgggttt    780

aatctgctca tgacgctgcg gctgtggtcc agctga                              816
```

<210> SEQ ID NO 138
<211> LENGTH: 831
<212> TYPE: DNA
<213> ORGANISM: Artificial Sequence
<220> FEATURE:
<223> OTHER INFORMATION: Synthetic sequence WT137-45 TCR14.1 Wild-type alpha-Chain (TRAV12-2 01 / TRAJ11 01)

<400> SEQUENCE: 138

```
atgaaatcct tgagagtttt actagtgatc ctgtggcttc agttgagctg ggtttggagc     60

caacagaagg aggtggagca gaattctgga cccctcagtg ttccagaggg agccattgcc    120

tctctcaact gcacttacag tgaccgaggt tcccagtcct tcttctggta cagacaatat    180

tctgggaaaa gccctgagtt gataatgttc atatactcca atggtgacaa agaagatgga    240

aggtttacag cacagctcaa taaagccagc cagtatgttt ctctgctcat cagagactcc    300
```

```
cagcccagtg attcagccac ctacctctgt gccgtgaacc tcctaggggc tacaggatac    360

agcaccctca cctttgggaa ggggactatg cttctagtct ctccagatat ccagaaccct    420

gaccctgccg tgtaccagct gagagactct aaatccagtg acaagtctgt ctgcctattc    480

accgattttg attctcaaac aaatgtgtca caaagtaagg attctgatgt gtatatcaca    540

gacaaaactg tgctagacat gaggtctatg gacttcaaga gcaacagtgc tgtggcctgg    600

agcaacaaat ctgactttgc atgtgcaaac gccttcaaca acagcattat tccagaagac    660

accttcttcc ccagcccaga aagttcctgt gatgtcaagc tggtcgagaa aagctttgaa    720

acagatacga acctaaactt tcaaaacctg tcagtgattg ggttccgaat cctcctcctg    780

aaagtggccg ggtttaatct gctcatgacg ctgcggctgt ggtccagctg a             831
```

```
<210> SEQ ID NO 139
<211> LENGTH: 807
<212> TYPE: DNA
<213> ORGANISM: Artificial Sequence
<220> FEATURE:
<223> OTHER INFORMATION: Synthetic sequence WT137-45 TCR15.1 Wild-type
      alpha-Chain (TRAV1-2 01 / TRAJ20 01)

<400> SEQUENCE: 139

atgtggggag ttttccttct ttatgtttcc atgaagatgg gaggcactac aggacaaaac     60

attgaccagc ccactgagat gacagctacg gaaggtgcca ttgtccagat caactgcacg    120

taccagacat ctgggttcaa cgggctgttc tggtaccagc aacatgctgg cgaagcaccc    180

acatttctgt cttacaatgt tctggatggt ttggaggaga aaggtcgttt ttcttcattc    240

cttagtcggt ctaaagggta cagttacctc cttttgaagg agctccagat gaaagactct    300

gcctcttacc tctgtgctgt gaggggcatt aacgactaca agctcagctt tggagccgga    360

accacagtaa ctgtaagagc aaatatccag aaccctgacc ctgccgtgta ccagctgaga    420

gactctaaat ccagtgacaa gtctgtctgc ctattcaccg attttgattc tcaaacaaat    480

gtgtcacaaa gtaaggattc tgatgtgtat atcacagaca aaactgtgct agacatgagg    540

tctatggact tcaagagcaa cagtgctgtg gcctggagca acaaatctga ctttgcatgt    600

gcaaacgcct tcaacaacag cattattcca gaagacacct tcttccccag cccagaaagt    660

tcctgtgatg tcaagctggt cgagaaaagc tttgaaacag atacgaacct aaactttcaa    720

aacctgtcag tgattgggtt ccgaatcctc ctcctgaaag tggccgggtt taatctgctc    780

atgacgctgc ggctgtggtc cagctga                                        807
```

```
<210> SEQ ID NO 140
<211> LENGTH: 816
<212> TYPE: DNA
<213> ORGANISM: Artificial Sequence
<220> FEATURE:
<223> OTHER INFORMATION: Synthetic sequence WT137-45 TCR16.1 Wild-type
      alpha-Chain (TRAV20 02 / TRAJ8 01)

<400> SEQUENCE: 140

atggagaaaa tgttggagtg tgcattcata gtcttgtggc ttcagcttgg ctggttgagt     60

ggagaagacc aggtgacgca gagtcccgag gccctgagac tccaggaggg agagagtagc    120

agtctcaact gcagttacac agtcagcggt ttaagagggc tgttctggta taggcaagat    180

cctgggaaag gccctgaatt cctcttcacc ctgtattcag ctggggaaga aaaggagaaa    240

gaaaggctaa aagccacatt aacaaagaag gaaagctttc tgcacatcac agcccctaaa    300

cctgaagact cagccactta tctctgtgct gtgatcacag gctttcagaa acttgtattt    360
```

```
ggaactggca cccgacttct ggtcagtcca aatatccaga accctgaccc tgccgtgtac    420

cagctgagag actctaaatc cagtgacaag tctgtctgcc tattcaccga ttttgattct    480

caaacaaatg tgtcacaaag taaggattct gatgtgtata tcacagacaa aactgtgcta    540

gacatgaggt ctatggactt caagagcaac agtgctgtgg cctggagcaa caaatctgac    600

tttgcatgtg caaacgcctt caacaacagc attattccag aagacacctt cttccccagc    660

ccagaaagtt cctgtgatgt caagctggtc gagaaaagct ttgaaacaga tacgaaccta    720

aactttcaaa acctgtcagt gattgggttc cgaatcctcc tcctgaaagt ggccgggttt    780

aatctgctca tgacgctgcg gctgtggtcc agctga                              816


<210> SEQ ID NO 141
<211> LENGTH: 807
<212> TYPE: DNA
<213> ORGANISM: Artificial Sequence
<220> FEATURE:
<223> OTHER INFORMATION: Synthetic sequence WT137-45 TCR16.2 Wild-type
      alpha-Chain (TRAV26-1 02 / TRAJ26 01)

<400> SEQUENCE: 141

atgaggctgg tggcaagagt aactgtgttt ctgacctttg gaactataat tgatgctaag     60

accacccagc ccacctccat ggattgcgct gaaggaagag ctgcaaacct gccttgtaat    120

cactctacca tcagtggaaa tgagtatgtg tattggtatc gacagattca ctcccagggg    180

ccacagtata tcattcatgg tctaaaaaac aatgaaacca atgaaatggc ctctctgatc    240

atcacagaag acagaaagtc cagcaccttg atcctgcccc acgctacgct gagagacact    300

gctgtgtact attgcatcgc cggtgtcggg cggggtcaga attttgtctt tggtcccgga    360

accagattgt ccgtgctgcc ctatatccag aaccctgacc ctgccgtgta ccagctgaga    420

gactctaaat ccagtgacaa gtctgtctgc ctattcaccg attttgattc tcaaacaaat    480

gtgtcacaaa gtaaggattc tgatgtgtat atcacagaca aaactgtgct agacatgagg    540

tctatggact tcaagagcaa cagtgctgtg gcctggagca acaaatctga ctttgcatgt    600

gcaaacgcct tcaacaacag cattattcca gaagacacct tcttccccag cccagaaagt    660

tcctgtgatg tcaagctggt cgagaaaagc tttgaaacag atacgaacct aaactttcaa    720

aacctgtcag tgattgggtt ccgaatcctc ctcctgaaag tggccgggtt taatctgctc    780

atgacgctgc ggctgtggtc cagctga                                        807


<210> SEQ ID NO 142
<211> LENGTH: 831
<212> TYPE: DNA
<213> ORGANISM: Artificial Sequence
<220> FEATURE:
<223> OTHER INFORMATION: Synthetic sequence WT137-45 TCR18.1 Wild-type
      alpha-Chain (TRAV24 01 / TRAJ48 01)

<400> SEQUENCE: 142

atggagaaga atcctttggc agccccatta ctaatcctct ggtttcatct tgactgcgtg     60

agcagcatac tgaacgtgga acaaagtcct cagtcactgc atgttcagga gggagacagc    120

accaatttca cctgcagctt cccttccagc aatttttatg ccttacactg gtacagatgg    180

gaaactgcaa aaagccccga ggccttgttt gtaatgactt taaatgggga tgaaaagaag    240

aaaggacgaa taagtgccac tcttaatacc aaggagggtt acagctattt gtacatcaaa    300

ggatcccagc ctgaagactc agccacatac ctctgtgcct ttcatcctaa ctttggaaat    360
```

gagaaattaa cctttgggac tggaacaaga ctcaccatca tacccaatat ccagaaccct 420
gaccctgccg tgtaccagct gagagactct aaatccagtg acaagtctgt ctgcctattc 480
accgattttg attctcaaac aaatgtgtca caaagtaagg attctgatgt gtatatcaca 540
gacaaaactg tgctagacat gaggtctatg gacttcaaga gcaacagtgc tgtggcctgg 600
agcaacaaat ctgactttgc atgtgcaaac gccttcaaca acagcattat tccagaagac 660
accttcttcc ccagcccaga aagttcctgt gatgtcaagc tggtcgagaa aagctttgaa 720
acagatacga acctaaactt tcaaaacctg tcagtgattg ggttccgaat cctcctcctg 780
aaagtggccg ggtttaatct gctcatgacg ctgcggctgt ggtccagctg a 831

<210> SEQ ID NO 143
<211> LENGTH: 834
<212> TYPE: DNA
<213> ORGANISM: Artificial Sequence
<220> FEATURE:
<223> OTHER INFORMATION: Synthetic sequence WT137-45 TCR19.1 Wild-type alpha-Chain (TRAV20 02 / TRAJ37 02)

<400> SEQUENCE: 143
atggagaaaa tgttggagtg tgcattcata gtcttgtggc ttcagcttgg ctggttgagt 60
ggagaagacc aggtgacgca gagtcccgag gccctgagac tccaggaggg agagagtagc 120
agtctcaact gcagttacac agtcagcggt ttaagagggc tgttctggta taggcaagat 180
cctgggaaag gccctgaatt cctcttcacc ctgtattcag ctggggaaga aaaggagaaa 240
gaaaggctaa aagccacatt aacaaagaag gaaagctttc tgcacatcac agcccctaaa 300
cctgaagact cagccactta tctctgtgct gtgcagccgc ggggggatgg gtctagcaac 360
acaggcaaac taatctttgg gcaagggaca actttacaag taaaaccaga tatccagaac 420
cctgaccctg ccgtgtacca gctgagagac tctaaatcca gtgacaagtc tgtctgccta 480
ttcaccgatt ttgattctca aacaaatgtg tcacaaagta aggattctga tgtgtatatc 540
acagacaaaa ctgtgctaga catgaggtct atggacttca agagcaacag tgctgtggcc 600
tggagcaaca aatctgactt tgcatgtgca aacgccttca acaacagcat tattccagaa 660
gacaccttct tccccagccc agaaagttcc tgtgatgtca agctggtcga gaaaagcttt 720
gaaacagata cgaacctaaa ctttcaaaac ctgtcagtga ttgggttccg aatcctcctc 780
ctgaaagtgg ccgggtttaa tctgctcatg acgctgcggc tgtggtccag ctga 834

<210> SEQ ID NO 144
<211> LENGTH: 819
<212> TYPE: DNA
<213> ORGANISM: Artificial Sequence
<220> FEATURE:
<223> OTHER INFORMATION: Synthetic sequence WT137-45 TCR10.1 - Codon Optimized alpha-Chain

<400> SEQUENCE: 144
atggagacac tgctgggact actgattctg tggctgcaac tgcaatgggt gagcagcaaa 60
caggaggtta cccagattcc tgctgctctg tctgttcctg aaggcgagaa tctggtgctg 120
aactgcagct tcacagatag cgccatctac aacctgcagt ggttcagaca ggatcctgga 180
aaaggcctga caagcctgct gctgattcag agctctcaga gagagcagac atctggaaga 240
ctgaatgcta gcctggacaa gtctagcggc agaagcaccc tgtatattgc cgcctctcaa 300
cctggagatt ctgccacata cctgtgtgct gtgaaggaga catctggctc tagactgacc 360
tttggcgagg gaacacaact gaccgtgaat cctgacatcc agaatcccga tcctgctgtg 420
taccagctgc gggacagcaa gagcagcgac aagagcgtgt gcctgttcac cgacttcgac 480
agccagacca acgtgtccca gagcaaggac agcgacgtgt acatcaccga taagtgcgtg 540
ctggacatgc ggagcatgga cttcaagagc aacagcgccg tggcctggtc caacaagagc 600
gacttcgcct gcgccaacgc cttcaacaac agcattatcc ccgaggacac attcttccca 660
agccccgaga gcagctgcga cgtgaagctg gtggaaaaga gcttcgagac agacaccaac 720
ctgaacttcc agaacctcag cgtgatcggc ttccggatcc tgctgctgaa ggtggccggc 780
ttcaacctgc tgatgaccct gcggctgtgg tccagctga 819

<210> SEQ ID NO 145
<211> LENGTH: 840
<212> TYPE: DNA
<213> ORGANISM: Artificial Sequence
<220> FEATURE:
<223> OTHER INFORMATION: Synthetic sequence WT137-45 TCR11.2 - Codon
Optimized alpha-Chain

<400> SEQUENCE: 145
atgaccagag ttagcctgtt atgggctgtg gtggtgagca catgtctgga atctggaatg 60
gcccagacag tgacacagtc tcagcctgaa atgtctgtgc aggaagccga aaccgttaca 120
ctgagctgca cctacgatac aagcgagaac aactactacc tgttctggta caagcagccc 180
ccctctaggc agatgatcct ggtgatcaga caggaggcct ataaacagca gaatgccaca 240
gagaaccggt tcagcgtgaa cttccagaaa gccgccaaga gcttcagcct gaagatctct 300
gattctcagc tgggcgatac agccatgtac ttttgcgcct tcatctaccc cagctacaca 360
agcggcacat acaagtacat cttcggcacc ggcacaagac tgaaggttct ggccaacatc 420
cagaatcccg atcctgctgt gtaccagctg cgggacagca agagcagcga caagagcgtg 480
tgcctgttca ccgacttcga cagccagacc aacgtgtccc agagcaagga cagcgacgtg 540
tacatcaccg ataagtgcgt gctggacatg cggagcatgg acttcaagag caacagcgcc 600
gtggcctggt ccaacaagag cgacttcgcc tgcgccaacg ccttcaacaa cagcattatc 660
cccgaggaca cattcttccc aagccccgag agcagctgcg acgtgaagct ggtggaaaag 720
agcttcgaga cagacaccaa cctgaacttc cagaacctca gcgtgatcgg cttccggatc 780
ctgctgctga aggtggccgg cttcaacctg ctgatgaccc tgcggctgtg gtccagctga 840

<210> SEQ ID NO 146
<211> LENGTH: 843
<212> TYPE: DNA
<213> ORGANISM: Artificial Sequence
<220> FEATURE:
<223> OTHER INFORMATION: Synthetic sequence WT137-45 TCR12.1 - Codon
Optimized alpha-Chain

<400> SEQUENCE: 146
atggccatgt tactaggagc gagcgtgctg attctgtggt tacagcctga ttgggtgaac 60
tctcagcaga agaacgatga tcagcaggtg aagcagaaca gcccctctct gtctgtgcag 120
gaaggcagaa tcagcatcct gaattgcgat tacaccaaca gcatgttcga ctacttcctg 180
tggtacaaga agtaccccgc cgagggccct acctttctga tcagcatctc tagcatcaag 240
gacaagaacg aagatggcag attcaccgtg ttcctgaaca agagcgccaa gcacctgagc 300
ctgcacattg tgccttctca acctggagat tctgccgtgt acttttgtgc tgcctctgga 360
acaggcggaa gctatatccc cacatttgga agaggaacaa gcctgatcgt gcacccttac 420
atccagaatc ccgatcctgc tgtgtaccag ctgcgggaca gcaagagcag cgacaagagc 480
gtgtgcctgt tcaccgactt cgacagccag accaacgtgt cccagagcaa ggacagcgac 540
gtgtacatca ccgataagtg cgtgctggac atgcggagca tggacttcaa gagcaacagc 600
gccgtggcct ggtccaacaa gagcgacttc gcctgcgcca acgccttcaa caacagcatt 660
atccccgagg acacattctt cccaagcccc gagagcagct gcgacgtgaa gctggtggaa 720
aagagcttcg agacagacac caacctgaac ttccagaacc tcagcgtgat cggcttccgg 780
atcctgctgc tgaaggtggc cggcttcaac ctgctgatga ccctgcggct gtggtccagc 840
tga 843

<210> SEQ ID NO 147
<211> LENGTH: 840
<212> TYPE: DNA
<213> ORGANISM: Artificial Sequence
<220> FEATURE:
<223> OTHER INFORMATION: Synthetic sequence WT137-45 TCR13.1 - Codon Optimized alpha-Chain

<400> SEQUENCE: 147
atggccatgt tactaggagc gagcgtgctg attctgtggt tacagcctga ttgggtgaac 60
tctcagcaga agaacgatga tcagcaggtg aagcagaaca gcccctctct gtctgtgcag 120
gaaggcagaa tcagcatcct gaattgcgat tacaccaaca gcatgttcga ctacttcctg 180
tggtacaaga agtaccccgc cgagggccct acctttctga tcagcatctc tagcatcaag 240
gacaagaacg aagatggcag attcaccgtg ttcctgaaca agagcgccaa gcacctgagc 300
ctgcacattg tgccttctca acctggagat tctgccgtgt acttttgtgc tgcctctggc 360
attggcgact acaaactgag ctttggagcc ggcacaacag tgaccgttag agccaatatc 420
cagaatcccg atcctgctgt gtaccagctg cgggacagca agagcagcga caagagcgtg 480
tgcctgttca ccgacttcga cagccagacc aacgtgtccc agagcaagga cagcgacgtg 540
tacatcaccg ataagtgcgt gctggacatg cggagcatgg acttcaagag caacagcgcc 600
gtggcctggt ccaacaagag cgacttcgcc tgcgccaacg ccttcaacaa cagcattatc 660
cccgaggaca cattcttccc aagccccgag agcagctgcg acgtgaagct ggtggaaaag 720
agcttcgaga cagacaccaa cctgaacttc cagaacctca gcgtgatcgg cttccggatc 780
ctgctgctga aggtggccgg cttcaacctg ctgatgaccc tgcggctgtg gtccagctga 840

<210> SEQ ID NO 148
<211> LENGTH: 816
<212> TYPE: DNA
<213> ORGANISM: Artificial Sequence
<220> FEATURE:
<223> OTHER INFORMATION: Synthetic sequence WT137-45 TCR13.2 -Codon Optimized alpha-Chain

<400> SEQUENCE: 148
atggtgaaga tccggcagtt cctcctggct attctgtggc tgcaactgtc ttgtgtgtct 60
gctgccaaga atgaagtgga gcagtctccc cagaacctta cagcccagga aggcgagttt 120
atcaccatca actgcagcta ttctgtgggc attagcgccc tgcattggct gcagcaacac 180
cctggaggag gaattgtgtc tctgtttatg ctgtcttctg gcaagaagaa gcacggccgg 240
ctgattgcca ccatcaacat ccaggagaag cactcttctc tgcacattac agcctctcat 300
cccagggatt ctgccgtgta catctgtgcc gtgagaacca gctacgataa ggtgattttc 360
ggaccaggca cctctctgag cgtgatcccc aatatccaga atcccgatcc tgctgtgtac 420
cagctgcggg acagcaagag cagcgacaag agcgtgtgcc tgttcaccga cttcgacagc 480
cagaccaacg tgtcccagag caaggacagc gacgtgtaca tcaccgataa gtgcgtgctg 540
gacatgcgga gcatggactt caagagcaac agcgccgtgg cctggtccaa caagagcgac 600
ttcgcctgcg ccaacgcctt caacaacagc attatccccg aggacacatt cttcccaagc 660
cccgagagca gctgcgacgt gaagctggtg gaaaagagct tcgagacaga caccaacctg 720
aacttccaga acctcagcgt gatcggcttc cggatcctgc tgctgaaggt ggccggcttc 780
aacctgctga tgaccctgcg gctgtggtcc agctga 816

<210> SEQ ID NO 149
<211> LENGTH: 831
<212> TYPE: DNA
<213> ORGANISM: Artificial Sequence
<220> FEATURE:
<223> OTHER INFORMATION: Synthetic sequence WT137-45 TCR14.1 -Codon Optimized alpha-Chain

<400> SEQUENCE: 149
atgaagagcc tgagagtcct gctggtgatt ttgtggctgc agctgtcttg ggtttggtct 60
cagcagaaag aagtggagca gaatagcggc cctctgtctg ttcctgaagg cgctattgct 120
agcctgaatt gcacatacag cgatagagga tctcagagct tcttctggta ccggcagtac 180
agcggcaaga gcccagaact gatcatgttc atctacagca atggcgacaa ggaggatggc 240
aggtttacag cccagctgaa caaggccagc cagtatgttt ctctgctgat cagagatagc 300
cagcctagcg attctgccac ctacctgtgt gccgtgaact tacttggagc tacaggatac 360
tctacactga ccttcggcaa aggcaccatg ctgctggtga gccctgatat ccagaatccc 420
gatcctgctg tgtaccagct gcgggacagc aagagcagcg acaagagcgt gtgcctgttc 480
accgacttcg acagccagac caacgtgtcc cagagcaagg acagcgacgt gtacatcacc 540
gataagtgcg tgctggacat gcggagcatg gacttcaaga gcaacagcgc cgtggcctgg 600
tccaacaaga gcgacttcgc ctgcgccaac gccttcaaca acagcattat ccccgaggac 660
acattcttcc caagccccga gagcagctgc gacgtgaagc tggtggaaaa gagcttcgag 720
acagacacca acctgaactt ccagaacctc agcgtgatcg gcttccggat cctgctgctg 780
aaggtggccg gcttcaacct gctgatgacc ctgcggctgt ggtccagctg a 831

<210> SEQ ID NO 150
<211> LENGTH: 807
<212> TYPE: DNA
<213> ORGANISM: Artificial Sequence
<220> FEATURE:
<223> OTHER INFORMATION: Synthetic sequence WT137-45 TCR15.1 - Codon Optimized alpha-Chain

<400> SEQUENCE: 150
atgtggggcg ttttccttct gtatgtgagc atgaagatgg gcggcacaac aggccagaac 60
atcgatcagc ctaccgagat gacagccaca gaaggagcta ttgttcagat caactgcacc 120
taccagacaa gcggcttcaa cggcctgttc tggtaccagc agcatgctgg agaagctcct 180
acatttctga gctacaatgt gctggatggc ctggaggaga aaggcaggtt tagcagcttc 240
ctgagcaggt ctaagggcta ttcttatctg ctgctgaagg agctgcagat gaaggattcc 300
gccagctacc tgtgtgccgt tagggggcatc aatgattaca agctgagctt tggagccgga 360
acaacagtga ccgtgagagc caacatccag aatcccgatc ctgctgtgta ccagctgcgg 420

```
gacagcaaga gcagcgacaa gagcgtgtgc ctgttcaccg acttcgacag ccagaccaac    480

gtgtcccaga gcaaggacag cgacgtgtac atcaccgata agtgcgtgct ggacatgcgg    540

agcatggact tcaagagcaa cagcgccgtg gcctggtcca acaagagcga cttcgcctgc    600

gccaacgcct tcaacaacag cattatcccc gaggacacat tcttcccaag ccccgagagc    660

agctgcgacg tgaagctggt ggaaaagagc ttcgagacag acaccaacct gaacttccag    720

aacctcagcg tgatcggctt ccggatcctg ctgctgaagg tggccggctt caacctgctg    780

atgaccctgc ggctgtggtc cagctga                                        807
```

<210> SEQ ID NO 151
<211> LENGTH: 816
<212> TYPE: DNA
<213> ORGANISM: Artificial Sequence
<220> FEATURE:
<223> OTHER INFORMATION: Synthetic sequence WT137-45 TCR16.1 - Codon Optimized alpha-Chain

<400> SEQUENCE: 151

```
atggagaaga tgctggagtg tgcgttcatc gttctgtggc tgcaacttgg atggctgtct     60

ggagaggatc aggttacaca gtctcctgaa gccctgagac tgcaagaagg agaaagctct    120

agcctgaact gcagctacac agtgtctgga ctgagaggcc tgttctggta cagacaggat    180

cctggaaaag gcccagagtt cctgtttacc ctgtattctg ccggcgagga gaaggagaaa    240

gagagactga aagctaccct gaccaagaag gagagcttcc tgcacattac cgcccccaaa    300

cctgaggatt ctgccacata tctgtgtgcc gtgattaccg gctttcagaa gctggtgttt    360

ggcacaggca ccagactgct ggtttctccc aatatccaga atcccgatcc tgctgtgtac    420

cagctgcggg acagcaagag cagcgacaag agcgtgtgcc tgttcaccga cttcgacagc    480

cagaccaacg tgtcccagag caaggacagc gacgtgtaca tcaccgataa gtgcgtgctg    540

gacatgcgga gcatggactt caagagcaac agcgccgtgg cctggtccaa caagagcgac    600

ttcgcctgcg ccaacgcctt caacaacagc attatccccg aggacacatt cttcccaagc    660

cccgagagca gctgcgacgt gaagctggtg gaaaagagct tcgagacaga caccaacctg    720

aacttccaga acctcagcgt gatcggcttc cggatcctgc tgctgaaggt ggccggcttc    780

aacctgctga tgaccctgcg gctgtggtcc agctga                              816
```

<210> SEQ ID NO 152
<211> LENGTH: 807
<212> TYPE: DNA
<213> ORGANISM: Artificial Sequence
<220> FEATURE:
<223> OTHER INFORMATION: Synthetic sequence WT137-45 TCR16.2 - Codon Optimized alpha-Chain

<400> SEQUENCE: 152

```
atgagactgg tggcacgcgt aactgtgttt ctgacctttg gcaccatcat cgatgccaag     60

acaacccagc ctacaagcat ggactgtgcc gagggaagag ctgctaatct gccatgtaat    120

cacagcacaa tcagcggcaa cgagtacgtg tactggtacc ggcagatcca ctctcaagga    180

cctcagtaca tcattcatgg cctgaagaac aacgagacca acgagatggc cagcctgatc    240

atcaccgagg acaggaagtc ttctaccctg attctgcctc atgctacact gagagatacc    300

gccgtgtact actgcattgc cggagtggga agaggccaga atttcgtgtt tggacctgga    360

acaagactga gcgttctgcc ctatatccag aatcccgatc ctgctgtgta ccagctgcgg    420

gacagcaaga gcagcgacaa gagcgtgtgc ctgttcaccg acttcgacag ccagaccaac    480
```

gtgtcccaga gcaaggacag cgacgtgtac atcaccgata agtgcgtgct ggacatgcgg 540
agcatggact tcaagagcaa cagcgccgtg gcctggtcca acaagagcga cttcgcctgc 600
gccaacgcct tcaacaacag cattatcccc gaggacacat tcttcccaag ccccgagagc 660
agctgcgacg tgaagctggt ggaaaagagc ttcgagacag acaccaacct gaacttccag 720
aacctcagcg tgatcggctt ccggatcctg ctgctgaagg tggccggctt caacctgctg 780
atgaccctgc ggctgtggtc cagctga 807

<210> SEQ ID NO 153
<211> LENGTH: 831
<212> TYPE: DNA
<213> ORGANISM: Artificial Sequence
<220> FEATURE:
<223> OTHER INFORMATION: Synthetic sequence WT137-45 TCR18.1 - Codon Optimized alpha-Chain

<400> SEQUENCE: 153
atggagaaga accccttggc agcacctctg cttattctgt ggttccacct ggattgtgtg 60
agcagcatcc tgaatgtgga gcagtctcct cagagcctgc atgtgcaaga aggcgatagc 120
accaatttca cctgcagctt tccaagcagc aacttctacg ccctgcactg gtacagatgg 180
gaaaccgcca aatctcctga agccctgttt gtgatgaccc tgaatggcga cgagaagaag 240
aagggcagaa ttagcgccac cctgaatacc aaggagggct acagctacct gtacatcaag 300
ggctctcaac ctgaggattc tgccacctac ctttgcgcct ttcaccccaa tttcggcaac 360
gagaaactga cctttggaac cggaacaagg ctgaccatca tccccaacat ccagaatccc 420
gatcctgctg tgtaccagct gcgggacagc aagagcagcg acaagagcgt gtgcctgttc 480
accgacttcg acagccagac caacgtgtcc cagagcaagg acagcgacgt gtacatcacc 540
gataagtgcg tgctggacat gcggagcatg gacttcaaga gcaacagcgc cgtggcctgg 600
tccaacaaga gcgacttcgc ctgcgccaac gccttcaaca acagcattat ccccgaggac 660
acattcttcc caagccccga gagcagctgc gacgtgaagc tggtggaaaa gagcttcgag 720
acagacacca acctgaactt ccagaacctc agcgtgatcg gcttccggat cctgctgctg 780
aaggtggccg gcttcaacct gctgatgacc ctgcggctgt ggtccagctg a 831

<210> SEQ ID NO 154
<211> LENGTH: 834
<212> TYPE: DNA
<213> ORGANISM: Artificial Sequence
<220> FEATURE:
<223> OTHER INFORMATION: Synthetic sequence WT137-45 TCR19.1 -Codon Optimized alpha-Chain

<400> SEQUENCE: 154
atggagaaga tgctggagtg tgcgttcatc gttctgtggc tgcaacttgg atggctgtct 60
ggagaggatc aggttacaca gtctcctgaa gccctgagac tgcaagaagg agaaagctct 120
agcctgaact gcagctacac agtgtctgga ctgagaggcc tgttctggta cagacaggat 180
cctggaaaag gcccagagtt cctgtttacc ctgtattctg ccggcgagga gaaggagaaa 240
gagagactga aagctaccct gaccaagaag gagagcttcc tgcacattac cgcccccaaa 300
cctgaggatt ctgccacata tctgtgtgct gttcagccta gaggagatgg ctctagcaat 360
accggcaagc tgatctttgg ccagggaaca acactgcagg tgaagcctga tatccagaat 420
cccgatcctg ctgtgtacca gctgcgggac agcaagagca gcgacaagag cgtgtgcctg 480
ttcaccgact tcgacagcca gaccaacgtg tcccagagca aggacagcga cgtgtacatc 540
accgataagt gcgtgctgga catgcggagc atggacttca agagcaacag cgccgtggcc 600
tggtccaaca agagcgactt cgcctgcgcc aacgccttca acaacagcat tatccccgag 660
gacacattct tcccaagccc cgagagcagc tgcgacgtga agctggtgga aaagagcttc 720
gagacagaca ccaacctgaa cttccagaac ctcagcgtga tcggcttccg gatcctgctg 780
ctgaaggtgg ccggcttcaa cctgctgatg accctgcggc tgtggtccag ctga 834

<210> SEQ ID NO 155
<211> LENGTH: 1859
<212> TYPE: DNA
<213> ORGANISM: Artificial Sequence
<220> FEATURE:
<223> OTHER INFORMATION: Synthetic sequence WT137-45 TCR10.1 Codon-
optimized TCRbeta-P2A-TCRalpha

<400> SEQUENCE: 155
ctcaataaaa gagcccacaa cccctcactc ggcgcgccac catgggcaca tctcttctct 60
gttgggtggt tctgggcttt ctgggcacag atcatacagg agctggagtt agccagtctc 120
ctaggtataa ggtgaccaag aggggacagg atgtggctct gagatgtgac cctattagcg 180
gacatgtgag cctgtactgg tacagacaag ctctgggaca aggacccgag tttctgacct 240
acttcaacta tgaggcccag caggacaaat ctggactgcc caacgacaga ttcagcgccg 300
aaagaccaga aggctctatt agcacactga ccatccagag aacagagcag agggattctg 360
ccatgtacag atgcgccagc agcttaacag gctcttacga gcagtacttt ggacctggca 420
caagactgac agtgacagag gacctgaaga acgtgttccc cccagaggtg gccgtgttcg 480
agcctagcga ggccgagatc agccacaccc agaaagccac cctcgtgtgc ctggccaccg 540
gcttttaccc cgaccacgtg gaactgtctt ggtgggtcaa cggcaaagag gtgcacagcg 600
gcgtctgcac cgacccccag cccctgaaag agcagcccgc cctgaacgac agccggtact 660
gtctgagcag cagactgaga gtgtccgcca ccttctggca gaacccccgg aaccacttca 720
gatgccaggt gcagttctac ggcctgagcg agaacgacga gtggacccag gaccgggcca 780
agcccgtgac ccagatcgtg tctgctgagg cctggggcag agccgattgc ggcttcacca 840
gcgagagcta ccagcagggc gtgctgagcg ccaccatcct gtacgagatc ctgctgggca 900
aggccaccct gtacgccgtg ctggtgtccg ccctggtgct gatggccatg gtcaagcgga 960
aggacagccg gggcggttcc ggagccacga acttctctct gttaaagcaa gcaggagacg 1020
tggaagaaaa ccccggtccc atggagacac tgctgggact actgattctg tggctgcaac 1080
tgcaatgggt gagcagcaaa caggaggtta cccagattcc tgctgctctg tctgttcctg 1140
aaggcgagaa tctggtgctg aactgcagct tcacagatag cgccatctac aacctgcagt 1200
ggttcagaca ggatcctgga aaaggcctga caagcctgct gctgattcag agctctcaga 1260
gagagcagac atctggaaga ctgaatgcta gcctggacaa gtctagcggc agaagcaccc 1320
tgtatattgc cgcctctcaa cctggagatt ctgccacata cctgtgtgct gtgaaggaga 1380
catctggctc tagactgacc tttggcgagg gaacacaact gaccgtgaat cctgacatcc 1440
agaatcctga tcctgccgtg taccagctgc gggacagcaa gagcagcgac aagagcgtgt 1500
gcctgttcac cgacttcgac agccagacca acgtgtccca gagcaaggac agcgacgtgt 1560
acatcaccga taagtgcgtg ctggacatgc ggagcatgga cttcaagagc aacagcgccg 1620
tggcctggtc caacaagagc gacttcgcct gcgccaacgc cttcaacaac agcattatcc 1680

```
ccgaggacac attcttccca agccccgaga gcagctgcga cgtgaagctg gtggaaaaga   1740

gcttcgagac agacaccaac ctgaacttcc agaacctcag cgtgatcggc ttccggatcc   1800

tgctgctgaa ggtggccggc ttcaacctgc tgatgaccct gcggctgtgg tccagctga    1859


<210> SEQ ID NO 156
<211> LENGTH: 1880
<212> TYPE: DNA
<213> ORGANISM: Artificial Sequence
<220> FEATURE:
<223> OTHER INFORMATION: Synthetic sequence WT137-45 TCR11.2 Codon-
      optimized TCRbeta-P2A-TCRalpha

<400> SEQUENCE: 156

ctcaataaaa gagcccacaa cccctcactc ggcgcgccac catgctgctt cttctcctcc     60

ttctcggacc tgctggatct ggattaggag ctgttgtgtc tcagcaccct tcttgggtga    120

tctgtaaaag cggcacaagc gtgaagatcg agtgcagaag cctggacttt caggccacaa    180

ccatgttctg gtataggcag ttccccaagc agtctctgat gctgatggcc acctctaatg    240

agggctctaa ggccacatat gaacagggag tggagaagga caagttcctg atcaaccacg    300

cctctctgac cctgtctacc ctgacagtta catctgccca ccctgaggat agcagctttt    360

acatctgtag cgccacacct gaagcctcta gcccatatga gcagtacttt ggccctggca    420

ccagattaac agtgacagag gacctgaaga acgtgttccc cccagaggtg gccgtgttcg    480

agcctagcga ggccgagatc agccacaccc agaaagccac cctcgtgtgc ctggccaccg    540

gcttttaccc cgaccacgtg gaactgtctt ggtgggtcaa cggcaaagag gtgcacagcg    600

gcgtctgcac cgacccccag cccctgaaag agcagcccgc cctgaacgac agccggtact    660

gtctgagcag cagactgaga gtgtccgcca ccttctggca gaacccccgg aaccacttca    720

gatgccaggt gcagttctac ggcctgagcg agaacgacga gtggacccag gaccgggcca    780

agcccgtgac ccagatcgtg tctgctgagg cctggggcag agccgattgc ggcttcacca    840

gcgagagcta ccagcagggc gtgctgagcg ccaccatcct gtacgagatc ctgctgggca    900

aggccaccct gtacgccgtg ctggtgtccg ccctggtgct gatggccatg gtcaagcgga    960

aggacagccg gggcggttcc ggagccacga acttctctct gttaaagcaa gcaggagacg   1020

tggaagaaaa ccccggtccc atgaccagag ttagcctgtt atgggctgtg gtggtgagca   1080

catgtctgga atctggaatg gcccagacag tgacacagtc tcagcctgaa atgtctgtgc   1140

aggaagccga aaccgttaca ctgagctgca cctacgatac aagcgagaac aactactacc   1200

tgttctggta caagcagccc ccctctaggc agatgatcct ggtgatcaga caggaggcct   1260

ataaacagca gaatgccaca gagaaccggt tcagcgtgaa cttccagaaa gccgccaaga   1320

gcttcagcct gaagatctct gattctcagc tgggcgatac agccatgtac ttttgcgcct   1380

tcatctaccc cagctacaca agcggcacat acaagtacat cttcggcacc ggcacaagac   1440

tgaaggttct ggccaacatc cagaatcctg accctgctgt gtaccagctg cgggacagca   1500

agagcagcga caagagcgtg tgcctgttca ccgacttcga cagccagacc aacgtgtccc   1560

agagcaagga cagcgacgtg tacatcaccg ataagtgcgt gctggacatg cggagcatgg   1620

acttcaagag caacagcgcc gtggcctggt ccaacaagag cgacttcgcc tgcgccaacg   1680

ccttcaacaa cagcattatc cccgaggaca cattcttccc aagccccgag agcagctgcg   1740

acgtgaagct ggtggaaaag agcttcgaga cagacaccaa cctgaacttc cagaacctca   1800

gcgtgatcgg cttccggatc ctgctgctga aggtggccgg cttcaacctg ctgatgaccc   1860
```

tgcggctgtg gtccagctga 1880

<210> SEQ ID NO 157
<211> LENGTH: 1877
<212> TYPE: DNA
<213> ORGANISM: Artificial Sequence
<220> FEATURE:
<223> OTHER INFORMATION: Synthetic sequence WT137-45 TCR12.1 Codon-
optimized TCRbeta-P2A-TCRalpha

<400> SEQUENCE: 157
ctcaataaaa gagcccacaa cccctcactc ggcgcgccac catgggacct ggactgcttc 60
attggatggc tctgtgtttg ctgggaacag gacatggaga tgctatggtg atccagaacc 120
ccaggtatca ggtgacccag tttggcaaac cagtgacact gagctgttct cagaccctga 180
accacaacgt gatgtactgg taccagcaga agtcttctca ggcccctaag ctgctgttcc 240
actactacga caaggacttc aacaacgagg ccgatacccc tgacaatttc cagagcagga 300
ggcccaatac cagcttctgt ttcctggaca ttagaagccc tggactggga gatgctgcca 360
tgtacctgtg tgccaccagc aatttacagg gaagacaacc tcagcacttt ggcgatggca 420
caaggctgtc tatcctggag gatctgaaca aggtgttccc cccagaggtg gccgtgttcg 480
agccttctga ggccgagatc tcccacaccc agaaagccac cctcgtgtgc ctggccaccg 540
gctttttccc cgaccacgtg gaactgtctt ggtgggtcaa cggcaaagag gtgcactccg 600
gcgtgtgcac cgatccccag cctctgaaag aacagcccgc cctgaacgac agccggtact 660
gcctgagcag cagactgaga gtgtccgcca ccttctggca gaacccccgg aaccacttca 720
gatgccaggt gcagttctac ggcctgagcg agaacgacga gtggacccag gacagagcca 780
agcccgtgac acagatcgtg tctgccgaag cctggggcag agccgattgc ggctttacct 840
ccgtgtccta tcagcagggc gtgctgagcg ccacaatcct gtacgagatc ctgctgggca 900
aggccaccct gtacgccgtg ctggtgtctg ccctggtgct gatggccatg gtcaagcgga 960
aggacttcgg ttccggagcc acgaacttct ctctgttaaa gcaagcagga gacgtggaag 1020
aaaaccccgg tcccatggcc atgttactag gagcgagcgt gctgattctg tggttacagc 1080
ctgattgggt gaactctcag cagaagaacg atgatcagca ggtgaagcag aacagcccct 1140
ctctgtctgt gcaggaaggc agaatcagca tcctgaattg cgattacacc aacagcatgt 1200
tcgactactt cctgtggtac aagaagtacc ccgccgaggg ccctaccttt ctgatcagca 1260
tctctagcat caaggacaag aacgaagatg gcagattcac cgtgttcctg aacaagagcg 1320
ccaagcacct gagcctgcac attgtgcctt ctcaacctgg agattctgcc gtgtactttt 1380
gtgctgcctc tggaacaggc ggaagctata tccccacatt tggaagagga acaagcctga 1440
tcgtgcaccc ttacatccag aatcccgacc ctgctgtgta ccagctgcgg gacagcaaga 1500
gcagcgacaa gagcgtgtgc ctgttcaccg acttcgacag ccagaccaac gtgtcccaga 1560
gcaaggacag cgacgtgtac atcaccgata agtgcgtgct ggacatgcgg agcatggact 1620
tcaagagcaa cagcgccgtg gcctggtcca acaagagcga cttcgcctgc gccaacgcct 1680
tcaacaacag cattatcccc gaggacacat tcttcccaag ccccgagagc agctgcgacg 1740
tgaagctggt ggaaaagagc ttcgagacag acaccaacct gaacttccag aacctcagcg 1800
tgatcggctt ccggatcctg ctgctgaagg tggccggctt caacctgctg atgaccctgc 1860
ggctgtggtc cagctga 1877

<210> SEQ ID NO 158

<211> LENGTH: 1910
<212> TYPE: DNA
<213> ORGANISM: Artificial Sequence
<220> FEATURE:
<223> OTHER INFORMATION: Synthetic sequence WT137-45 TCR13.1 Codon-
optimized TCRbeta-P2A-TCRalpha

<400> SEQUENCE: 158
ctcaataaaa gagcccacaa cccctcactc ggcgcgccac catgctgagc cctgatctcc 60
ctgattctgc ctggaatacc agactgctgt gtcatgtgat gctgtgtctg cttggagccg 120
tttctgtggc tgctggcgtg attcaatctc ctagacacct gatcaaggag aagagagaaa 180
cagccaccct gaagtgctac cccatcccca gacacgatac agtgtactgg tatcagcaag 240
gacctggaca agatccccag ttcctgatca gcttctacga gaagatgcag agcgacaaag 300
gcagcatccc agacagattt agcgcccagc agtttagcga ctatcactct gagctgaaca 360
tgagcagcct ggaactgggc gattctgctc tgtacttctg tgcctcttct ctgagactgg 420
gaagagaaac ccagtacttt ggacccggca caagactgct ggttcttgag gacctgaaga 480
acgtgttccc cccagaggtg gccgtgttcg agcctagcga ggccgagatc agccacaccc 540
agaaagccac cctcgtgtgc ctggccaccg gcttttaccc cgaccacgtg gaactgtctt 600
ggtgggtcaa cggcaaagag gtgcacagcg gcgtctgcac cgacccccag cccctgaaag 660
agcagcccgc cctgaacgac agccggtact gtctgagcag cagactgaga gtgtccgcca 720
ccttctggca gaacccccgg aaccacttca gatgccaggt gcagttctac ggcctgagcg 780
agaacgacga gtggacccag gaccgggcca agcccgtgac ccagatcgtg tctgctgagg 840
cctggggcag agccgattgc ggcttcacca gcgagagcta ccagcagggc gtgctgagcg 900
ccaccatcct gtacgagatc ctgctgggca aggccaccct gtacgccgtg ctggtgtccg 960
ccctggtgct gatggccatg gtcaagcgga aggacagccg gggcggttcc ggagccacga 1020
acttctctct gttaaagcaa gcaggagacg tggaagaaaa ccccggtccc atggccatgt 1080
tactaggagc gagcgtgctg attctgtggt tacagcctga ttgggtgaac tctcagcaga 1140
agaacgatga tcagcaggtg aagcagaaca gcccctctct gtctgtgcag gaaggcagaa 1200
tcagcatcct gaattgcgat tacaccaaca gcatgttcga ctacttcctg tggtacaaga 1260
agtaccccgc cgagggccct acctttctga tcagcatctc tagcatcaag gacaagaacg 1320
aagatggcag attcaccgtg ttcctgaaca agagcgccaa gcacctgagc ctgcacattg 1380
tgccttctca acctggagat tctgccgtgt acttttgtgc tgcctctggc attggcgact 1440
acaaactgag ctttggagcc ggcacaacag tgaccgttag agccaatatc cagaaccctg 1500
atcctgccgt gtaccagctg cgggacagca agagcagcga caagagcgtg tgcctgttca 1560
ccgacttcga cagccagacc aacgtgtccc agagcaagga cagcgacgtg tacatcaccg 1620
ataagtgcgt gctggacatg cggagcatgg acttcaagag caacagcgcc gtggcctggt 1680
ccaacaagag cgacttcgcc tgcgccaacg ccttcaacaa cagcattatc cccgaggaca 1740
cattcttccc aagccccgag agcagctgcg acgtgaagct ggtggaaaag agcttcgaga 1800
cagacaccaa cctgaacttc cagaacctca gcgtgatcgg cttccggatc ctgctgctga 1860
aggtggccgg cttcaacctg ctgatgaccc tgcggctgtg gtccagctga 1910

<210> SEQ ID NO 159
<211> LENGTH: 1856
<212> TYPE: DNA
<213> ORGANISM: Artificial Sequence
<220> FEATURE:

<223> OTHER INFORMATION: Synthetic sequence WT137-45 TCR13.2 Codon-optimized TCRbeta-P2A-TCRalpha

<400> SEQUENCE: 159

```
ctcaataaaa gagcccacaa cccctcactc ggcgcgccac catgggcaca agacttctct     60
gctgggtggt gcttggattt ctgggcacag atcatacagg agctggagtt agccagtctc    120
ctaggtacaa agtggccaag agaggacagg atgtggctct gagatgtgac cctattagcg    180
gacatgtgag cctgttttgg taccagcaag ctctgggaca aggacccgag tttctgacct    240
acttccagaa tgaagcccag ctggataaat ctggactgcc tagcgaccgg ttcttcgccg    300
aaagacctga aggatctgtt agcaccctga agattcagag aacacagcag gaggactctg    360
ccgtgtacct gtgtgcctct tctttaggac aggcctatga gcagtatttt ggacctggca    420
ccagactgac cgtgacagag gacctgaaga acgtgttccc cccagaggtg gccgtgttcg    480
agcctagcga ggccgagatc agccacaccc agaaagccac cctcgtgtgc ctggccaccg    540
gcttttaccc cgaccacgtg gaactgtctt ggtgggtcaa cggcaaagag gtgcacagcg    600
gcgtctgcac cgacccccag cccctgaaag agcagcccgc cctgaacgac agccggtact    660
gtctgagcag cagactgaga gtgtccgcca ccttctggca gaacccccgg aaccacttca    720
gatgccaggt gcagttctac ggcctgagcg agaacgacga gtggacccag gaccgggcca    780
agcccgtgac ccagatcgtg tctgctgagg cctggggcag agccgattgc ggcttcacca    840
gcgagagcta ccagcagggc gtgctgagcg ccaccatcct gtacgagatc ctgctgggca    900
aggccaccct gtacgccgtg ctggtgtccg ccctggtgct gatggccatg gtcaagcgga    960
aggacagccg gggcggttcc ggagccacga acttctctct gttaaagcaa gcaggagacg   1020
tggaagaaaa ccccggtccc atggtgaaga tccggcagtt cctcctggct attctgtggc   1080
tgcaactgtc ttgtgtgtct gctgccaaga atgaagtgga gcagtctccc cagaacctta   1140
cagcccagga aggcgagttt atcaccatca actgcagcta ttctgtgggc attagcgccc   1200
tgcattggct gcagcaacac cctggaggag gaattgtgtc tctgtttatg ctgtcttctg   1260
gcaagaagaa gcacggccgg ctgattgcca ccatcaacat ccaggagaag cactcttctc   1320
tgcacattac agcctctcat cccagggatt ctgccgtgta catctgtgcc gtgagaacca   1380
gctacgataa ggtgattttc ggaccaggca cctctctgag cgtgatcccc aatatccaga   1440
accctgatcc tgctgtgtac cagctgcggg acagcaagag cagcgacaag agcgtgtgcc   1500
tgttcaccga cttcgacagc cagaccaacg tgtcccagag caaggacagc gacgtgtaca   1560
tcaccgataa gtgcgtgctg gacatgcgga gcatggactt caagagcaac agcgccgtgg   1620
cctggtccaa caagagcgac ttcgcctgcg ccaacgcctt caacaacagc attatccccg   1680
aggacacatt cttcccaagc cccgagagca gctgcgacgt gaagctggtg gaaaagagct   1740
tcgagacaga caccaacctg aacttccaga acctcagcgt gatcggcttc cggatcctgc   1800
tgctgaaggt ggccggcttc aacctgctga tgaccctgcg gctgtggtcc agctga       1856
```

<210> SEQ ID NO 160
<211> LENGTH: 1865
<212> TYPE: DNA
<213> ORGANISM: Artificial Sequence
<220> FEATURE:
<223> OTHER INFORMATION: Synthetic sequence WT137-45 TCR14.1 Codon-optimized TCRbeta-P2A-TCRalpha

<400> SEQUENCE: 160

```
ctcaataaaa gagcccacaa cccctcactc ggcgcgccac catgggcaca agacttctct     60
```

```
gctgggtggc cttttgtctg ctggtggaag agctgattga agctggagtt gtgcagtctc    120

ctaggtacaa gatcatcgag aagaagcagc ccgtggcctt ctggtgtaat cccatttctg    180

gccacaacac cctgtactgg tatctgcaga atctgggaca gggccctgaa ctgctgatca    240

gatacgagaa cgaagaagcc gtggacgatt ctcaactgcc taaggaccgc ttttctgccg    300

agaggctgaa aggagtggat tctaccctga agatccaacc tgctgaactg ggcgattctg    360

ctgtgtacct gtgcgcttct agcctgacaa gaggagctga agcctttttt ggacagggca    420

caagactgac agtggtggag gatctgaaca aggtgttccc cccagaggtg gccgtgttcg    480

agccttctga ggccgagatc tcccacaccc agaaagccac cctcgtgtgc ctggccaccg    540

gctttttccc cgaccacgtg gaactgtctt ggtgggtcaa cggcaaagag gtgcactccg    600

gcgtgtgcac cgatccccag cctctgaaag aacagcccgc cctgaacgac agccggtact    660

gcctgagcag cagactgaga gtgtccgcca ccttctggca gaacccccgg aaccacttca    720

gatgccaggt gcagttctac ggcctgagcg agaacgacga gtggacccag gacagagcca    780

agcccgtgac acagatcgtg tctgccgaag cctggggcag agccgattgc ggctttacct    840

ccgtgtccta tcagcagggc gtgctgagcg ccacaatcct gtacgagatc ctgctgggca    900

aggccaccct gtacgccgtg ctggtgtctg ccctggtgct gatggccatg gtcaagcgga    960

aggacttcgg ttccggagcc acgaacttct ctctgttaaa gcaagcagga gacgtggaag   1020

aaaaccccgg tcccatgaag agcctgagag tcctgctggt gattttgtgg ctgcagctgt   1080

cttgggtttg gtctcagcag aaagaagtgg agcagaatag cggccctctg tctgttcctg   1140

aaggcgctat tgctagcctg aattgcacat acagcgatag aggatctcag agcttcttct   1200

ggtaccggca gtacagcggc aagagcccag aactgatcat gttcatctac agcaatggcg   1260

acaaggagga tggcaggttt acagcccagc tgaacaaggc cagccagtat gtttctctgc   1320

tgatcagaga tagccagcct agcgattctg ccacctacct gtgtgccgtg aacttacttg   1380

gagctacagg atactctaca ctgaccttcg gcaaaggcac catgctgctg gtgagccctg   1440

atatccagaa tcctgatcct gctgtgtacc agctgcggga cagcaagagc agcgacaaga   1500

gcgtgtgcct gttcaccgac ttcgacagcc agaccaacgt gtcccagagc aaggacagcg   1560

acgtgtacat caccgataag tgcgtgctgg acatgcggag catggacttc aagagcaaca   1620

gcgccgtggc ctggtccaac aagagcgact tcgcctgcgc caacgccttc aacaacagca   1680

ttatccccga ggacacattc ttcccaagcc ccgagagcag ctgcgacgtg aagctggtgg   1740

aaaagagctt cgagacagac accaacctga acttccagaa cctcagcgtg atcggcttcc   1800

ggatcctgct gctgaaggtg gccggcttca acctgctgat gaccctgcgg ctgtggtcca   1860

gctga                                                               1865
```

<210> SEQ ID NO 161
<211> LENGTH: 1844
<212> TYPE: DNA
<213> ORGANISM: Artificial Sequence
<220> FEATURE:
<223> OTHER INFORMATION: Synthetic sequence WT137-45 TCR15.1 Codon-
      optimized TCRbeta-P2A-TCRalpha

<400> SEQUENCE: 161

```
ctcaataaaa gagcccacaa cccctcactc ggcgcgccac catgagcaac caggtcttgt     60

gctgtgtggt gctgtgcttt cttggcgcca atacagtgga tggcggcatt acacaaagcc    120

ccaagtacct gttcaggaaa gagggccaga atgtgacact gagctgtgag cagaacctga    180
```

atcacgacgc catgtactgg tacagacagg atccaggaca aggactgagg ctgatctact 240
actcccagat cgtgaacgac ttccagaagg gcgatattgc cgagggctat agcgtgagca 300
gagagaagaa agagagcttc ccactgacag tgacatctgc ccagaagaac cctaccgcct 360
tctacctgtg tgcctcttct agagatagag agcaggagtc tcctctgcac ttcggaaatg 420
gcaccagact gacagtgacc gaggatctga acaaggtgtt ccccccagag gtggccgtgt 480
tcgagccttc tgaggccgag atctcccaca cccagaaagc caccctcgtg tgcctggcca 540
ccggcttttt ccccgaccac gtggaactgt cttggtgggt caacggcaaa gaggtgcact 600
ccggcgtgtg caccgatccc cagcctctga aagaacagcc cgccctgaac gacagccggt 660
actgcctgag cagcagactg agagtgtccg ccaccttctg gcagaacccc cggaaccact 720
tcagatgcca ggtgcagttc tacggcctga gcgagaacga cgagtggacc caggacagag 780
ccaagcccgt gacacagatc gtgtctgccg aagcctgggg cagagccgat tgcggcttta 840
cctccgtgtc ctatcagcag ggcgtgctga gcgccacaat cctgtacgag atcctgctgg 900
gcaaggccac cctgtacgcc gtgctggtgt ctgccctggt gctgatggcc atggtcaagc 960
ggaaggactt cggttccgga gccacgaact tctctctgtt aaagcaagca ggagacgtgg 1020
aagaaaaccc cggtcccatg tggggcgttt tccttctgta tgtgagcatg aagatgggcg 1080
gcacaacagg ccagaacatc gatcagccta ccgagatgac agccacagaa ggagctattg 1140
ttcagatcaa ctgcacctac cagacaagcg gcttcaacgg cctgttctgg taccagcagc 1200
atgctggaga agctcctaca tttctgagct acaatgtgct ggatggcctg gaggagaaag 1260
gcaggtttag cagcttcctg agcaggtcta agggctattc ttatctgctg ctgaaggagc 1320
tgcagatgaa ggattccgcc agctacctgt gtgccgttag gggcatcaat gattacaagc 1380
tgagctttgg agccggaaca acagtgaccg tgagagccaa catccagaac cccgatcctg 1440
ctgtgtacca gctgcgggac agcaagagca gcgacaagag cgtgtgcctg ttcaccgact 1500
tcgacagcca gaccaacgtg tcccagagca aggacagcga cgtgtacatc accgataagt 1560
gcgtgctgga catgcggagc atggacttca agagcaacag cgccgtggcc tggtccaaca 1620
agagcgactt cgcctgcgcc aacgccttca acaacagcat tatccccgag gacacattct 1680
tcccaagccc cgagagcagc tgcgacgtga agctggtgga aaagagcttc gagacagaca 1740
ccaacctgaa cttccagaac ctcagcgtga tcggcttccg gatcctgctg ctgaaggtgg 1800
ccggcttcaa cctgctgatg accctgcggc tgtggtccag ctga 1844

<210> SEQ ID NO 162
<211> LENGTH: 1856
<212> TYPE: DNA
<213> ORGANISM: Artificial Sequence
<220> FEATURE:
<223> OTHER INFORMATION: Synthetic sequence WT137-45 TCR16.1 Codon-optimized TCRbeta-P2A-TCRalpha

<400> SEQUENCE: 162
ctcaataaaa gagcccacaa cccctcactc ggcgcgccac catgggacct cagcttcttg 60
gatacgttgt gctgtgtctg cttggagctg gacctcttga agctcaggtt acccagaacc 120
ccagatacct gattaccgtg acaggcaaaa agctgaccgt gacatgtagc cagaacatga 180
accacgagta catgagctgg taccggcagg atcctggatt aggcctgaga cagatctact 240
acagcatgaa cgtggaggtg accgataaag gcgacgtgcc tgagggatac aaggtgagca 300
gaaaggagaa gaggaatttc cccctgatcc tggaaagccc aagccccaat cagacaagcc 360
tgtacttttg tgccagcagc ttttctggcg gcacatatga gcagtacttc ggccctggca 420
caagactgac agttacagag gacctgaaga acgtgttccc cccagaggtg gccgtgttcg 480
agcctagcga ggccgagatc agccacaccc agaaagccac cctcgtgtgc ctggccaccg 540
gcttttaccc cgaccacgtg gaactgtctt ggtgggtcaa cggcaaagag gtgcacagcg 600
gcgtctgcac cgacccccag cccctgaaag agcagcccgc cctgaacgac agccggtact 660
gtctgagcag cagactgaga gtgtccgcca ccttctggca gaacccccgg aaccacttca 720
gatgccaggt gcagttctac ggcctgagcg agaacgacga gtggacccag gaccgggcca 780
agcccgtgac ccagatcgtg tctgctgagg cctggggcag agccgattgc ggcttcacca 840
gcgagagcta ccagcagggc gtgctgagcg ccaccatcct gtacgagatc ctgctgggca 900
aggccaccct gtacgccgtg ctggtgtccg ccctggtgct gatggccatg gtcaagcgga 960
aggacagccg gggcggttcc ggagccacga acttctctct gttaaagcaa gcaggagacg 1020
tggaagaaaa ccccggtccc atggagaaga tgctggagtg tgcgttcatc gttctgtggc 1080
tgcaacttgg atggctgtct ggagaggatc aggttacaca gtctcctgaa gccctgagac 1140
tgcaagaagg agaaagctct agcctgaact gcagctacac agtgtctgga ctgagaggcc 1200
tgttctggta cagacaggat cctggaaaag gcccagagtt cctgtttacc ctgtattctg 1260
ccggcgagga gaaggagaaa gagagactga aagctaccct gaccaagaag gagagcttcc 1320
tgcacattac cgcccccaaa cctgaggatt ctgccacata tctgtgtgcc gtgattaccg 1380
gctttcagaa gctggtgttt ggcacaggca ccagactgct ggtttctccc aatatccaga 1440
atcccgatcc tgctgtgtac cagctgcggg acagcaagag cagcgacaag agcgtgtgcc 1500
tgttcaccga cttcgacagc cagaccaacg tgtcccagag caaggacagc gacgtgtaca 1560
tcaccgataa gtgcgtgctg gacatgcgga gcatggactt caagagcaac agcgccgtgg 1620
cctggtccaa caagagcgac ttcgcctgcg ccaacgcctt caacaacagc attatccccg 1680
aggacacatt cttcccaagc cccgagagca gctgcgacgt gaagctggtg gaaaagagct 1740
tcgagacaga caccaacctg aacttccaga acctcagcgt gatcggcttc cggatcctgc 1800
tgctgaaggt ggccggcttc aacctgctga tgaccctgcg gctgtggtcc agctga 1856

<210> SEQ ID NO 163
<211> LENGTH: 1880
<212> TYPE: DNA
<213> ORGANISM: Artificial Sequence
<220> FEATURE:
<223> OTHER INFORMATION: Synthetic sequence WT137-45 TCR16.2 Codon-
optimized TCRbeta-P2A-TCRalpha

<400> SEQUENCE: 163
ctcaataaaa gagcccacaa cccctcactc ggcgcgccac catgctgagc cctgatctcc 60
ctgattctgc ctggaatacc agactgctgt gtcatgtgat gctgtgtctg cttggagccg 120
tttctgtggc tgctggcgtg attcaatctc ctagacacct gatcaaggag aagagagaaa 180
cagccaccct gaagtgctac cccatcccca gacacgatac agtgtactgg tatcagcaag 240
gacctggaca agatccccag ttcctgatca gcttctacga gaagatgcag agcgacaaag 300
gcagcatccc agacagattt agcgcccagc agtttagcga ctatcactct gagctgaaca 360
tgagcagcct ggaactgggc gattctgctc tgtacttctg tgccagcagc tatagaggag 420
gcagcacata tgagcagtac tttggccctg gcacaagact gacagtgaca gaggacctga 480
agaacgtgtt ccccccagag gtggccgtgt tcgagcctag cgaggccgag atcagccaca 540

```
cccagaaagc caccctcgtg tgcctggcca ccggctttta ccccgaccac gtggaactgt    600
cttggtgggt caacggcaaa gaggtgcaca gcggcgtctg caccgacccc cagcccctga    660
aagagcagcc cgccctgaac gacagccggt actgtctgag cagcagactg agagtgtccg    720
ccaccttctg gcagaacccc cggaaccact tcagatgcca ggtgcagttc tacggcctga    780
gcgagaacga cgagtggacc caggaccggg ccaagcccgt gacccagatc gtgtctgctg    840
aggcctgggg cagagccgat tgcggcttca ccagcgagag ctaccagcag ggcgtgctga    900
gcgccaccat cctgtacgag atcctgctgg gcaaggccac cctgtacgcc gtgctggtgt    960
ccgccctggt gctgatggcc atggtcaagc ggaaggacag ccggggcggt tccggagcca   1020
cgaacttctc tctgttaaag caagcaggag acgtggaaga aaaccccggt cccatgagac   1080
tggtggcacg cgtaactgtg tttctgacct ttggcaccat catcgatgcc aagacaaccc   1140
agcctacaag catggactgt gccgagggaa gagctgctaa tctgccatgt aatcacagca   1200
caatcagcgg caacgagtac gtgtactggt accggcagat ccactctcaa ggacctcagt   1260
acatcattca tggcctgaag aacaacgaga ccaacgagat ggccagcctg atcatcaccg   1320
aggacaggaa gtcttctacc ctgattctgc ctcatgctac actgagagat accgccgtgt   1380
actactgcat tgccggagtg ggaagaggcc agaatttcgt gtttggacct ggaacaagac   1440
tgagcgttct gccctatatc cagaaccccg atcctgccgt gtaccagctg cgggacagca   1500
agagcagcga caagagcgtg tgcctgttca ccgacttcga cagccagacc aacgtgtccc   1560
agagcaagga cagcgacgtg tacatcaccg ataagtgcgt gctggacatg cggagcatgg   1620
acttcaagag caacagcgcc gtggcctggt ccaacaagag cgacttcgcc tgcgccaacg   1680
ccttcaacaa cagcattatc cccgaggaca cattcttccc aagccccgag agcagctgcg   1740
acgtgaagct ggtggaaaag agcttcgaga cagacaccaa cctgaacttc cagaacctca   1800
gcgtgatcgg cttccggatc ctgctgctga aggtggccgg cttcaacctg ctgatgaccc   1860
tgcggctgtg gtccagctga                                               1880
```

<210> SEQ ID NO 164
<211> LENGTH: 1871
<212> TYPE: DNA
<213> ORGANISM: Artificial Sequence
<220> FEATURE:
<223> OTHER INFORMATION: Synthetic sequence WT137-45 TCR18.1 Codon-
optimized TCRbeta-P2A-TCRalpha

<400> SEQUENCE: 164

```
ctcaataaaa gagcccacaa cccctcactc ggcgcgccac catgagcacc agactccttt     60
gctggatggc tttgtgtctg cttggagctg agctgtctga agctgaagtt gcccagtctc    120
ccagatacaa gatcaccgag aaatctcagg ctgtggcctt ctggtgtgac cctatttctg    180
gacacgccac cctgtactgg tataggcaaa ttctgggaca aggccctgaa ctgctggtgc    240
aatttcagga tgagagcgtg gtggacgatt ctcaactgcc taaggacagg ttttctgccg    300
agcggctgaa aggagttgat agcaccctga agatccaacc tgctgaactg ggcgattctg    360
ctatgtacct gtgcgcctct tctcagagag atagccctaa cgagaagctg ttctttggct    420
ctggaaccca gctgtctgtg ctggaggatc tgaacaaggt gttccccccc gaggtggccg    480
tgttcgagcc ttctgaggcc gagatctccc acacccagaa agccaccctc gtgtgcctgg    540
ccaccggctt tttccccgac cacgtggaac tgtcttggtg ggtcaacggc aaagaggtgc    600
actccggcgt gtgcaccgat ccccagcctc tgaaagaaca gcccgccctg aacgacagcc    660
```

ggtactgcct gagcagcaga ctgagagtgt ccgccacctt ctggcagaac ccccggaacc 720
acttcagatg ccaggtgcag ttctacggcc tgagcgagaa cgacgagtgg acccaggaca 780
gagccaagcc cgtgacacag atcgtgtctg ccgaagcctg gggcagagcc gattgcggct 840
ttacctccgt gtcctatcag cagggcgtgc tgagcgccac aatcctgtac gagatcctgc 900
tgggcaaggc caccctgtac gccgtgctgg tgtctgccct ggtgctgatg gccatggtca 960
agcggaagga cttcggttcc ggagccacga acttctctct gttaaagcaa gcaggagacg 1020
tggaagaaaa ccccggtccc atggagaaga acccccttggc agcacctctg cttattctgt 1080
ggttccacct ggattgtgtg agcagcatcc tgaatgtgga gcagtctcct cagagcctgc 1140
atgtgcaaga aggcgatagc accaatttca cctgcagctt tccaagcagc aacttctacg 1200
ccctgcactg gtacagatgg gaaaccgcca aatctcctga agccctgttt gtgatgaccc 1260
tgaatggcga cgagaagaag aagggcagaa ttagcgccac cctgaatacc aaggagggct 1320
acagctacct gtacatcaag ggctctcaac ctgaggattc tgccacctac ctttgcgcct 1380
ttcaccccaa tttcggcaac gagaaactga cctttggaac cggaacaagg ctgaccatca 1440
tccccaacat ccagaaccct gatcctgccg tgtaccagct gcgggacagc aagagcagcg 1500
acaagagcgt gtgcctgttc accgacttcg acagccagac caacgtgtcc cagagcaagg 1560
acagcgacgt gtacatcacc gataagtgcg tgctggacat gcggagcatg gacttcaaga 1620
gcaacagcgc cgtggcctgg tccaacaaga gcgacttcgc ctgcgccaac gccttcaaca 1680
acagcattat ccccgaggac acattcttcc caagccccga gagcagctgc gacgtgaagc 1740
tggtggaaaa gagcttcgag acagacacca acctgaactt ccagaacctc agcgtgatcg 1800
gcttccggat cctgctgctg aaggtggccg gcttcaacct gctgatgacc ctgcggctgt 1860
ggtccagctg a 1871

<210> SEQ ID NO 165
<211> LENGTH: 1877
<212> TYPE: DNA
<213> ORGANISM: Artificial Sequence
<220> FEATURE:
<223> OTHER INFORMATION: Synthetic sequence WT137-45 TCR19.1 Codon-
      optimized TCRbeta-P2A-TCRalpha

<400> SEQUENCE: 165
ctcaataaaa gagcccacaa cccctcactc ggcgcgccac catgggctgt agactgttgt 60
gttgtgctgt gctgtgtctg ttgggagctg tgcctatgga aacaggcgtt acccagacac 120
ctagacatct ggttatgggc atgaccaaca agaagagcct gaagtgcgag cagcatctgg 180
gccataacgc catgtactgg tataagcaga gcgccaagaa accactggaa ctgatgttcg 240
tgtacagcct ggaggagagg gtggagaata atagcgtgcc cagcagattt agccctgagt 300
gcccaaattc ttctcacctg ttcctgcacc tgcacacatt acagcccgag gattctgccc 360
tgtacctgtg tgcttcttct caagaccctt acaagctgag cggcaatacc atctacttcg 420
gcgaaggctc ttggctgaca gtggttgaag atctgaacaa ggtgttcccc ccagaggtgg 480
ccgtgttcga gccttctgag gccgagatct cccacaccca gaaagccacc ctcgtgtgcc 540
tggccaccgg ctttttcccc gaccacgtgg aactgtcttg gtgggtcaac ggcaaagagg 600
tgcactccgg cgtgtgcacc gatccccagc ctctgaaaga acagcccgcc ctgaacgaca 660
gccggtactg cctgagcagc agactgagag tgtccgccac cttctggcag aacccccgga 720
accacttcag atgccaggtg cagttctacg gcctgagcga gaacgacgag tggacccagg 780
acagagccaa gcccgtgaca cagatcgtgt ctgccgaagc ctggggcaga gccgattgcg 840
gctttacctc cgtgtcctat cagcagggcg tgctgagcgc cacaatcctg tacgagatcc 900
tgctgggcaa ggccaccctg tacgccgtgc tggtgtctgc cctggtgctg atggccatgg 960
tcaagcggaa ggacttcggt tccggagcca cgaacttctc tctgttaaag caagcaggag 1020
acgtggaaga aaaccccggt cccatggaga agatgctgga gtgtgcgttc atcgttctgt 1080
ggctgcaact tggatggctg tctggagagg atcaggttac acagtctcct gaagccctga 1140
gactgcaaga aggagaaagc tctagcctga actgcagcta cacagtgtct ggactgagag 1200
gcctgttctg gtacagacag gatcctggaa aaggcccaga gttcctgttt accctgtatt 1260
ctgccggcga ggagaaggag aaagagagac tgaaagctac cctgaccaag aaggagagct 1320
tcctgcacat taccgccccc aaacctgagg attctgccac atatctgtgt gctgttcagc 1380
ctagaggaga tggctctagc aataccggca agctgatctt tggccaggga acaacactgc 1440
aggtgaagcc tgatatccag aaccccgatc ctgctgtgta ccagctgcgg gacagcaaga 1500
gcagcgacaa gagcgtgtgc ctgttcaccg acttcgacag ccagaccaac gtgtcccaga 1560
gcaaggacag cgacgtgtac atcaccgata agtgcgtgct ggacatgcgg agcatggact 1620
tcaagagcaa cagcgccgtg gcctggtcca acaagagcga cttcgcctgc gccaacgcct 1680
tcaacaacag cattatcccc gaggacacat tcttcccaag ccccgagagc agctgcgacg 1740
tgaagctggt ggaaaagagc ttcgagacag acaccaacct gaacttccag aacctcagcg 1800
tgatcggctt ccggatcctg ctgctgaagg tggccggctt caacctgctg atgaccctgc 1860
ggctgtggtc cagctga 1877

<210> SEQ ID NO 166
<211> LENGTH: 66
<212> TYPE: DNA
<213> ORGANISM: Artificial Sequence
<220> FEATURE:
<223> OTHER INFORMATION: Synthetic sequence Porcine teschovirus-1 2A (P2A)

<400> SEQUENCE: 166
ggaagcggag ctactaactt cagcctgctg aagcaggctg gagacgtgga ggagaaccct 60
ggacct 66

<210> SEQ ID NO 167
<211> LENGTH: 66
<212> TYPE: DNA
<213> ORGANISM: Artificial Sequence
<220> FEATURE:
<223> OTHER INFORMATION: Synthetic sequence Porcine teschovirus-1 2A (P2A) peptide - Codon Optimized

<400> SEQUENCE: 167
ggttccggag ccacgaactt ctctctgtta aagcaagcag gagacgtgga agaaaacccc 60
ggtccc 66

<210> SEQ ID NO 168
<211> LENGTH: 63
<212> TYPE: DNA
<213> ORGANISM: Artificial Sequence
<220> FEATURE:
<223> OTHER INFORMATION: Synthetic sequence Thoseaasigna virus 2A (T2A)

<400> SEQUENCE: 168
ggaagcggag agggcagagg aagtctgcta acatgcggtg acgtcgagga gaatcctgga 60
cct 63

<210> SEQ ID NO 169
<211> LENGTH: 69
<212> TYPE: DNA
<213> ORGANISM: Artificial Sequence
<220> FEATURE:
<223> OTHER INFORMATION: Synthetic sequence Equine rhinitis A virus (ERAV) 2A (E2A)

<400> SEQUENCE: 169
ggaagcggac agtgtactaa ttatgctctc ttgaaattgg ctggagatgt tgagagcaac 60
cctggacct 69

<210> SEQ ID NO 170
<211> LENGTH: 75
<212> TYPE: DNA
<213> ORGANISM: Artificial Sequence
<220> FEATURE:
<223> OTHER INFORMATION: Synthetic sequence Foot-and-Mouth disease virus 2A (F2A)

<400> SEQUENCE: 170
ggaagcggag tgaaacagac tttgaatttt gaccttctca agttggcggg agacgtggag 60
tccaaccctg gacct 75

<210> SEQ ID NO 171
<211> LENGTH: 5
<212> TYPE: PRT
<213> ORGANISM: Artificial Sequence
<220> FEATURE:
<223> OTHER INFORMATION: Gly-Ser linker

<400> SEQUENCE: 171

Gly Gly Gly Gly Ser
1               5

<210> SEQ ID NO 172
<211> LENGTH: 4
<212> TYPE: PRT
<213> ORGANISM: Artificial Sequence
<220> FEATURE:
<223> OTHER INFORMATION: Gly-Ser linker

<400> SEQUENCE: 172

Gly Gly Gly Ser
1

<210> SEQ ID NO 173
<211> LENGTH: 45
<212> TYPE: PRT
<213> ORGANISM: Artificial Sequence
<220> FEATURE:
<223> OTHER INFORMATION: Gly-Ser linker
<220> FEATURE:
<221> NAME/KEY: VARIANT
<222> LOCATION: (5)..(40)
<223> OTHER INFORMATION: Any one or all of amino acids 5-40 can either be present or absent.

<400> SEQUENCE: 173

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser

```
            20                  25                  30

Gly Gly Gly Ser Gly Gly Gly Ser Gly Gly Gly Gly Ser
        35                  40                  45


<210> SEQ ID NO 174
<211> LENGTH: 70
<212> TYPE: PRT
<213> ORGANISM: Artificial Sequence
<220> FEATURE:
<223> OTHER INFORMATION: Gly-Ser linker
<220> FEATURE:
<221> NAME/KEY: VARIANT
<222> LOCATION: (5)..(40)
<223> OTHER INFORMATION: Any one or all of amino acids 5-40 can either
      be present or absent.
<220> FEATURE:
<221> NAME/KEY: VARIANT
<222> LOCATION: (44)..(70)
<223> OTHER INFORMATION: Any one or all of amino acids 44-70 can either
      be present or absent.

<400> SEQUENCE: 174

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Ser Gly Gly Ser Gly Gly
        35                  40                  45

Ser Gly Gly Ser Gly Gly Ser Gly Gly Ser Gly Gly Ser Gly Gly Ser
    50                  55                  60

Gly Gly Ser Gly Gly Ser
65                  70


<210> SEQ ID NO 175
<211> LENGTH: 90
<212> TYPE: PRT
<213> ORGANISM: Artificial Sequence
<220> FEATURE:
<223> OTHER INFORMATION: Gly-Ser linker
<220> FEATURE:
<221> NAME/KEY: VARIANT
<222> LOCATION: (5)..(40)
<223> OTHER INFORMATION: Any one or all of amino acids 5-40 can either
      be present or absent.
<220> FEATURE:
<221> NAME/KEY: VARIANT
<222> LOCATION: (46)..(90)
<223> OTHER INFORMATION: Any one or all of amino acids 46-90 can either
      be present or absent.

<400> SEQUENCE: 175

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser
                85                  90
```

<210> SEQ ID NO 176
<211> LENGTH: 6
<212> TYPE: PRT
<213> ORGANISM: Artificial Sequence
<220> FEATURE:
<223> OTHER INFORMATION: Synthetic sequence WT137-45 TCR15.1 - alpha CDR1

<400> SEQUENCE: 176

Thr Ser Gly Phe Asn Gly
1 5

<210> SEQ ID NO 177
<211> LENGTH: 6
<212> TYPE: PRT
<213> ORGANISM: Artificial Sequence
<220> FEATURE:
<223> OTHER INFORMATION: Synthetic sequence WT137-45 TCR15.1 - alpha CDR2

<400> SEQUENCE: 177

Asn Val Leu Asp Gly Leu
1 5

<210> SEQ ID NO 178
<211> LENGTH: 11
<212> TYPE: PRT
<213> ORGANISM: Artificial Sequence
<220> FEATURE:
<223> OTHER INFORMATION: Synthetic sequence WT137-45 TCR15.1 - alpha CDR3

<400> SEQUENCE: 178

Ala Val Arg Gly Ile Asn Asp Tyr Lys Leu Ser
1 5 10

<210> SEQ ID NO 179
<211> LENGTH: 5
<212> TYPE: PRT
<213> ORGANISM: Artificial Sequence
<220> FEATURE:
<223> OTHER INFORMATION: Synthetic sequence WT137-45 TCR15.1 - beta CDR1

<400> SEQUENCE: 179

Leu Asn His Asp Ala
1 5

<210> SEQ ID NO 180
<211> LENGTH: 6
<212> TYPE: PRT
<213> ORGANISM: Artificial Sequence
<220> FEATURE:
<223> OTHER INFORMATION: Synthetic sequence WT137-45 TCR15.1 - beta CDR2

<400> SEQUENCE: 180

Ser Gln Ile Val Asn Asp
1 5

<210> SEQ ID NO 181
<211> LENGTH: 13
<212> TYPE: PRT
<213> ORGANISM: Artificial Sequence
<220> FEATURE:
<223> OTHER INFORMATION: Synthetic sequence WT137-45 TCR15.1 - beta CDR3

<400> SEQUENCE: 181

Ala Ser Ser Arg Asp Arg Glu Gln Glu Ser Pro Leu His
1 5 10

<210> SEQ ID NO 182
<211> LENGTH: 7
<212> TYPE: PRT
<213> ORGANISM: Artificial Sequence
<220> FEATURE:
<223> OTHER INFORMATION: Synthetic sequence WT137-45 TCR16.2 - alpha CDR1

<400> SEQUENCE: 182

Thr Ile Ser Gly Asn Glu Tyr
1 5

<210> SEQ ID NO 183
<211> LENGTH: 5
<212> TYPE: PRT
<213> ORGANISM: Artificial Sequence
<220> FEATURE:
<223> OTHER INFORMATION: Synthetic sequence WT137-45 TCR16.2 - alpha CDR2

<400> SEQUENCE: 183

Gly Leu Lys Asn Asn
1 5

<210> SEQ ID NO 184
<211> LENGTH: 11
<212> TYPE: PRT
<213> ORGANISM: Artificial Sequence
<220> FEATURE:
<223> OTHER INFORMATION: Synthetic sequence WT137-45 TCR16.2 - alpha CDR3

<400> SEQUENCE: 184

Ile Ala Gly Val Gly Arg Gly Gln Asn Phe Val
1 5 10

<210> SEQ ID NO 185
<211> LENGTH: 5
<212> TYPE: PRT
<213> ORGANISM: Artificial Sequence
<220> FEATURE:
<223> OTHER INFORMATION: Synthetic sequence WT137-45 TCR16.2 - beta CDR1

<400> SEQUENCE: 185

Pro Arg His Asp Thr
1 5

<210> SEQ ID NO 186
<211> LENGTH: 6
<212> TYPE: PRT
<213> ORGANISM: Artificial Sequence
<220> FEATURE:
<223> OTHER INFORMATION: Synthetic sequence WT137-45 TCR16.2 - beta CDR2

<400> SEQUENCE: 186

Phe Tyr Glu Lys Met Gln
1 5

<210> SEQ ID NO 187
<211> LENGTH: 13
<212> TYPE: PRT
<213> ORGANISM: Artificial Sequence
<220> FEATURE:
<223> OTHER INFORMATION: Synthetic sequence WT137-45 TCR16.2 - beta CDR3

<400> SEQUENCE: 187

Ala Ser Ser Tyr Arg Gly Gly Ser Thr Tyr Glu Gln Tyr
1 5 10

<210> SEQ ID NO 188
<211> LENGTH: 6
<212> TYPE: PRT
<213> ORGANISM: Artificial Sequence
<220> FEATURE:
<223> OTHER INFORMATION: Synthetic sequence WT137-45 TCR18.1 - alpha CDR1

<400> SEQUENCE: 188

Ser Ser Asn Phe Tyr Ala
1 5

<210> SEQ ID NO 189
<211> LENGTH: 7
<212> TYPE: PRT
<213> ORGANISM: Artificial Sequence
<220> FEATURE:
<223> OTHER INFORMATION: Synthetic sequence WT137-45 TCR18.1 - alpha CDR2

<400> SEQUENCE: 189

Met Thr Leu Asn Gly Asp Glu
1 5

<210> SEQ ID NO 190
<211> LENGTH: 12
<212> TYPE: PRT
<213> ORGANISM: Artificial Sequence
<220> FEATURE:
<223> OTHER INFORMATION: Synthetic sequence WT137-45 TCR18.1 - alpha CDR3

<400> SEQUENCE: 190

Ala Phe His Pro Asn Phe Gly Asn Glu Lys Leu Thr
1 5 10

<210> SEQ ID NO 191
<211> LENGTH: 5
<212> TYPE: PRT
<213> ORGANISM: Artificial Sequence
<220> FEATURE:
<223> OTHER INFORMATION: Synthetic sequence WT137-45 TCR18.1 - beta CDR1

<400> SEQUENCE: 191

Ser Gly His Ala Thr
1 5

<210> SEQ ID NO 192
<211> LENGTH: 6
<212> TYPE: PRT
<213> ORGANISM: Artificial Sequence
<220> FEATURE:
<223> OTHER INFORMATION: Synthetic sequence WT137-45 TCR18.1 - beta CDR2

<400> SEQUENCE: 192

Phe Gln Asp Glu Ser Val
1 5

<210> SEQ ID NO 193
<211> LENGTH: 13
<212> TYPE: PRT
<213> ORGANISM: Artificial Sequence
<220> FEATURE:
<223> OTHER INFORMATION: Synthetic sequence WT137-45 TCR18.1 - beta CDR3

<400> SEQUENCE: 193

Ala Ser Ser Gln Arg Asp Ser Pro Asn Glu Lys Leu Phe
1 5 10

<210> SEQ ID NO 194
<211> LENGTH: 6
<212> TYPE: PRT
<213> ORGANISM: Artificial Sequence
<220> FEATURE:
<223> OTHER INFORMATION: Synthetic sequence WT137-45 TCR10.1 - alpha CDR1

<400> SEQUENCE: 194

Asp Ser Ala Ile Tyr Asn
1 5

<210> SEQ ID NO 195
<211> LENGTH: 7
<212> TYPE: PRT
<213> ORGANISM: Artificial Sequence
<220> FEATURE:
<223> OTHER INFORMATION: Synthetic sequence WT137-45 TCR10.1 - alpha CDR2

<400> SEQUENCE: 195

Ile Gln Ser Ser Gln Arg Glu
1 5

<210> SEQ ID NO 196
<211> LENGTH: 11
<212> TYPE: PRT
<213> ORGANISM: Artificial Sequence
<220> FEATURE:
<223> OTHER INFORMATION: Synthetic sequence WT137-45 TCR10.1 - alpha CDR3

<400> SEQUENCE: 196

Ala Val Lys Glu Thr Ser Gly Ser Arg Leu Thr
1 5 10

<210> SEQ ID NO 197
<211> LENGTH: 5
<212> TYPE: PRT
<213> ORGANISM: Artificial Sequence
<220> FEATURE:
<223> OTHER INFORMATION: Synthetic sequence WT137-45 TCR10.1 - beta CDR1

<400> SEQUENCE: 197

Ser Gly His Val Ser
1 5

<210> SEQ ID NO 198
<211> LENGTH: 6
<212> TYPE: PRT
<213> ORGANISM: Artificial Sequence
<220> FEATURE:
<223> OTHER INFORMATION: Synthetic sequence WT137-45 TCR10.1 - beta CDR2

<400> SEQUENCE: 198

Phe Asn Tyr Glu Ala Gln
1 5

<210> SEQ ID NO 199
<211> LENGTH: 11
<212> TYPE: PRT
<213> ORGANISM: Artificial Sequence
<220> FEATURE:
<223> OTHER INFORMATION: Synthetic sequence WT137-45 TCR10.1 - beta
CDR3

<400> SEQUENCE: 199

Ala Ser Ser Leu Thr Gly Ser Tyr Glu Gln Tyr
1 5 10

<210> SEQ ID NO 200
<211> LENGTH: 7
<212> TYPE: PRT
<213> ORGANISM: Artificial Sequence
<220> FEATURE:
<223> OTHER INFORMATION: Synthetic sequence WT137-45 TCR11.2 - alpha
CDR1

<400> SEQUENCE: 200

Thr Ser Glu Asn Asn Tyr Tyr
1 5

<210> SEQ ID NO 201
<211> LENGTH: 8
<212> TYPE: PRT
<213> ORGANISM: Artificial Sequence
<220> FEATURE:
<223> OTHER INFORMATION: Synthetic sequence WT137-45 TCR11.2 - alpha
CDR2

<400> SEQUENCE: 201

Gln Glu Ala Tyr Lys Gln Gln Asn
1 5

<210> SEQ ID NO 202
<211> LENGTH: 15
<212> TYPE: PRT
<213> ORGANISM: Artificial Sequence
<220> FEATURE:
<223> OTHER INFORMATION: Synthetic sequence WT137-45 TCR11.2 - alpha
CDR3

<400> SEQUENCE: 202

Ala Phe Ile Tyr Pro Ser Tyr Thr Ser Gly Thr Tyr Lys Tyr Ile
1 5 10 15

<210> SEQ ID NO 203
<211> LENGTH: 6
<212> TYPE: PRT
<213> ORGANISM: Artificial Sequence
<220> FEATURE:
<223> OTHER INFORMATION: Synthetic sequence WT137-45 TCR11.2 - beta
CDR1

<400> SEQUENCE: 203

Asp Phe Gln Ala Thr Thr
1 5

<210> SEQ ID NO 204
<211> LENGTH: 7
<212> TYPE: PRT
<213> ORGANISM: Artificial Sequence
<220> FEATURE:
<223> OTHER INFORMATION: Synthetic sequence WT137-45 TCR11.2 - beta
CDR2

<400> SEQUENCE: 204

Ser Asn Glu Gly Ser Lys Ala
1 5

```
<210> SEQ ID NO 205
<211> LENGTH: 13
<212> TYPE: PRT
<213> ORGANISM: Artificial Sequence
<220> FEATURE:
<223> OTHER INFORMATION: Synthetic sequence WT137-45 TCR11.2 - beta
      CDR3

<400> SEQUENCE: 205

Ser Ala Thr Pro Glu Ala Ser Ser Pro Tyr Glu Gln Tyr
1               5                   10


<210> SEQ ID NO 206
<211> LENGTH: 6
<212> TYPE: PRT
<213> ORGANISM: Artificial Sequence
<220> FEATURE:
<223> OTHER INFORMATION: Synthetic sequence WT137-45 TCR12.1 - alpha
      CDR1

<400> SEQUENCE: 206

Asn Ser Met Phe Asp Tyr
1               5


<210> SEQ ID NO 207
<211> LENGTH: 7
<212> TYPE: PRT
<213> ORGANISM: Artificial Sequence
<220> FEATURE:
<223> OTHER INFORMATION: Synthetic sequence WT137-45 TCR12.1 - alpha
      CDR2

<400> SEQUENCE: 207

Ile Ser Ser Ile Lys Asp Lys
1               5


<210> SEQ ID NO 208
<211> LENGTH: 12
<212> TYPE: PRT
<213> ORGANISM: Artificial Sequence
<220> FEATURE:
<223> OTHER INFORMATION: Synthetic sequence WT137-45 TCR12.1 - alpha
      CDR3

<400> SEQUENCE: 208

Ala Ala Ser Gly Thr Gly Gly Ser Tyr Ile Pro Thr
1               5                   10


<210> SEQ ID NO 209
<211> LENGTH: 5
<212> TYPE: PRT
<213> ORGANISM: Artificial Sequence
<220> FEATURE:
<223> OTHER INFORMATION: Synthetic sequence WT137-45 TCR12.1 - beta
      CDR1

<400> SEQUENCE: 209

Leu Asn His Asn Val
1               5


<210> SEQ ID NO 210
<211> LENGTH: 6
<212> TYPE: PRT
<213> ORGANISM: Artificial Sequence
<220> FEATURE:
<223> OTHER INFORMATION: Synthetic sequence WT137-45 TCR12.1 - beta
      CDR2
```

<400> SEQUENCE: 210

Tyr Tyr Asp Lys Asp Phe
1 5

<210> SEQ ID NO 211
<211> LENGTH: 12
<212> TYPE: PRT
<213> ORGANISM: Artificial Sequence
<220> FEATURE:
<223> OTHER INFORMATION: Synthetic sequence WT137-45 TCR12.1 - beta CDR3

<400> SEQUENCE: 211

Ala Thr Ser Asn Leu Gln Gly Arg Gln Pro Gln His
1 5 10

<210> SEQ ID NO 212
<211> LENGTH: 6
<212> TYPE: PRT
<213> ORGANISM: Artificial Sequence
<220> FEATURE:
<223> OTHER INFORMATION: Synthetic sequence WT137-45 TCR13.1 - alpha CDR1

<400> SEQUENCE: 212

Asn Ser Met Phe Asp Tyr
1 5

<210> SEQ ID NO 213
<211> LENGTH: 7
<212> TYPE: PRT
<213> ORGANISM: Artificial Sequence
<220> FEATURE:
<223> OTHER INFORMATION: Synthetic sequence WT137-45 TCR13.1 - alpha CDR2

<400> SEQUENCE: 213

Ile Ser Ser Ile Lys Asp Lys
1 5

<210> SEQ ID NO 214
<211> LENGTH: 11
<212> TYPE: PRT
<213> ORGANISM: Artificial Sequence
<220> FEATURE:
<223> OTHER INFORMATION: Synthetic sequence WT137-45 TCR13.1 - alpha CDR3

<400> SEQUENCE: 214

Ala Ala Ser Gly Ile Gly Asp Tyr Lys Leu Ser
1 5 10

<210> SEQ ID NO 215
<211> LENGTH: 5
<212> TYPE: PRT
<213> ORGANISM: Artificial Sequence
<220> FEATURE:
<223> OTHER INFORMATION: Synthetic sequence WT137-45 TCR13.1 - beta CDR1

<400> SEQUENCE: 215

Pro Arg His Asp Thr
1 5

<210> SEQ ID NO 216
<211> LENGTH: 6
<212> TYPE: PRT

```
<213> ORGANISM: Artificial Sequence
<220> FEATURE:
<223> OTHER INFORMATION: Synthetic sequence WT137-45 TCR13.1 - beta
      CDR2

<400> SEQUENCE: 216

Phe Tyr Glu Lys Met Gln
1               5


<210> SEQ ID NO 217
<211> LENGTH: 12
<212> TYPE: PRT
<213> ORGANISM: Artificial Sequence
<220> FEATURE:
<223> OTHER INFORMATION: Synthetic sequence WT137-45 TCR13.1 - beta
      CDR3

<400> SEQUENCE: 217

Ala Ser Ser Leu Arg Leu Gly Arg Glu Thr Gln Tyr
1               5                   10


<210> SEQ ID NO 218
<211> LENGTH: 6
<212> TYPE: PRT
<213> ORGANISM: Artificial Sequence
<220> FEATURE:
<223> OTHER INFORMATION: Synthetic sequence WT137-45 TCR14.1 - alpha
      CDR1

<400> SEQUENCE: 218

Asp Arg Gly Ser Gln Ser
1               5


<210> SEQ ID NO 219
<211> LENGTH: 6
<212> TYPE: PRT
<213> ORGANISM: Artificial Sequence
<220> FEATURE:
<223> OTHER INFORMATION: Synthetic sequence WT137-45 TCR14.1 - alpha
      CDR2

<400> SEQUENCE: 219

Ile Tyr Ser Asn Gly Asp
1               5


<210> SEQ ID NO 220
<211> LENGTH: 14
<212> TYPE: PRT
<213> ORGANISM: Artificial Sequence
<220> FEATURE:
<223> OTHER INFORMATION: Synthetic sequence WT137-45 TCR14.1 - alpha
      CDR3

<400> SEQUENCE: 220

Ala Val Asn Leu Leu Gly Ala Thr Gly Tyr Ser Thr Leu Thr
1               5                   10


<210> SEQ ID NO 221
<211> LENGTH: 5
<212> TYPE: PRT
<213> ORGANISM: Artificial Sequence
<220> FEATURE:
<223> OTHER INFORMATION: Synthetic sequence WT137-45 TCR14.1 - beta
      CDR1

<400> SEQUENCE: 221

Ser Gly His Asn Thr
1               5
```

<210> SEQ ID NO 222
<211> LENGTH: 6
<212> TYPE: PRT
<213> ORGANISM: Artificial Sequence
<220> FEATURE:
<223> OTHER INFORMATION: Synthetic sequence WT137-45 TCR14.1 - beta CDR2

<400> SEQUENCE: 222

Tyr Glu Asn Glu Glu Ala
1               5

<210> SEQ ID NO 223
<211> LENGTH: 11
<212> TYPE: PRT
<213> ORGANISM: Artificial Sequence
<220> FEATURE:
<223> OTHER INFORMATION: Synthetic sequence WT137-45 TCR14.1 - beta CDR3

<400> SEQUENCE: 223

Ala Ser Ser Leu Thr Arg Gly Ala Glu Ala Phe
1               5                   10

<210> SEQ ID NO 224
<211> LENGTH: 6
<212> TYPE: PRT
<213> ORGANISM: Artificial Sequence
<220> FEATURE:
<223> OTHER INFORMATION: Synthetic sequence WT137-45 TCR16.1 - alpha CDR1

<400> SEQUENCE: 224

Val Ser Gly Leu Arg Gly
1               5

<210> SEQ ID NO 225
<211> LENGTH: 7
<212> TYPE: PRT
<213> ORGANISM: Artificial Sequence
<220> FEATURE:
<223> OTHER INFORMATION: Synthetic sequence WT137-45 TCR16.1 - alpha CDR2

<400> SEQUENCE: 225

Leu Tyr Ser Ala Gly Glu Glu
1               5

<210> SEQ ID NO 226
<211> LENGTH: 10
<212> TYPE: PRT
<213> ORGANISM: Artificial Sequence
<220> FEATURE:
<223> OTHER INFORMATION: Synthetic sequence WT137-45 TCR16.1 - alpha CDR3

<400> SEQUENCE: 226

Ala Val Ile Thr Gly Phe Gln Lys Leu Val
1               5                   10

<210> SEQ ID NO 227
<211> LENGTH: 5
<212> TYPE: PRT
<213> ORGANISM: Artificial Sequence
<220> FEATURE:
<223> OTHER INFORMATION: Synthetic sequence WT137-45 TCR16.1 - beta CDR1

<400> SEQUENCE: 227

Met Asn His Glu Tyr
1 5

<210> SEQ ID NO 228
<211> LENGTH: 6
<212> TYPE: PRT
<213> ORGANISM: Artificial Sequence
<220> FEATURE:
<223> OTHER INFORMATION: Synthetic sequence WT137-45 TCR16.1 - beta CDR2

<400> SEQUENCE: 228

Ser Met Asn Val Glu Val
1 5

<210> SEQ ID NO 229
<211> LENGTH: 12
<212> TYPE: PRT
<213> ORGANISM: Artificial Sequence
<220> FEATURE:
<223> OTHER INFORMATION: Synthetic sequence WT137-45 TCR16.1 - beta CDR3

<400> SEQUENCE: 229

Ala Ser Ser Phe Ser Gly Gly Thr Tyr Glu Gln Tyr
1 5 10

<210> SEQ ID NO 230
<211> LENGTH: 6
<212> TYPE: PRT
<213> ORGANISM: Artificial Sequence
<220> FEATURE:
<223> OTHER INFORMATION: Synthetic sequence WT137-45 TCR19.1 - alpha CDR1

<400> SEQUENCE: 230

Val Ser Gly Leu Arg Gly
1 5

<210> SEQ ID NO 231
<211> LENGTH: 7
<212> TYPE: PRT
<213> ORGANISM: Artificial Sequence
<220> FEATURE:
<223> OTHER INFORMATION: Synthetic sequence WT137-45 TCR19.1 - alpha CDR2

<400> SEQUENCE: 231

Leu Tyr Ser Ala Gly Glu Glu
1 5

<210> SEQ ID NO 232
<211> LENGTH: 16
<212> TYPE: PRT
<213> ORGANISM: Artificial Sequence
<220> FEATURE:
<223> OTHER INFORMATION: Synthetic sequence WT137-45 TCR19.1 - alpha CDR3

<400> SEQUENCE: 232

Ala Val Gln Pro Arg Gly Asp Gly Ser Ser Asn Thr Gly Lys Leu Ile
1 5 10 15

<210> SEQ ID NO 233
<211> LENGTH: 5

```
<212> TYPE: PRT
<213> ORGANISM: Artificial Sequence
<220> FEATURE:
<223> OTHER INFORMATION: Synthetic sequence WT137-45 TCR19.1 - beta
      CDR1

<400> SEQUENCE: 233

Leu Gly His Asn Ala
1               5


<210> SEQ ID NO 234
<211> LENGTH: 6
<212> TYPE: PRT
<213> ORGANISM: Artificial Sequence
<220> FEATURE:
<223> OTHER INFORMATION: Synthetic sequence WT137-45 TCR19.1 - beta
      CDR2

<400> SEQUENCE: 234

Tyr Ser Leu Glu Glu Arg
1               5


<210> SEQ ID NO 235
<211> LENGTH: 15
<212> TYPE: PRT
<213> ORGANISM: Artificial Sequence
<220> FEATURE:
<223> OTHER INFORMATION: Synthetic sequence WT137-45 TCR19.1 - beta
      CDR3

<400> SEQUENCE: 235

Ala Ser Ser Gln Asp Pro Tyr Lys Leu Ser Gly Asn Thr Ile Tyr
1               5                   10                  15


<210> SEQ ID NO 236
<211> LENGTH: 5
<212> TYPE: PRT
<213> ORGANISM: Artificial Sequence
<220> FEATURE:
<223> OTHER INFORMATION: Synthetic sequence WT137-45 TCR13.2 - alpha
      CDR1

<400> SEQUENCE: 236

Val Gly Ile Ser Ala
1               5


<210> SEQ ID NO 237
<211> LENGTH: 5
<212> TYPE: PRT
<213> ORGANISM: Artificial Sequence
<220> FEATURE:
<223> OTHER INFORMATION: Synthetic sequence WT137-45 TCR13.2 - alpha
      CDR2

<400> SEQUENCE: 237

Leu Ser Ser Gly Lys
1               5


<210> SEQ ID NO 238
<211> LENGTH: 10
<212> TYPE: PRT
<213> ORGANISM: Artificial Sequence
<220> FEATURE:
<223> OTHER INFORMATION: Synthetic sequence WT137-45 TCR13.2 - alpha
      CDR3

<400> SEQUENCE: 238

Ala Val Arg Thr Ser Tyr Asp Lys Val Ile
```

1 5 10

<210> SEQ ID NO 239
<211> LENGTH: 5
<212> TYPE: PRT
<213> ORGANISM: Artificial Sequence
<220> FEATURE:
<223> OTHER INFORMATION: Synthetic sequence WT137-45 TCR13.2 - beta CDR1

<400> SEQUENCE: 239

Ser Gly His Val Ser
1 5

<210> SEQ ID NO 240
<211> LENGTH: 6
<212> TYPE: PRT
<213> ORGANISM: Artificial Sequence
<220> FEATURE:
<223> OTHER INFORMATION: Synthetic sequence WT137-45 TCR13.2 - beta CDR2

<400> SEQUENCE: 240

Phe Gln Asn Glu Ala Gln
1 5

<210> SEQ ID NO 241
<211> LENGTH: 11
<212> TYPE: PRT
<213> ORGANISM: Artificial Sequence
<220> FEATURE:
<223> OTHER INFORMATION: Synthetic sequence WT137-45 TCR13.2 - beta CDR3

<400> SEQUENCE: 241

Ala Ser Ser Leu Gly Gln Ala Tyr Glu Gln Tyr
1 5 10

<210> SEQ ID NO 242
<211> LENGTH: 114
<212> TYPE: PRT
<213> ORGANISM: Artificial Sequence
<220> FEATURE:
<223> OTHER INFORMATION: Synthetic sequence WT137-45 TCR10.1 - Vbeta (mature)

<400> SEQUENCE: 242

Gly Ala Gly Val Ser Gln Ser Pro Arg Tyr Lys Val Thr Lys Arg Gly
1 5 10 15

Gln Asp Val Ala Leu Arg Cys Asp Pro Ile Ser Gly His Val Ser Leu
20 25 30

Tyr Trp Tyr Arg Gln Ala Leu Gly Gln Gly Pro Glu Phe Leu Thr Tyr
35 40 45

Phe Asn Tyr Glu Ala Gln Gln Asp Lys Ser Gly Leu Pro Asn Asp Arg
50 55 60

Phe Ser Ala Glu Arg Pro Glu Gly Ser Ile Ser Thr Leu Thr Ile Gln
65 70 75 80

Arg Thr Glu Gln Arg Asp Ser Ala Met Tyr Arg Cys Ala Ser Ser Leu
85 90 95

Thr Gly Ser Tyr Glu Gln Tyr Phe Gly Pro Gly Thr Arg Leu Thr Val
100 105 110

Thr Glu

<210> SEQ ID NO 243
<211> LENGTH: 118
<212> TYPE: PRT
<213> ORGANISM: Artificial Sequence
<220> FEATURE:
<223> OTHER INFORMATION: Synthetic sequence WT137-45 TCR11.2 - Vbeta
(mature)

<400> SEQUENCE: 243

```
Gly Ala Val Val Ser Gln His Pro Ser Trp Val Ile Cys Lys Ser Gly
1               5                   10                  15

Thr Ser Val Lys Ile Glu Cys Arg Ser Leu Asp Phe Gln Ala Thr Thr
            20                  25                  30

Met Phe Trp Tyr Arg Gln Phe Pro Lys Gln Ser Leu Met Leu Met Ala
        35                  40                  45

Thr Ser Asn Glu Gly Ser Lys Ala Thr Tyr Glu Gln Gly Val Glu Lys
    50                  55                  60

Asp Lys Phe Leu Ile Asn His Ala Ser Leu Thr Leu Ser Thr Leu Thr
65                  70                  75                  80

Val Thr Ser Ala His Pro Glu Asp Ser Ser Phe Tyr Ile Cys Ser Ala
                85                  90                  95

Thr Pro Glu Ala Ser Ser Pro Tyr Glu Gln Tyr Phe Gly Pro Gly Thr
            100                 105                 110

Arg Leu Thr Val Thr Glu
        115
```

<210> SEQ ID NO 244
<211> LENGTH: 114
<212> TYPE: PRT
<213> ORGANISM: Artificial Sequence
<220> FEATURE:
<223> OTHER INFORMATION: Synthetic sequence WT137-45 TCR12.1 - Vbeta
(mature)

<400> SEQUENCE: 244

```
Asp Ala Met Val Ile Gln Asn Pro Arg Tyr Gln Val Thr Gln Phe Gly
1               5                   10                  15

Lys Pro Val Thr Leu Ser Cys Ser Gln Thr Leu Asn His Asn Val Met
            20                  25                  30

Tyr Trp Tyr Gln Gln Lys Ser Ser Gln Ala Pro Lys Leu Leu Phe His
        35                  40                  45

Tyr Tyr Asp Lys Asp Phe Asn Asn Glu Ala Asp Thr Pro Asp Asn Phe
    50                  55                  60

Gln Ser Arg Arg Pro Asn Thr Ser Phe Cys Phe Leu Asp Ile Arg Ser
65                  70                  75                  80

Pro Gly Leu Gly Asp Ala Ala Met Tyr Leu Cys Ala Thr Ser Asn Leu
                85                  90                  95

Gln Gly Arg Gln Pro Gln His Phe Gly Asp Gly Thr Arg Leu Ser Ile
            100                 105                 110

Leu Glu
```

<210> SEQ ID NO 245
<211> LENGTH: 114
<212> TYPE: PRT
<213> ORGANISM: Artificial Sequence
<220> FEATURE:
<223> OTHER INFORMATION: Synthetic sequence WT137-45 TCR13.1 - Vbeta
(mature

<400> SEQUENCE: 245

```
Ala Ala Gly Val Ile Gln Ser Pro Arg His Leu Ile Lys Glu Lys Arg
1               5                   10                  15

Glu Thr Ala Thr Leu Lys Cys Tyr Pro Ile Pro Arg His Asp Thr Val
            20                  25                  30

Tyr Trp Tyr Gln Gln Gly Pro Gly Gln Asp Pro Gln Phe Leu Ile Ser
        35                  40                  45

Phe Tyr Glu Lys Met Gln Ser Asp Lys Gly Ser Ile Pro Asp Arg Phe
    50                  55                  60

Ser Ala Gln Gln Phe Ser Asp Tyr His Ser Glu Leu Asn Met Ser Ser
65                  70                  75                  80

Leu Glu Leu Gly Asp Ser Ala Leu Tyr Phe Cys Ala Ser Ser Leu Arg
                85                  90                  95

Leu Gly Arg Glu Thr Gln Tyr Phe Gly Pro Gly Thr Arg Leu Leu Val
            100                 105                 110

Leu Glu


<210> SEQ ID NO 246
<211> LENGTH: 114
<212> TYPE: PRT
<213> ORGANISM: Artificial Sequence
<220> FEATURE:
<223> OTHER INFORMATION: Synthetic sequence WT137-45 TCR13.2 - Vbeta
      (mature)

<400> SEQUENCE: 246

Gly Ala Gly Val Ser Gln Ser Pro Arg Tyr Lys Val Ala Lys Arg Gly
1               5                   10                  15

Gln Asp Val Ala Leu Arg Cys Asp Pro Ile Ser Gly His Val Ser Leu
            20                  25                  30

Phe Trp Tyr Gln Gln Ala Leu Gly Gln Gly Pro Glu Phe Leu Thr Tyr
        35                  40                  45

Phe Gln Asn Glu Ala Gln Leu Asp Lys Ser Gly Leu Pro Ser Asp Arg
    50                  55                  60

Phe Phe Ala Glu Arg Pro Glu Gly Ser Val Ser Thr Leu Lys Ile Gln
65                  70                  75                  80

Arg Thr Gln Gln Glu Asp Ser Ala Val Tyr Leu Cys Ala Ser Ser Leu
                85                  90                  95

Gly Gln Ala Tyr Glu Gln Tyr Phe Gly Pro Gly Thr Arg Leu Thr Val
            100                 105                 110

Thr Glu


<210> SEQ ID NO 247
<211> LENGTH: 114
<212> TYPE: PRT
<213> ORGANISM: Artificial Sequence
<220> FEATURE:
<223> OTHER INFORMATION: Synthetic sequence WT137-45 TCR14.1 - Vbeta
      (mature)

<400> SEQUENCE: 247

Glu Ala Gly Val Val Gln Ser Pro Arg Tyr Lys Ile Ile Glu Lys Lys
1               5                   10                  15

Gln Pro Val Ala Phe Trp Cys Asn Pro Ile Ser Gly His Asn Thr Leu
            20                  25                  30

Tyr Trp Tyr Leu Gln Asn Leu Gly Gln Gly Pro Glu Leu Leu Ile Arg
        35                  40                  45

Tyr Glu Asn Glu Glu Ala Val Asp Asp Ser Gln Leu Pro Lys Asp Arg
    50                  55                  60
```

Phe Ser Ala Glu Arg Leu Lys Gly Val Asp Ser Thr Leu Lys Ile Gln
65 70 75 80

Pro Ala Glu Leu Gly Asp Ser Ala Val Tyr Leu Cys Ala Ser Ser Leu
85 90 95

Thr Arg Gly Ala Glu Ala Phe Phe Gly Gln Gly Thr Arg Leu Thr Val
100 105 110

Val Glu

<210> SEQ ID NO 248
<211> LENGTH: 115
<212> TYPE: PRT
<213> ORGANISM: Artificial Sequence
<220> FEATURE:
<223> OTHER INFORMATION: Synthetic sequence WT137-45 TCR15.1 - Vbeta (mature)

<400> SEQUENCE: 248

Asp Gly Gly Ile Thr Gln Ser Pro Lys Tyr Leu Phe Arg Lys Glu Gly
1 5 10 15

Gln Asn Val Thr Leu Ser Cys Glu Gln Asn Leu Asn His Asp Ala Met
20 25 30

Tyr Trp Tyr Arg Gln Asp Pro Gly Gln Gly Leu Arg Leu Ile Tyr Tyr
35 40 45

Ser Gln Ile Val Asn Asp Phe Gln Lys Gly Asp Ile Ala Glu Gly Tyr
50 55 60

Ser Val Ser Arg Glu Lys Lys Glu Ser Phe Pro Leu Thr Val Thr Ser
65 70 75 80

Ala Gln Lys Asn Pro Thr Ala Phe Tyr Leu Cys Ala Ser Ser Arg Asp
85 90 95

Arg Glu Gln Glu Ser Pro Leu His Phe Gly Asn Gly Thr Arg Leu Thr
100 105 110

Val Thr Glu
115

<210> SEQ ID NO 249
<211> LENGTH: 114
<212> TYPE: PRT
<213> ORGANISM: Artificial Sequence
<220> FEATURE:
<223> OTHER INFORMATION: Synthetic sequence WT137-45 TCR16.1 - Vbeta (mature)

<400> SEQUENCE: 249

Glu Ala Gln Val Thr Gln Asn Pro Arg Tyr Leu Ile Thr Val Thr Gly
1 5 10 15

Lys Lys Leu Thr Val Thr Cys Ser Gln Asn Met Asn His Glu Tyr Met
20 25 30

Ser Trp Tyr Arg Gln Asp Pro Gly Leu Gly Leu Arg Gln Ile Tyr Tyr
35 40 45

Ser Met Asn Val Glu Val Thr Asp Lys Gly Asp Val Pro Glu Gly Tyr
50 55 60

Lys Val Ser Arg Lys Glu Lys Arg Asn Phe Pro Leu Ile Leu Glu Ser
65 70 75 80

Pro Ser Pro Asn Gln Thr Ser Leu Tyr Phe Cys Ala Ser Ser Phe Ser
85 90 95

Gly Gly Thr Tyr Glu Gln Tyr Phe Gly Pro Gly Thr Arg Leu Thr Val
100 105 110

Thr Glu

<210> SEQ ID NO 250
<211> LENGTH: 115
<212> TYPE: PRT
<213> ORGANISM: Artificial Sequence
<220> FEATURE:
<223> OTHER INFORMATION: Synthetic sequence WT137-45 TCR16.2 - Vbeta
(mature)

<400> SEQUENCE: 250

```
Ala Ala Gly Val Ile Gln Ser Pro Arg His Leu Ile Lys Glu Lys Arg
1               5                   10                  15

Glu Thr Ala Thr Leu Lys Cys Tyr Pro Ile Pro Arg His Asp Thr Val
            20                  25                  30

Tyr Trp Tyr Gln Gln Gly Pro Gly Gln Asp Pro Gln Phe Leu Ile Ser
        35                  40                  45

Phe Tyr Glu Lys Met Gln Ser Asp Lys Gly Ser Ile Pro Asp Arg Phe
    50                  55                  60

Ser Ala Gln Gln Phe Ser Asp Tyr His Ser Glu Leu Asn Met Ser Ser
65                  70                  75                  80

Leu Glu Leu Gly Asp Ser Ala Leu Tyr Phe Cys Ala Ser Ser Tyr Arg
                85                  90                  95

Gly Gly Ser Thr Tyr Glu Gln Tyr Phe Gly Pro Gly Thr Arg Leu Thr
            100                 105                 110

Val Thr Glu
        115
```

<210> SEQ ID NO 251
<211> LENGTH: 116
<212> TYPE: PRT
<213> ORGANISM: Artificial Sequence
<220> FEATURE:
<223> OTHER INFORMATION: Synthetic sequence WT137-45 TCR18.1 - Vbeta
(mature)

<400> SEQUENCE: 251

```
Glu Ala Glu Val Ala Gln Ser Pro Arg Tyr Lys Ile Thr Glu Lys Ser
1               5                   10                  15

Gln Ala Val Ala Phe Trp Cys Asp Pro Ile Ser Gly His Ala Thr Leu
            20                  25                  30

Tyr Trp Tyr Arg Gln Ile Leu Gly Gln Gly Pro Glu Leu Leu Val Gln
        35                  40                  45

Phe Gln Asp Glu Ser Val Val Asp Asp Ser Gln Leu Pro Lys Asp Arg
    50                  55                  60

Phe Ser Ala Glu Arg Leu Lys Gly Val Asp Ser Thr Leu Lys Ile Gln
65                  70                  75                  80

Pro Ala Glu Leu Gly Asp Ser Ala Met Tyr Leu Cys Ala Ser Ser Gln
                85                  90                  95

Arg Asp Ser Pro Asn Glu Lys Leu Phe Phe Gly Ser Gly Thr Gln Leu
            100                 105                 110

Ser Val Leu Glu
        115
```

<210> SEQ ID NO 252
<211> LENGTH: 117
<212> TYPE: PRT
<213> ORGANISM: Artificial Sequence
<220> FEATURE:
<223> OTHER INFORMATION: Synthetic sequence WT137-45 TCR19.1 - Vbeta (mature)

<400> SEQUENCE: 252

Glu Thr Gly Val Thr Gln Thr Pro Arg His Leu Val Met Gly Met Thr
1 5 10 15

Asn Lys Lys Ser Leu Lys Cys Glu Gln His Leu Gly His Asn Ala Met
20 25 30

Tyr Trp Tyr Lys Gln Ser Ala Lys Lys Pro Leu Glu Leu Met Phe Val
35 40 45

Tyr Ser Leu Glu Glu Arg Val Glu Asn Asn Ser Val Pro Ser Arg Phe
50 55 60

Ser Pro Glu Cys Pro Asn Ser Ser His Leu Phe Leu His Leu His Thr
65 70 75 80

Leu Gln Pro Glu Asp Ser Ala Leu Tyr Leu Cys Ala Ser Ser Gln Asp
85 90 95

Pro Tyr Lys Leu Ser Gly Asn Thr Ile Tyr Phe Gly Glu Gly Ser Trp
100 105 110

Leu Thr Val Val Glu
115

<210> SEQ ID NO 253
<211> LENGTH: 112
<212> TYPE: PRT
<213> ORGANISM: Artificial Sequence
<220> FEATURE:
<223> OTHER INFORMATION: Synthetic sequence WT137-45 TCR10.1 Valpha
(mature)

<400> SEQUENCE: 253

Lys Gln Glu Val Thr Gln Ile Pro Ala Ala Leu Ser Val Pro Glu Gly
1 5 10 15

Glu Asn Leu Val Leu Asn Cys Ser Phe Thr Asp Ser Ala Ile Tyr Asn
20 25 30

Leu Gln Trp Phe Arg Gln Asp Pro Gly Lys Gly Leu Thr Ser Leu Leu
35 40 45

Leu Ile Gln Ser Ser Gln Arg Glu Gln Thr Ser Gly Arg Leu Asn Ala
50 55 60

Ser Leu Asp Lys Ser Ser Gly Arg Ser Thr Leu Tyr Ile Ala Ala Ser
65 70 75 80

Gln Pro Gly Asp Ser Ala Thr Tyr Leu Cys Ala Val Lys Glu Thr Ser
85 90 95

Gly Ser Arg Leu Thr Phe Gly Glu Gly Thr Gln Leu Thr Val Asn Pro
100 105 110

<210> SEQ ID NO 254
<211> LENGTH: 119
<212> TYPE: PRT
<213> ORGANISM: Artificial Sequence
<220> FEATURE:
<223> OTHER INFORMATION: Synthetic sequence WT137-45 TCR11.2 Valpha
(mature)

<400> SEQUENCE: 254

Ala Gln Thr Val Thr Gln Ser Gln Pro Glu Met Ser Val Gln Glu Ala
1 5 10 15

Glu Thr Val Thr Leu Ser Cys Thr Tyr Asp Thr Ser Glu Asn Asn Tyr
20 25 30

Tyr Leu Phe Trp Tyr Lys Gln Pro Pro Ser Arg Gln Met Ile Leu Val
35 40 45

```
Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Thr Ala Met Tyr Phe Cys Ala Phe Ile Tyr
                85                  90                  95

Pro Ser Tyr Thr Ser Gly Thr Tyr Lys Tyr Ile Phe Gly Thr Gly Thr
            100                 105                 110

Arg Leu Lys Val Leu Ala Asn
        115


<210> SEQ ID NO 255
<211> LENGTH: 114
<212> TYPE: PRT
<213> ORGANISM: Artificial Sequence
<220> FEATURE:
<223> OTHER INFORMATION: Synthetic sequence WT137-45 TCR12.1 Valpha
      (mature)

<400> SEQUENCE: 255

Asp Gln Gln Val Lys Gln Asn Ser Pro Ser Leu Ser Val Gln Glu Gly
1               5                   10                  15

Arg Ile Ser Ile Leu Asn Cys Asp Tyr Thr Asn Ser Met Phe Asp Tyr
            20                  25                  30

Phe Leu Trp Tyr Lys Lys Tyr Pro Ala Glu Gly Pro Thr Phe Leu Ile
        35                  40                  45

Ser Ile Ser Ser Ile Lys Asp Lys Asn Glu Asp Gly Arg Phe Thr Val
    50                  55                  60

Phe Leu Asn Lys Ser Ala Lys His Leu Ser Leu His Ile Val Pro Ser
65                  70                  75                  80

Gln Pro Gly Asp Ser Ala Val Tyr Phe Cys Ala Ala Ser Gly Thr Gly
                85                  90                  95

Gly Ser Tyr Ile Pro Thr Phe Gly Arg Gly Thr Ser Leu Ile Val His
            100                 105                 110

Pro Tyr


<210> SEQ ID NO 256
<211> LENGTH: 113
<212> TYPE: PRT
<213> ORGANISM: Artificial Sequence
<220> FEATURE:
<223> OTHER INFORMATION: Synthetic sequence WT137-45 TCR13.1 Valpha
      (mature)

<400> SEQUENCE: 256

Asp Gln Gln Val Lys Gln Asn Ser Pro Ser Leu Ser Val Gln Glu Gly
1               5                   10                  15

Arg Ile Ser Ile Leu Asn Cys Asp Tyr Thr Asn Ser Met Phe Asp Tyr
            20                  25                  30

Phe Leu Trp Tyr Lys Lys Tyr Pro Ala Glu Gly Pro Thr Phe Leu Ile
        35                  40                  45

Ser Ile Ser Ser Ile Lys Asp Lys Asn Glu Asp Gly Arg Phe Thr Val
    50                  55                  60

Phe Leu Asn Lys Ser Ala Lys His Leu Ser Leu His Ile Val Pro Ser
65                  70                  75                  80

Gln Pro Gly Asp Ser Ala Val Tyr Phe Cys Ala Ala Ser Gly Ile Gly
                85                  90                  95
```

```
Asp Tyr Lys Leu Ser Phe Gly Ala Gly Thr Thr Val Thr Val Arg Ala
            100                 105                 110

Asn


<210> SEQ ID NO 257
<211> LENGTH: 109
<212> TYPE: PRT
<213> ORGANISM: Artificial Sequence
<220> FEATURE:
<223> OTHER INFORMATION: Synthetic sequence WT137-45 TCR13.2 Valpha
      (mature)

<400> SEQUENCE: 257

Lys Asn Glu Val Glu Gln Ser Pro Gln Asn Leu Thr Ala Gln Glu Gly
1               5                   10                  15

Glu Phe Ile Thr Ile Asn Cys Ser Tyr Ser Val Gly Ile Ser Ala Leu
            20                  25                  30

His Trp Leu Gln Gln His Pro Gly Gly Gly Ile Val Ser Leu Phe Met
        35                  40                  45

Leu Ser Ser Gly Lys Lys Lys His Gly Arg Leu Ile Ala Thr Ile Asn
    50                  55                  60

Ile Gln Glu Lys His Ser Ser Leu His Ile Thr Ala Ser His Pro Arg
65                  70                  75                  80

Asp Ser Ala Val Tyr Ile Cys Ala Val Arg Thr Ser Tyr Asp Lys Val
                85                  90                  95

Ile Phe Gly Pro Gly Thr Ser Leu Ser Val Ile Pro Asn
            100                 105


<210> SEQ ID NO 258
<211> LENGTH: 114
<212> TYPE: PRT
<213> ORGANISM: Artificial Sequence
<220> FEATURE:
<223> OTHER INFORMATION: Synthetic sequence WT137-45 TCR14.1 Valpha
      (mature)

<400> SEQUENCE: 258

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Phe Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Asn Leu Leu Gly Ala
                85                  90                  95

Thr Gly Tyr Ser Thr Leu Thr Phe Gly Lys Gly Thr Met Leu Leu Val
            100                 105                 110

Ser Pro


<210> SEQ ID NO 259
<211> LENGTH: 111
<212> TYPE: PRT
<213> ORGANISM: Artificial Sequence
<220> FEATURE:
<223> OTHER INFORMATION: Synthetic sequence WT137-45 TCR15.1 Valpha
      (mature)
```

<400> SEQUENCE: 259

Gly Gln Asn Ile Asp Gln Pro Thr Glu Met Thr Ala Thr Glu Gly Ala
1               5                   10                  15

Ile Val Gln Ile Asn Cys Thr Tyr Gln Thr Ser Gly Phe Asn Gly Leu
            20                  25                  30

Phe Trp Tyr Gln Gln His Ala Gly Glu Ala Pro Thr Phe Leu Ser Tyr
        35                  40                  45

Asn Val Leu Asp Gly Leu Glu Glu Lys Gly Arg Phe Ser Ser Phe Leu
    50                  55                  60

Ser Arg Ser Lys Gly Tyr Ser Tyr Leu Leu Leu Lys Glu Leu Gln Met
65                  70                  75                  80

Lys Asp Ser Ala Ser Tyr Leu Cys Ala Val Arg Gly Ile Asn Asp Tyr
                85                  90                  95

Lys Leu Ser Phe Gly Ala Gly Thr Thr Val Thr Val Arg Ala Asn
            100                 105                 110

<210> SEQ ID NO 260
<211> LENGTH: 110
<212> TYPE: PRT
<213> ORGANISM: Artificial Sequence
<220> FEATURE:
<223> OTHER INFORMATION: Synthetic sequence WT137-45 TCR16.1 Valpha (mature)

<400> SEQUENCE: 260

Glu Asp Gln Val Thr Gln Ser Pro Glu Ala Leu Arg Leu Gln Glu Gly
1               5                   10                  15

Glu Ser Ser Ser Leu Asn Cys Ser Tyr Thr Val Ser Gly Leu Arg Gly
            20                  25                  30

Leu Phe Trp Tyr Arg Gln Asp Pro Gly Lys Gly Pro Glu Phe Leu Phe
        35                  40                  45

Thr Leu Tyr Ser Ala Gly Glu Glu Lys Glu Lys Glu Arg Leu Lys Ala
    50                  55                  60

Thr Leu Thr Lys Lys Glu Ser Phe Leu His Ile Thr Ala Pro Lys Pro
65                  70                  75                  80

Glu Asp Ser Ala Thr Tyr Leu Cys Ala Val Ile Thr Gly Phe Gln Lys
                85                  90                  95

Leu Val Phe Gly Thr Gly Thr Arg Leu Leu Val Ser Pro Asn
            100                 105                 110

<210> SEQ ID NO 261
<211> LENGTH: 111
<212> TYPE: PRT
<213> ORGANISM: Artificial Sequence
<220> FEATURE:
<223> OTHER INFORMATION: Synthetic sequence WT137-45 TCR16.2 Valpha (mature)

<400> SEQUENCE: 261

Asp Ala Lys Thr Thr Gln Pro Thr Ser Met Asp Cys Ala Glu Gly Arg
1               5                   10                  15

Ala Ala Asn Leu Pro Cys Asn His Ser Thr Ile Ser Gly Asn Glu Tyr
            20                  25                  30

Val Tyr Trp Tyr Arg Gln Ile His Ser Gln Gly Pro Gln Tyr Ile Ile
        35                  40                  45

His Gly Leu Lys Asn Asn Glu Thr Asn Glu Met Ala Ser Leu Ile Ile
    50                  55                  60

Thr Glu Asp Arg Lys Ser Ser Thr Leu Ile Leu Pro His Ala Thr Leu
65 70 75 80

Arg Asp Thr Ala Val Tyr Tyr Cys Ile Ala Gly Val Gly Arg Gly Gln
85 90 95

Asn Phe Val Phe Gly Pro Gly Thr Arg Leu Ser Val Leu Pro Tyr
100 105 110

<210> SEQ ID NO 262
<211> LENGTH: 114
<212> TYPE: PRT
<213> ORGANISM: Artificial Sequence
<220> FEATURE:
<223> OTHER INFORMATION: Synthetic sequence WT137-45 TCR18.1 Valpha (mature)

<400> SEQUENCE: 262

Ile Leu Asn Val Glu Gln Ser Pro Gln Ser Leu His Val Gln Glu Gly
1 5 10 15

Asp Ser Thr Asn Phe Thr Cys Ser Phe Pro Ser Ser Asn Phe Tyr Ala
20 25 30

Leu His Trp Tyr Arg Trp Glu Thr Ala Lys Ser Pro Glu Ala Leu Phe
35 40 45

Val Met Thr Leu Asn Gly Asp Glu Lys Lys Lys Gly Arg Ile Ser Ala
50 55 60

Thr Leu Asn Thr Lys Glu Gly Tyr Ser Tyr Leu Tyr Ile Lys Gly Ser
65 70 75 80

Gln Pro Glu Asp Ser Ala Thr Tyr Leu Cys Ala Phe His Pro Asn Phe
85 90 95

Gly Asn Glu Lys Leu Thr Phe Gly Thr Gly Thr Arg Leu Thr Ile Ile
100 105 110

Pro Asn

<210> SEQ ID NO 263
<211> LENGTH: 115
<212> TYPE: PRT
<213> ORGANISM: Artificial Sequence
<220> FEATURE:
<223> OTHER INFORMATION: Synthetic sequence WT137-45 TCR19.1 Valpha (mature)

<400> SEQUENCE: 263

Glu Asp Gln Val Thr Gln Ser Pro Glu Ala Leu Arg Leu Gln Glu Gly
1 5 10 15

Glu Ser Ser Ser Leu Asn Cys Ser Tyr Thr Val Ser Gly Leu Arg Gly
20 25 30

Leu Phe Trp Tyr Arg Gln Asp Pro Gly Lys Gly Pro Glu Phe Leu Phe
35 40 45

Thr Leu Tyr Ser Ala Gly Glu Glu Lys Glu Lys Glu Arg Leu Lys Ala
50 55 60

Thr Leu Thr Lys Lys Glu Ser Phe Leu His Ile Thr Ala Pro Lys Pro
65 70 75 80

Glu Asp Ser Ala Thr Tyr Leu Cys Ala Val Gln Pro Arg Gly Asp Gly
85 90 95

Ser Ser Asn Thr Gly Lys Leu Ile Phe Gly Gln Gly Thr Thr Leu Gln
100 105 110

Val Lys Pro
115